US010457963B2

(12) United States Patent
Shaw, IV et al.

(10) Patent No.: US 10,457,963 B2
(45) Date of Patent: Oct. 29, 2019

(54) HETEROLOGOUS PRODUCTION OF 10-METHYLSTEARIC ACID

(71) Applicant: Novogy, Inc., Cambridge, MA (US)

(72) Inventors: Arthur J. Shaw, IV, Belmont, MA (US); Hannah Blitzblau, Arlington, MA (US); Donald V. Crabtree, Cambridge, MA (US)

(73) Assignee: Novogy, Inc., Camden, MA (US)

( * ) Notice: Subject to any disclaimer, the term of this patent is extended or adjusted under 35 U.S.C. 154(b) by 0 days.

(21) Appl. No.: 15/710,734

(22) Filed: Sep. 20, 2017

(65) Prior Publication Data

US 2018/0105848 A1 Apr. 19, 2018

Related U.S. Application Data

(60) Provisional application No. 62/396,870, filed on Sep. 20, 2016.

(51) Int. Cl.

| | |
|---|---|
| ***C12P 7/64*** | (2006.01) |
| ***C11B 1/10*** | (2006.01) |
| ***A23D 9/02*** | (2006.01) |
| ***C12Q 1/686*** | (2018.01) |
| ***C12N 9/10*** | (2006.01) |
| ***C11C 3/00*** | (2006.01) |
| ***C12N 9/02*** | (2006.01) |

(52) U.S. Cl.

CPC .............. *C12P 7/6409* (2013.01); *A23D 9/02* (2013.01); *C11B 1/10* (2013.01); *C11C 3/00* (2013.01); *C12N 9/001* (2013.01); *C12N 9/1007* (2013.01); *C12Q 1/686* (2013.01)

(58) Field of Classification Search

CPC .... A23D 9/02; C11B 1/10; C11C 3/00; C12Q 1/686; C12N 9/1007; C12N 9/001; C12P 7/6409

See application file for complete search history.

(56) References Cited

U.S. PATENT DOCUMENTS

| | | | | |
|---|---|---|---|---|
| 7,166,766 B1 | 1/2007 | Duhot et al. | | |
| 8,530,221 B2 * | 9/2013 | Hu | ......................... | C12N 15/52 435/243 |
| 2010/0115669 A1 | 5/2010 | Bao et al. | | |
| 2011/0195880 A1 | 8/2011 | Kawamura et al. | | |

FOREIGN PATENT DOCUMENTS

| | | |
|---|---|---|
| EP | 1108790 A2 | 6/2001 |
| WO | WO/00/061740 A1 | 10/2000 |
| WO | WO/15/184277 A1 | 12/2015 |

OTHER PUBLICATIONS

Chertkov et al., Complete genome sequence of Thermomonospora curvata type starin (B9T). Stand. Genom. Sci., 2011, vol. 4: 13-22. (Year: 2011).*

Korn-Wendisch et al., *Thermocrispum* gen. nov., a new genus of the order Actinomycetales and description of *Thermocrispum agreste* sp. nov. Int. J. System. Bacteriol., 1995, vol. 45(1): 67-77. (Year: 1995).*

Abghari et al., Yarrowia lipolytica as an oleaginous cell factory platform for production of fatty acid-based biofuel and bioproducts. Frontiers in Energy Res., 2014, vol. 2, Article 21: pp. 1-21. (Year: 2014).*

Actinobacteria/Wikipedia; 8 (eight) pages downloaded from https://en.wikipedia.org/wiki/Actinobacteria on Feb. 12, 2019. (Year: 2019).*

International Search Report and Written Opinion in International Application No. PCT/US2017/052491 dated Dec. 21, 2017.

* cited by examiner

*Primary Examiner* — Ganapathirama Raghu
(74) *Attorney, Agent, or Firm* — Albert Shung

(57) ABSTRACT

Nucleic acids and cells comprising a methyltransferase gene and/or a reductase gene are disclosed. These nucleic acids and cells may be used to produce branched (methyl)lipids, such as 10-methylstearate.

14 Claims, 32 Drawing Sheets

Specification includes a Sequence Listing.

PHOSPHOLIPID-ACYL OLEIC ACID

PHOSPHOLIPID - ACYL 10 - METHYLENE STEARIC ACID

PHOSPHOLIPID - ACYL 10 - METHYLSTEARIC ACID

A) *MYCOBACTERIUM SMEGMATIS*

MYCOBACTERIUM SMEGMATIS mc2 155 tms opero.gb FROM 1 TO 5601

MSMEI_6118 (tmsA) FAD/FMN OXIDOREDUCTASE

MSMEI_6119 (tmsB) cfa SYNTHASE

B) *AGROMYCES SUBBETICUS*

AGROMYCES SUBBETICUS DSM 16689 tms operon.gb FROM 1 TO 4550

HYDROLASE    tmsA FAD-LINKED OXIDASE    tmsB CYCLOPROPANE SYNTHASE    HYP PROTEIN

HYP PROTEIN

C) *AMYCOLICICOCCUS SUBFLAVUS*

AMYCOLICICOCCUS SUBFLAVUS tms operon.gb FROM 1 TO 5428

DNA POL III    tmsB (CYCLOPROPANE SYNTHASE)    POLYKETIDE CYCLASE    HYP PROTEIN    RecR    URIDINE KINASE
SUBUNIT
tmsA (FAD OXIDASE)

D) *CORYNEBACTERIUM GLUTAMICUM*

CORYNEBACTERIUM GLUTAMICUM DSM 20300 tms operon.gb FROM 1 TO 5164

TYPE VII SECRETION    tmsA DEHYDROGENASE    tmsB CYCLOPROPANE SYNTHASE    MEMBRANE PROTEIN
PROTEIN EccB

E) *CORYNEBACTERIUM GLYCINIPHILIUM*

CORYNEBACTERIUM GLYCINIPHILIUM tms operon.gb FROM 1 TO 5458

HELICASE    Gly tmsA (FMN/FAD)    Cgly tmsB (CYCLOPROPANE SYN)    HYP PROTEIN    TRANS- AMINASE Ggly tmsC (HYP PROTEIN)

F) *KNOELLA AEROLATA*

KNOELLA AEROLATA DSM 18566 tms operon.gb FROM 1 TO 8859

HYPOTHETICAL    tmsA FAD-LINKED    NUCLEOTIDE-DISULFIDE OXIDOR
PROTEIN    OXIDASE    tmsB CYCLOPROPANE    METHYL-    ACYL-CoA
SYNTHASE    TRANSFERASE TYPE 12    OXIDASE

G) *MYCOBACTERIUM AUSTROAFRICANUM*

M AUSTROAFRICANUM tms operon.gb FROM 1 TO 7475

DNA POL III SUBUNIT    tmsC    tmsB CYCLOPROPANE    tmsA FAD-    POLYKETIDE    NUCLEOID RecR
HYP PROTEIN    SYNTHASE    LINKED OXIDASE    CYCLASE    PROTEIN
AMIDASE

H) *MYCOBACTERIUM GILVUM*

MYCOBACTERIUM GILVUM spyr1 DSM 45189 tms operon.gb FROM 1 TO 5798

AMIDASE    tmsA FAD/FMN    tmsC    DNA POL III
POLYKETIDE    DEHYDROG-    tmsB METHYLTRANSFERASE    HYP    SUBUNIT
CYCLASE    ENASE    PROTEIN

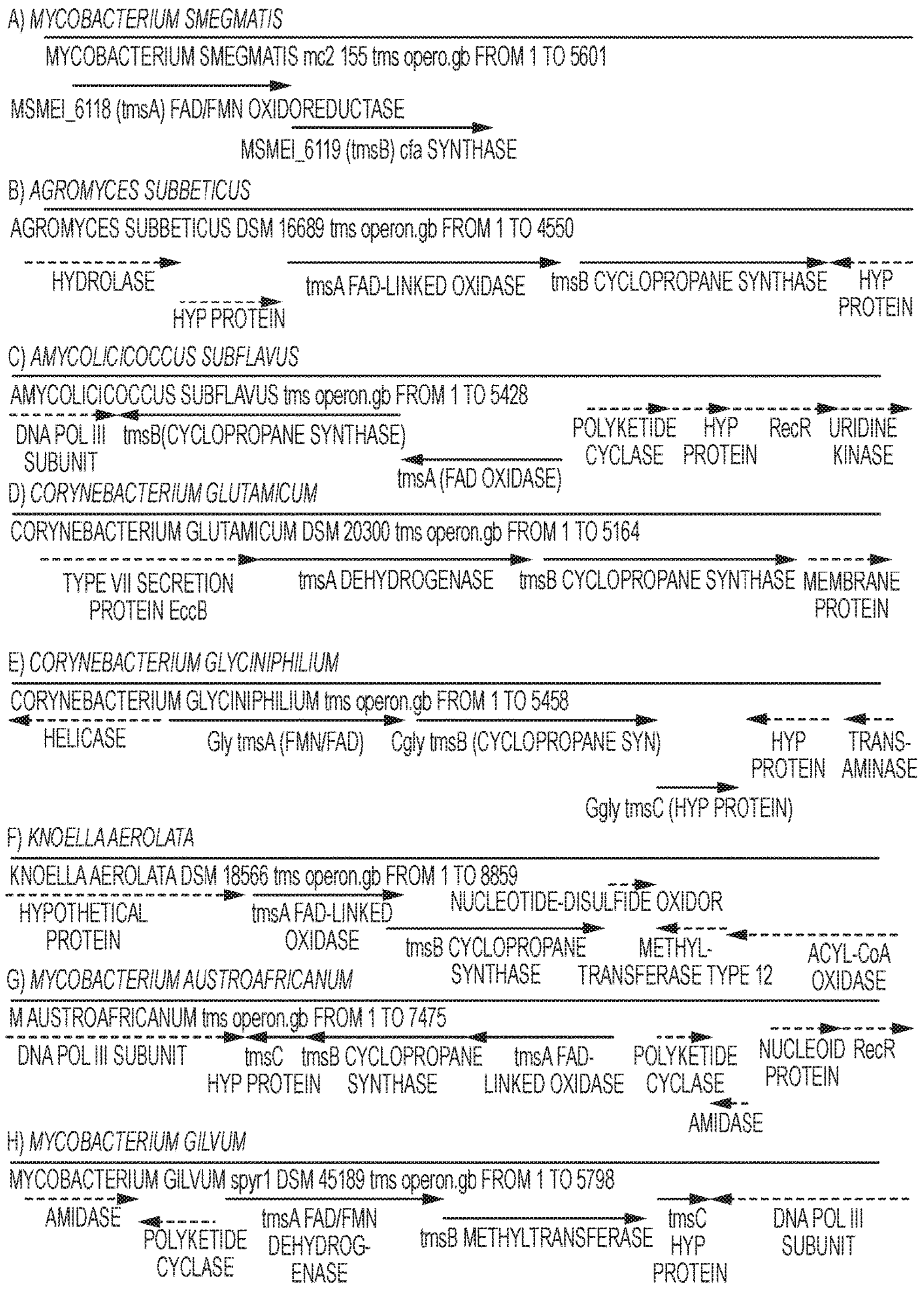

FIG. 3A

I) *MYCOBACTERIUM INDICUS PRANII*

MYCOBACTERIUM INDICUS PRANII DSM 45239 tsm operon.gb FROM 1 TO 5148

KanY PROTEIN | tmsA FAD/FMN DEHYDROGENASE | tmsB CYCLOPROPANE SYNTHASE | DNA POL III SUBUNIT

J) *MYCOBACTERIUM PHLEI*

MYCOBACTERIUM PHLEI tms operon.gb FROM 1 TO 3450 tmsA MPHLEI_RS13765 FAD OXIDASE | tmsB MPHLEI_RS13770 cfa SYNTHASE

K) *MYCOBACTERIUM TUBERCULOSIS*

MYCOBACTERIUM TUBERCULOSIS H37Rv tms operon.gb FROM 1 TO 4777

HYP PROTEIN | CONSERVED PROTEIN | Mt tmsA CONSERVED PROTEIN | Mt tmsB (FATTY ACID SYNTHASE) | DNA POL III SUBUNIT

L) *MYCOBACTERIUM VANBAALENII*

MYCOBACTERIUM VANBAALENII tms operon.gb FROM 1 TO 3825 tmsA Mvan_5531 FAD OXIDASE | tmsB Mvan_5532 (cfa SYNTHASE) | tmsB Mvan_5533 UNKNOWN

M) *RHODOCOCCUS OPACUS*

RHODOCOCCUS OPACUS M213 tms operon.gb FROM 1 TO 5276

HYP PROTEIN | tmsA HYP PROTEIN | tmsB CYCLOPROPANE SYNTHASE | HYP PROTEIN | FATTY OXODATION SUBUNIT ALPHA

N) *STREPTOMYCES REGNSIS*

STREPTOMYCES REGNSIS tms operon.gb FROM 1 TO 4481

HYP PROTEIN | tmsA FAD-LINKED OXIDASE | tmsB CYCLOPROPANE SYNTHASE | tmsC HYP PROTEIN

O) *THERMOBIFIDE FUSCA*

THERMOBIFIDA FUSCA YX tms operon.gb FROM 1 TO 4401

Tf tmsC HYPOTHETICAL PROTEIN | Tf tmsB CYCLOPROPANE SYNTHASE | Tf tmsA HYPOTHETICAL PRO | GLUTAMATE RACEMASE

P) *THERMOMONOSPORA CURVATA*

THERMOMONOSPORA CURVATA DSM 43183 tms operon.gb FROM 1 TO 5044

PYRIDOXAMINE OXIDASE | tmsA FAD LINKED OXIDASE | tmsB CYCLOPROPANE SYNTHASE | RNA POLYMERASE II | RNA POLYMERASE

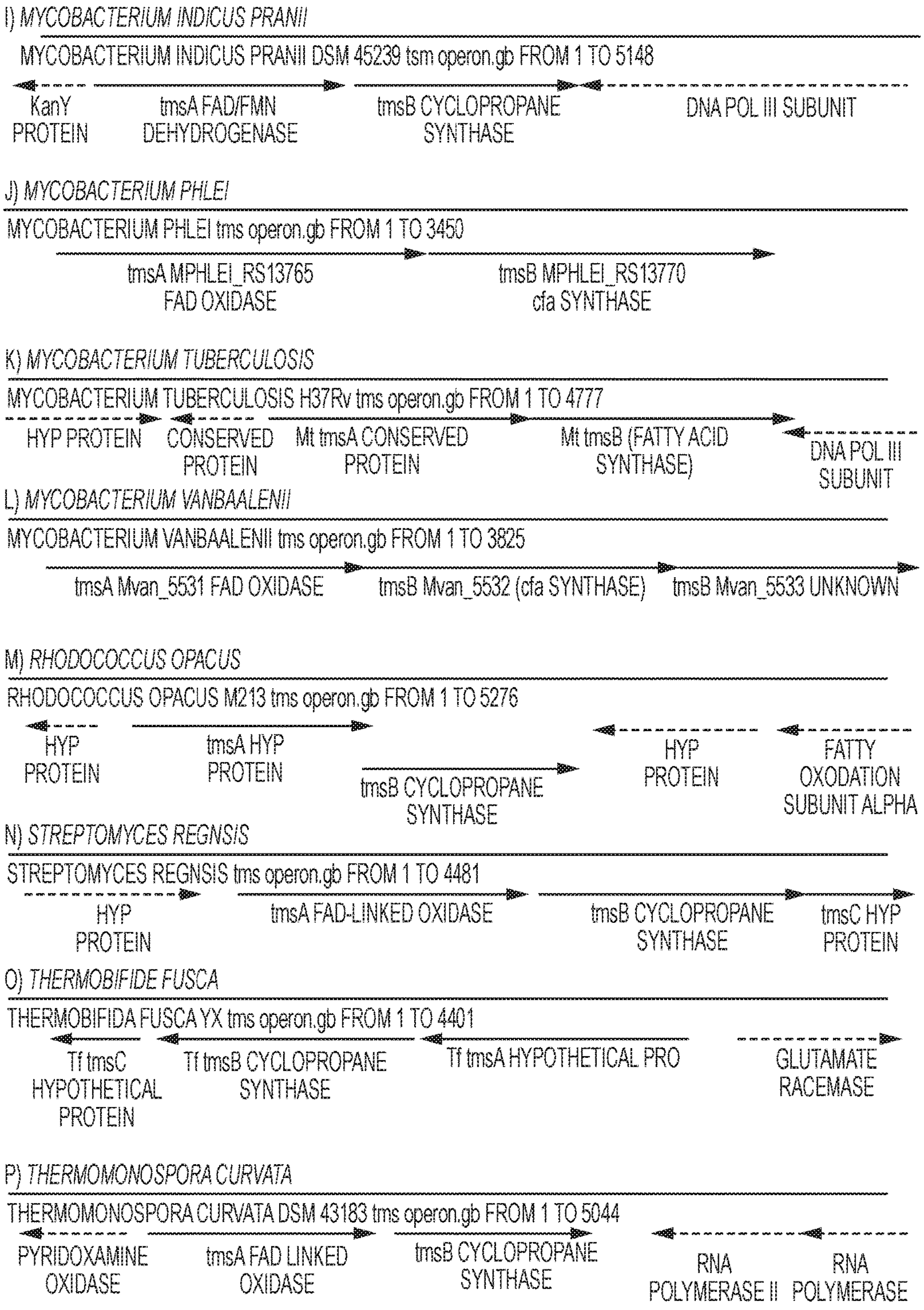

FIG. 3B

```
Ecoli_cfa       ------------------MSSS-CIEEVSVPDDNWYRIANELLSRAGIAINGSAPADIRV   41
Cglycini_tmsB   ----------MS--RGFTPLTVGQIVDKVI-TPPAPFRVTAFDGS---TAGPADAELALEI   45
Cglut_tmsB      ----------MSNAVAQDLMTIADIVEATT-TAPIPFHITAFDGS---FTGPEDAPYQLFV   47
Tfus_tmsB       ------------------MRLAEVFERVV-GPDAPVHFRAYDGS---TAGDPRSEVAIVV   38
Tcurv_tmsB      ------------------MTLAKVFEELV-GADAPVELTAYDGS---RAGRLGSDLRVHV   38
Kaero_tmsB      ----------MSHTTDEIRTVADLVDEVV-VGPLPVRVTAYDGS---KTGPDSAPRTIHI   46
Asubflav_tmsB   ---MKAVLTAFTAPQLERMNVAEILSAVL-GRDFPIRFTAYDGS---ALGPETARYGLHL   53
Rop_tmsB        MTTLK-----ASRSQDHKLTIAEILETLS-DGMLPLRFSAYDGS---AAGPEDAPYGLHL   51
Mind_tmsB       --------------------MAEILEVFAATGRHPLKFTAYDGS---IAGNEDAELGLDL   37
Asubb_tmsB      ----------------------MLEIVV-AGRLPLRFTAYDGS---SAGPPDALFGLDL   33
Msmeg_tmsB      MTTFKERE---TSTADRKLTLAEILEIFA-AGKEPLKFTAYDGS---SAGPEDATMGLDL   53
Mvan_tmsB       MTTFRDGAADTGLHGDRKLTLAEVLEVFA-SGRLPLKFTAYDGS---SAGPDDATLGLDL   56
Mgliv_tmsB      MTTFREHTDSSASDPDRKLTLAEVLEIFA-AGRRPLKFTAYDGS---SCGPEDATLGLDL   56
                                        ..          ..     *         :   : :

Ecoli_cfa       KNPDFFK-RVLQEGSLGLGESYMDGWWECDRLDM------------FFSKVLRA------   82
Cglycini_tmsB   TSPDALAYIVTAPGDLGLARAYITGSLRVTGDEPGHPYLVFDHLQHLYDQIRRP--SAKD  103
Cglut_tmsB      ANTDAVSYIATAPGDLGLARAYLMGDLIVEGEHPGHPYGIFDALKEFYRCFKRP--DAST  105
Tfus_tmsB       RHPAAVNYIVQAPGALGLTRAYVAGYLDVE----GDMYTALRAMADVVF-QDRPRLSPGE   93
Tcurv_tmsB      KSPYAVSYLVHSPSALGLARAYVAGHLDAY----GDMYTLLREMTQLTE-AL----TPKA   89
Kaero_tmsB      ANQRAVAYLATAPGDLGMARAYTTGDLVVEGVHPGNPYEALVDL-ERVH-FRRP--DPRL  102
Asubflav_tmsB   TTPRGLTYLATAPGDLGLARAYVSGDLEVSGVHQGDPYEIMKILAHDVR-VRRP--SPAT  110
Rop_tmsB        KTTRGTTYLATAPGDLGMARAYVSGDLEARGVHPGDPYEILRVMGDELH-FRRP--SALT  108
Mind_tmsB       RSPRGATYLATAPGELGLARAYVSGDLQAYGVHPGDPYQLLKTLTDRVE-FKRP--PVRV   94
Asubb_tmsB      KTPRGTTYLATGRGDLGLARAYIAGDLEIQGVHPGDPYELLKALADSLV-FKLP--PPRV   90
Msmeg_tmsB      KTPRGTTYLATAPGDLGLARAYVSGDLEPHGVHPGDPYPLLRALAERME-FKRP--PARV  110
Mvan_tmsB       LTPRGTTYLATAPGDLGLARAYVSGDLQLQGVHPGDPYDLLNALVQKLD-FKRP--SARV  113
Mgliv_tmsB      LTPRGTTYLATAPGDLGLARAYIAGDLRLSGVHPGDPHDLLTALTERLE-YRRP--PVRV  113
                          .   . **:.:*  *
```

HIGHLIGHTED = ACTIVE SITE BICARBONATE ION BINDING AMINO ACID, CONSERVED IN BOTH TmsB AND *E. coli* Cfa UNDERLINED = TmsB CONSERVED ONLY, NOT PRESENT IN *E. coli* Cfa
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 19A

```
Ecoli_cfa       ---------GLEN---------QLPH---HFKDTLRIAGARLFNLQSKKRAWIVGKEHYDL  122
Cglycini_tmsB   LLDIARSLKAMG-----AIKVQPAPEQETLPGWKRAILEGL-SRHSPERDKEVVSRHYDV  157
Cglut_tmsB      TLQIMWTLRKMN-----ALKFQEIPPMEQAPAWRKALINGLASRHSKSRDKKAISYHYDV  160
Tfus_tmsB       LLRIIRGIG-----WVKFVNRLPPPPQE-VRQSRLAAL---GWRHSKQRDAEAIQHHYDV  144
Tcurv_tmsB      RLRLLAGVLQDPLLRAAASRRLPPPPQE-VRTGRTS-----WFRHTKRRDAKAISHHYDV  143
Kaero_tmsB      LLDLARIVGPRN------LAPPPPPPQEAVPRWRRVAE---GLRHSYGRDSEAIRHHYDV  153
Asubflav_tmsB   IASIMRSLGWER------LRPVAPPPQENMPRWRRMAL---GLLHSKSRDAAAIHHHYDV  161
Rop_tmsB        LAAITRSLGWDL------LRPIAPPPQEHLPRWRRVAE---GLRHSKSRDAEVIHHHYDV  159
Mind_tmsB       LANVVRSLGFER------LLPVAPPPQEALPRWRRIAD---GLMHTRTRDAEAIHHHYDV  145
Asubb_tmsB      MTQIIRSIGVEH------LRPIAPPPQEVPPRWRRIAE---GLRHSKGRDAEAIHHHYDV  141
Msmeg_tmsB      LANIVRSIGIEH------LKPIAPPPQEALPRWRRIME---GLRHSKTRDAEAIHHHYDV  161
Mvan_tmsB       LAQVVRSIGIEH------LKPIAPPPQEALPRWRRIAE---GLRHSKTRDADAIHHHYDV  164
Mgliv_tmsB      LANVLRSIGIEH------LKPVAPPPQEHLPRWRRIAE---GLRHSKTRDAEAIQHHYDV  164
                                                            ::  *   .    ***:

Ecoli_cfa       GNDLFSRMLDPFMQYSCAYWKDAD-------------------------NLESAQQAKLK  157
Cglycini_tmsB   GNDFYELFLGDSMAYTCAYYPEFDGENQVTGPTGGWRYDDWEKGPTAMGPLTQAQDNKHR  217
Cglut_tmsB      GNEFYSLFLDDSMTYTCAYYPTPE------------------------SSLEEAQENKYR  196
Tfus_tmsB       SNAFYALVLGESMTYTCAVYPTEQ------------------------ATLEQAQFFKHE  180
Tcurv_tmsB      SNTFYEWVLGPSMTYTCACFPTED------------------------ATLEEAQFHKHD  179
Kaero_tmsB      SNHFYEQVLGPSMTYTCAVFPDHD------------------------TGLDEAQEEKYR  189
Asubflav_tmsB   SNEFYEHILGPSMTYTCAAYPSAD------------------------SSLEEAQDNKYR  197
Rop_tmsB        SNTFYEYVLGPSMTYTCACYENAE------------------------QTLEEAQDNKYR  195
Mind_tmsB       SNTFYELVLGPSNTYTCAVYPDAD------------------------ATLEQAQENKYR  181
Asubb_tmsB      SNTFYEWVLGPSMTYTCACYPGLD------------------------ASLDEAQQNKYR  177
Msmeg_tmsB      SNTFYEWVLGPSMTYTCACYPTED------------------------ATLEEAQDNKYR  197
Mvan_tmsB       SNTFYEWVLGPSMTYTCACYPHPD------------------------ATLEEAQENKYR  200
Mgliv_tmsB      SNTFYSWVLGPSMTYTCACYPHPD------------------------ATLEEAQENKYR  200
                .* ::  .*.  * *:** :   :                          * .**  *
```

HIGHLIGHTED = ACTIVE SITE BICARBONATE ION BINDING AMINO ACID, CONSERVED IN BOTH TmsB AND *E. coli* Cfa UNDERLINED = TmsB CONSERVED ONLY, NOT PRESENT IN *E. coli* Cfa

* = SINGLE, FULLY CONSERVED RESIDUE IN ALL SEQUENCES

: = AMINO ACIDS WITH STRONGLY SIMILAR PROPERTIES

. = AMINO ACIDS WITH WEAKLY SIMILAR PROPERTIES

FIG. 19B

```
Ecoli_cfa        MICEKLQLKPGMRVLDIGCGWGGLAHYMASNYDVSVVGVTISAEQQKMAQERCEGLD---  214
Cglycini_tmsB    LVFDKLRLNPGDRLLDVGCGWGGMVRYAAR-HGVKAIGVTLSREQYEWGKAKIEEEGLQD  276
Cglut_tmsB       LIFEKLRLKEGDRLLDVGCGWGGMVRYAAK-HGVKAIGVTLSEQQYEWGQAEIKRQGLED  255
Tfus_tmsB        LIARKLGLAPGIRLLDVGCGWGGMVIHAAREHGVKALGVTLSEEQAEWAQKRIAHEGLGD  240
Tcurv_tmsB       LVAKKLGLRPGMRLLDVGCGWGGMVMHAAKHYGVRALGVTLSKQQAEWAQKAIAEAGLSD  239
Kaero_tmsB       LVFEKLALRPGDRLLDIGCGWGGMVRYAAR-RGVRALGVTLSGEQAAWAQVAIAREGLGE  248
Asubflav_tmsB    LVFEKLGLKAGDRLLDVGCGWGGMVRFAAK-RGVHVIGATLSRKQAEWAQKMIAHEGLGD  256
Rop_tmsB         LVFEKLGLQPGDRLLDIGCGWGSMVRYAAR-RGVKVIGATLSREQAEWAQKAIAEEGLSD  254
Mind_tmsB        LIFEKLRLKAGDRLLDVGCGWGGMVRYAAR-RGVRATGATLSAEQAKWAQKAIAEEGLAD  240
Asubb_tmsB       LVFEKLRLKPGDRLLDVGCGWGGMVRYAAR-HGVQALGVTLSREQTAWAQQAIAVEGLAD  236
Msmeg_tmsB       LVFEKLRLKPGDRLLDVGCGWGGMVRYAAR-HGVKALGVTLSREQATWAQKAIAQEGLTD  256
Mvan_tmsB        LVFEKLRLKPGDRLLDVGCGWGGMVRYAAR-HGVKAIGVTLSREQAQWARAAIERDGLGD  259
Mgliv_tmsB       LVFEKLRLKPGDRLLDVGCGWGGMVRYAAR-HGVKVLGVTLSKEQAQWAADAVERDGLGE  259
                 ::  ** *  * *:**:*****.:. .  *    .*  . *.*:* :*    .       .


Ecoli_cfa        -VTILLQDYRDLN-DQFDRIVSVGMFEHVGPKNYDTYFAVVDRNLKPEGIFLLHTIGSKK  272
Cglycini_tmsB    LAEVRCMDYRDVPESDFDAVSAIGILEHIGVPNYEDYFTRLFAKLRPGGRMLNHCITRPH  336
Cglut_tmsB       LAEIRFMDYRDVPETGFDAISAIGIIEHIGVNNYPDYFELLSSKLKTGGLMLNHSITYPD  315
Tfus_tmsB        LAEVRHMDYRDLPDGEYDAISSIGLTEHVGKKNVPAYFASLYRKLVPGGRLLNHCITRPR  300
Tcurv_tmsB       LAEVRHQDYRDVTEGDFDAISSIGLTEHIGKANLPSYFGFLYGKLKPGGRLLNHCITRPD  299
Kaero_tmsB       LAAVRHEDYRHVAETGFDAISSIGITEHIGVRNYPTYFDWMLHHVKPGGLVLNHCITRPE  308
Asubflav_tmsB    LAEVRFCDYRDVTEAGFDAVSSIGLTEHIGLANYPSYFGFLKDKLRPGGRLLNHCITRPN  316
Rop_tmsB         LAEVRFSDYRDVPETGFDAISSIGLTEHIGVGNYPAYFGLLQSKLREGGRLLNHCITRPD  314
Mind_tmsB        LAEVRHTDYRDVGEAAFDAVSSIGLTEHIGVKNYPAYFGFLKSKLRTGGLLLNHCITRHD  300
Asubb_tmsB       LAEVRYGDYRDIAEDGFDAVSSIGLLEHIGVRNYASYFGFLQSRLRPGGLLLNHCITRPD  296
Msmeg_tmsB       LAEVRHGDYRDVIESGFDAVSSIGLTEHIGVHNYPAYFNFLKSKLRTGGLLLNHCITRPD  316
Mvan_tmsB        LAEVRHSDYRDVRESQFDAVSSLGLTEHIGVANYPSYFRFLKSKLRPGGLLLNHCITRHN  319
Mgliv_tmsB       LAEVRHGDYRDVRESHFDAVSSLGLTEHIGVANYPSYFRFLKSKLRPGGLLLNHCITRNN  319
                  . :   ***.:     :* : ::*: **:*   *    **   :   .:    * .* * *
```

HIGHLIGHTED = ACTIVE SITE BICARBONATE ION BINDING AMINO ACID, CONSERVED IN BOTH TmsB AND *E. coli* Cfa UNDERLINED = TmsB CONSERVED ONLY, NOT PRESENT IN *E. coli* Cfa
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 19C

```
Ecoli_cfa       T---DLNVDPWINKYIFPNGCLPSVRQ-IAQSSEPHFVMEDWHNFGADYDTTLMAWYERF    328
Cglycini_tmsB   NRKT--KTGQFIDRYIFPDGELTGSGRIITIMQDTGFDVVHEENLRPHYQRTLHDWCELL    394
Cglut_tmsB      NRPR--HAGAFIDRYIFPDGELTGSGTLIKHMQDNGFEVLHEENLRFDYQRTLHAWCENL    373
Tfus_tmsB       NDLPPFKRGGVINRYVFPDGELEGPGWLQAAMNDAGFEIRHQENLREHYARTLRDWLANL    360
Tcurv_tmsB      NTQPAMKKDGFINRYVFPDGELEGPGYLQTQMNDAGFEIRHQENLREHYARTLAGWCRNL    359
Kaero_tmsB      NRAK--SVGRFIDRYIFPDGELTGSGRIITTMQDNGFEVVHSENLREHYALTLAAWGENL    366
Asubflav_tmsB   NLQSN-RAGDFIDRYVFPDGELAGPGFIISAVHDAGFEVRHEENLREHYALTLRDWNRNL    375
Rop_tmsB        NQSQA-RAGGFIDRYVFPDGELTGSGRIITEIQNVGLEVRHEENLREHYALTLAGWCQNL    373
Mind_tmsB       NTSTS-FAGGFTDRYVFPDGELTGSGRITCDVQDCGFEVLHAENFRHHYANTLRDWCRNL    359
Asubb_tmsB      NRSEP-SARGFIDRYVFPDGELTGSGRIITEAQDVGFEVLHEENLRQHYALTLRDWCANL    355
Msmeg_tmsB      NRSAP-SAGGFIDRYVFPDGELTGSGRIITEAQDVGLEVIHEENLRNHYAMTLRDWCRNL    375
Mvan_tmsB       NRTGP-AAGGFIDRYVFPDGELTGSGRIITEIQDVGLEVMHEENLRRHYALTLRDWCRNL    378
Mgliv_tmsB      NRSHA-TAGGFIDRYVFPDGELTGSGRIITEMQDVGLEVVHEENLRHHYALTLRDWSRNL    378
                .           ::*:**:* * .         :  : : . .*:  .*  **   *   :

Ecoli_cfa       LAAWPEIADNYSERFKRMFTYYLNACAGAFRARDIQLWQVVFSRGVENGLRVAR----------    382
Cglycini_tmsB   ATNWDQAVHLVGEETARLFGLYMAGSEWGFEHNVIQLHQVLGVKPDAAGSSG-VPVRQWWRS---    455
Cglut_tmsB      KENWEEAVELAGEPTARLFGLYMAGSEWGFAHNIVQLHQVLGVKLDEQGSRGEVPERMWWTI---    435
Tfus_tmsB       DRNWDAAVREVGEGTARVWRLYMAGCVLGFERNVVQLHQILGVKLDG-TE-ARMPLRPDFEPPLP    423
Tcurv_tmsB      DEHWDEAVAEVGEGTARVWRLYMAGSRLGFELNWIQLHQILGVKLGERGE-SRMPLRPDWGV---    420
Kaero_tmsB      VEHWASCVADVGEGTAKVWGLYLAGSRRGFERNVVQLHQVLAARPVPSRL-PQVPLRQWWTS---    427
Asubflav_tmsB   ARDWDACVHASDEGTARVWGLYISGSRVAFETNSIQLHQVLAVKTARNGE-AQVPLGQWWTR---    436
Rop_tmsB        VDNWDACVAEVGEGTARVWGLYMAGSRLGFERNVVQLHQVLAVKLGPKGE-AHVPLRPWWK----    433
Mind_tmsB       VENWDAAVSEVGLPTAKVWGLYMAASRVAFEQNNLQLHHVLAAKTDARGD-DDLPLRPWWTA---    420
Asubb_tmsB      VAHWEEAVAEVGLPTAKVWGLYMAGSRLAFESGGIQLHQVLAVRPDDRSDAAQLPLRPWWTP---    417
Msmeg_tmsB      VEHWDEAVEEVGLPTAKVWGLYMAGSRLGFETNVVQLHQVLAVKLDDQGKDGGLPLRPWWSA---    437
Mvan_tmsB       VQHWDEAVAEVGLPTAKVWGLYMAASRVGFEQNSIQLHQVLAVKLDERGGDGGLPLRPWWTA---    440
Mgliv_tmsB      VAHWDDAVTEVGLPTAKVWGLYIAASRVGFEQNAIQLHQVLSVKLDERGSDGGLPLRPWWNA---    440
                   *   .   .    :::  *: ..  .*    :** :::  :
```

HIGHLIGHTED = ACTIVE SITE BICARBONATE ION BINDING AMINO ACID, CONSERVED IN BOTH TmsB AND *E. coli* Cfa UNDERLINED = TmsB CONSERVED ONLY, NOT PRESENT IN *E. coli* Cfa
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 19D

```
Eco_GlcD         MSILYEE-----RLDGALPDV--------DRTSVLMALREHVPGLEILHTDEEIIPYECD   47
Cglycini_tmsA    -----------VTVAGRITDAVRIGNGLDQRDLAPVGWYAHEQAVARLKASFDAVPAGRR   49
Cglut_tmsA       MSGLVDPDSTFLKTIGKLSNSLSIGRGVDQKEVIPKGWNAHWEAITKLKRSFDAIPAGER   60
Kaero_tmsA       -----------------------------MSMDRTGPARVRTVGERRLLESFAAVPPGER   31
Asubflav_tmsA    -------------------------------MTPEASAAAHAAAVDRLIHSYRAIPDDAP   29
Rop_tmsA         MREGGRPFRAH-------------------RTLPVTGIDAHRAGVERLLASYRAIPTDAT   41
Asubb_tmsA       -----------------------------VSAPATDARTAHADGVERLLESYRAVPAAAS   31
Mind_tmsA        MHGLLSKTRVY------------------VVPVLGSALSAHKSGVDRLLASYRSIPATSA   42
Msmeg_tmsA       -----------------------------VSVVTTDAQAAHAAGVSRLLASYRIPPSAT    31
Mvan_tmsA        -----------------------------VSVPSTDARSAHADGVQRLLASYRAIPQDAT   31
Mgilv_tmsA       -----------------------------VSVAVTDARSAYAHGVQRLVASYRAIPAGAT   31
Tcurv_tmsA       -------------------------------MSQLAVTDHHERAVEALRRSYAAIPPGTP   29
Tfus_tmsA        ----------V------------------NCQSSASNLANHINAVYELRRAYARLSADKP   32
                                                            .   *      :

Eco_GlcD         GLSAYRTRPLLVVLPKQMEQVTAILAVCHRLRVPVVTRGAGTGLSGGALPLEKGVLLVMA  107
Cglycini_tmsA    -----------VRLAKKT---------SNLFRGRSG-EAV---------------GLDVS   73
Cglut_tmsA       -----------VRLAKKT---------SNLFRGRSD-AGH---------------GLDVA   84
Kaero_tmsA       -----------VRLAKRT---------SNLFRAREGTSTR---------------GLDTS   56
Asubflav_tmsA    -----------VRLAKKT---------SNLFRHREKTSAP---------------GLDVS   54
Rop_tmsA         -----------VRLAKKT---------SNLFRARAQTSAP---------------GLDVS   66
Asubb_tmsA       -----------VRLAKRT---------SNLFRSRAATDAP---------------GLDTS   56
Mind_tmsA        -----------VRLAKPT---------SNLFRARTKRDAP---------------GLDTS   67
Msmeg_tmsA       -----------VRLAKPT---------SNLFRARARTNVK---------------GLDVS   56
Mvan_tmsA        -----------VRLAKPT---------SNLFRARAKTRTK---------------GLDTS   56
Mgilv_tmsA       -----------VRLAKPT---------SNLFRARAKSTAA---------------GLDTS   56
Tcurv_tmsA       -----------VRLAKQT---------SNLFRFREPTAAP---------------GLDVS   54
Tfus_tmsA        -----------VRLAKTT---------SNLFRFRSRDDAA---------------RLDVS   57
                             ^ ^            ^^^^  ^                       ^
                            * * *           .: :*                       *  :
```

^ = CONSERVED IN TmsA SEQUENCE BUT NOT *E. coli* GlcD SEQUENCE
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20A

```
Eco_GlcD        RFKEILDINPVGRRARVQPGVRNLAISQAVAPHNLYYAPDPSSQIACSIGGNVAENAGGV 167
Cglycini_tmsA   GLHGVIAVDPVEGTADVQGMCTYEDLVDVLLPYGLAPTVVPQ-LKTITLGGAVTGMGVES 132
Cglut_tmsA      ALGGVIAIDPVNATADVQGMCTYEDLVDATLSYGLMPLVVPQ-LKTITLGGAVTGMGVES 143
Kaero_tmsA      GLTGVRVVDAGTLTADVDGMCTYEDLVAATLPLGLAPLVVPQ-LRTITVGGAVTGLGIES 115
Asubflav_tmsA   GLARVIGIDSDTRTADVGGMCTYEDLVAATLEYDLVPLVVPQ-LKTITLGGAVTGLGIES 113
Rop_tmsA        GLGGVISVDEQDRTADVAGMCTYEDLVDATLPYGLAPLVVPQ-LKTITLGGAVTGLGIES 125
Asubb_tmsA      GLTHVIAVDPGARTADVAGMCTYDDLVAATLPHGLAPLVVPQ-LKTITLGGAVTGLGIES 115
Mind_tmsA       GLTGVLSVDPETRTADVAGMCTYADLVAATLPYGLSPLVVPQ-LKTITLGGAVSGLGIES 126
Msmeg_tmsA      GLTGVIGVDPDARTADVAGMCTYEDLVAATLPYGLAPLVVPQ-LKTITLGGAVTGLGIES 115
Mvan_tmsA       GLTNVIAVDAEARTADVAGMCTYEDLVAATLPHGLSPLVVPQ-LKTITLGGAVTGLGIES 115
Mgilv_tmsA      GLTHVIAVDPETRTAEVAGMCTYEDLVAATLPHGLSPLVVPQ-LKTITLGGAVTGLGIES 115
Tcurv_tmsA      GFNRVLAVDPDARTADVQGMTTYEDLVDATLPHGLMPLVVPQ-LKTITLGGAVTGLGIES 113
Tfus_tmsA       AFTSVISIDTEARVAEVGGMTTYEDLVAATLRHGLMPPVVPQ-LRTITLGGAVTGLGIES 116
                    ^   ^         ^^ ^^ ^^^   ^     ^ ^^ ^ ^ ^^^   ^  ^ ^ ^^
                 :  :  ::     * *        :  .    .*     *.   : ::** *:  .

Eco_GlcD        HCLKYGLTVHNLLKIEVQTLDGEALTLGSDALDSPGFDLLALFTGSEGMLGVTTEVTVKL 227
Cglycini_tmsA   TSFRNGLPHEAVLEMDVLTGTGDILTCSPT----QNTDLYRGFPNSYGSLGYSVRLKVRC 188
Cglut_tmsA      TSFRNGLPHESVLEMDIFTGTGEIVTCSPT----ENVDLYRGFPNSYGSLGYAVRLKIEL 199
Kaero_tmsA      TSFRNGLPHESVLEMDVLTGAGEIVTATAD---NEHADLFRGFPNSYGSLGYATCLRIEL 172
Asubflav_tmsA   TSFRNGLPHESVLEMDILTGAGEVVTAGPE---GPHSDLYWGFPNSYGTLGYATRLRIEL 170
Rop_tmsA        TSFRNGLPHESVLEIDVLTGSGDIVTARPE---GENSDLFWGFPNSYGTLGYSTRLRIQL 182
Asubb_tmsA      TSFRNGLPHESVLEIDVLTGAGEIITASPI----EHAELFRAFPNSYGTLGYAVRLRIEL 171
Mind_tmsA       ASFRNGLPHESVLEMDILTGAGDLLTASRT----QHPDLFRAFPNSYGTLGYSTRLRIEL 182
Msmeg_tmsA      TSFRNGLPHESVLEMDILTGSGEIVTASPD----QHSDLFHAFPNSYGTLGYSTRLRIEL 171
Mvan_tmsA       ASFRNGLPHESVLEMDVLTGTGDVVRASPD----ENPDLFRAFPNSYGTLGYSVRLKIEL 171
Mgilv_tmsA      ASFRNGLPHESVLEMDILTGTGDIVRAAPD----ENPDLFRTFPNSYGTLGYSVRLKIEL 171
Tcurv_tmsA      TSFRNGLPHESVLEMQIITGAGEVVTATPD---GEHSDLFWGFPNSYGTLGYALKLKIEL 170
Tfus_tmsA       SSFRNGLPHESVEEMEILTGSGQVVVARRD---NEHRDLFYGFPNSYGTLGYALRLRIQL 173
                 ^^^^  ^^^ ^ ^     ^                       ^^ ^    ^   ^
                 .:: **  . : :::: *  *: :            :*   * .* * ** :  : :.
```

^ = CONSERVED IN TmsA SEQUENCE BUT NOT *E. coli* GlcD SEQUENCE
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20B

```
Eco_GlcD        LPKPPVARVLLASFDSVEKAGLAVGDIIANGIIPGG-LEMMDNLSIRAAEDFIHAGYPVD    286
Cglycini_tmsA   ERVEPYVDLRHVRFDDVQSLTDALDNIVVDKEYEGERVDYLDGVVFSLEESYLVLGRATS    248
Cglut_tmsA      EPVQDYVQLRHVRFNDLESLTKAIEEVASSLEFDNQPVDYLDGVVFSPTEAYLVLGTQTS    259
Kaero_tmsA      ERVGTCVEVRHVRFHDLDALCAAIAEVVATRSHEGEEVDHVDGVVFSRDEAYLTLGRHSD    232
Asubflav_tmsA   EPVEPYVELRHLRFTSLDELQETLDTVSYEHTYDGEPVHYVDGVMFSATESYLTLGRQTS    230
Rop_tmsA        EPVKRYVALRHLRFDSLDELQSAMDRIVTERVHDGIPVDYLDGVVFTASESYLTLGHQTD    242
Asubb_tmsA      EPVEPFVALTHLRFHALTDLIEAMERIIETGRLDGVAVDSLDGVVFSAEESYLCVGTQTA    231
Mind_tmsA       EPVAPFVALRHIRFRSLPALIAAAERIVDTGGQGGTPVDYLDGVVFSADESYLCVGRRTT    242
Msmeg_tmsA      EPVHPFVALRHLRFHSITDLVAAMDRIIETGGLDGEPVDYLDGVVFSATESYLCVGFKTK    231
Mvan_tmsA       EPVKPFVALRHLRFHSISALIEAMDRIVETGGLNGEPVDYLDGVVFSAEESYLCVGQRSA    231
Mgilv_tmsA      EPVKPFVALRHLRFHSLSTLIATMDRIVDTGSLDGEQVDYLDGVVFSAEESYLCVGTRSA    231
Tcurv_tmsA      EPVKPYVRLRHLRFDDAGECAAKLAELSESREHEGDEVHFLDGTFFGPREMYLTLGTFTD    230
Tfus_tmsA       EPVRPYVHLRHLRFTDAAAAMAALEQICADRTHDGETVDFVDGVVFARNELYLTLGTFTD    233
                ^ ^   ^   ^ ^                        ^    ^  ^     ^^
                      . :    *            :       .  :. :*.  :   *  ::  *

Eco_GlcD        AEAILLCELDGV---ESDVQEDCE----------RVNDILLKAGATDVRLAQDEAERVRF    333
Cglycini_tmsA   EAGPV-SDYTRERSYYRSLQHPSG----VLRDKLTIRDYLWR------------WDVDWF    291
Cglut_tmsA      QPGPT-SDYTRDLSYYRSLQHPEG----ITYDRLTIRDYIWR------------WDTDWF    302
Kaero_tmsA      RTGPT-SDYTGQQVYYRSIQHDGPS---PRRDLLTTHDYLWR------------WDTDWF    276
Asubflav_tmsA   EPGPV-SDYTGNQIYYRSIQHGGA--ETPVVDRMTIHDYLWR------------WDTDWF    275
Rop_tmsA        EGGPV-SDYTGQNIFYRSIQHSSV--NHPKTDKLTIRDYLWR------------WDTDWF    287
Asubb_tmsA      ASGPV-SDYTRQQIFYRSIQHD----DGAKHDRLTMHDYLWR------------WDADWF    274
Mind_tmsA       TPGPV-SDYTGKDIYYQSIRHDAPGLEATKDDRLTMHDYFWR------------WDTDWF    289
Msmeg_tmsA      TPGPV-SDYTGQQIFYRSIQHDGDT-GAEKHDRLTIHDYLWR------------WDTDWF    277
Mvan_tmsA       TPGPV-SDYTGKQIYYRSIQHDGPTDGAEKHDRLTIHDYLWR------------WDTDWF    278
Mgilv_tmsA      TPGPV-SDYTGEHIFYRSIQHDCPTEGGQKHDRLTAHDYFWR------------WDTDWF    278
Tcurv_tmsA      TAPYV-SDYTGQHIYYRSIQQ-------RSIDFLTIRDYLWR------------WDTDWF    270
Tfus_tmsA       RAPWT-SDYTGTDIYYRSIPRYAG---PGPGDYLTTHDYLWR------------WDTDWF    277
                      ^^^^     ^ ^             ^  ^   ^ ^^            ^^ ^^
                      .:          .: .                 .* : :             :   *
```

^ = CONSERVED IN TmsA SEQUENCE BUT NOT *E. coli* GlcD SEQUENCE
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20C

```
Eco_GlcD        WAGRKNA--FPAVGRISP-------DYYCMDGTIPRRALPGVLEGI------ARLSQQYD 378
Cglycini_tmsA   WCNRAFGTQNPTIRTLWPRDLLRSSFYWKIIGWDRRFDIADRIEAHNGRPARERVVQDIE 351
Cglut_tmsA      WCSRAFGTQNPVVRKLWPRDLLRSSFYWKIIGWDRKYSIADRLEERKGRPARERVVQDVE 362
Kaero_tmsA      WCSRAFGAQDPRVRRWWPRRWRRSSVYWRLVAADRRVGFSDRLEARRGNPPRERVVQDVE 336
Asubflav_tmsA   WCSRAFGTQHPVVRRFWPRRYRRSSFYWKLIALDRQVGLADFIEQRKGNLPRERVVQDIE 335
Rop_tmsA        WCSRAFGAQNPTIRRLWPKNLLRSSFYWKLIALDHKYDIGDRLEKRKGNPPRERVVQDVE 347
Asubb_tmsA      WCSQAFGAQHPLIRRFWPRRYRRSRSYSTLMRLERRFDLGDRLEKLKGRPARERVIQDVE 334
Mind_tmsA       WCSRAFGVQDPRVRRFWPRRYRRSSFYWKLISLDRRFGISDRIEARNGRPPRERVVQDIE 349
Msmeg_tmsA      WCSRAFGAQHPVIRRFWPRRLRRSSFYWKLVAYDQRYDIADRIEKRNGRPPRERVVQDVE 337
Mvan_tmsA       WCSRAFGAQNPRIRRWWPRRYRRSSVYWKLIGYDRRFGIADRIEKRNGRPPRERVVQDIE 338
Mgilv_tmsA      WCSRAFGAQNPKVRRWWPRRLRRSSFYWKLVGYDQRFGIADRIEKHHGRPPRERVVQDVE 338
Tcurv_tmsA      WCSRALGVQNPLIRRVWPKSAKRSDVYRKLVAYEKRYQFKARIDRWTGKPPREDVIQDIE 330
Tfus_tmsA       WCSRAFGLQHPVVRRLWPRSLKRSDVYRKLVAWDRRTDASRLLDYYRGRPPKEPVIQDIE 337
                 ^  ^ ^ ^    ^  ^     ^^                       ^    ^ ^  ^ ^

                *..:  .   * :    *        *  :     :      ::          : *: :

Eco_GlcD        LRVANV-----FHAGDGNMHPLILF-----DANEPGEFA----RA--------EELGG-- 414
Cglycini_tmsA   VTPDNLPEFLTWFFTHCEIEPVWLCPIRLADDS-------------------GERTPWPL 392
Cglut_tmsA      VTIDKLPEFLKWFFESSDIEPLWLCPIKLREVPGSSVGAGEILSSAEAIDSGAAEHPWPL 422
Kaero_tmsA      IPLGQTAAFLHWFLDEVPIEPIWLCPLRLRDH-----------------------QRWPL 373
Asubflav_tmsA   VPIENTASFLRWFLANVPIEPVWLCPLRLRKTRSPGLP----------SPTSPASRPWPL 385
Rop_tmsA        VPIERTADFVRWFLDEIPIEPLWLCPLRLREPAPAGA---------------SSQRPWPL 392
Asubb_tmsA      VPIGRTVGFLEWFLANVPIEPIWLCPLRLRGD-----------------------RGWPL 371
Mind_tmsA       IPIERTCDFLEWFLDNVPITPIWLCPLRLRDR-----------------------DGWPL 386
Msmeg_tmsA      VPIERCADFVEWFLQNVPIEPIWLCPLRLRDSADGG-------------------ASWPL 378
Mvan_tmsA       VPIERTVEFLQWFLDTVPIEPIWLCPLRLRDD-----------------------RDWPL 375
Mgilv_tmsA      VPIERTVEFLQWFLDTIPIEPLWLCPLRLRDD-----------------------NSWSL 375
Tcurv_tmsA      VPAERLPEFLEFFHDKIGMSPVWLCPLRAR-------------------------HRWPL 365
Tfus_tmsA       VEVGRAAEFLDFFHTEIGMSPVWLCPLRLREDTAD-----------------DTEPVWPL 380
                        ^   ^         ^ ^^                               ^ ^
                :   .      :.     : *: *
```

^ = CONSERVED IN TmsA SEQUENCE BUT NOT *E. coli* GlcD SEQUENCE
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20D

```
Eco_GlcD        ---KILELCVEVG--GSIS-------GEHGIGREKINQMC------------AQFNSDE-   449
Cglycini_tmsA   YPLSPGDTWVNVGFWSSVPADLMGKDAPTGAFNREVERVVSDLGGHKSLYSEAFYSEEQF   452
Cglut_tmsA      YPLKKDVLWVNIGFWSSVPVDLMGSDAPEGAFNREIERVMAELGGHKSLYSEAFYTREDF   482
Kaero_tmsA      YPLEPGRTYVNVGFWSTVPGP--GPGEELGATNRAIERRVDEVGGHKSLYSDSYYSRSDF   431
Asubflav_tmsA   YPLEPQRTYVNVGFWSAVPV---VAGQPEGHTNRMIENEVDRLDGHKSLYSDAFYERKEF   442
Rop_tmsA        YPLEPKRTYVNIGFWSSVPI---VPGRPEGAANRLIEDKVSDFDGHKSLYSDSYYSREDF   449
Asubb_tmsA      YPIRPQQTYVNIGFWSTVPV---G--GSEGETNRSIERAVSEFDGHKSLYSDSYYSREEF   426
Mind_tmsA       YPMRPDHTYVNVGFWSSVPG---G--ATEGAANRMIEEKVSELDGHKSLYSDSFYSREDF   441
Msmeg_tmsA      YPLKAHHTYVNIGFWSSVPV---G--PEEGHTNRLIEKKVAELDGHKSLYSDAYYTRDEF   433
Mvan_tmsA       YPIRPHHTYVNVGFWSSVPV---G--PEEGYTNRMIERKVSDLDGHKSLYSDAYYSPEEF   430
Mgilv_tmsA      YPLRPHRTYVNVGFWSSVPV---G--PEEGHTNKLIERRISELEGHKSLYSDAFYSADEF   430
Tcurv_tmsA      YPLKPGVTYVNAGFWGTVPL---QPGQMPEYHNRLIERKVAQLDGHKSLYSTAFYSREEF   422
Tfus_tmsA       YPLKPRRLYVNFGFWGLVPI---RPGGGRTYHNRLIEKEVTRLGGHKSLYSDAFYDEDEF   437
                ^^        ^  ^^  ^^             ^   ^       ^^^^^^^   ^    ^

                         *: *  , :              .. ::               : :  .:

Eco_GlcD        ------ITTFHAVKAAFDPDGLLNPGKNIPTLHRCAEFGAMHVHHGHLPFPELERF       227
Cglycini_tmsA   AAL-YGGERPAQLKAVFDPDDRFPGLYEKTVGGV----------------------       188
Cglut_tmsA      EKL-YGGTIPALLKKQWDPHSRFPGLYEKTVKGA----------------------       199
Kaero_tmsA      DAL-YGGDAYAVLKATYDPDGRFPHLYDKAVRHA----------------------       172
Asubflav_tmsA   DAL-YGGDTYRELKETYDPNSRLLDLYAKAVQGR----------------------       170
Rop_tmsA        ERLYYGGDRYTELKKRYDPKSRLLDLFSKAVQRR----------------------       182
Asubb_tmsA      EEL-YGGEAYRAVKRRYDPDSRLLDLYAKAVQRR----------------------       171
Mind_tmsA       DEL-YGGETYNTVKKTYDPDSRLLDLYAKAVQRR----------------------       182
Msmeg_tmsA      DEL-YGGEVYNTVKKTYDPDSRLLDLYSKAVQRQ----------------------       171
Mvan_tmsA       DSL-YGGETYKTVKKTYDPDSRFLDLYGKAVGRQ----------------------       171
Mgilv_tmsA      DAL-YGGEIYRTVKKTYDPDSRFLDLYAKAVRRQ----------------------       171
Tcurv_tmsA      WRH-YDGETYRRLKDTYDPDARLLDLYDKCVRGR----------------------       170
Tfus_tmsA       WEL-YNGEIYRKLKAAYDPDGRLLDLYTKCVGGG----------------------       173
                    ^ ^              ^   ^    ^
                            :*  :**,  :       .
```

^ = CONSERVED IN TmsA SEQUENCE BUT NOT *E. coli* GlcD SEQUENCE
* = SINGLE, FULLY CONSERVED RESIDUE IN ALL SEQUENCES
: = AMINO ACIDS WITH STRONGLY SIMILAR PROPERTIES
. = AMINO ACIDS WITH WEAKLY SIMILAR PROPERTIES

FIG. 20E

SEQUENCE LISTING

```
<160> NUMBER OF SEQ ID NOS: 98

<210> SEQ ID NO 1
<211> LENGTH: 1401
<212> TYPE: DNA
<213> ORGANISM: Mycobacterium smegmatis

<400> SEQUENCE: 1

gtgtctgtgg ttactactga cgcacaggct gcccatgccg ccggcgtctc gcgtcttctg      60

gccagctacc gggcgatccc gcccagcgcg acagtgcgcc ttgcgaaacc gacgtccaac     120

ctgttccgcg cccgcgcccg caccaatgtg aagggtctcg acgtctcggg cctgaccggt     180

gtgatcggtg tcgacccgga cgcgcgcacc gccgatgtgg cgggcatgtg cacctacgag     240

gacctggtgg cggccacgct tccgtacggc cttgccccac tggtggtgcc gcagctcaag     300

accatcacgc tcggtggcgc ggtcaccggt ctgggcatcg agtccacgtc gttccgcaac     360

ggtctgccgc acgaaagtgt cctggagatg gacatcttga ccggttcggg cgagatcgtc     420

acggcctcac cggatcagca ctcggatctg ttccatgcgt tccccaattc atatggaacc     480

cttggttatt ccacccggct gcgcatcgaa ctggagcccg tgcacccgtt tgtggcgttg     540

cgccacctgc gctttcactc gatcaccgat ctggtcgcgg cgatggaccg gatcatcgag     600

accggcgggc tggacggtga acccgtcgac tacctcgacg gcgtggtgtt cagcgcgact     660
```

-continued

```
gagagttacc tgtgtgttgg cttcaagacg aaaacgccgg ggccggtcag cgattacaca    720

ggtcagcaga tcttctaccg gtcgatccag catgacggcg acaccggcgc cgagaaacac    780

gaccggctga ccatccacga ctacctgtgg cgctgggaca ccgactggtt ctggtgctca    840

cgggcattcg gcgctcagca tccggtgatc cgcaggttct ggccgcggcg gctgcgccgc    900

agcagcttct actggaagct ggtggcctac gaccagcggt acgacatcgc cgaccgtatc    960

gagaagcgca acgggcgccc gccgcgcgag cgggtggtcc aggacgtcga ggtgcccatc   1020

gagcggtgcg cggacttcgt cgagtggttc ctgcagaatg tgccgatcga gccgatctgg   1080

ctgtgccccc tacggttgcg tgacagcgcc gacggcggtg cctcgtggcc cctgtatccg   1140

ctgaaggcgc accacaccta cgtcaacatc ggtttctggt catcagtgcc ggtgggcccc   1200

gaggagggcc acaccaaccg cctcatcgag aaaaaagtcg cggagctgga cgggcacaaa   1260

tctttgtact cggacgctta ttacacacgt gacgaattcg acgagctgta cggcggtgag   1320

gtctacaaca ccgtcaagaa gacgtacgac ccggattcac gtctgctaga cctgtattcg   1380

aaggcggtgc aaagacaatg a                                             1401


<210> SEQ ID NO 2
<211> LENGTH: 466
<212> TYPE: PRT
<213> ORGANISM: Mycobacterium smegmatis

<400> SEQUENCE: 2

Val Ser Val Val Thr Thr Asp Ala Gln Ala Ala His Ala Ala Gly Val
1               5                   10                  15

Ser Arg Leu Leu Ala Ser Tyr Arg Ala Ile Pro Pro Ser Ala Thr Val
            20                  25                  30

Arg Leu Ala Lys Pro Thr Ser Asn Leu Phe Arg Ala Arg Ala Arg Thr
        35                  40                  45

Asn Val Lys Gly Leu Asp Val Ser Gly Leu Thr Gly Val Ile Gly Val
    50                  55                  60

Asp Pro Asp Ala Arg Thr Ala Asp Val Ala Gly Met Cys Thr Tyr Glu
65                  70                  75                  80

Asp Leu Val Ala Ala Thr Leu Pro Tyr Gly Leu Ala Pro Leu Val Val
                85                  90                  95

Pro Gln Leu Lys Thr Ile Thr Leu Gly Gly Ala Val Thr Gly Leu Gly
            100                 105                 110

Ile Glu Ser Thr Ser Phe Arg Asn Gly Leu Pro His Glu Ser Val Leu
        115                 120                 125

Glu Met Asp Ile Leu Thr Gly Ser Gly Glu Ile Val Thr Ala Ser Pro
    130                 135                 140

Asp Gln His Ser Asp Leu Phe His Ala Phe Pro Asn Ser Tyr Gly Thr
145                 150                 155                 160

Leu Gly Tyr Ser Thr Arg Leu Arg Ile Glu Leu Glu Pro Val His Pro
                165                 170                 175

Phe Val Ala Leu Arg His Leu Arg Phe His Ser Ile Thr Asp Leu Val
            180                 185                 190

Ala Ala Met Asp Arg Ile Ile Glu Thr Gly Gly Leu Asp Gly Glu Pro
        195                 200                 205

Val Asp Tyr Leu Asp Gly Val Val Phe Ser Ala Thr Glu Ser Tyr Leu
    210                 215                 220

Cys Val Gly Phe Lys Thr Lys Thr Pro Gly Pro Val Ser Asp Tyr Thr
225                 230                 235                 240
```

```
Gly Gln Gln Ile Phe Tyr Arg Ser Ile Gln His Asp Gly Asp Thr Gly
                245                 250                 255

Ala Glu Lys His Asp Arg Leu Thr Ile His Asp Tyr Leu Trp Arg Trp
            260                 265                 270

Asp Thr Asp Trp Phe Trp Cys Ser Arg Ala Phe Gly Ala Gln His Pro
        275                 280                 285

Val Ile Arg Arg Phe Trp Pro Arg Arg Leu Arg Arg Ser Ser Phe Tyr
    290                 295                 300

Trp Lys Leu Val Ala Tyr Asp Gln Arg Tyr Asp Ile Ala Asp Arg Ile
305                 310                 315                 320

Glu Lys Arg Asn Gly Arg Pro Pro Arg Glu Arg Val Val Gln Asp Val
                325                 330                 335

Glu Val Pro Ile Glu Arg Cys Ala Asp Phe Val Glu Trp Phe Leu Gln
            340                 345                 350

Asn Val Pro Ile Glu Pro Ile Trp Leu Cys Pro Leu Arg Leu Arg Asp
        355                 360                 365

Ser Ala Asp Gly Gly Ala Ser Trp Pro Leu Tyr Pro Leu Lys Ala His
    370                 375                 380

His Thr Tyr Val Asn Ile Gly Phe Trp Ser Ser Val Pro Val Gly Pro
385                 390                 395                 400

Glu Glu Gly His Thr Asn Arg Leu Ile Glu Lys Lys Val Ala Glu Leu
                405                 410                 415

Asp Gly His Lys Ser Leu Tyr Ser Asp Ala Tyr Tyr Thr Arg Asp Glu
            420                 425                 430

Phe Asp Glu Leu Tyr Gly Gly Glu Val Tyr Asn Thr Val Lys Lys Thr
        435                 440                 445

Tyr Asp Pro Asp Ser Arg Leu Leu Asp Leu Tyr Ser Lys Ala Val Gln
    450                 455                 460

Arg Gln
465
```

<210> SEQ ID NO 3
<211> LENGTH: 1314
<212> TYPE: DNA
<213> ORGANISM: Mycobacterium smegmatis

<400> SEQUENCE: 3

```
atgaccacat tcaaagaacg cgagacgtcc acagcggacc gcaagctcac cctggccgag      60

atcctcgaga tcttcgccgc gggtaaggag ccgctgaagt tcactgcgta cgacggcagc     120

tcggccggtc ccgaggacgc cacgatgggt ctggacctca agaccccgcg tgggaccacc     180

tatctggcca cggcacccgg cgatctgggc ctggcccgtg cgtatgtctc cggtgacctg     240

gagccgcacg gcgtgcatcc cggcgatccc tacccgctgc tgcgcgccct ggccgaacgc     300

atggagttca agcgcccgcc tgcgcgtgtg ctggcgaaca tcgtgcgctc catcggcatc     360

gagcacctca agccgatcgc accgccgccg caggaggcgc tgccccggtg gcgccgcatc     420

atggagggcc tgcggcacag caagacccgc gacgccgagg ccatccacca ccactacgac     480

gtgtcgaaca cgttctacga gtgggtgctg ggcccgtcga tgacctacac gtgcgcgtgc     540

taccccaccg aggacgcgac cctcgaagag gcccaggaca acaagtaccg cctggtgttc     600

gagaagctgc gcctgaagcc cggtgaccgg ttgctcgacg tgggctgcgg ctggggcggc     660

atggtccgct acgcggcccg ccacggcgtc aaggcgctcg gtgtcacgct cagccgcgaa     720

caggcgacgt gggcgcagaa ggccatcgcc caggaaggtc tcaccgatct ggccgaggtg     780
```

-continued cgtcacggtg attaccgcga cgtcatcgaa tccgggttcg acgcggtgtc ctcgatcggg 840
ctgaccgagc acatcggcgt gcacaactac ccggcgtact tcaacttcct caagtcgaag 900
ctgcgcaccg gtggcctgct gctcaaccac tgcatcaccc gcccggacaa ccggtcggcg 960
ccatcggccg gcgggttcat cgacaggtac gtgttccccg acggggagct caccggctcg 1020
ggccgcatca tcaccgaggc ccaggacgtg ggccttgagg tgatccacga ggagaaccta 1080
cgcaatcact atgcgatgac gctgcgcgac tggtgccgca acctggtcga gcactgggac 1140
gaggcggtcg aagaggtcgg gctgcccacc gcgaaggtgt ggggcctgta catggccggc 1200
tcacgtctgg gcttcgagac caatgtggtt cagctgcacc aggttctggc ggtcaagctt 1260
gacgatcagg gcaaggacgg cggactgccg ttgcggccct ggtggtccgc ctag 1314

<210> SEQ ID NO 4
<211> LENGTH: 437
<212> TYPE: PRT
<213> ORGANISM: Mycobacterium smegmatis

<400> SEQUENCE: 4

Met Thr Thr Phe Lys Glu Arg Glu Thr Ser Thr Ala Asp Arg Lys Leu
1 5 10 15

Thr Leu Ala Glu Ile Leu Glu Ile Phe Ala Ala Gly Lys Glu Pro Leu
20 25 30

Lys Phe Thr Ala Tyr Asp Gly Ser Ser Ala Gly Pro Glu Asp Ala Thr
35 40 45

Met Gly Leu Asp Leu Lys Thr Pro Arg Gly Thr Thr Tyr Leu Ala Thr
50 55 60

Ala Pro Gly Asp Leu Gly Leu Ala Arg Ala Tyr Val Ser Gly Asp Leu
65 70 75 80

Glu Pro His Gly Val His Pro Gly Asp Pro Tyr Pro Leu Leu Arg Ala
85 90 95

Leu Ala Glu Arg Met Glu Phe Lys Arg Pro Pro Ala Arg Val Leu Ala
100 105 110

Asn Ile Val Arg Ser Ile Gly Ile Glu His Leu Lys Pro Ile Ala Pro
115 120 125

Pro Pro Gln Glu Ala Leu Pro Arg Trp Arg Arg Ile Met Glu Gly Leu
130 135 140

Arg His Ser Lys Thr Arg Asp Ala Glu Ala Ile His His His Tyr Asp
145 150 155 160

Val Ser Asn Thr Phe Tyr Glu Trp Val Leu Gly Pro Ser Met Thr Tyr
165 170 175

Thr Cys Ala Cys Tyr Pro Thr Glu Asp Ala Thr Leu Glu Glu Ala Gln
180 185 190

Asp Asn Lys Tyr Arg Leu Val Phe Glu Lys Leu Arg Leu Lys Pro Gly
195 200 205

Asp Arg Leu Leu Asp Val Gly Cys Gly Trp Gly Gly Met Val Arg Tyr
210 215 220

Ala Ala Arg His Gly Val Lys Ala Leu Gly Val Thr Leu Ser Arg Glu
225 230 235 240

Gln Ala Thr Trp Ala Gln Lys Ala Ile Ala Gln Glu Gly Leu Thr Asp
245 250 255

Leu Ala Glu Val Arg His Gly Asp Tyr Arg Asp Val Ile Glu Ser Gly
260 265 270

Phe Asp Ala Val Ser Ser Ile Gly Leu Thr Glu His Ile Gly Val His

-continued

```
        275                 280                 285

Asn Tyr Pro Ala Tyr Phe Asn Phe Leu Lys Ser Lys Leu Arg Thr Gly
    290                 295                 300

Gly Leu Leu Leu Asn His Cys Ile Thr Arg Pro Asp Asn Arg Ser Ala
305                 310                 315                 320

Pro Ser Ala Gly Gly Phe Ile Asp Arg Tyr Val Phe Pro Asp Gly Glu
                325                 330                 335

Leu Thr Gly Ser Gly Arg Ile Ile Thr Glu Ala Gln Asp Val Gly Leu
            340                 345                 350

Glu Val Ile His Glu Glu Asn Leu Arg Asn His Tyr Ala Met Thr Leu
        355                 360                 365

Arg Asp Trp Cys Arg Asn Leu Val Glu His Trp Asp Glu Ala Val Glu
    370                 375                 380

Glu Val Gly Leu Pro Thr Ala Lys Val Trp Gly Leu Tyr Met Ala Gly
385                 390                 395                 400

Ser Arg Leu Gly Phe Glu Thr Asn Val Val Gln Leu His Gln Val Leu
                405                 410                 415

Ala Val Lys Leu Asp Asp Gln Gly Lys Asp Gly Gly Leu Pro Leu Arg
            420                 425                 430

Pro Trp Trp Ser Ala
        435
```

<210> SEQ ID NO 5
<211> LENGTH: 1380
<212> TYPE: DNA
<213> ORGANISM: Unknown
<220> FEATURE:
<223> OTHER INFORMATION: Agromyces subbeticus

<400> SEQUENCE: 5

```
gtgtccgctc ctgcgaccga tgcacgaacc gcccacgccg acggcgtgga gcgattgctc     60

gagagttatc gggcggtgcc ggcggccgca tcggtgcggc tcgccaagcg cacctcgaac    120

ctcttccggt cccgagcggc gacggatgcc cctggcctcg acacctccgg cctgacccac    180

gtcatcgcgg tcgaccccgg ggcgcgcacg gccgacgtcg ccggcatgtg cacctacgac    240

gacctcgtcg ccgcgacact gccgcatggg ctcgcgccac tcgtggtgcc gcaactgaag    300

accatcaccc tcgggggcgc cgtaacggga ctcggcatcg agtcgacgtc gttccgcaac    360

ggtctgccgc acgagtcggt gctcgagatc gacgtgctca ccggcgcagg cgagatcatc    420

acggcgtcgc cgatcgagca cgcagagctg ttccgcgcct tccccaactc gtacggcacc    480

ctcggctacg ccgtgcgcct gcgcatcgag ctcgagccgg tcgagccgtt cgtcgcactc    540

acgcaccttc ggttccatgc gctcaccgac ctcatcgagg caatggagcg catcatcgag    600

accggtcgac tcgacggggt tgccgtcgat tccctcgacg gcgtggtgtt cagcgctgaa    660

gagagctacc tgtgcgtcgg cacgcagacc gcggcatccg gcccggtcag cgactacacc    720

cgccagcaga tcttctatcg ctccatccag catgacgacg gtgcgaagca cgaccggctc    780

accatgcacg actacctgtg gcgctgggac gccgactggt tctggtgctc gcaggcgttc    840

ggcgcgcagc atccgctgat tcgccggttc tggccgcggc gataccggcg cagccgctcg    900

tactcgacgc tcatgcgcct cgaacggcga ttcgacctcg gcgatcgcct cgagaagctc    960

aagggccggc cggcgcgcga acgcgtgatc caagacgtcg aggtgccgat cgggcgcacc   1020

gtcggcttcc tcgaatggtt cctcgcgaac gtgccgatcg agccgatctg gttgtgcccg   1080

ctgcgcctgc ggggcgaccg cggctggcct ctctacccga tccggccgca gcagacctac   1140
```

```
gtcaacatcg gcttctggtc gacggttccg gtgggcggct ccgagggcga gacgaaccgc   1200

tcgatcgagc gcgccgtgag cgagttcgac ggacacaagt cgctgtactc cgactcgtac   1260

tactcgcgcg aggagttcga ggagctctac ggcggcgagg cgtaccgggc cgtgaagcgg   1320

cgatacgacc ccgactctcg actgctcgac ctctatgcga aggcggtgca acggcgatga   1380


<210> SEQ ID NO 6
<211> LENGTH: 459
<212> TYPE: PRT
<213> ORGANISM: Unknown
<220> FEATURE:
<223> OTHER INFORMATION: Agromyces subbeticus

<400> SEQUENCE: 6

Val Ser Ala Pro Ala Thr Asp Ala Arg Thr Ala His Ala Asp Gly Val
1               5                   10                  15

Glu Arg Leu Leu Glu Ser Tyr Arg Ala Val Pro Ala Ala Ala Ser Val
            20                  25                  30

Arg Leu Ala Lys Arg Thr Ser Asn Leu Phe Arg Ser Arg Ala Ala Thr
        35                  40                  45

Asp Ala Pro Gly Leu Asp Thr Ser Gly Leu Thr His Val Ile Ala Val
    50                  55                  60

Asp Pro Gly Ala Arg Thr Ala Asp Val Ala Gly Met Cys Thr Tyr Asp
65                  70                  75                  80

Asp Leu Val Ala Ala Thr Leu Pro His Gly Leu Ala Pro Leu Val Val
                85                  90                  95

Pro Gln Leu Lys Thr Ile Thr Leu Gly Gly Ala Val Thr Gly Leu Gly
            100                 105                 110

Ile Glu Ser Thr Ser Phe Arg Asn Gly Leu Pro His Glu Ser Val Leu
        115                 120                 125

Glu Ile Asp Val Leu Thr Gly Ala Gly Glu Ile Ile Thr Ala Ser Pro
    130                 135                 140

Ile Glu His Ala Glu Leu Phe Arg Ala Phe Pro Asn Ser Tyr Gly Thr
145                 150                 155                 160

Leu Gly Tyr Ala Val Arg Leu Arg Ile Glu Leu Glu Pro Val Glu Pro
                165                 170                 175

Phe Val Ala Leu Thr His Leu Arg Phe His Ala Leu Thr Asp Leu Ile
            180                 185                 190

Glu Ala Met Glu Arg Ile Ile Glu Thr Gly Arg Leu Asp Gly Val Ala
        195                 200                 205

Val Asp Ser Leu Asp Gly Val Val Phe Ser Ala Glu Glu Ser Tyr Leu
    210                 215                 220

Cys Val Gly Thr Gln Thr Ala Ala Ser Gly Pro Val Ser Asp Tyr Thr
225                 230                 235                 240

Arg Gln Gln Ile Phe Tyr Arg Ser Ile Gln His Asp Asp Gly Ala Lys
                245                 250                 255

His Asp Arg Leu Thr Met His Asp Tyr Leu Trp Arg Trp Asp Ala Asp
            260                 265                 270

Trp Phe Trp Cys Ser Gln Ala Phe Gly Ala Gln His Pro Leu Ile Arg
        275                 280                 285

Arg Phe Trp Pro Arg Arg Tyr Arg Arg Ser Arg Ser Tyr Ser Thr Leu
    290                 295                 300

Met Arg Leu Glu Arg Arg Phe Asp Leu Gly Asp Arg Leu Glu Lys Leu
305                 310                 315                 320
```

-continued

```
Lys Gly Arg Pro Ala Arg Glu Arg Val Ile Gln Asp Val Glu Val Pro
                325                 330                 335

Ile Gly Arg Thr Val Gly Phe Leu Glu Trp Phe Leu Ala Asn Val Pro
            340                 345                 350

Ile Glu Pro Ile Trp Leu Cys Pro Leu Arg Leu Arg Gly Asp Arg Gly
        355                 360                 365

Trp Pro Leu Tyr Pro Ile Arg Pro Gln Gln Thr Tyr Val Asn Ile Gly
    370                 375                 380

Phe Trp Ser Thr Val Pro Val Gly Gly Ser Glu Gly Glu Thr Asn Arg
385                 390                 395                 400

Ser Ile Glu Arg Ala Val Ser Glu Phe Asp Gly His Lys Ser Leu Tyr
                405                 410                 415

Ser Asp Ser Tyr Tyr Ser Arg Glu Glu Phe Glu Glu Leu Tyr Gly Gly
            420                 425                 430

Glu Ala Tyr Arg Ala Val Lys Arg Arg Tyr Asp Pro Asp Ser Arg Leu
        435                 440                 445

Leu Asp Leu Tyr Ala Lys Ala Val Gln Arg Arg
    450                 455
```

<210> SEQ ID NO 7
<211> LENGTH: 1254
<212> TYPE: DNA
<213> ORGANISM: Unknown
<220> FEATURE:
<223> OTHER INFORMATION: Agromyces subbeticus

<400> SEQUENCE: 7

```
atcctcgaga tcgtcgtcgc cggtcggctg ccgctgaggt tcaccgccta cgacgggagc      60

tcggcggggc cgcctgacgc cctgttcggc ctcgacctga agactccgcg aggaacgacc     120

tatctcgcca ccggccgcgg cgatctcggc ctcgcccgcg cctacatcgc gggcgacctc     180

gagatacagg gggtgcaccc cggagacccc tacgagctgc tcaaggcact cgccgacagc     240

ctggtcttca agctgccacc gccgcgggtg atgacccaga tcatccgttc gatcggcgtc     300

gaacatctgc ggccgatcgc gccgccgccg caagaggtgc cgccccggtg gcgccgcatc     360

gccgaggggc tccgacacag caagggccgc gacgccgaag cgatccacca ccactacgac     420

gtgtcgaaca ccttctacga atgggtgctc gggccgtcga tgacctacac gtgcgcgtgc     480

tacccgggcc tcgacgcatc cctcgacgag gcgcagcaga acaagtaccg gctcgtgttc     540

gagaagctgc ggctgaagcc gggcgaccga ctgctcgacg tcggctgcgg gtggggcggc     600

atggtgcgct acgccgcgcg ccacggcgtg caggcgttgg gcgtgaccct gtcgcgagag     660

cagacggcgt gggcgcagca ggcgatcgcc gtcgagggcc tcgccgacct cgccgaggtg     720

cgctacggcg actaccgcga catcgccgaa gacggcttcg atgcggtgtc atcgatcggg     780

ctgctcgagc acatcggcgt gcgcaactac gcttcgtatt tcggctttct gcagtcgcgc     840

ttgcggcccg ggggactctt gctcaaccac tgcatcaccc ggcccgacaa tcgctccgag     900

ccgtcggcgc gcggcttcat cgaccggtac gtgttccccg acggagagct caccggctcg     960

ggccgcatca tcaccgaggc gcaggatgtc ggcttcgaag tgctgcacga agagaacctg    1020

cgtcagcatt atgcactgac actgcgcgat tggtgcgcca acctcgtcgc gcactgggaa    1080

gaggcggtcg ccgaggtcgg gctgccgacc gcgaaggtgt ggggcctcta catggccggg    1140

tcacggctcg cgttcgagag cggcggcatc cagttgcacc aggtgctggc ggtcagacca    1200

gacgatcgca gcgacgccgc ccagctgccg ctgcggccgt ggtggacgcc atag          1254
```

<210> SEQ ID NO 8
<211> LENGTH: 417
<212> TYPE: PRT
<213> ORGANISM: Unknown
<220> FEATURE:
<223> OTHER INFORMATION: Agromyces subbeticus

<400> SEQUENCE: 8

```
Ile Leu Glu Ile Val Val Ala Gly Arg Leu Pro Leu Arg Phe Thr Ala
1               5                   10                  15

Tyr Asp Gly Ser Ser Ala Gly Pro Pro Asp Ala Leu Phe Gly Leu Asp
            20                  25                  30

Leu Lys Thr Pro Arg Gly Thr Thr Tyr Leu Ala Thr Gly Arg Gly Asp
        35                  40                  45

Leu Gly Leu Ala Arg Ala Tyr Ile Ala Gly Asp Leu Glu Ile Gln Gly
    50                  55                  60

Val His Pro Gly Asp Pro Tyr Glu Leu Leu Lys Ala Leu Ala Asp Ser
65                  70                  75                  80

Leu Val Phe Lys Leu Pro Pro Pro Arg Val Met Thr Gln Ile Ile Arg
                85                  90                  95

Ser Ile Gly Val Glu His Leu Arg Pro Ile Ala Pro Pro Pro Gln Glu
            100                 105                 110

Val Pro Pro Arg Trp Arg Arg Ile Ala Glu Gly Leu Arg His Ser Lys
        115                 120                 125

Gly Arg Asp Ala Glu Ala Ile His His His Tyr Asp Val Ser Asn Thr
    130                 135                 140

Phe Tyr Glu Trp Val Leu Gly Pro Ser Met Thr Tyr Thr Cys Ala Cys
145                 150                 155                 160

Tyr Pro Gly Leu Asp Ala Ser Leu Asp Glu Ala Gln Gln Asn Lys Tyr
                165                 170                 175

Arg Leu Val Phe Glu Lys Leu Arg Leu Lys Pro Gly Asp Arg Leu Leu
            180                 185                 190

Asp Val Gly Cys Gly Trp Gly Gly Met Val Arg Tyr Ala Ala Arg His
        195                 200                 205

Gly Val Gln Ala Leu Gly Val Thr Leu Ser Arg Glu Gln Thr Ala Trp
    210                 215                 220

Ala Gln Gln Ala Ile Ala Val Glu Gly Leu Ala Asp Leu Ala Glu Val
225                 230                 235                 240

Arg Tyr Gly Asp Tyr Arg Asp Ile Ala Glu Asp Gly Phe Asp Ala Val
                245                 250                 255

Ser Ser Ile Gly Leu Leu Glu His Ile Gly Val Arg Asn Tyr Ala Ser
            260                 265                 270

Tyr Phe Gly Phe Leu Gln Ser Arg Leu Arg Pro Gly Gly Leu Leu Leu
        275                 280                 285

Asn His Cys Ile Thr Arg Pro Asp Asn Arg Ser Glu Pro Ser Ala Arg
    290                 295                 300

Gly Phe Ile Asp Arg Tyr Val Phe Pro Asp Gly Glu Leu Thr Gly Ser
305                 310                 315                 320

Gly Arg Ile Ile Thr Glu Ala Gln Asp Val Gly Phe Glu Val Leu His
                325                 330                 335

Glu Glu Asn Leu Arg Gln His Tyr Ala Leu Thr Leu Arg Asp Trp Cys
            340                 345                 350

Ala Asn Leu Val Ala His Trp Glu Glu Ala Val Ala Glu Val Gly Leu
        355                 360                 365
```

```
Pro Thr Ala Lys Val Trp Gly Leu Tyr Met Ala Gly Ser Arg Leu Ala
    370                 375                 380

Phe Glu Ser Gly Gly Ile Gln Leu His Gln Val Leu Ala Val Arg Pro
385                 390                 395                 400

Asp Asp Arg Ser Asp Ala Ala Gln Leu Pro Leu Arg Pro Trp Trp Thr
                405                 410                 415

Pro
```

<210> SEQ ID NO 9
<211> LENGTH: 1428
<212> TYPE: DNA
<213> ORGANISM: Unknown
<220> FEATURE:
<223> OTHER INFORMATION: Amycolicicoccus subflavus

<400> SEQUENCE: 9

```
atgacgcctg aagctagtgc ggcggcgcac gccgctgcgg tggatcgcct catccatagc     60

tatcgggcga ttcctgatga cgcgccggtg cggctggcga agaagacgtc aaacctattc    120

cgccacaggg aaaagacttc tgctcctggg cttgacgtat ccggcctggc tcgcgtgatt    180

gggatcgact cagacactcg cactgccgac gttggcggca tgtgcacata cgaggacctt    240

gtcgcggcga cgctcgaata cgatctggtc cccctggtcg tcccgcaact caaaacgatc    300

actctcggcg gcgcggtgac gggcctggga attgagtcca cctcgttccg caatgggctt    360

ccccatgaat ctgttctcga aatggatatc ctgacgggcg ccggggaggt cgtcacggcc    420

ggcccggaag gcccccatag cgatttgtac tgggggtttc cgaattcgta cggcacgctc    480

ggctatgcga cgcgcctgcg catcgaacta gaaccggtcg agccgtacgt cgaactcagg    540

cacctgcggt tcactagcct cgatgagctt caggagacac ttgacaccgt ttcgtacgaa    600

cacacgtatg acggggaacc cgttcattac gtcgatggag tcatgttctc agccacggaa    660

agctacctca cgcttggccg tcagacgagc gaacccggcc cggtcagcga ctacaccgga    720

aaccagatct actaccgttc aatacagcac ggtggcgctg aaactcccgt cgtcgaccgg    780

atgaccattc atgactatct atggcgctgg gatactgact ggttctggtg ctcgcgtgcc    840

ttcggaacgc aacacccagt ggtccggaga ttctggccac gccgctatcg ccgcagcagc    900

ttctactgga agctgatcgc gcttgaccgc caggttgggc tcgcggactt catcgaacaa    960

cggaagggca acctcccccg ggaacgcgta gtccaggaca tcgaggtccc gatcgagaac   1020

actgcgagct tcttgcggtg gttcttggcg aacgtgccga tcgagccggt atggctatgc   1080

ccgctgcgcc tgcgaaaaac acgcagcccc ggcctgcctt cgccgacgtc cccggcttca   1140

cgcccatggc ccctctatcc gctcgagcct cagcgcacat acgtcaatgt tggcttctgg   1200

tcagcggtgc cggtcgtggc cggccagccc gaggggcaca ccaaccggat gatcgagaac   1260

gaagtcgatc gccttgacgg tcacaaatcg ctgtactcag atgcgtttta cgagcgaaaa   1320

gagtttgacg cgctgtacgg cggcgatacc tatagagaac tcaaagagac ctacgaccca   1380

aacagccggt tacttgatct ctatgcaaag gcggtgcaag gacgatga                1428
```

<210> SEQ ID NO 10
<211> LENGTH: 475
<212> TYPE: PRT
<213> ORGANISM: Unknown
<220> FEATURE:
<223> OTHER INFORMATION: Amycolicicoccus subflavus

<400> SEQUENCE: 10

-continued

```
Met Thr Pro Glu Ala Ser Ala Ala Ala His Ala Ala Ala Val Asp Arg
1               5                   10                  15

Leu Ile His Ser Tyr Arg Ala Ile Pro Asp Asp Ala Pro Val Arg Leu
            20                  25                  30

Ala Lys Lys Thr Ser Asn Leu Phe Arg His Arg Glu Lys Thr Ser Ala
        35                  40                  45

Pro Gly Leu Asp Val Ser Gly Leu Ala Arg Val Ile Gly Ile Asp Ser
    50                  55                  60

Asp Thr Arg Thr Ala Asp Val Gly Gly Met Cys Thr Tyr Glu Asp Leu
65                  70                  75                  80

Val Ala Ala Thr Leu Glu Tyr Asp Leu Val Pro Leu Val Val Pro Gln
                85                  90                  95

Leu Lys Thr Ile Thr Leu Gly Gly Ala Val Thr Gly Leu Gly Ile Glu
            100                 105                 110

Ser Thr Ser Phe Arg Asn Gly Leu Pro His Glu Ser Val Leu Glu Met
        115                 120                 125

Asp Ile Leu Thr Gly Ala Gly Glu Val Val Thr Ala Gly Pro Glu Gly
    130                 135                 140

Pro His Ser Asp Leu Tyr Trp Gly Phe Pro Asn Ser Tyr Gly Thr Leu
145                 150                 155                 160

Gly Tyr Ala Thr Arg Leu Arg Ile Glu Leu Glu Pro Val Glu Pro Tyr
                165                 170                 175

Val Glu Leu Arg His Leu Arg Phe Thr Ser Leu Asp Glu Leu Gln Glu
            180                 185                 190

Thr Leu Asp Thr Val Ser Tyr Glu His Thr Tyr Asp Gly Glu Pro Val
        195                 200                 205

His Tyr Val Asp Gly Val Met Phe Ser Ala Thr Glu Ser Tyr Leu Thr
    210                 215                 220

Leu Gly Arg Gln Thr Ser Glu Pro Gly Pro Val Ser Asp Tyr Thr Gly
225                 230                 235                 240

Asn Gln Ile Tyr Tyr Arg Ser Ile Gln His Gly Gly Ala Glu Thr Pro
                245                 250                 255

Val Val Asp Arg Met Thr Ile His Asp Tyr Leu Trp Arg Trp Asp Thr
            260                 265                 270

Asp Trp Phe Trp Cys Ser Arg Ala Phe Gly Thr Gln His Pro Val Val
        275                 280                 285

Arg Arg Phe Trp Pro Arg Arg Tyr Arg Arg Ser Ser Phe Tyr Trp Lys
    290                 295                 300

Leu Ile Ala Leu Asp Arg Gln Val Gly Leu Ala Asp Phe Ile Glu Gln
305                 310                 315                 320

Arg Lys Gly Asn Leu Pro Arg Glu Arg Val Val Gln Asp Ile Glu Val
                325                 330                 335

Pro Ile Glu Asn Thr Ala Ser Phe Leu Arg Trp Phe Leu Ala Asn Val
            340                 345                 350

Pro Ile Glu Pro Val Trp Leu Cys Pro Leu Arg Leu Arg Lys Thr Arg
        355                 360                 365

Ser Pro Gly Leu Pro Ser Pro Thr Ser Pro Ala Ser Arg Pro Trp Pro
    370                 375                 380

Leu Tyr Pro Leu Glu Pro Gln Arg Thr Tyr Val Asn Val Gly Phe Trp
385                 390                 395                 400

Ser Ala Val Pro Val Val Ala Gly Gln Pro Glu Gly His Thr Asn Arg
                405                 410                 415

Met Ile Glu Asn Glu Val Asp Arg Leu Asp Gly His Lys Ser Leu Tyr
```

```
            420                 425                 430

Ser Asp Ala Phe Tyr Glu Arg Lys Glu Phe Asp Ala Leu Tyr Gly Gly
        435                 440                 445

Asp Thr Tyr Arg Glu Leu Lys Glu Thr Tyr Asp Pro Asn Ser Arg Leu
    450                 455                 460

Leu Asp Leu Tyr Ala Lys Ala Val Gln Gly Arg
465                 470                 475
```

<210> SEQ ID NO 11
<211> LENGTH: 1311
<212> TYPE: DNA
<213> ORGANISM: Unknown
<220> FEATURE:
<223> OTHER INFORMATION: Amycolicicoccus subflavus

<400> SEQUENCE: 11

```
atgaaggcag tgttgacggc gtttacggct ccccaactcg aaaggatgaa cgtcgctgag      60
atactcagcg cggtactcgg gcgagatttc ccgatccggt tcactgcgta cgacggcagc     120
gcgctcggcc ccgaaaccgc ccgctacggc ttgcacctca cgacgccgcg cgggctgacc     180
tacctcgcta ccgcgcccgg tgatctcggg ctcgcacgcg cgtacgtgtc cggcgacctc     240
gaggtcagtg gggttcatca gggtgacccg tacgagataa tgaagatcct cgcgcatgac     300
gtccgggtgc ggcggccctc gccagcaacg atcgcttcga tcatgcggtc cctcggctgg     360
gaacgcttgc gaccggtcgc gccgcccccg caagagaaca tgccccgttg gcgccggatg     420
gcccttggcc tgctgcactc gaagagccgt gatgctgcgg caatccacca tcattacgac     480
gtgtcgaacg agttttacga gcacatcctc ggcccgtcga tgacgtacac atgcgcggcc     540
taccccagcg cagacagttc cctggaggaa gcacaggaca acaagtaccg actcgtcttc     600
gagaaacttg gcctgaaagc cggggatcgc ctgcttgacg tcgggtgcgg gtggggcggc     660
atggtgcggt tcgccgctaa gcgcggcgtt catgtcatcg gtgcgacatt gtcccgcaaa     720
caggcggaat gggctcagaa gatgattgcc catgaaggat tgggcgatct ggcggaagtc     780
cgtttctgcg actaccgcga tgtcacagag gcgggcttcg acgcagtgtc gtcgatcggc     840
ctcactgaac acatcggttt ggcgaactac ccgtcgtact tcggcttcct gaaggacaag     900
ttgcggccag gcggacgact gctgaaccat tgcatcactc gcccgaacaa ccttcaaagc     960
aaccgcgcag gtgacttcat tgaccggtac gttttccctg acggagagct cgccggacct    1020
ggcttcatca tttcagctgt ccacgacgcc ggtttcgagg tgcggcacga agagaacctc    1080
cgcgagcact acgcactgac gctgcgggac tggaaccgca acctcgctcg cgactgggac    1140
gcgtgtgtgc acgcctccga cgagggcacc gcccgcgtct ggggactgta catttccggt    1200
tcacgagtcg cgtttgaaac gaactcgatt cagctgcacc aggtcctggc ggtcaaaacc    1260
gcgcggaatg gcgaagcgca ggtcccgttg ggtcagtggt ggacccgctg a             1311
```

<210> SEQ ID NO 12
<211> LENGTH: 436
<212> TYPE: PRT
<213> ORGANISM: Unknown
<220> FEATURE:
<223> OTHER INFORMATION: Amycolicicoccus subflavus

<400> SEQUENCE: 12

```
Met Lys Ala Val Leu Thr Ala Phe Thr Ala Pro Gln Leu Glu Arg Met
1               5                   10                  15

Asn Val Ala Glu Ile Leu Ser Ala Val Leu Gly Arg Asp Phe Pro Ile
```

-continued

```
            20                  25                  30

Arg Phe Thr Ala Tyr Asp Gly Ser Ala Leu Gly Pro Glu Thr Ala Arg
        35                  40                  45

Tyr Gly Leu His Leu Thr Thr Pro Arg Gly Leu Thr Tyr Leu Ala Thr
    50                  55                  60

Ala Pro Gly Asp Leu Gly Leu Ala Arg Ala Tyr Val Ser Gly Asp Leu
65                  70                  75                  80

Glu Val Ser Gly Val His Gln Gly Asp Pro Tyr Glu Ile Met Lys Ile
                85                  90                  95

Leu Ala His Asp Val Arg Val Arg Arg Pro Ser Pro Ala Thr Ile Ala
            100                 105                 110

Ser Ile Met Arg Ser Leu Gly Trp Glu Arg Leu Arg Pro Val Ala Pro
        115                 120                 125

Pro Pro Gln Glu Asn Met Pro Arg Trp Arg Arg Met Ala Leu Gly Leu
    130                 135                 140

Leu His Ser Lys Ser Arg Asp Ala Ala Ala Ile His His His Tyr Asp
145                 150                 155                 160

Val Ser Asn Glu Phe Tyr Glu His Ile Leu Gly Pro Ser Met Thr Tyr
                165                 170                 175

Thr Cys Ala Ala Tyr Pro Ser Ala Asp Ser Ser Leu Glu Glu Ala Gln
            180                 185                 190

Asp Asn Lys Tyr Arg Leu Val Phe Glu Lys Leu Gly Leu Lys Ala Gly
        195                 200                 205

Asp Arg Leu Leu Asp Val Gly Cys Gly Trp Gly Gly Met Val Arg Phe
    210                 215                 220

Ala Ala Lys Arg Gly Val His Val Ile Gly Ala Thr Leu Ser Arg Lys
225                 230                 235                 240

Gln Ala Glu Trp Ala Gln Lys Met Ile Ala His Glu Gly Leu Gly Asp
                245                 250                 255

Leu Ala Glu Val Arg Phe Cys Asp Tyr Arg Asp Val Thr Glu Ala Gly
            260                 265                 270

Phe Asp Ala Val Ser Ser Ile Gly Leu Thr Glu His Ile Gly Leu Ala
        275                 280                 285

Asn Tyr Pro Ser Tyr Phe Gly Phe Leu Lys Asp Lys Leu Arg Pro Gly
    290                 295                 300

Gly Arg Leu Leu Asn His Cys Ile Thr Arg Pro Asn Asn Leu Gln Ser
305                 310                 315                 320

Asn Arg Ala Gly Asp Phe Ile Asp Arg Tyr Val Phe Pro Asp Gly Glu
                325                 330                 335

Leu Ala Gly Pro Gly Phe Ile Ile Ser Ala Val His Asp Ala Gly Phe
            340                 345                 350

Glu Val Arg His Glu Glu Asn Leu Arg Glu His Tyr Ala Leu Thr Leu
        355                 360                 365

Arg Asp Trp Asn Arg Asn Leu Ala Arg Asp Trp Asp Ala Cys Val His
    370                 375                 380

Ala Ser Asp Glu Gly Thr Ala Arg Val Trp Gly Leu Tyr Ile Ser Gly
385                 390                 395                 400

Ser Arg Val Ala Phe Glu Thr Asn Ser Ile Gln Leu His Gln Val Leu
                405                 410                 415

Ala Val Lys Thr Ala Arg Asn Gly Glu Ala Gln Val Pro Leu Gly Gln
            420                 425                 430

Trp Trp Thr Arg
        435
```

<210> SEQ ID NO 13
<211> LENGTH: 1548
<212> TYPE: DNA
<213> ORGANISM: Corynebacterium glutamicum

<400> SEQUENCE: 13
atgagcggat tagttgaccc ggatagtact tttttaaaga ccatcggaaa actgagcaac 60
agcttgtcca ttggtcgtgg agtagatcaa aaagaggtaa tccccaaagg ctggaacgcc 120
cattgggagg caattacaaa gcttaagaga agctttgacg cgattcctgc tggggagcgg 180
gtgcgtttag ctaagaaaac ctccaacctg ttccgtggac gctccgatgc aggtcacggc 240
ctagatgtgg cagcgcttgg gggagtgatt gccattgatc cggtcaatgc caccgccgat 300
gtacagggca tgtgcacgta tgaagacctg gtagatgcca ctttaagtta tggtctgatg 360
ccgttggttg tgcctcaact gaaaaccatc acgcttggtg gcgcagtgac cggaatgggc 420
gtggaatcca catccttccg caacggtttg ccacacgaat cagtgctgga gatggatatt 480
tttaccggca ctggtgagat cgtgacttgc tcgcccacag aaaatgtcga cctttacaga 540
ggttttccca actcttatgg ttcgctggga tacgcggtgc ggctaaaaat tgagctggaa 600
ccagtgcaag attacgtcca gctgcgccac gtgcgcttca acgatttaga gtctttgacc 660
aaagcgattg aggaagtcgc gtcttctctg gagtttgata accaacccgt cgattacctt 720
gacggcgtgg tgttttcacc cacggaagcc tacttagttc ttggcacgca aacctcacaa 780
cctggcccca ccagcgatta caccagggat ttaagctact accgctccct gcaacaccca 840
gagggcatca cctatgaccg cctgacaatc cgcgattaca tctggcgctg ggacaccgac 900
tggttctggt gttcacgcgc attcggcacc caaaaccccg tggtgcgcaa actctggccc 960
agggatctgc tgcgctcgag tttctattgg aagatcatcg gctgggatcg aaaatactcc 1020
atcgctgatc gcctggaaga gcgcaaaggc cgcccggcta gggaacgggt ggtccaagac 1080
gtggaagtta cgattgataa actgccagaa tttttgaaat ggttctttga aagcagcgac 1140
atcgagccgc tgtggctgtg cccgatcaag cttcgggagg taccaggtag ttcggttggt 1200
gctggagaaa ttttgagctc cgctgaagca atcgactccg gtgctgctga acacccttgg 1260
ccgctgtatc ccttgaagaa ggacgtgctg tgggtcaaca tcggattctg gtcctcagtg 1320
ccggttgatc tgatgggctc cgatgcacca gagggagcat ttaacagaga aatcgaacgc 1380
gtcatggcag agctaggcgg acataaatcg ctgtactccg aagcgttcta caccagggaa 1440
gactttgaaa aactttatgg cggaaccatc ccggcgctgc taaaaaagca gtgggatccc 1500
cacagccgat tccccggttt gtatgaaaag acagtaaaag gcgcctag 1548

<210> SEQ ID NO 14
<211> LENGTH: 515
<212> TYPE: PRT
<213> ORGANISM: Corynebacterium glutamicum

<400> SEQUENCE: 14

Met Ser Gly Leu Val Asp Pro Asp Ser Thr Phe Leu Lys Thr Ile Gly
1               5                   10                  15

Lys Leu Ser Asn Ser Leu Ser Ile Gly Arg Gly Val Asp Gln Lys Glu
            20                  25                  30

Val Ile Pro Lys Gly Trp Asn Ala His Trp Glu Ala Ile Thr Lys Leu
        35                  40                  45

Lys Arg Ser Phe Asp Ala Ile Pro Ala Gly Glu Arg Val Arg Leu Ala

-continued

```
    50                  55                  60

Lys Lys Thr Ser Asn Leu Phe Arg Gly Arg Ser Asp Ala Gly His Gly
65                  70                  75                  80

Leu Asp Val Ala Ala Leu Gly Gly Val Ile Ala Ile Asp Pro Val Asn
                85                  90                  95

Ala Thr Ala Asp Val Gln Gly Met Cys Thr Tyr Glu Asp Leu Val Asp
            100                 105                 110

Ala Thr Leu Ser Tyr Gly Leu Met Pro Leu Val Val Pro Gln Leu Lys
        115                 120                 125

Thr Ile Thr Leu Gly Gly Ala Val Thr Gly Met Gly Val Glu Ser Thr
    130                 135                 140

Ser Phe Arg Asn Gly Leu Pro His Glu Ser Val Leu Glu Met Asp Ile
145                 150                 155                 160

Phe Thr Gly Thr Gly Glu Ile Val Thr Cys Ser Pro Thr Glu Asn Val
                165                 170                 175

Asp Leu Tyr Arg Gly Phe Pro Asn Ser Tyr Gly Ser Leu Gly Tyr Ala
            180                 185                 190

Val Arg Leu Lys Ile Glu Leu Glu Pro Val Gln Asp Tyr Val Gln Leu
        195                 200                 205

Arg His Val Arg Phe Asn Asp Leu Glu Ser Leu Thr Lys Ala Ile Glu
    210                 215                 220

Glu Val Ala Ser Ser Leu Glu Phe Asp Asn Gln Pro Val Asp Tyr Leu
225                 230                 235                 240

Asp Gly Val Val Phe Ser Pro Thr Glu Ala Tyr Leu Val Leu Gly Thr
                245                 250                 255

Gln Thr Ser Gln Pro Gly Pro Thr Ser Asp Tyr Thr Arg Asp Leu Ser
            260                 265                 270

Tyr Tyr Arg Ser Leu Gln His Pro Glu Gly Ile Thr Tyr Asp Arg Leu
        275                 280                 285

Thr Ile Arg Asp Tyr Ile Trp Arg Trp Asp Thr Asp Trp Phe Trp Cys
    290                 295                 300

Ser Arg Ala Phe Gly Thr Gln Asn Pro Val Val Arg Lys Leu Trp Pro
305                 310                 315                 320

Arg Asp Leu Leu Arg Ser Ser Phe Tyr Trp Lys Ile Ile Gly Trp Asp
                325                 330                 335

Arg Lys Tyr Ser Ile Ala Asp Arg Leu Glu Glu Arg Lys Gly Arg Pro
            340                 345                 350

Ala Arg Glu Arg Val Val Gln Asp Val Glu Val Thr Ile Asp Lys Leu
        355                 360                 365

Pro Glu Phe Leu Lys Trp Phe Phe Glu Ser Ser Asp Ile Glu Pro Leu
    370                 375                 380

Trp Leu Cys Pro Ile Lys Leu Arg Glu Val Pro Gly Ser Ser Val Gly
385                 390                 395                 400

Ala Gly Glu Ile Leu Ser Ser Ala Glu Ala Ile Asp Ser Gly Ala Ala
                405                 410                 415

Glu His Pro Trp Pro Leu Tyr Pro Leu Lys Lys Asp Val Leu Trp Val
            420                 425                 430

Asn Ile Gly Phe Trp Ser Ser Val Pro Val Asp Leu Met Gly Ser Asp
        435                 440                 445

Ala Pro Glu Gly Ala Phe Asn Arg Glu Ile Glu Arg Val Met Ala Glu
    450                 455                 460

Leu Gly Gly His Lys Ser Leu Tyr Ser Glu Ala Phe Tyr Thr Arg Glu
465                 470                 475                 480
```

```
Asp Phe Glu Lys Leu Tyr Gly Gly Thr Ile Pro Ala Leu Leu Lys Lys
                485                 490                 495

Gln Trp Asp Pro His Ser Arg Phe Pro Gly Leu Tyr Glu Lys Thr Val
            500                 505                 510

Lys Gly Ala
        515


<210> SEQ ID NO 15
<211> LENGTH: 1308
<212> TYPE: DNA
<213> ORGANISM: Corynebacterium glutamicum

<400> SEQUENCE: 15

atgagtaacg ccgtagcgca ggacctcatg accatcgccg acatcgtcga ggccacgacc      60

actgcaccca tcccattcca catcactgcc ttcgatggaa gcttcactgg ccctgaagat     120

gctccctacc agctgtttgt tgccaacacg gatgcagtat cctacatcgc aacagcgcca     180

ggagatttgg gtttggcacg tgcctacctc atgggagacc tcatcgtgga aggtgagcat     240

cccggccatc cttatgggat ctttgatgcg ttgaaggagt tctaccgctg cttcaaacgc     300

ccagatgcat ccaccacctt gcagatcatg tggactctgc ggaaaatgaa tgccttaaaa     360

ttccaggaaa ttccaccaat ggaacaagcc cctgcatggc gtaaagcact gatcaacggg     420

ctagcatcca ggcactcgaa atcccgcgac aagaaagcca ttagctacca ctacgacgtg     480

ggcaatgagt tctactccct gtttttagat gattccatga cctatacctg cgcgtattat     540

ccaacgccag aatcaagttt ggaagaagcc caagaaaaca aataccgcct catctttgaa     600

aaactgcgtc tgaaagaagg cgatcgcctc ctagacgtgg gatgcggttg ggaggcatg      660

gtccgctacg ccgccaaaca cggtgtgaaa gccatcggag ttacgctgtc tgaacagcaa     720

tatgagtggg gtcaagcaga gatcaaacgc caaggtttgg aagacctcgc ggaaattcgc     780

ttcatggatt accgcgatgt tccagaaact ggattcgatg cgatctcagc aatcggcatc     840

attgaacaca tcggtgtgaa caactatccc gactactttg aattgctcag cagcaaactc     900

aaaacaggcg gactgatgct caaccacagc atcacctacc cagacaaccg cccccgccac     960

gcaggtgcat ttattgatcg ctacattttc cccgacggtg aactcactgg ctctggcacc    1020

ctgatcaagc acatgcagga caacggtttc gaagtgctgc acgaagaaaa cctccgcttt    1080

gattaccaac gcaccctgca cgcgtggtgc gaaaacctca aagaaaattg ggaggaagca    1140

gttgaactcg ccggtgaacc cactgcacga ctctttggcc tgtacatggc aggttcggaa    1200

tggggatttg cccacaacat cgtccagctg caccaagtac tgggtgtgaa actcgatgag    1260

cagggaagtc gcggagaagt tcctgaaaga atgtggtgga ctatctaa                 1308


<210> SEQ ID NO 16
<211> LENGTH: 435
<212> TYPE: PRT
<213> ORGANISM: Corynebacterium glutamicum

<400> SEQUENCE: 16

Met Ser Asn Ala Val Ala Gln Asp Leu Met Thr Ile Ala Asp Ile Val
1               5                   10                  15

Glu Ala Thr Thr Thr Ala Pro Ile Pro Phe His Ile Thr Ala Phe Asp
            20                  25                  30

Gly Ser Phe Thr Gly Pro Glu Asp Ala Pro Tyr Gln Leu Phe Val Ala
        35                  40                  45
```

```
Asn Thr Asp Ala Val Ser Tyr Ile Ala Thr Ala Pro Gly Asp Leu Gly
    50                  55                  60

Leu Ala Arg Ala Tyr Leu Met Gly Asp Leu Ile Val Glu Gly Glu His
65                  70                  75                  80

Pro Gly His Pro Tyr Gly Ile Phe Asp Ala Leu Lys Glu Phe Tyr Arg
                85                  90                  95

Cys Phe Lys Arg Pro Asp Ala Ser Thr Thr Leu Gln Ile Met Trp Thr
            100                 105                 110

Leu Arg Lys Met Asn Ala Leu Lys Phe Gln Glu Ile Pro Pro Met Glu
        115                 120                 125

Gln Ala Pro Ala Trp Arg Lys Ala Leu Ile Asn Gly Leu Ala Ser Arg
    130                 135                 140

His Ser Lys Ser Arg Asp Lys Lys Ala Ile Ser Tyr His Tyr Asp Val
145                 150                 155                 160

Gly Asn Glu Phe Tyr Ser Leu Phe Leu Asp Asp Ser Met Thr Tyr Thr
                165                 170                 175

Cys Ala Tyr Tyr Pro Thr Pro Glu Ser Ser Leu Glu Glu Ala Gln Glu
            180                 185                 190

Asn Lys Tyr Arg Leu Ile Phe Glu Lys Leu Arg Leu Lys Glu Gly Asp
        195                 200                 205

Arg Leu Leu Asp Val Gly Cys Gly Trp Gly Gly Met Val Arg Tyr Ala
    210                 215                 220

Ala Lys His Gly Val Lys Ala Ile Gly Val Thr Leu Ser Glu Gln Gln
225                 230                 235                 240

Tyr Glu Trp Gly Gln Ala Glu Ile Lys Arg Gln Gly Leu Glu Asp Leu
                245                 250                 255

Ala Glu Ile Arg Phe Met Asp Tyr Arg Asp Val Pro Glu Thr Gly Phe
            260                 265                 270

Asp Ala Ile Ser Ala Ile Gly Ile Ile Glu His Ile Gly Val Asn Asn
        275                 280                 285

Tyr Pro Asp Tyr Phe Glu Leu Leu Ser Ser Lys Leu Lys Thr Gly Gly
    290                 295                 300

Leu Met Leu Asn His Ser Ile Thr Tyr Pro Asp Asn Arg Pro Arg His
305                 310                 315                 320

Ala Gly Ala Phe Ile Asp Arg Tyr Ile Phe Pro Asp Gly Glu Leu Thr
                325                 330                 335

Gly Ser Gly Thr Leu Ile Lys His Met Gln Asp Asn Gly Phe Glu Val
            340                 345                 350

Leu His Glu Glu Asn Leu Arg Phe Asp Tyr Gln Arg Thr Leu His Ala
        355                 360                 365

Trp Cys Glu Asn Leu Lys Glu Asn Trp Glu Glu Ala Val Glu Leu Ala
    370                 375                 380

Gly Glu Pro Thr Ala Arg Leu Phe Gly Leu Tyr Met Ala Gly Ser Glu
385                 390                 395                 400

Trp Gly Phe Ala His Asn Ile Val Gln Leu His Gln Val Leu Gly Val
                405                 410                 415

Lys Leu Asp Glu Gln Gly Ser Arg Gly Glu Val Pro Glu Arg Met Trp
            420                 425                 430

Trp Thr Ile
        435
```

<210> SEQ ID NO 17
<211> LENGTH: 1458
<212> TYPE: DNA

<213> ORGANISM: Unknown
<220> FEATURE:
<223> OTHER INFORMATION: Corynebacterium glyciniphilium

<400> SEQUENCE: 17
gtgaccgtcg ccggcaggat cactgacgcg gtacgcatag gaaatggact tgaccagcga 60
gatctagccc ccgtcgggtg gtacgcacac gaacaggccg tggcgcgact gaaggccagt 120
ttcgacgcgg tccccgccgg gcgtcgcgtg cggctggcga agaagacgtc caaccttttc 180
cgcgggcgtt ccggcgaggc agtcgggctc gacgtgtcgg ggctgcacgg cgtcatcgcc 240
gtcgaccccg ttgagggcac cgctgacgtc cagggcatgt gcacgtacga ggacctggtg 300
gacgtcctgc tgccctacgg tctggcgccc accgtcgttc cgcagctgaa gaccatcact 360
ctcggcggtg cggtgaccgg catgggggtg gaatccacct ccttccgcaa cggcctgccg 420
cacgaagccg tcctggaaat ggatgtgctc accggtaccg gagacatcct cacctgttcg 480
ccgacccaga acaccgacct ctaccgcggc ttccccaact cctacggttc cctgggatac 540
agcgtgcggc tgaaggtgcg gtgcgaacgg gtggaaccct acgtcgacct gcggcatgta 600
cgcttcgatg acgttcagtc gctcaccgac gccctcgaca acatcgtcgt ggacaaggag 660
tacgagggtg aacgggtcga ctatctcgac ggtgtggtct tcagcctgga ggagagctac 720
ctcgtcctgg gacgggcgac cagcgaggcc ggccccgtta gcgactacac ccgcgagcgc 780
agttactacc gttctctgca gcatccgtcg ggggtcctgc gcgacaagtt gaccatccgc 840
gactacctct ggcggtggga cgtcgactgg ttctggtgca accgggcctt cggtacccag 900
aaccccacca tccgtactct gtggccgcgg gatctcctgc ggtcgagctt ctactggaag 960
atcatcggct gggaccgacg cttcgacatc gcggaccgga tcgaggcaca caacgggcgc 1020
cccgcacgcg agcgcgtcgt ccaggacatc gaggtcaccc ccgacaacct gccggagttc 1080
ctcacgtggt tcttcaccca ctgcgagatc gagccggtgt ggctgtgccc cattcgactg 1140
gccgacgact cgggcgagcg gacaccgtgg cccctgtacc cgctgtcacc cggcgacacc 1200
tgggtcaacg tgggattctg gagctcggtg cccgccgacc tgatggggaa ggacgccccg 1260
accggagcct tcaaccggga ggtggagaga gtcgtctcgg acctcggcgg acacaagtcg 1320
ttgtactccg aggcattcta ttctgaggaa cagttcgccg ccctctacgg cggtgaacgt 1380
cccgcacaac tcaaggcggt cttcgacccg gatgaccggt tccccgggtt gtacgagaag 1440
accgtgggcg gcgtctga 1458

<210> SEQ ID NO 18
<211> LENGTH: 485
<212> TYPE: PRT
<213> ORGANISM: Unknown
<220> FEATURE:
<223> OTHER INFORMATION: Corynebacterium glyciniphilium

<400> SEQUENCE: 18

Val Thr Val Ala Gly Arg Ile Thr Asp Ala Val Arg Ile Gly Asn Gly
1 5 10 15

Leu Asp Gln Arg Asp Leu Ala Pro Val Gly Trp Tyr Ala His Glu Gln
20 25 30

Ala Val Ala Arg Leu Lys Ala Ser Phe Asp Ala Val Pro Ala Gly Arg
35 40 45

Arg Val Arg Leu Ala Lys Lys Thr Ser Asn Leu Phe Arg Gly Arg Ser
50 55 60

Gly Glu Ala Val Gly Leu Asp Val Ser Gly Leu His Gly Val Ile Ala

-continued

```
65                  70                  75                  80

Val Asp Pro Val Glu Gly Thr Ala Asp Val Gln Gly Met Cys Thr Tyr
                85                  90                  95

Glu Asp Leu Val Asp Val Leu Leu Pro Tyr Gly Leu Ala Pro Thr Val
            100                 105                 110

Val Pro Gln Leu Lys Thr Ile Thr Leu Gly Gly Ala Val Thr Gly Met
        115                 120                 125

Gly Val Glu Ser Thr Ser Phe Arg Asn Gly Leu Pro His Glu Ala Val
    130                 135                 140

Leu Glu Met Asp Val Leu Thr Gly Thr Gly Asp Ile Leu Thr Cys Ser
145                 150                 155                 160

Pro Thr Gln Asn Thr Asp Leu Tyr Arg Gly Phe Pro Asn Ser Tyr Gly
                165                 170                 175

Ser Leu Gly Tyr Ser Val Arg Leu Lys Val Arg Cys Glu Arg Val Glu
            180                 185                 190

Pro Tyr Val Asp Leu Arg His Val Arg Phe Asp Asp Val Gln Ser Leu
        195                 200                 205

Thr Asp Ala Leu Asp Asn Ile Val Val Asp Lys Glu Tyr Glu Gly Glu
    210                 215                 220

Arg Val Asp Tyr Leu Asp Gly Val Val Phe Ser Leu Glu Glu Ser Tyr
225                 230                 235                 240

Leu Val Leu Gly Arg Ala Thr Ser Glu Ala Gly Pro Val Ser Asp Tyr
                245                 250                 255

Thr Arg Glu Arg Ser Tyr Tyr Arg Ser Leu Gln His Pro Ser Gly Val
            260                 265                 270

Leu Arg Asp Lys Leu Thr Ile Arg Asp Tyr Leu Trp Arg Trp Asp Val
        275                 280                 285

Asp Trp Phe Trp Cys Asn Arg Ala Phe Gly Thr Gln Asn Pro Thr Ile
    290                 295                 300

Arg Thr Leu Trp Pro Arg Asp Leu Leu Arg Ser Ser Phe Tyr Trp Lys
305                 310                 315                 320

Ile Ile Gly Trp Asp Arg Arg Phe Asp Ile Ala Asp Arg Ile Glu Ala
                325                 330                 335

His Asn Gly Arg Pro Ala Arg Glu Arg Val Val Gln Asp Ile Glu Val
            340                 345                 350

Thr Pro Asp Asn Leu Pro Glu Phe Leu Thr Trp Phe Phe Thr His Cys
        355                 360                 365

Glu Ile Glu Pro Val Trp Leu Cys Pro Ile Arg Leu Ala Asp Asp Ser
    370                 375                 380

Gly Glu Arg Thr Pro Trp Pro Leu Tyr Pro Leu Ser Pro Gly Asp Thr
385                 390                 395                 400

Trp Val Asn Val Gly Phe Trp Ser Ser Val Pro Ala Asp Leu Met Gly
                405                 410                 415

Lys Asp Ala Pro Thr Gly Ala Phe Asn Arg Glu Val Glu Arg Val Val
            420                 425                 430

Ser Asp Leu Gly Gly His Lys Ser Leu Tyr Ser Glu Ala Phe Tyr Ser
        435                 440                 445

Glu Glu Gln Phe Ala Ala Leu Tyr Gly Gly Glu Arg Pro Ala Gln Leu
    450                 455                 460

Lys Ala Val Phe Asp Pro Asp Asp Arg Phe Pro Gly Leu Tyr Glu Lys
465                 470                 475                 480

Thr Val Gly Gly Val
                485
```

<210> SEQ ID NO 19
<211> LENGTH: 1368
<212> TYPE: DNA
<213> ORGANISM: Unknown
<220> FEATURE:
<223> OTHER INFORMATION: Corynebacterium glyciniphilium

<400> SEQUENCE: 19
atgagcaggg gattcacgcc gctgacggtg ggacagatcg tggacaaggt catcacaccg 60
ccggcaccgt tccgggtgac cgctttcgac ggatccaccg cggggccggc agacgcggaa 120
ctggcactgg agatcacatc gccggacgcc ctggcctata tcgtgaccgc gccgggcgac 180
ctcggactgg cacgcgccta catcaccgga agcctccgcg tcaccggtga cgagcccggc 240
cacccgtacc tcgtctttga ccacctccag cacctttacg accagatccg acgcccctcg 300
gcgaaggacc tgctggatat cgcccgctcg ctgaaggcca tgggggcgat caaggtgcag 360
ccggcaccgg agcaggagac cctcccgggc tggaagaggg ccatactcga ggggctgtcc 420
cggcactctc cggaacggga caaggaggtc gtgagccgcc actacgacgt gggcaatgac 480
ttctacgagc tcttcctcgg cgattccatg gcctacacct gtgcctacta tcccgagttt 540
gacggtgaga accaggtcac cggtcccacc ggcgggtggc ggtacgacga ctgggagaaa 600
gggccgaccg ccaacgggcc gttgacccag gcgcaggaca acaagcatcg cctggtcttc 660
gacaagctgc gactcaaccc gggtgaccgg ttgttggacg tcggctgcgg gtggggcggt 720
atggtgcggt acgccgcccg ccacggcgtg aaggccatcg gtgtcacgct gtcccgagag 780
cagtacgagt ggggtaaggc gaagatcgag gaggagggtc tgcaggacct cgccgaggtc 840
cggtgtatgg actaccgtga cgtgccggag tccgacttcg acgcggtcag tgccatcggc 900
atcctcgagc acatcggcgt gcccaactac gaggactact tcacccgcct gttcgccaag 960
ctgcgcccgg gcggtcggat gctgaaccac tgcatcaccc gtccgcacaa ccggaagacg 1020
aagaccggcc agttcatcga ccgctacatc ttccccgacg gtgagctgac cggctcgggc 1080
cggatcatca cgatcatgca ggacaccgga ttcgacgtcg tccacgagga gaatctgcga 1140
ccgcactacc agcgcacgtt gcatgactgg tgtgaactgt tggccaccaa ctgggaccag 1200
gccgtccatc tcgtgggcga ggagacggct cgtctgttcg gcctgtacat ggcggggtcg 1260
gaatggggtt tcgaacacaa cgtgatccag ctccaccagg ttctcggcgt gaagccggac 1320
gcggcaggca gttccggggt gccggtccgc cagtggtgga ggtcctga 1368

<210> SEQ ID NO 20
<211> LENGTH: 455
<212> TYPE: PRT
<213> ORGANISM: Unknown
<220> FEATURE:
<223> OTHER INFORMATION: Corynebacterium glyciniphilium

<400> SEQUENCE: 20

Met Ser Arg Gly Phe Thr Pro Leu Thr Val Gly Gln Ile Val Asp Lys
1 5 10 15

Val Ile Thr Pro Pro Ala Pro Phe Arg Val Thr Ala Phe Asp Gly Ser
20 25 30

Thr Ala Gly Pro Ala Asp Ala Glu Leu Ala Leu Glu Ile Thr Ser Pro
35 40 45

Asp Ala Leu Ala Tyr Ile Val Thr Ala Pro Gly Asp Leu Gly Leu Ala
50 55 60

-continued

```
Arg Ala Tyr Ile Thr Gly Ser Leu Arg Val Thr Gly Asp Glu Pro Gly
65                  70                  75                  80

His Pro Tyr Leu Val Phe Asp His Leu Gln His Leu Tyr Asp Gln Ile
                85                  90                  95

Arg Arg Pro Ser Ala Lys Asp Leu Leu Asp Ile Ala Arg Ser Leu Lys
            100                 105                 110

Ala Met Gly Ala Ile Lys Val Gln Pro Ala Pro Glu Gln Glu Thr Leu
        115                 120                 125

Pro Gly Trp Lys Arg Ala Ile Leu Glu Gly Leu Ser Arg His Ser Pro
    130                 135                 140

Glu Arg Asp Lys Glu Val Val Ser Arg His Tyr Asp Val Gly Asn Asp
145                 150                 155                 160

Phe Tyr Glu Leu Phe Leu Gly Asp Ser Met Ala Tyr Thr Cys Ala Tyr
                165                 170                 175

Tyr Pro Glu Phe Asp Gly Glu Asn Gln Val Thr Gly Pro Thr Gly Gly
            180                 185                 190

Trp Arg Tyr Asp Asp Trp Glu Lys Gly Pro Thr Ala Asn Gly Pro Leu
        195                 200                 205

Thr Gln Ala Gln Asp Asn Lys His Arg Leu Val Phe Asp Lys Leu Arg
    210                 215                 220

Leu Asn Pro Gly Asp Arg Leu Leu Asp Val Gly Cys Gly Trp Gly Gly
225                 230                 235                 240

Met Val Arg Tyr Ala Ala Arg His Gly Val Lys Ala Ile Gly Val Thr
                245                 250                 255

Leu Ser Arg Glu Gln Tyr Glu Trp Gly Lys Ala Lys Ile Glu Glu Glu
            260                 265                 270

Gly Leu Gln Asp Leu Ala Glu Val Arg Cys Met Asp Tyr Arg Asp Val
        275                 280                 285

Pro Glu Ser Asp Phe Asp Ala Val Ser Ala Ile Gly Ile Leu Glu His
    290                 295                 300

Ile Gly Val Pro Asn Tyr Glu Asp Tyr Phe Thr Arg Leu Phe Ala Lys
305                 310                 315                 320

Leu Arg Pro Gly Gly Arg Met Leu Asn His Cys Ile Thr Arg Pro His
                325                 330                 335

Asn Arg Lys Thr Lys Thr Gly Gln Phe Ile Asp Arg Tyr Ile Phe Pro
            340                 345                 350

Asp Gly Glu Leu Thr Gly Ser Gly Arg Ile Ile Thr Ile Met Gln Asp
        355                 360                 365

Thr Gly Phe Asp Val Val His Glu Glu Asn Leu Arg Pro His Tyr Gln
    370                 375                 380

Arg Thr Leu His Asp Trp Cys Glu Leu Leu Ala Thr Asn Trp Asp Gln
385                 390                 395                 400

Ala Val His Leu Val Gly Glu Glu Thr Ala Arg Leu Phe Gly Leu Tyr
                405                 410                 415

Met Ala Gly Ser Glu Trp Gly Phe Glu His Asn Val Ile Gln Leu His
            420                 425                 430

Gln Val Leu Gly Val Lys Pro Asp Ala Ala Gly Ser Ser Gly Val Pro
        435                 440                 445

Val Arg Gln Trp Trp Arg Ser
    450                 455
```

<210> SEQ ID NO 21
<211> LENGTH: 588
<212> TYPE: DNA

<213> ORGANISM: Unknown
<220> FEATURE:
<223> OTHER INFORMATION: Corynebacterium glyciniphilium

<400> SEQUENCE: 21
gtggcggtgc tgtgcacacc gttgctgctc ggagcctgca ccatcggcga cgcgggaccg 60
ggggacgaga ccacggaccc tgtcgtggac actgaagcac cgcccgataa accggtgccg 120
gactctgcgg cggaatccgg cgctgaagac ggacctgatt ctgaggtgcc ggacgacccc 180
gaccagcctg atgctgagcc ggtggagact gatcccgacg ccccgggggc ccggggactg 240
gcgatcggtg actgcgtcgc cgacatggac cagctcgacg gcaccggcga catcgacgtc 300
gtcgactgcg ccggccccca tgccggcgag gtgtacgcac aggcggatat cgcaggtaag 360
aacctgttcc ccggcaacga gccgttgggg caggaggcgg gagcgatctg cgggggtgac 420
tccttcaccg gctatgtcgg catcggattc cccgagtcct cgctggacgt cgtcacgatg 480
atgccgtcca aggagagctg ggcgcaggag gaccggacgg tgacctgtgt ggtcaccgac 540
ccgaacctcg agcagatcgc cggcacgctc gagcagagct ggcgttag 588

<210> SEQ ID NO 22
<211> LENGTH: 195
<212> TYPE: PRT
<213> ORGANISM: Unknown
<220> FEATURE:
<223> OTHER INFORMATION: Corynebacterium glyciniphilium

<400> SEQUENCE: 22

Val Ala Val Leu Cys Thr Pro Leu Leu Leu Gly Ala Cys Thr Ile Gly
1 5 10 15

Asp Ala Gly Pro Gly Asp Glu Thr Thr Asp Pro Val Val Asp Thr Glu
20 25 30

Ala Pro Pro Asp Lys Pro Val Pro Asp Ser Ala Ala Glu Ser Gly Ala
35 40 45

Glu Asp Gly Pro Asp Ser Glu Val Pro Asp Asp Pro Asp Gln Pro Asp
50 55 60

Ala Glu Pro Val Glu Thr Asp Pro Asp Ala Pro Gly Ala Arg Gly Leu
65 70 75 80

Ala Ile Gly Asp Cys Val Ala Asp Met Asp Gln Leu Asp Gly Thr Gly
85 90 95

Asp Ile Asp Val Val Asp Cys Ala Gly Pro His Ala Gly Glu Val Tyr
100 105 110

Ala Gln Ala Asp Ile Ala Gly Lys Asn Leu Phe Pro Gly Asn Glu Pro
115 120 125

Leu Gly Gln Glu Ala Gly Ala Ile Cys Gly Gly Asp Ser Phe Thr Gly
130 135 140

Tyr Val Gly Ile Gly Phe Pro Glu Ser Ser Leu Asp Val Val Thr Met
145 150 155 160

Met Pro Ser Lys Glu Ser Trp Ala Gln Glu Asp Arg Thr Val Thr Cys
165 170 175

Val Val Thr Asp Pro Asn Leu Glu Gln Ile Ala Gly Thr Leu Glu Gln
180 185 190

Ser Trp Arg
195

<210> SEQ ID NO 23
<211> LENGTH: 1395
<212> TYPE: DNA

-continued

<213> ORGANISM: Unknown
<220> FEATURE:
<223> OTHER INFORMATION: Knoella aerolata

<400> SEQUENCE: 23
atgagcatgg accggaccgg accggccagg gtgcggaccg tgggggagcg gcggctgctc 60
gagagcttcg ccgccgtccc cccgggcgaa cgcgtgcggc tggccaagcg cacgtccaac 120
ctcttccgcg cccgggaggg cacctcgaca cgcgggctcg acacgagcgg actgaccggc 180
gtgcgcgtgg tcgacgcagg caccctcacg gccgacgtcg acggaatgtg cacgtacgag 240
gacctcgtcg ccgcaacgct gccgctcggg ctcgcgccgc tcgtcgtgcc ccagctgcgg 300
accatcaccg tcggcggggc ggtcaccggt ctcgggatcg agtcgacgtc gttccgcaac 360
gggttgccgc acgagtccgt cctcgagatg gacgtcctca cgggtgccgg cgagatcgtc 420
actgccacag cggacaacga gcacgccgac ctcttccgcg gcttccccaa ctcctacggg 480
tcgctgggct acgcgacgtg cctgcgcatc gagctcgagc gtgtgggtac ctgtgtggag 540
gtgaggcacg tccgcttcca cgacctcgac gccctgtgcg ccgccatcgc cgaggtcgtg 600
gcgacgagat cgcacgaggg cgaggaggtc gaccacgtgg acggggtggt cttctcccgc 660
gacgaggcgt acctcacgct gggtcgtcac tccgaccgga ccggaccgac cagcgactac 720
accgggcagc aggtctacta ccggtcgatc cagcacgacg gcccctctcc acggcgcgac 780
ctgctcacca ctcacgacta cctctggcgc tgggacaccg actggttctg gtgctcgcgc 840
gccttcgggg cccaggaccc gcgcgtccgg cggtggtggc cgcgccggtg gcgccggtcg 900
agcgtgtact ggaggctcgt ggcggcggac cggcgcgtcg ggttctcgga ccgcctcgag 960
gcacgtcggg gcaacccgcc gcgggagcgg gtggtccagg acgtcgagat cccgctcggg 1020
cagaccgcgg ccttcctcca ctggttcctc gacgaggtgc cgatcgaacc gatctggctg 1080
tgcccgttgc gtcttcgcga ccatcagagg tggccgctct atccgctcga gcccggacgc 1140
acctacgtca acgtggggtt ctggtcgacc gtgccggggc ccggaccggg cgaggagctg 1200
ggcgccacca accgcgccat cgagcgccgt gtcgacgagg tcggcggcca caagtccctg 1260
tactccgact cctactactc ccggtccgac ttcgacgccc tctacggcgg ggacgcgtat 1320
gccgtgctga aggccaccta cgacccggac gggcggttcc ctcacctcta cgacaaggcg 1380
gtgcgacacg catga 1395

<210> SEQ ID NO 24
<211> LENGTH: 464
<212> TYPE: PRT
<213> ORGANISM: Unknown
<220> FEATURE:
<223> OTHER INFORMATION: Knoella aerolata

<400> SEQUENCE: 24

Met Ser Met Asp Arg Thr Gly Pro Ala Arg Val Arg Thr Val Gly Glu
1 5 10 15

Arg Arg Leu Leu Glu Ser Phe Ala Ala Val Pro Pro Gly Glu Arg Val
20 25 30

Arg Leu Ala Lys Arg Thr Ser Asn Leu Phe Arg Ala Arg Glu Gly Thr
35 40 45

Ser Thr Arg Gly Leu Asp Thr Ser Gly Leu Thr Gly Val Arg Val Val
50 55 60

Asp Ala Gly Thr Leu Thr Ala Asp Val Asp Gly Met Cys Thr Tyr Glu
65 70 75 80

-continued

```
Asp Leu Val Ala Ala Thr Leu Pro Leu Gly Leu Ala Pro Leu Val Val
                85                  90                  95

Pro Gln Leu Arg Thr Ile Thr Val Gly Gly Ala Val Thr Gly Leu Gly
            100                 105                 110

Ile Glu Ser Thr Ser Phe Arg Asn Gly Leu Pro His Glu Ser Val Leu
        115                 120                 125

Glu Met Asp Val Leu Thr Gly Ala Gly Glu Ile Val Thr Ala Thr Ala
    130                 135                 140

Asp Asn Glu His Ala Asp Leu Phe Arg Gly Phe Pro Asn Ser Tyr Gly
145                 150                 155                 160

Ser Leu Gly Tyr Ala Thr Cys Leu Arg Ile Glu Leu Glu Arg Val Gly
                165                 170                 175

Thr Cys Val Glu Val Arg His Val Arg Phe His Asp Leu Asp Ala Leu
            180                 185                 190

Cys Ala Ala Ile Ala Glu Val Val Ala Thr Arg Ser His Glu Gly Glu
        195                 200                 205

Glu Val Asp His Val Asp Gly Val Val Phe Ser Arg Asp Glu Ala Tyr
    210                 215                 220

Leu Thr Leu Gly Arg His Ser Asp Arg Thr Gly Pro Thr Ser Asp Tyr
225                 230                 235                 240

Thr Gly Gln Gln Val Tyr Tyr Arg Ser Ile Gln His Asp Gly Pro Ser
                245                 250                 255

Pro Arg Arg Asp Leu Leu Thr Thr His Asp Tyr Leu Trp Arg Trp Asp
            260                 265                 270

Thr Asp Trp Phe Trp Cys Ser Arg Ala Phe Gly Ala Gln Asp Pro Arg
        275                 280                 285

Val Arg Arg Trp Trp Pro Arg Arg Trp Arg Arg Ser Ser Val Tyr Trp
    290                 295                 300

Arg Leu Val Ala Ala Asp Arg Arg Val Gly Phe Ser Asp Arg Leu Glu
305                 310                 315                 320

Ala Arg Arg Gly Asn Pro Pro Arg Glu Arg Val Val Gln Asp Val Glu
                325                 330                 335

Ile Pro Leu Gly Gln Thr Ala Ala Phe Leu His Trp Phe Leu Asp Glu
            340                 345                 350

Val Pro Ile Glu Pro Ile Trp Leu Cys Pro Leu Arg Leu Arg Asp His
        355                 360                 365

Gln Arg Trp Pro Leu Tyr Pro Leu Glu Pro Gly Arg Thr Tyr Val Asn
    370                 375                 380

Val Gly Phe Trp Ser Thr Val Pro Gly Pro Gly Pro Gly Glu Glu Leu
385                 390                 395                 400

Gly Ala Thr Asn Arg Ala Ile Glu Arg Arg Val Asp Glu Val Gly Gly
                405                 410                 415

His Lys Ser Leu Tyr Ser Asp Ser Tyr Tyr Ser Arg Ser Asp Phe Asp
            420                 425                 430

Ala Leu Tyr Gly Gly Asp Ala Tyr Ala Val Leu Lys Ala Thr Tyr Asp
        435                 440                 445

Pro Asp Gly Arg Phe Pro His Leu Tyr Asp Lys Ala Val Arg His Ala
    450                 455                 460
```

<210> SEQ ID NO 25
<211> LENGTH: 1284
<212> TYPE: DNA
<213> ORGANISM: Unknown
<220> FEATURE:
<223> OTHER INFORMATION: Knoella aerolata

<400> SEQUENCE: 25
atgagccaca cgaccgatga gatccgcacg gtcgccgacc tcgtcgacga ggtggtcgtc 60
ggcccgctgc cggtgcgggt cacggcctac gacgggtcga agacggggcc ggacagcgcc 120
ccgcgaacca tccacatcgc caaccagcga gcggtcgcct acctcgccac cgcgcccggg 180
gacctcggca tggcccgcgc ctacaccacc ggtgacctcg tcgtcgaggg cgtgcacccg 240
ggcaacccct acgaggccct ggtcgacctc gaacgtgtgc acttccgccg cccggacccg 300
cggctgctcc tcgacctcgc gcgcatcgtc gggccacgca acctcgcgcc cccgcccccg 360
ccgccgcagg aggctgtgcc gaggtggcgg cgggtggccg agggcctgcg ccactcgtac 420
gggcgggaca gcgaggcgat ccgccaccac tacgacgtct ccaaccactt ctacgagcag 480
gtgctcggcc cgagcatgac ctacacctgc gcggtcttcc ccgaccacga caccgggctc 540
gacgaggcgc aggaggagaa gtaccgcctc gtcttcgaga agctcgcgct gcgtcccggt 600
gaccggttgc tcgacatcgg ctgcgggtgg ggcgggatgg tccggtacgc cgcacggcgg 660
ggggtgcgag cgctcggcgt gacactgtcc ggtgagcagg cggcgtgggc acaggtcgcc 720
atcgcccgcg aggggctggg ggagctcgcc gccgtccggc acgaggacta ccgccacgtc 780
gccgagaccg ggttcgacgc catctcctcg atcggcatca ccgagcacat cggggtgcgc 840
aactacccca cgtacttcga ctggatgctc caccacgtca agccgggagg gctcgtgctc 900
aaccactgca tcaccagacc cgagaaccgg gccaagagcg tcggccggtt catcgaccgc 960
tacatcttcc ccgacggcga gctcaccggg tccggccgga tcatcacgac catgcaggac 1020
aacggtttcg aggtcgtgca ctccgagaac ctgcgagagc actacgccct caccctggcg 1080
gcctggggcg agaacctcgt cgagcactgg gcctcctgcg tggccgacgt gggggagggg 1140
acggcgaagg tctggggcct ctacctcgcg ggctcgcgtc gtggcttcga gcgcaacgtc 1200
gtccagctgc accaggtgct ggccgcgagg ccggtgccgt cccgactccc gcaggtgccg 1260
ctgcgccagt ggtggacctc gtga 1284

<210> SEQ ID NO 26
<211> LENGTH: 427
<212> TYPE: PRT
<213> ORGANISM: Unknown
<220> FEATURE:
<223> OTHER INFORMATION: Knoella aerolata

<400> SEQUENCE: 26

Met Ser His Thr Thr Asp Glu Ile Arg Thr Val Ala Asp Leu Val Asp
1 5 10 15

Glu Val Val Val Gly Pro Leu Pro Val Arg Val Thr Ala Tyr Asp Gly
20 25 30

Ser Lys Thr Gly Pro Asp Ser Ala Pro Arg Thr Ile His Ile Ala Asn
35 40 45

Gln Arg Ala Val Ala Tyr Leu Ala Thr Ala Pro Gly Asp Leu Gly Met
50 55 60

Ala Arg Ala Tyr Thr Thr Gly Asp Leu Val Val Glu Gly Val His Pro
65 70 75 80

Gly Asn Pro Tyr Glu Ala Leu Val Asp Leu Glu Arg Val His Phe Arg
85 90 95

Arg Pro Asp Pro Arg Leu Leu Leu Asp Leu Ala Arg Ile Val Gly Pro
100 105 110

Arg Asn Leu Ala Pro Pro Pro Pro Pro Pro Gln Glu Ala Val Pro Arg

```
        115                 120                 125

Trp Arg Arg Val Ala Glu Gly Leu Arg His Ser Tyr Gly Arg Asp Ser
    130                 135                 140

Glu Ala Ile Arg His His Tyr Asp Val Ser Asn His Phe Tyr Glu Gln
145                 150                 155                 160

Val Leu Gly Pro Ser Met Thr Tyr Thr Cys Ala Val Phe Pro Asp His
                165                 170                 175

Asp Thr Gly Leu Asp Glu Ala Gln Glu Glu Lys Tyr Arg Leu Val Phe
            180                 185                 190

Glu Lys Leu Ala Leu Arg Pro Gly Asp Arg Leu Leu Asp Ile Gly Cys
        195                 200                 205

Gly Trp Gly Gly Met Val Arg Tyr Ala Ala Arg Arg Gly Val Arg Ala
    210                 215                 220

Leu Gly Val Thr Leu Ser Gly Glu Gln Ala Ala Trp Ala Gln Val Ala
225                 230                 235                 240

Ile Ala Arg Glu Gly Leu Gly Glu Leu Ala Ala Val Arg His Glu Asp
                245                 250                 255

Tyr Arg His Val Ala Glu Thr Gly Phe Asp Ala Ile Ser Ser Ile Gly
            260                 265                 270

Ile Thr Glu His Ile Gly Val Arg Asn Tyr Pro Thr Tyr Phe Asp Trp
        275                 280                 285

Met Leu His His Val Lys Pro Gly Gly Leu Val Leu Asn His Cys Ile
    290                 295                 300

Thr Arg Pro Glu Asn Arg Ala Lys Ser Val Gly Arg Phe Ile Asp Arg
305                 310                 315                 320

Tyr Ile Phe Pro Asp Gly Glu Leu Thr Gly Ser Gly Arg Ile Ile Thr
                325                 330                 335

Thr Met Gln Asp Asn Gly Phe Glu Val Val His Ser Glu Asn Leu Arg
            340                 345                 350

Glu His Tyr Ala Leu Thr Leu Ala Ala Trp Gly Glu Asn Leu Val Glu
        355                 360                 365

His Trp Ala Ser Cys Val Ala Asp Val Gly Glu Gly Thr Ala Lys Val
    370                 375                 380

Trp Gly Leu Tyr Leu Ala Gly Ser Arg Arg Gly Phe Glu Arg Asn Val
385                 390                 395                 400

Val Gln Leu His Gln Val Leu Ala Ala Arg Pro Val Pro Ser Arg Leu
                405                 410                 415

Pro Gln Val Pro Leu Arg Gln Trp Trp Thr Ser
            420                 425
```

<210> SEQ ID NO 27
<211> LENGTH: 1392
<212> TYPE: DNA
<213> ORGANISM: Mycobacterium austroafricanum

<400> SEQUENCE: 27

```
gtgtctgttc cttcgaccga cgcacgttct gctcacgccg acggcgtgca gcggcttctc      60

gccagctatc gggcgattcc ccaagacgcc acggtccggc tggccaaacc cacgtcgaac     120

ctcttccgtg cccgcgcgaa aaccaggacc aagggtctgg acacgtctgg gttgacgaac     180

gtgatcgcgg tcgacgcgga ggcacgcacc gccgatgtgg cagggatgtg cacctacgaa     240

gacctggtcg cggccacgct gccgcatgga ctttcgccgc tggtggtgcc gcagttgaag     300

acgatcaccc tcggcggggc ggtcaccgga ctcgggatcg agtccgcctc gttccgcaac     360
```

```
ggcctgccac acgaatcggt tctcgagatg gacgtcctca ccggcaccgg tgatgtcgtg    420

cgcgcctccc ccgacgagaa ccctgacctg tttcgggcgt ttccgaattc ctatggcacg    480

ttgggctatt cggttcggct caagatcgag ctggaaccgg tgaagccgtt cgtcgcgctg    540

cgccacctcc gtttccattc gctgtcggct ctcatcgagg cgatggaccg catcgtcgaa    600

accggcggcc tcaacggcga accggtggac tacctcgacg gcgtcgtgtt cagtgccgag    660

gagagttacc tgtgcgtggg gcagcgctcc gcgacaccgg gcccggtcag cgactacacg    720

ggcaagcaga tctactaccg ctcgattcag cacgacggcc cgaccgatgg cgccgagaag    780

cacgaccggc tgaccatcca cgactacctg tggcgctggg acaccgactg gttctggtgc    840

tcaagggcat tcggcgcgca gaacccgcgg atccggcgct ggtggccgcg ccggtaccgg    900

cgcagcagtg tgtactggaa gctgatcggc tacgaccggc gtttcggtat cgccgatcgc    960

atcgagaagc gcaacggccg acccccgcgc gagcgggtgg tccaggacat cgaggtgccc   1020

atcgagcgga ccgtcgagtt tctgcagtgg tttctcgaca ccgtgcccat cgaaccgatc   1080

tggttgtgcc cgttgcggct ccgcgacgac cgcgattggc ccctgtatcc gatccgaccc   1140

caccacacct acgtcaacgt gggtttctgg tcgtcggtgc cggtgggccc ggaggagggc   1200

tacaccaaca ggatgatcga acggaaagtc agcgacctcg acggtcacaa atcgctgtat   1260

tccgatgcgt actactcgcc ggaagagttt gattcgctct atggcgggga gacgtacaag   1320

acggtgaaga agacatacga cccagactct cgtttcctgg acctgtacgg caaagcagtg   1380

gggcggcaat ga                                                       1392


<210> SEQ ID NO 28
<211> LENGTH: 463
<212> TYPE: PRT
<213> ORGANISM: Mycobacterium austroafricanum

<400> SEQUENCE: 28

Val Ser Val Pro Ser Thr Asp Ala Arg Ser Ala His Ala Asp Gly Val
1               5                   10                  15

Gln Arg Leu Leu Ala Ser Tyr Arg Ala Ile Pro Gln Asp Ala Thr Val
            20                  25                  30

Arg Leu Ala Lys Pro Thr Ser Asn Leu Phe Arg Ala Arg Ala Lys Thr
        35                  40                  45

Arg Thr Lys Gly Leu Asp Thr Ser Gly Leu Thr Asn Val Ile Ala Val
    50                  55                  60

Asp Ala Glu Ala Arg Thr Ala Asp Val Ala Gly Met Cys Thr Tyr Glu
65                  70                  75                  80

Asp Leu Val Ala Ala Thr Leu Pro His Gly Leu Ser Pro Leu Val Val
                85                  90                  95

Pro Gln Leu Lys Thr Ile Thr Leu Gly Gly Ala Val Thr Gly Leu Gly
            100                 105                 110

Ile Glu Ser Ala Ser Phe Arg Asn Gly Leu Pro His Glu Ser Val Leu
        115                 120                 125

Glu Met Asp Val Leu Thr Gly Thr Gly Asp Val Val Arg Ala Ser Pro
    130                 135                 140

Asp Glu Asn Pro Asp Leu Phe Arg Ala Phe Pro Asn Ser Tyr Gly Thr
145                 150                 155                 160

Leu Gly Tyr Ser Val Arg Leu Lys Ile Glu Leu Glu Pro Val Lys Pro
                165                 170                 175

Phe Val Ala Leu Arg His Leu Arg Phe His Ser Leu Ser Ala Leu Ile
            180                 185                 190
```

```
Glu Ala Met Asp Arg Ile Val Glu Thr Gly Gly Leu Asn Gly Glu Pro
        195                 200                 205

Val Asp Tyr Leu Asp Gly Val Val Phe Ser Ala Glu Glu Ser Tyr Leu
    210                 215                 220

Cys Val Gly Gln Arg Ser Ala Thr Pro Gly Pro Val Ser Asp Tyr Thr
225                 230                 235                 240

Gly Lys Gln Ile Tyr Tyr Arg Ser Ile Gln His Asp Gly Pro Thr Asp
                245                 250                 255

Gly Ala Glu Lys His Asp Arg Leu Thr Ile His Asp Tyr Leu Trp Arg
            260                 265                 270

Trp Asp Thr Asp Trp Phe Trp Cys Ser Arg Ala Phe Gly Ala Gln Asn
        275                 280                 285

Pro Arg Ile Arg Arg Trp Trp Pro Arg Arg Tyr Arg Arg Ser Ser Val
    290                 295                 300

Tyr Trp Lys Leu Ile Gly Tyr Asp Arg Arg Phe Gly Ile Ala Asp Arg
305                 310                 315                 320

Ile Glu Lys Arg Asn Gly Arg Pro Pro Arg Glu Arg Val Val Gln Asp
                325                 330                 335

Ile Glu Val Pro Ile Glu Arg Thr Val Glu Phe Leu Gln Trp Phe Leu
            340                 345                 350

Asp Thr Val Pro Ile Glu Pro Ile Trp Leu Cys Pro Leu Arg Leu Arg
        355                 360                 365

Asp Asp Arg Asp Trp Pro Leu Tyr Pro Ile Arg Pro His His Thr Tyr
    370                 375                 380

Val Asn Val Gly Phe Trp Ser Ser Val Pro Val Gly Pro Glu Glu Gly
385                 390                 395                 400

Tyr Thr Asn Arg Met Ile Glu Arg Lys Val Ser Asp Leu Asp Gly His
                405                 410                 415

Lys Ser Leu Tyr Ser Asp Ala Tyr Tyr Ser Pro Glu Glu Phe Asp Ser
            420                 425                 430

Leu Tyr Gly Gly Glu Thr Tyr Lys Thr Val Lys Lys Thr Tyr Asp Pro
        435                 440                 445

Asp Ser Arg Phe Leu Asp Leu Tyr Gly Lys Ala Val Gly Arg Gln
    450                 455                 460
```

<210> SEQ ID NO 29
<211> LENGTH: 1323
<212> TYPE: DNA
<213> ORGANISM: Mycobacterium austroafricanum

<400> SEQUENCE: 29

```
ttgacgacat ttcgggacgg cgcggccgac accggcctgc acggagaccg caagctcacc     60

ctggcggagg tcttggaggt cttcgcctcg ggccgactgc ctctgaagtt cacggcgtac    120

gacggcagca gcgcgggccc ggacgacgcc acgctcgggc tggacctgct gaccccccgc    180

gggaccacgt acctcgcaac ggctcccggc gatctcggcc tggcccgggc ctacgtctcc    240

ggtgacctgc agttgcaggg ggtgcaccct ggcgacccgt acgacctgct caacgcactg    300

gtgcagaaac tggacttcaa gcgaccgtcc gcccgggtgc tggcgcaggt cgtccgatcg    360

atcgggatcg agcacctgaa accgatcgcg ccaccgccgc aggaggcgct gccgcggtgg    420

cggcgcatcg cagaaggact gcggcacagc aagacccgtg acgccgacgc gatccaccac    480

cattacgatg tctccaacac cttctacgag tgggtgctcg ggccgtcgat gacctacacc    540

tgcgcctgct acccgcatcc cgacgccacc ctcgaggagg cgcaggagaa caaatatcgg    600
```

-continued

```
ctggtgttcg agaaactgcg cctcaagccg ggcgaccgcc ttctcgacgt gggttgcggg    660

tggggcggaa tggtgcgcta cgcggcccgt cacggcgtca aggcgatcgg ggtgacgctg    720

tccagggagc aggcgcagtg ggcacgcgcc gccatcgaac gggacggcct gggtgacctc    780

gccgaggtcc gccacagcga ctaccgcgat gtgcgcgagt cccagttcga cgccgtgtct    840

tcgctggggc tcaccgagca catcggggtc gccaactatc cgtcgtactt ccggttcctc    900

aagtcgaagt tgcgcccggg cggcctactg ctcaaccact gcatcacccg gcacaacaat    960

cgcaccggcc ccgccgccgg gggattcatc gaccggtatg tgttcccgga cggggagctg   1020

accggatcgg gccggatcat caccgagatc caggacgtcg gtttggaggt gatgcacgaa   1080

gagaacctgc gccggcacta tgcgctgaca cttcgggact ggtgccggaa tctggtgcag   1140

cactgggacg aagcggtcgc agaggtcggc ctgcccaccg ccaaggtgtg ggtctgtac    1200

atggctgcct cgcgggtcgg cttcgagcag aacagcattc agctgcatca ggtactggcg   1260

gtgaagctcg acgaacgtgg cggggacggc ggtttgccgt tgcggccctg gtggaccgcg   1320

tag                                                                 1323
```

<210> SEQ ID NO 30
<211> LENGTH: 440
<212> TYPE: PRT
<213> ORGANISM: Mycobacterium austroafricanum

<400> SEQUENCE: 30

```
Leu Thr Thr Phe Arg Asp Gly Ala Ala Asp Thr Gly Leu His Gly Asp
1               5                   10                  15

Arg Lys Leu Thr Leu Ala Glu Val Leu Glu Val Phe Ala Ser Gly Arg
            20                  25                  30

Leu Pro Leu Lys Phe Thr Ala Tyr Asp Gly Ser Ser Ala Gly Pro Asp
        35                  40                  45

Asp Ala Thr Leu Gly Leu Asp Leu Leu Thr Pro Arg Gly Thr Thr Tyr
    50                  55                  60

Leu Ala Thr Ala Pro Gly Asp Leu Gly Leu Ala Arg Ala Tyr Val Ser
65                  70                  75                  80

Gly Asp Leu Gln Leu Gln Gly Val His Pro Gly Asp Pro Tyr Asp Leu
                85                  90                  95

Leu Asn Ala Leu Val Gln Lys Leu Asp Phe Lys Arg Pro Ser Ala Arg
            100                 105                 110

Val Leu Ala Gln Val Val Arg Ser Ile Gly Ile Glu His Leu Lys Pro
        115                 120                 125

Ile Ala Pro Pro Pro Gln Glu Ala Leu Pro Arg Trp Arg Arg Ile Ala
    130                 135                 140

Glu Gly Leu Arg His Ser Lys Thr Arg Asp Ala Asp Ala Ile His His
145                 150                 155                 160

His Tyr Asp Val Ser Asn Thr Phe Tyr Glu Trp Val Leu Gly Pro Ser
                165                 170                 175

Met Thr Tyr Thr Cys Ala Cys Tyr Pro His Pro Asp Ala Thr Leu Glu
            180                 185                 190

Glu Ala Gln Glu Asn Lys Tyr Arg Leu Val Phe Glu Lys Leu Arg Leu
        195                 200                 205

Lys Pro Gly Asp Arg Leu Leu Asp Val Gly Cys Gly Trp Gly Gly Met
    210                 215                 220

Val Arg Tyr Ala Ala Arg His Gly Val Lys Ala Ile Gly Val Thr Leu
225                 230                 235                 240
```

```
Ser Arg Glu Gln Ala Gln Trp Ala Arg Ala Ala Ile Glu Arg Asp Gly
                245                 250                 255

Leu Gly Asp Leu Ala Glu Val Arg His Ser Asp Tyr Arg Asp Val Arg
            260                 265                 270

Glu Ser Gln Phe Asp Ala Val Ser Ser Leu Gly Leu Thr Glu His Ile
        275                 280                 285

Gly Val Ala Asn Tyr Pro Ser Tyr Phe Arg Phe Leu Lys Ser Lys Leu
    290                 295                 300

Arg Pro Gly Gly Leu Leu Leu Asn His Cys Ile Thr Arg His Asn Asn
305                 310                 315                 320

Arg Thr Gly Pro Ala Ala Gly Gly Phe Ile Asp Arg Tyr Val Phe Pro
                325                 330                 335

Asp Gly Glu Leu Thr Gly Ser Gly Arg Ile Ile Thr Glu Ile Gln Asp
            340                 345                 350

Val Gly Leu Glu Val Met His Glu Glu Asn Leu Arg Arg His Tyr Ala
        355                 360                 365

Leu Thr Leu Arg Asp Trp Cys Arg Asn Leu Val Gln His Trp Asp Glu
    370                 375                 380

Ala Val Ala Glu Val Gly Leu Pro Thr Ala Lys Val Trp Gly Leu Tyr
385                 390                 395                 400

Met Ala Ala Ser Arg Val Gly Phe Glu Gln Asn Ser Ile Gln Leu His
                405                 410                 415

Gln Val Leu Ala Val Lys Leu Asp Glu Arg Gly Gly Asp Gly Gly Leu
            420                 425                 430

Pro Leu Arg Pro Trp Trp Thr Ala
        435                 440
```

<210> SEQ ID NO 31
<211> LENGTH: 381
<212> TYPE: DNA
<213> ORGANISM: Mycobacterium austroafricanum

<400> SEQUENCE: 31

```
gtgatccgct ttctgctgcg cgtcgcggtc tttctcggat cgtcggcgat cgggctactg      60

gtggccggct ggctggtgcc gggggtgtcg ctgtcggtgc tgggcttcgt caccgcggtg     120

gtgatcttca cggtggcaca agggattctg tcgccgttct tcctgaagat ggccagccgc     180

tacgcgtcgg ccttcctcgg cggcatcggc ctggtgtcca cgttcgtggc gctgctgctc     240

gcgtcgctgc tgtccaacgg gctcagcatc cgcggcgtcg ggtcgtggat cgcggccacg     300

gtggtggtct ggctggtcac agccctggcg accgtcgtgc tgcccgttct ggtgctgcgg     360

gagaagaaga aagcagcctg a                                                381
```

<210> SEQ ID NO 32
<211> LENGTH: 126
<212> TYPE: PRT
<213> ORGANISM: Mycobacterium austroafricanum

<400> SEQUENCE: 32

```
Val Ile Arg Phe Leu Leu Arg Val Ala Val Phe Leu Gly Ser Ser Ala
1               5                   10                  15

Ile Gly Leu Leu Val Ala Gly Trp Leu Val Pro Gly Val Ser Leu Ser
            20                  25                  30

Val Leu Gly Phe Val Thr Ala Val Val Ile Phe Thr Val Ala Gln Gly
        35                  40                  45
```

```
Ile Leu Ser Pro Phe Phe Leu Lys Met Ala Ser Arg Tyr Ala Ser Ala
    50                  55                  60

Phe Leu Gly Gly Ile Gly Leu Val Ser Thr Phe Val Ala Leu Leu Leu
65                  70                  75                  80

Ala Ser Leu Leu Ser Asn Gly Leu Ser Ile Arg Gly Val Gly Ser Trp
                85                  90                  95

Ile Ala Ala Thr Val Val Val Trp Leu Val Thr Ala Leu Ala Thr Val
            100                 105                 110

Val Leu Pro Val Leu Val Leu Arg Glu Lys Lys Lys Ala Ala
        115                 120                 125
```

<210> SEQ ID NO 33
<211> LENGTH: 1392
<212> TYPE: DNA
<213> ORGANISM: Mycobacterium gilvum

<400> SEQUENCE: 33

```
gtgtctgttg ccgtaaccga cgcacgatcc gcctacgccc acggcgtgca gcggctggtc     60
gcgagttacc gcgccatccc cgccggcgcc accgtccgcc tggccaaacc cacgtccaac    120
ctgttccgcg ccagggcgaa gagcaccgcg gcgggcctcg acacctccgg cctgacacat    180
gtgatcgccg tggaccccga gacgcgcacc gccgaggtcg cggggatgtg cacctacgag    240
gacctggtgg cggcgacgct gccccacggg ctttcaccgc tggtggtccc gcaactcaag    300
acgatcaccc tcggcggcgc cgtcaccggg ctcggcatcg agtcggcgtc gttccgcaac    360
ggccttccgc acgaatcggt cctggagatg gacatcctca ccgggaccgg cgacatcgtg    420
cgcgccgcgc ccgacgagaa tcccgacctt ttccgcacct tcccgaattc ttatggaacg    480
ctgggttact cggttcggct gaagatcgag ctggagccgg tgaagccgtt cgtggcgtta    540
cgccatctcc gcttccactc actgtcgaca ctcatcgcga cgatggaccg catcgtcgac    600
accgggagtc tcgacggtga gcaggtcgac tatctcgacg gagtggtgtt cagcgccgag    660
gagagctacc tgtgcgtcgg aacacgttcc gcgacaccgg gtcctgtcag cgactacacc    720
ggcgagcaca tcttctaccg gtcgatccag cacgattgcc cgaccgaagg cggacagaag    780
cacgaccggc tgacggcgca cgactacttc tggcgctggg acaccgactg gttctggtgc    840
tcaagggcat tcggcgcgca gaacccgaag gtccgtcggt ggtggccccg acggctccgg    900
cgcagcagct tctactggaa gctcgtcggc tacgaccagc gtttcggcat cgccgaccgg    960
atcgagaaac accacggccg gccaccgcgc gaacgcgtcg tccaggacgt cgaggtcccc   1020
atcgagcgca ccgtcgaatt cctgcagtgg ttcctcgaca cgatcccgat agagccgctc   1080
tggttgtgcc cgttgcgact tcgcgatgac aacagctggt cgctgtaccc gctccggccc   1140
catcgcacgt atgtcaacgt gggattctgg tcgtcggtgc ccgtcgggcc ggaggagggt   1200
cacaccaaca agctgatcga acgcaggatc agcgagctgg agggacacaa gtcgctgtac   1260
tccgacgcct tctattcggc cgacgagttc gacgcgctgt acggcggcga gatctaccgg   1320
accgtgaaga agacctacga cccagattct cgtttcctcg acctctatgc gaaggcggtg   1380
cgacggcaat ga                                                       1392
```

<210> SEQ ID NO 34
<211> LENGTH: 463
<212> TYPE: PRT
<213> ORGANISM: Mycobacterium gilvum

<400> SEQUENCE: 34

-continued

```
Val Ser Val Ala Val Thr Asp Ala Arg Ser Ala Tyr Ala His Gly Val
1               5                   10                  15

Gln Arg Leu Val Ala Ser Tyr Arg Ala Ile Pro Ala Gly Ala Thr Val
            20                  25                  30

Arg Leu Ala Lys Pro Thr Ser Asn Leu Phe Arg Ala Arg Ala Lys Ser
        35                  40                  45

Thr Ala Ala Gly Leu Asp Thr Ser Gly Leu Thr His Val Ile Ala Val
    50                  55                  60

Asp Pro Glu Thr Arg Thr Ala Glu Val Ala Gly Met Cys Thr Tyr Glu
65                  70                  75                  80

Asp Leu Val Ala Ala Thr Leu Pro His Gly Leu Ser Pro Leu Val Val
                85                  90                  95

Pro Gln Leu Lys Thr Ile Thr Leu Gly Gly Ala Val Thr Gly Leu Gly
            100                 105                 110

Ile Glu Ser Ala Ser Phe Arg Asn Gly Leu Pro His Glu Ser Val Leu
        115                 120                 125

Glu Met Asp Ile Leu Thr Gly Thr Gly Asp Ile Val Arg Ala Ala Pro
    130                 135                 140

Asp Glu Asn Pro Asp Leu Phe Arg Thr Phe Pro Asn Ser Tyr Gly Thr
145                 150                 155                 160

Leu Gly Tyr Ser Val Arg Leu Lys Ile Glu Leu Glu Pro Val Lys Pro
                165                 170                 175

Phe Val Ala Leu Arg His Leu Arg Phe His Ser Leu Ser Thr Leu Ile
            180                 185                 190

Ala Thr Met Asp Arg Ile Val Asp Thr Gly Ser Leu Asp Gly Glu Gln
        195                 200                 205

Val Asp Tyr Leu Asp Gly Val Val Phe Ser Ala Glu Glu Ser Tyr Leu
    210                 215                 220

Cys Val Gly Thr Arg Ser Ala Thr Pro Gly Pro Val Ser Asp Tyr Thr
225                 230                 235                 240

Gly Glu His Ile Phe Tyr Arg Ser Ile Gln His Asp Cys Pro Thr Glu
                245                 250                 255

Gly Gly Gln Lys His Asp Arg Leu Thr Ala His Asp Tyr Phe Trp Arg
            260                 265                 270

Trp Asp Thr Asp Trp Phe Trp Cys Ser Arg Ala Phe Gly Ala Gln Asn
        275                 280                 285

Pro Lys Val Arg Arg Trp Trp Pro Arg Arg Leu Arg Arg Ser Ser Phe
    290                 295                 300

Tyr Trp Lys Leu Val Gly Tyr Asp Gln Arg Phe Gly Ile Ala Asp Arg
305                 310                 315                 320

Ile Glu Lys His His Gly Arg Pro Pro Arg Glu Arg Val Val Gln Asp
                325                 330                 335

Val Glu Val Pro Ile Glu Arg Thr Val Glu Phe Leu Gln Trp Phe Leu
            340                 345                 350

Asp Thr Ile Pro Ile Glu Pro Leu Trp Leu Cys Pro Leu Arg Leu Arg
        355                 360                 365

Asp Asp Asn Ser Trp Ser Leu Tyr Pro Leu Arg Pro His Arg Thr Tyr
    370                 375                 380

Val Asn Val Gly Phe Trp Ser Ser Val Pro Val Gly Pro Glu Glu Gly
385                 390                 395                 400

His Thr Asn Lys Leu Ile Glu Arg Arg Ile Ser Glu Leu Glu Gly His
                405                 410                 415

Lys Ser Leu Tyr Ser Asp Ala Phe Tyr Ser Ala Asp Glu Phe Asp Ala
```

```
            420                 425                 430

Leu Tyr Gly Gly Glu Ile Tyr Arg Thr Val Lys Lys Thr Tyr Asp Pro
        435                 440                 445

Asp Ser Arg Phe Leu Asp Leu Tyr Ala Lys Ala Val Arg Arg Gln
    450                 455                 460


<210> SEQ ID NO 35
<211> LENGTH: 1323
<212> TYPE: DNA
<213> ORGANISM: Mycobacterium gilvum

<400> SEQUENCE: 35

atgacgactt ttcgggaaca taccgacagt tcggcgtccg acccggatcg gaaactcact      60

ttggcagagg tgttggagat cttcgccgcg ggtcgccgtc cgctgaagtt caccgcctat     120

gacggaagta gttgcgggcc tgaggatgcg acactgggcc tcgacctgct gaccccgcgg     180

ggcacgacct acctggccac ggcgccgggt gatctcggcc tggcgcgggc ctacatcgcc     240

ggcgatctgc gcctcagtgg tgtgcatccc ggcgatcccc atgacctgct cacggcgctg     300

acggaacgcc tggagtacag gcgtccgccg gtgcgagtgc tggccaatgt tctgcgctcc     360

atcgggatcg agcacctcaa gcccgtcgcg ccgccacccc aggagcacct gccgcggtgg     420

cggcggatcg cagaggggtt gcggcacagc aagacccgtg acgctgaggc catccagcac     480

cactacgacg tctcgaacac gttctactca tgggtcctgg gtccgtcgat gacctacacc     540

tgcgcctgct atccacaccc ggatgccacg ctggaggagg cgcaggagaa caagtaccgg     600

ctggtgttcg agaagcttcg actcaagccc ggtgaccggc tgctcgacgt cggttgcggc     660

tggggcggaa tggtccgcta cgccgcccgg cacggggtca aggtcctggg ggtgacgctg     720

tcgaaggagc aggcgcagtg ggcggccgac gcagtcgagc gggacggcct gggtgagttg     780

gccgaggtcc gccacggcga ctaccgcgac gtgcgcgagt cgcacttcga cgcagtgtcc     840

tcgctcgggc tcaccgagca catcggcgtc gcgaactacc cgtcgtactt ccgcttcctg     900

aagtcgaaac tgcggccggg tggcctgctg ctcaaccact gcatcacccg aaacaacaac     960

cggagtcacg ccaccgcagg cggattcatc gatcgctatg tctttcccga cggggagctg    1020

acggggtcgg ggcgaatcat caccgaaatg caggacgtcg gactcgaggt cgtgcacgag    1080

gagaatctgc gtcaccacta cgcgctgacg ctgcgcgact ggagccgcaa cctggtcgcg    1140

cactgggacg acgcggtgac cgaggtcggt ctgccgactg ccaaggtgtg ggcctctac     1200

atcgccgcgt cgcgagtcgg cttcgagcag aacgccattc agctgcacca ggtgctgtcg    1260

gtcaagctcg acgagcgtgg ctcggacggc ggactgccgt tacgaccctg gtggaacgcc    1320

tag                                                                  1323


<210> SEQ ID NO 36
<211> LENGTH: 440
<212> TYPE: PRT
<213> ORGANISM: Mycobacterium gilvum

<400> SEQUENCE: 36

Met Thr Thr Phe Arg Glu His Thr Asp Ser Ser Ala Ser Asp Pro Asp
1               5                   10                  15

Arg Lys Leu Thr Leu Ala Glu Val Leu Glu Ile Phe Ala Ala Gly Arg
            20                  25                  30

Arg Pro Leu Lys Phe Thr Ala Tyr Asp Gly Ser Ser Cys Gly Pro Glu
        35                  40                  45
```

-continued

```
Asp Ala Thr Leu Gly Leu Asp Leu Leu Thr Pro Arg Gly Thr Thr Tyr
    50                  55                  60

Leu Ala Thr Ala Pro Gly Asp Leu Gly Leu Ala Arg Ala Tyr Ile Ala
65                  70                  75                  80

Gly Asp Leu Arg Leu Ser Gly Val His Pro Gly Asp Pro His Asp Leu
                85                  90                  95

Leu Thr Ala Leu Thr Glu Arg Leu Glu Tyr Arg Arg Pro Pro Val Arg
            100                 105                 110

Val Leu Ala Asn Val Leu Arg Ser Ile Gly Ile Glu His Leu Lys Pro
        115                 120                 125

Val Ala Pro Pro Pro Gln Glu His Leu Pro Arg Trp Arg Arg Ile Ala
    130                 135                 140

Glu Gly Leu Arg His Ser Lys Thr Arg Asp Ala Glu Ala Ile Gln His
145                 150                 155                 160

His Tyr Asp Val Ser Asn Thr Phe Tyr Ser Trp Val Leu Gly Pro Ser
                165                 170                 175

Met Thr Tyr Thr Cys Ala Cys Tyr Pro His Pro Asp Ala Thr Leu Glu
            180                 185                 190

Glu Ala Gln Glu Asn Lys Tyr Arg Leu Val Phe Glu Lys Leu Arg Leu
        195                 200                 205

Lys Pro Gly Asp Arg Leu Leu Asp Val Gly Cys Gly Trp Gly Gly Met
    210                 215                 220

Val Arg Tyr Ala Ala Arg His Gly Val Lys Val Leu Gly Val Thr Leu
225                 230                 235                 240

Ser Lys Glu Gln Ala Gln Trp Ala Ala Asp Ala Val Glu Arg Asp Gly
                245                 250                 255

Leu Gly Glu Leu Ala Glu Val Arg His Gly Asp Tyr Arg Asp Val Arg
            260                 265                 270

Glu Ser His Phe Asp Ala Val Ser Ser Leu Gly Leu Thr Glu His Ile
        275                 280                 285

Gly Val Ala Asn Tyr Pro Ser Tyr Phe Arg Phe Leu Lys Ser Lys Leu
    290                 295                 300

Arg Pro Gly Gly Leu Leu Leu Asn His Cys Ile Thr Arg Asn Asn Asn
305                 310                 315                 320

Arg Ser His Ala Thr Ala Gly Gly Phe Ile Asp Arg Tyr Val Phe Pro
                325                 330                 335

Asp Gly Glu Leu Thr Gly Ser Gly Arg Ile Ile Thr Glu Met Gln Asp
            340                 345                 350

Val Gly Leu Glu Val Val His Glu Glu Asn Leu Arg His His Tyr Ala
        355                 360                 365

Leu Thr Leu Arg Asp Trp Ser Arg Asn Leu Val Ala His Trp Asp Asp
    370                 375                 380

Ala Val Thr Glu Val Gly Leu Pro Thr Ala Lys Val Trp Gly Leu Tyr
385                 390                 395                 400

Ile Ala Ala Ser Arg Val Gly Phe Glu Gln Asn Ala Ile Gln Leu His
                405                 410                 415

Gln Val Leu Ser Val Lys Leu Asp Glu Arg Gly Ser Asp Gly Gly Leu
            420                 425                 430

Pro Leu Arg Pro Trp Trp Asn Ala
        435                 440
```

<210> SEQ ID NO 37
<211> LENGTH: 387
<212> TYPE: DNA

<213> ORGANISM: Mycobacterium gilvum

<400> SEQUENCE: 37
atgatccggt tcctgctgcg catcgcggtc tttctgggct catcagcgat cgggctcctc 60
gtcgccggat ggctggtgcc cggggtgtcg ctgtcggtgt ggggcttcgt cacggcagtg 120
gtgatcttca ccgtggcgca ggcgatcctg tccccgttct tcctcaagat ggccagccgc 180
tacgcctcgg cgttcctcgg cgggatcggt ctggtgtcga cgtttgccgc gctgctgctc 240
gtctcgctgc tgtccaacgg tctgagcatc cgcggcatcg gatcctggat cgccgcaacc 300
gtggtggtct ggttggtgac cgccctggcg acgctggtgc tgccgatgtt ggtgctgcgc 360
gagaagaaaa ccgcgtcgcg cgtctga 387

<210> SEQ ID NO 38
<211> LENGTH: 128
<212> TYPE: PRT
<213> ORGANISM: Mycobacterium gilvum

<400> SEQUENCE: 38

Met Ile Arg Phe Leu Leu Arg Ile Ala Val Phe Leu Gly Ser Ser Ala
1 5 10 15

Ile Gly Leu Leu Val Ala Gly Trp Leu Val Pro Gly Val Ser Leu Ser
20 25 30

Val Trp Gly Phe Val Thr Ala Val Val Ile Phe Thr Val Ala Gln Ala
35 40 45

Ile Leu Ser Pro Phe Phe Leu Lys Met Ala Ser Arg Tyr Ala Ser Ala
50 55 60

Phe Leu Gly Gly Ile Gly Leu Val Ser Thr Phe Ala Ala Leu Leu Leu
65 70 75 80

Val Ser Leu Leu Ser Asn Gly Leu Ser Ile Arg Gly Ile Gly Ser Trp
85 90 95

Ile Ala Ala Thr Val Val Val Trp Leu Val Thr Ala Leu Ala Thr Leu
100 105 110

Val Leu Pro Met Leu Val Leu Arg Glu Lys Lys Thr Ala Ser Arg Val
115 120 125

<210> SEQ ID NO 39
<211> LENGTH: 1425
<212> TYPE: DNA
<213> ORGANISM: Unknown
<220> FEATURE:
<223> OTHER INFORMATION: Mycobacterium indicus pranii

<400> SEQUENCE: 39
atgcacgggc tgttgtcgaa gactagggta tatgtggtgc ctgtccttgg atctgcactc 60
tcggcccaca agtcgggcgt tgaccggctg ctggcaagct atcgatccat tcccgcaacg 120
tccgcggtcc ggctggccaa accgacgtca aacctgttcc gcgcccgcac caaacgtgac 180
gcgcccggct tggacacctc ggggctgacc ggcgtcctga gcgtggatcc cgaaacccgc 240
accgcggacg tcgccggcat gtgcacctac gcggacctgg tggccgcaac gctgccctac 300
ggcctgtcgc cgctggtcgt cccgcagctg aagaccatca ccctcggcgg ggcggtcagc 360
ggcctgggga tcgagtcggc gtcgtttcgc aacgggctgc cgcacgaatc ggtgctggag 420
atggatatcc tcaccggcgc tggcgatttg ctcaccgcat cacgtaccca gcacccggac 480
ctgttccgcg ccttcccgaa ttcctatggg acactggggt attcgacccg gcttcggatc 540
gagctggaac ccgtcgcacc gttcgtcgcg ctgcgccaca tccgcttccg ctcgctgccc 600

-continued

```
gcgctgatcg ccgcggccga acgcatcgtc gacaccggcg ggcagggcgg aaccccggtc    660

gactacctcg acggggtggt cttcagcgcc gacgaaagct acctgtgcgt gggccggcgg    720

accaccaccc ccggcccggt cagcgactac accggcaagg acatctacta ccagtccatc    780

cggcacgacg ccccgggcct ggaggcgacc aaggatgacc ggctgaccat gcacgactac    840

ttctggcgct gggacaccga ttggttctgg tgctcgcgcg cgttcggcgt gcaggacccg    900

cgggtgcgac gcttctggcc gcgccgttat cggcgcagca gcttctactg gaagctgatt    960

tccctggacc ggcgcttcgg gatctccgac cgcatcgagg cgcgcaacgg gcggccccca   1020

cgcgaacggg tggtgcaaga catcgagatt ccaatcgaac ggacctgcga cttcctggag   1080

tggttcctgg acaacgtgcc aatcacgccg atctggttgt gcccgttgcg ccttcgcgac   1140

cgcgacggct ggccgttgta cccgatgcgg ccggatcaca cgtacgtcaa cgtcggcttc   1200

tggtcgtcgg tgccgggggg cgcgaccgag ggcgccgcca accggatgat cgaagaaaag   1260

gtgagcgaac tcgacgggca caagtccctg tactccgatt ccttctactc ccgcgaggac   1320

ttcgacgagc tgtacggcgg cgagacctac aacaccgtca agaaaaccta cgaccccgat   1380

tctcgtttac tcgacctcta cgcaaaggcg gtgcaacggc gatga                   1425
```

```
<210> SEQ ID NO 40
<211> LENGTH: 474
<212> TYPE: PRT
<213> ORGANISM: Unknown
<220> FEATURE:
<223> OTHER INFORMATION: Mycobacterium indicus pranii

<400> SEQUENCE: 40

Met His Gly Leu Leu Ser Lys Thr Arg Val Tyr Val Val Pro Val Leu
1               5                   10                  15

Gly Ser Ala Leu Ser Ala His Lys Ser Gly Val Asp Arg Leu Leu Ala
            20                  25                  30

Ser Tyr Arg Ser Ile Pro Ala Thr Ser Ala Val Arg Leu Ala Lys Pro
        35                  40                  45

Thr Ser Asn Leu Phe Arg Ala Arg Thr Lys Arg Asp Ala Pro Gly Leu
    50                  55                  60

Asp Thr Ser Gly Leu Thr Gly Val Leu Ser Val Asp Pro Glu Thr Arg
65                  70                  75                  80

Thr Ala Asp Val Ala Gly Met Cys Thr Tyr Ala Asp Leu Val Ala Ala
                85                  90                  95

Thr Leu Pro Tyr Gly Leu Ser Pro Leu Val Val Pro Gln Leu Lys Thr
            100                 105                 110

Ile Thr Leu Gly Gly Ala Val Ser Gly Leu Gly Ile Glu Ser Ala Ser
        115                 120                 125

Phe Arg Asn Gly Leu Pro His Glu Ser Val Leu Glu Met Asp Ile Leu
    130                 135                 140

Thr Gly Ala Gly Asp Leu Leu Thr Ala Ser Arg Thr Gln His Pro Asp
145                 150                 155                 160

Leu Phe Arg Ala Phe Pro Asn Ser Tyr Gly Thr Leu Gly Tyr Ser Thr
                165                 170                 175

Arg Leu Arg Ile Glu Leu Glu Pro Val Ala Pro Phe Val Ala Leu Arg
            180                 185                 190

His Ile Arg Phe Arg Ser Leu Pro Ala Leu Ile Ala Ala Ala Glu Arg
        195                 200                 205

Ile Val Asp Thr Gly Gly Gln Gly Gly Thr Pro Val Asp Tyr Leu Asp
```

-continued

```
    210                 215                 220

Gly Val Val Phe Ser Ala Asp Glu Ser Tyr Leu Cys Val Gly Arg Arg
225                 230                 235                 240

Thr Thr Thr Pro Gly Pro Val Ser Asp Tyr Thr Gly Lys Asp Ile Tyr
                245                 250                 255

Tyr Gln Ser Ile Arg His Asp Ala Pro Gly Leu Glu Ala Thr Lys Asp
            260                 265                 270

Asp Arg Leu Thr Met His Asp Tyr Phe Trp Arg Trp Asp Thr Asp Trp
        275                 280                 285

Phe Trp Cys Ser Arg Ala Phe Gly Val Gln Asp Pro Arg Val Arg Arg
    290                 295                 300

Phe Trp Pro Arg Arg Tyr Arg Arg Ser Ser Phe Tyr Trp Lys Leu Ile
305                 310                 315                 320

Ser Leu Asp Arg Arg Phe Gly Ile Ser Asp Arg Ile Glu Ala Arg Asn
                325                 330                 335

Gly Arg Pro Pro Arg Glu Arg Val Val Gln Asp Ile Glu Ile Pro Ile
            340                 345                 350

Glu Arg Thr Cys Asp Phe Leu Glu Trp Phe Leu Asp Asn Val Pro Ile
        355                 360                 365

Thr Pro Ile Trp Leu Cys Pro Leu Arg Leu Arg Asp Arg Asp Gly Trp
    370                 375                 380

Pro Leu Tyr Pro Met Arg Pro Asp His Thr Tyr Val Asn Val Gly Phe
385                 390                 395                 400

Trp Ser Ser Val Pro Gly Gly Ala Thr Glu Gly Ala Ala Asn Arg Met
                405                 410                 415

Ile Glu Glu Lys Val Ser Glu Leu Asp Gly His Lys Ser Leu Tyr Ser
            420                 425                 430

Asp Ser Phe Tyr Ser Arg Glu Asp Phe Asp Glu Leu Tyr Gly Gly Glu
        435                 440                 445

Thr Tyr Asn Thr Val Lys Lys Thr Tyr Asp Pro Asp Ser Arg Leu Leu
    450                 455                 460

Asp Leu Tyr Ala Lys Ala Val Gln Arg Arg
465                 470
```

<210> SEQ ID NO 41
<211> LENGTH: 1263
<212> TYPE: DNA
<213> ORGANISM: Unknown
<220> FEATURE:
<223> OTHER INFORMATION: Mycobacterium indicus pranii

<400> SEQUENCE: 41

```
atggccgaga tcctggaggt cttcgccgcc accggccgac atccgctgaa gttcaccgcc      60

tacgacggca gcatcgccgg caacgaggac gccgaactgg gcctggacct tcgcagcccc     120

cgcggcgcca cctatctggc gaccgccccc ggcgaactcg gcctcgcccg cgcctacgtg     180

tcgggcgacc tgcaggccta cggcgtccat cccggcgacc cgtaccaact gctcaagacg     240

ctcaccgatc gggtggaatt caagcggccc ccggtgcggg tgctggccaa cgtcgtgcgg     300

tcgctggggt tcgagcggtt gctgccggtc gcgccgcccc cgcaggaggc gctgccccgg     360

tggcggcgca tcgccgacgg gctgatgcac acgaggaccc gcgacgccga ggccatccac     420

caccactacg acgtgtccaa caccttctac gaattggtgt tggggccgtc gatgacctac     480

acctgcgcgg tgtatcccga tgccgacgcg acactcgaac aggcgcagga gaacaagtac     540

cggctgatct tcgagaagct gcggctgaag gcgggcgacc ggctgctcga cgtcggctgc     600
```

-continued

```
ggctggggcg gcatggtgcg ctacgcggcc cggcgcggcg tccgggccac cggcgccacc    660

ctgtcggccg aacaggcgaa gtgggcgcag aaggcgatcg ccgaggaagg ccttgcggac    720

ctggccgagg tgcgccacac cgactatcgg gacgtgggcg aggcggcgtt cgacgccgtg    780

tcctcgatcg ggctgaccga gcacatcggc gtcaagaatt accccgccta cttcggcttc    840

ttgaagtcga agctgcgcac cggcggcctg ctgctcaatc actgcatcac ccgccacgac    900

aacacgtcga cgtcgttcgc gggcggattc accgatcgct atgtcttccc ggacggggag    960

ctgaccggct cgggccgcat cacctgcgac gtccaggact gcggcttcga ggtgctgcac   1020

gcggagaact tccgccacca ctacgcgatg acgctgcgcg actggtgccg caatctggtc   1080

gagaactggg acgccgcggt cagcgaggtc ggcctaccga ccgcgaaggt ctggggcctg   1140

tacatggcgg cgtcacgggt tgcgttcgag cagaacaacc ttcagctgca tcacgtgctg   1200

gcggccaaga ccgacgcgcg gggcgacgac gacctgccgc tgcggccgtg gtggacggcc   1260

tga                                                                 1263
```

```
<210> SEQ ID NO 42
<211> LENGTH: 420
<212> TYPE: PRT
<213> ORGANISM: Unknown
<220> FEATURE:
<223> OTHER INFORMATION: Mycobacterium indicus pranii

<400> SEQUENCE: 42

Met Ala Glu Ile Leu Glu Val Phe Ala Ala Thr Gly Arg His Pro Leu
1               5                   10                  15

Lys Phe Thr Ala Tyr Asp Gly Ser Ile Ala Gly Asn Glu Asp Ala Glu
            20                  25                  30

Leu Gly Leu Asp Leu Arg Ser Pro Arg Gly Ala Thr Tyr Leu Ala Thr
        35                  40                  45

Ala Pro Gly Glu Leu Gly Leu Ala Arg Ala Tyr Val Ser Gly Asp Leu
    50                  55                  60

Gln Ala Tyr Gly Val His Pro Gly Asp Pro Tyr Gln Leu Leu Lys Thr
65                  70                  75                  80

Leu Thr Asp Arg Val Glu Phe Lys Arg Pro Pro Val Arg Val Leu Ala
                85                  90                  95

Asn Val Val Arg Ser Leu Gly Phe Glu Arg Leu Leu Pro Val Ala Pro
            100                 105                 110

Pro Pro Gln Glu Ala Leu Pro Arg Trp Arg Arg Ile Ala Asp Gly Leu
        115                 120                 125

Met His Thr Arg Thr Arg Asp Ala Glu Ala Ile His His His Tyr Asp
    130                 135                 140

Val Ser Asn Thr Phe Tyr Glu Leu Val Leu Gly Pro Ser Met Thr Tyr
145                 150                 155                 160

Thr Cys Ala Val Tyr Pro Asp Ala Asp Ala Thr Leu Glu Gln Ala Gln
                165                 170                 175

Glu Asn Lys Tyr Arg Leu Ile Phe Glu Lys Leu Arg Leu Lys Ala Gly
            180                 185                 190

Asp Arg Leu Leu Asp Val Gly Cys Gly Trp Gly Gly Met Val Arg Tyr
        195                 200                 205

Ala Ala Arg Arg Gly Val Arg Ala Thr Gly Ala Thr Leu Ser Ala Glu
    210                 215                 220

Gln Ala Lys Trp Ala Gln Lys Ala Ile Ala Glu Glu Gly Leu Ala Asp
225                 230                 235                 240
```

-continued

```
Leu Ala Glu Val Arg His Thr Asp Tyr Arg Asp Val Gly Glu Ala Ala
                245                 250                 255

Phe Asp Ala Val Ser Ser Ile Gly Leu Thr Glu His Ile Gly Val Lys
            260                 265                 270

Asn Tyr Pro Ala Tyr Phe Gly Phe Leu Lys Ser Lys Leu Arg Thr Gly
        275                 280                 285

Gly Leu Leu Leu Asn His Cys Ile Thr Arg His Asp Asn Thr Ser Thr
    290                 295                 300

Ser Phe Ala Gly Gly Phe Thr Asp Arg Tyr Val Phe Pro Asp Gly Glu
305                 310                 315                 320

Leu Thr Gly Ser Gly Arg Ile Thr Cys Asp Val Gln Asp Cys Gly Phe
                325                 330                 335

Glu Val Leu His Ala Glu Asn Phe Arg His His Tyr Ala Met Thr Leu
            340                 345                 350

Arg Asp Trp Cys Arg Asn Leu Val Glu Asn Trp Asp Ala Ala Val Ser
        355                 360                 365

Glu Val Gly Leu Pro Thr Ala Lys Val Trp Gly Leu Tyr Met Ala Ala
    370                 375                 380

Ser Arg Val Ala Phe Glu Gln Asn Asn Leu Gln Leu His His Val Leu
385                 390                 395                 400

Ala Ala Lys Thr Asp Ala Arg Gly Asp Asp Asp Leu Pro Leu Arg Pro
                405                 410                 415

Trp Trp Thr Ala
            420


<210> SEQ ID NO 43
<211> LENGTH: 1380
<212> TYPE: DNA
<213> ORGANISM: Mycobacterium phlei

<400> SEQUENCE: 43

gtgtctgaac cccgaaccga cgcacgtgtt gttcaggccg cgggcgtgca caagctgctg      60

gagagctacc gcgcgatccc gcccgaggcc accgtccggc tggccaaacc cacctcgaac     120

ctgttccggg cgcgcgccaa gacctcggtc aagggtctcg atgtctcggg cctgacccat     180

gtgatctccg tcgaccccga cgagcgcacc gctgaggtgg ccgggatgtg cacctacgag     240

gacctggtcg ccgcgacgct gccgtacggg ctgtcaccgc tggtggtgcc gcagctcaag     300

accatcaccc tcggcggcgc cgtgacgggt ctgggcatcg agtcggcgtc gttccgtaac     360

ggcctgccgc acgagtcggt gctggagatg gacatcctca ccggatcggg cgagatcctc     420

accgcctccc gcgaccagca ccccgacctg ttccgggcgt tcccgaactc ctatggcacg     480

ctgggctatt cggtgcggct gaagatcgag ttggagaccg tcaaaccgtt cgtcgcggtc     540

cgtcacctgc ggttccacga catcgaggac ctggtcgccg agatggaccg cattgtcgag     600

accggcggct acgacggcac cccggtcgac tatctcgacg gtgtggtgtt ctcggcccgc     660

gagagctacc tgacgctggg cttccagacc gccaccccgg gcccggtcag cgactacacc     720

ggccagcaga tctactaccg ctcgatccag cacgaggacg gcgtcaagga cgaccggctg     780

acgatccacg actacttctg gcgctgggac accgactggt tctggtgctc gcgggcgttc     840

ggcgtgcaga acccgacgat ccgccggttc tggccgcgcc ggctcaagcg cagcagcttc     900

tactggaagc tggtcgccta cgaccgcaag ttcaacatcg ccgatcgcat cgagatgcac     960

aacggccgcc cgccccgcga gcgcgtcgtg caggacatcg aggtgccgat cgagcgggtc    1020
```

gccgagtttt tgggctggtt cctcgacaac gtgccgatcg agccgatctg gctgtgcccg 1080
ttgcgtcttc gcgacgacgc cggctggccg ctgtacccga tccgggcgca gcacacctac 1140
gtcaacgtgg ggttctggtc ctcggtgccg gtggggccca ccgaggggca cacgaaccgg 1200
ctgatcgagc gcaaggtcag cgagctcgac gggcacaagt cgctgtactc ggacgcgtac 1260
tactcgcgcg acgagttcga ccagctctac ggcggcgaaa tctacaaaac cgttaaaaag 1320
gcctacgatc cagattcacg actgctcgac ctgtacgcga aggcggtgca gcgccagtga 1380

<210> SEQ ID NO 44
<211> LENGTH: 459
<212> TYPE: PRT
<213> ORGANISM: Mycobacterium phlei

<400> SEQUENCE: 44

Val Ser Glu Pro Arg Thr Asp Ala Arg Val Val Gln Ala Ala Gly Val
1 5 10 15

His Lys Leu Leu Glu Ser Tyr Arg Ala Ile Pro Pro Glu Ala Thr Val
20 25 30

Arg Leu Ala Lys Pro Thr Ser Asn Leu Phe Arg Ala Arg Ala Lys Thr
35 40 45

Ser Val Lys Gly Leu Asp Val Ser Gly Leu Thr His Val Ile Ser Val
50 55 60

Asp Pro Asp Glu Arg Thr Ala Glu Val Ala Gly Met Cys Thr Tyr Glu
65 70 75 80

Asp Leu Val Ala Ala Thr Leu Pro Tyr Gly Leu Ser Pro Leu Val Val
85 90 95

Pro Gln Leu Lys Thr Ile Thr Leu Gly Gly Ala Val Thr Gly Leu Gly
100 105 110

Ile Glu Ser Ala Ser Phe Arg Asn Gly Leu Pro His Glu Ser Val Leu
115 120 125

Glu Met Asp Ile Leu Thr Gly Ser Gly Glu Ile Leu Thr Ala Ser Arg
130 135 140

Asp Gln His Pro Asp Leu Phe Arg Ala Phe Pro Asn Ser Tyr Gly Thr
145 150 155 160

Leu Gly Tyr Ser Val Arg Leu Lys Ile Glu Leu Glu Thr Val Lys Pro
165 170 175

Phe Val Ala Val Arg His Leu Arg Phe His Asp Ile Glu Asp Leu Val
180 185 190

Ala Glu Met Asp Arg Ile Val Glu Thr Gly Gly Tyr Asp Gly Thr Pro
195 200 205

Val Asp Tyr Leu Asp Gly Val Val Phe Ser Ala Arg Glu Ser Tyr Leu
210 215 220

Thr Leu Gly Phe Gln Thr Ala Thr Pro Gly Pro Val Ser Asp Tyr Thr
225 230 235 240

Gly Gln Gln Ile Tyr Tyr Arg Ser Ile Gln His Glu Asp Gly Val Lys
245 250 255

Asp Asp Arg Leu Thr Ile His Asp Tyr Phe Trp Arg Trp Asp Thr Asp
260 265 270

Trp Phe Trp Cys Ser Arg Ala Phe Gly Val Gln Asn Pro Thr Ile Arg
275 280 285

Arg Phe Trp Pro Arg Arg Leu Lys Arg Ser Ser Phe Tyr Trp Lys Leu
290 295 300

Val Ala Tyr Asp Arg Lys Phe Asn Ile Ala Asp Arg Ile Glu Met His
305 310 315 320

-continued

```
Asn Gly Arg Pro Pro Arg Glu Arg Val Val Gln Asp Ile Glu Val Pro
                325                 330                 335

Ile Glu Arg Val Ala Glu Phe Leu Gly Trp Phe Leu Asp Asn Val Pro
            340                 345                 350

Ile Glu Pro Ile Trp Leu Cys Pro Leu Arg Leu Arg Asp Asp Ala Gly
        355                 360                 365

Trp Pro Leu Tyr Pro Ile Arg Ala Gln His Thr Tyr Val Asn Val Gly
    370                 375                 380

Phe Trp Ser Ser Val Pro Val Gly Pro Thr Glu Gly His Thr Asn Arg
385                 390                 395                 400

Leu Ile Glu Arg Lys Val Ser Glu Leu Asp Gly His Lys Ser Leu Tyr
                405                 410                 415

Ser Asp Ala Tyr Tyr Ser Arg Asp Glu Phe Asp Gln Leu Tyr Gly Gly
            420                 425                 430

Glu Ile Tyr Lys Thr Val Lys Lys Ala Tyr Asp Pro Asp Ser Arg Leu
        435                 440                 445

Leu Asp Leu Tyr Ala Lys Ala Val Gln Arg Gln
    450                 455


<210> SEQ ID NO 45
<211> LENGTH: 1314
<212> TYPE: DNA
<213> ORGANISM: Mycobacterium phlei

<400> SEQUENCE: 45

atgacggcga tcaaagagaa cccggtcctg acttcggcca ggaagctgtc cctggccgag     60

attctggaaa tccttgccgg gggcgaactc ccggtgcgtt tcacggccta cgacggcagc    120

tcggcgggcc cggcggactc cccgctcggc ctggagctgc tgaccccgcg cggcaccacc    180

tatctggcca ccgccccggg cgatctcggg ctggcacgcg cctacatcgc cggtgacctg    240

cagccgcacg gcgtgcatcc gggcgatccg tacgagctgc tcaaggccct gtcggagaag    300

atggagttca agcggccgcc cgcgaaggtg ctggccaaca tcgtgcgctc catcggtatc    360

gagcacctca agccgatcgc accgccgccg caggaggcgc agccgcgctg gcgccggatc    420

gcggaagggt tgcggcacag caagactcgc gacgccgagg cgatccacca ccactacgac    480

gtgtccaaca cgttctacga gtgggtgctc ggcccgtcga tgacctacac ctgcgcgtgc    540

tacccggacg tcgacgcaac cctggagcag gcgcaggaga acaagtaccg cctggtgttc    600

gagaagctgc gcctgaagcc gggcgaccgg ctgctcgacg tgggctgcgg ctggggcggc    660

atggtgcgct acgccgccca gcacggggtc aaggccatcg gcgtcacgct gtctcgggag    720

caggcgacgt gggcgcagaa ggcgatcgcc gagcaggggc tcagcgatct ggccgaggtc    780

cgccacggcg actaccgcga cattcgcgag tccgggttcg acgcggtgtc ctcgatcggg    840

ctgaccgagc acatcggcgt ggccaactac ccgtcgtact tccggttcct gcagtccaag    900

ctgcgtgtcg gcgggctgct gctcaaccac tgcatcaccc ggccggacaa caagtcgcag    960

gccagcgcgg gcgggttcat cgaccgctac gtgttccccg acggggagct caccgggtcc   1020

ggccgcatca tcgccgcggc ccaggacgtc ggcctcgagg tggtgcacga ggagaacctg   1080

cgccagcact acgcgatgac gctgcgcgac tggtgccgca acctcgtcga gcactgggac   1140

gaggcggtcg ccgaggtcgg cctggaacgc gccaagatct ggggcctgta catggccggc   1200

tcccggctcg gcttcgagac gaacatcgtg cagctgcacc aggtgctggc ggtcaagctg   1260

gaccgcaggg gcggcgacgg cgggctgccg ttgcgcccgt ggtggacgcc ctag          1314
```

<210> SEQ ID NO 46
<211> LENGTH: 437
<212> TYPE: PRT
<213> ORGANISM: Mycobacterium phlei

<400> SEQUENCE: 46

Met Thr Ala Ile Lys Glu Asn Pro Val Leu Thr Ser Ala Arg Lys Leu
1 5 10 15

Ser Leu Ala Glu Ile Leu Glu Ile Leu Ala Gly Gly Glu Leu Pro Val
20 25 30

Arg Phe Thr Ala Tyr Asp Gly Ser Ser Ala Gly Pro Ala Asp Ser Pro
35 40 45

Leu Gly Leu Glu Leu Leu Thr Pro Arg Gly Thr Thr Tyr Leu Ala Thr
50 55 60

Ala Pro Gly Asp Leu Gly Leu Ala Arg Ala Tyr Ile Ala Gly Asp Leu
65 70 75 80

Gln Pro His Gly Val His Pro Gly Asp Pro Tyr Glu Leu Leu Lys Ala
85 90 95

Leu Ser Glu Lys Met Glu Phe Lys Arg Pro Pro Ala Lys Val Leu Ala
100 105 110

Asn Ile Val Arg Ser Ile Gly Ile Glu His Leu Lys Pro Ile Ala Pro
115 120 125

Pro Pro Gln Glu Ala Gln Pro Arg Trp Arg Arg Ile Ala Glu Gly Leu
130 135 140

Arg His Ser Lys Thr Arg Asp Ala Glu Ala Ile His His His Tyr Asp
145 150 155 160

Val Ser Asn Thr Phe Tyr Glu Trp Val Leu Gly Pro Ser Met Thr Tyr
165 170 175

Thr Cys Ala Cys Tyr Pro Asp Val Asp Ala Thr Leu Glu Gln Ala Gln
180 185 190

Glu Asn Lys Tyr Arg Leu Val Phe Glu Lys Leu Arg Leu Lys Pro Gly
195 200 205

Asp Arg Leu Leu Asp Val Gly Cys Gly Trp Gly Gly Met Val Arg Tyr
210 215 220

Ala Ala Gln His Gly Val Lys Ala Ile Gly Val Thr Leu Ser Arg Glu
225 230 235 240

Gln Ala Thr Trp Ala Gln Lys Ala Ile Ala Glu Gln Gly Leu Ser Asp
245 250 255

Leu Ala Glu Val Arg His Gly Asp Tyr Arg Asp Ile Arg Glu Ser Gly
260 265 270

Phe Asp Ala Val Ser Ser Ile Gly Leu Thr Glu His Ile Gly Val Ala
275 280 285

Asn Tyr Pro Ser Tyr Phe Arg Phe Leu Gln Ser Lys Leu Arg Val Gly
290 295 300

Gly Leu Leu Leu Asn His Cys Ile Thr Arg Pro Asp Asn Lys Ser Gln
305 310 315 320

Ala Ser Ala Gly Gly Phe Ile Asp Arg Tyr Val Phe Pro Asp Gly Glu
325 330 335

Leu Thr Gly Ser Gly Arg Ile Ile Ala Ala Ala Gln Asp Val Gly Leu
340 345 350

Glu Val Val His Glu Glu Asn Leu Arg Gln His Tyr Ala Met Thr Leu
355 360 365

Arg Asp Trp Cys Arg Asn Leu Val Glu His Trp Asp Glu Ala Val Ala

-continued

```
    370                 375                 380

Glu Val Gly Leu Glu Arg Ala Lys Ile Trp Gly Leu Tyr Met Ala Gly
385                 390                 395                 400

Ser Arg Leu Gly Phe Glu Thr Asn Ile Val Gln Leu His Gln Val Leu
                405                 410                 415

Ala Val Lys Leu Asp Arg Arg Gly Gly Asp Gly Gly Leu Pro Leu Arg
            420                 425                 430

Pro Trp Trp Thr Pro
        435
```

<210> SEQ ID NO 47
<211> LENGTH: 1413
<212> TYPE: DNA
<213> ORGANISM: Mycobacterium tuberculosis

<400> SEQUENCE: 47

```
atgcaggggc agttgtcgag gactagggta tatacggtgc ctgtccctgg atctgcacag     60
tcggcttacg cctgcggcgt cgagcggttg ctggcgagct atcgatccat ccccgcgact    120
gcatccatcc ggcttgccaa gcccacctca aatctgttcc gcgcccgcgt caaacacgat    180
gcacgcggcc tggacgcatc gggactgacc ggtgtcatcg gtatcgatcc cgaggcccgc    240
accgccgacg tggccggcat gtgcacatac gaggacctaa tcgccgcgac actgcactac    300
ggtctgtcac cattggtggt tccgcagctg aggacgatca cattgggcgg agcggtcacc    360
ggcttgggta tcgagtcggc gtcgttccgc aacggcctgc cccacgagtc ggtgctggag    420
atggatatcc tcaccggcgc aggagaactt ctcaccgtct cgcccggaca gcactccgac    480
ttgtaccgtg cattccctaa ctcgtatggg acactgggct attcaacccg gcttcgaatc    540
cagctggagc cggtccggcc gtttgtcgcg ctgcggcaca tccgatttag ctcgttgacg    600
gcgatggtgg ccgcaatgga gcgcatcatc gacaccggcg gactggacgg cgaatcggtg    660
gactatctcg acggggtggt tttcagcgct gacgaaagct acctgtgcat cggcatgcag    720
acgagcgtac cgggcccggt cagcgactac accggacaag acatctacta ccggtcgatc    780
caacacgagg cggggatcaa ggaagaccgg ttgaccatcc acgattactt ctggcgctgg    840
gacaccgatt ggttctggtg ctcacgatcg tttggtgccc aaaacccgcg gctgcgccgc    900
tggtggccgc ggcgctaccg gcgtagcagt gtctactgga ggttgatggc gctcgatcag    960
cgcttcggga tcgccgaccg gttcgagaac agcaggggtc gtcccgcgcg tgaacgggtg   1020
gtgcaggata tcgaagtgcc gatcgaacgg acctgcgagt ttctggagtg gttcggggaa   1080
aacgtgccca tttcgccaat ctggttgtgc ccgttgcggc tacgcgatca cgccggctgg   1140
ccgctgtacc cgatccggcc tgaccgtagc tatgtcaaca tcgggttctg gtcgtcggtg   1200
ccggttggcg ccaccgaggg cgccaccaac cgcaagatcg agaacaaggt gagtgcgctc   1260
gacgggcaca agtcgctcta ctccgactcc ttctataccc gcgaggagtt cgacgagctc   1320
tacggcggcg agacttacaa cactgtgaag aaagcctacg atcccgattc gcgtctcctc   1380
gatctttacg caaaggcggt gcaacgacga tga                                1413
```

<210> SEQ ID NO 48
<211> LENGTH: 470
<212> TYPE: PRT
<213> ORGANISM: Mycobacterium tuberculosis

<400> SEQUENCE: 48

```
Met Gln Gly Gln Leu Ser Arg Thr Arg Val Tyr Thr Val Pro Val Pro
```

-continued

```
1               5                   10                  15

Gly Ser Ala Gln Ser Ala Tyr Ala Cys Gly Val Glu Arg Leu Leu Ala
            20                  25                  30

Ser Tyr Arg Ser Ile Pro Ala Thr Ala Ser Ile Arg Leu Ala Lys Pro
        35                  40                  45

Thr Ser Asn Leu Phe Arg Ala Arg Val Lys His Asp Ala Arg Gly Leu
    50                  55                  60

Asp Ala Ser Gly Leu Thr Gly Val Ile Gly Ile Asp Pro Glu Ala Arg
65                  70                  75                  80

Thr Ala Asp Val Ala Gly Met Cys Thr Tyr Glu Asp Leu Ile Ala Ala
                85                  90                  95

Thr Leu His Tyr Gly Leu Ser Pro Leu Val Val Pro Gln Leu Arg Thr
            100                 105                 110

Ile Thr Leu Gly Gly Ala Val Thr Gly Leu Gly Ile Glu Ser Ala Ser
        115                 120                 125

Phe Arg Asn Gly Leu Pro His Glu Ser Val Leu Glu Met Asp Ile Leu
    130                 135                 140

Thr Gly Ala Gly Glu Leu Leu Thr Val Ser Pro Gly Gln His Ser Asp
145                 150                 155                 160

Leu Tyr Arg Ala Phe Pro Asn Ser Tyr Gly Thr Leu Gly Tyr Ser Thr
                165                 170                 175

Arg Leu Arg Ile Gln Leu Glu Pro Val Arg Pro Phe Val Ala Leu Arg
            180                 185                 190

His Ile Arg Phe Ser Ser Leu Thr Ala Met Val Ala Ala Met Glu Arg
        195                 200                 205

Ile Ile Asp Thr Gly Gly Leu Asp Gly Glu Ser Val Asp Tyr Leu Asp
    210                 215                 220

Gly Val Val Phe Ser Ala Asp Glu Ser Tyr Leu Cys Ile Gly Met Gln
225                 230                 235                 240

Thr Ser Val Pro Gly Pro Val Ser Asp Tyr Thr Gly Gln Asp Ile Tyr
                245                 250                 255

Tyr Arg Ser Ile Gln His Glu Ala Gly Ile Lys Glu Asp Arg Leu Thr
            260                 265                 270

Ile His Asp Tyr Phe Trp Arg Trp Asp Thr Asp Trp Phe Trp Cys Ser
        275                 280                 285

Arg Ser Phe Gly Ala Gln Asn Pro Arg Leu Arg Arg Trp Trp Pro Arg
    290                 295                 300

Arg Tyr Arg Arg Ser Ser Val Tyr Trp Arg Leu Met Ala Leu Asp Gln
305                 310                 315                 320

Arg Phe Gly Ile Ala Asp Arg Phe Glu Asn Ser Arg Gly Arg Pro Ala
                325                 330                 335

Arg Glu Arg Val Val Gln Asp Ile Glu Val Pro Ile Glu Arg Thr Cys
            340                 345                 350

Glu Phe Leu Glu Trp Phe Gly Glu Asn Val Pro Ile Ser Pro Ile Trp
        355                 360                 365

Leu Cys Pro Leu Arg Leu Arg Asp His Ala Gly Trp Pro Leu Tyr Pro
    370                 375                 380

Ile Arg Pro Asp Arg Ser Tyr Val Asn Ile Gly Phe Trp Ser Ser Val
385                 390                 395                 400

Pro Val Gly Ala Thr Glu Gly Ala Thr Asn Arg Lys Ile Glu Asn Lys
                405                 410                 415

Val Ser Ala Leu Asp Gly His Lys Ser Leu Tyr Ser Asp Ser Phe Tyr
            420                 425                 430
```

-continued

Thr Arg Glu Glu Phe Asp Glu Leu Tyr Gly Gly Glu Thr Tyr Asn Thr
        435                 440                 445

Val Lys Lys Ala Tyr Asp Pro Asp Ser Arg Leu Leu Asp Leu Tyr Ala
    450                 455                 460

Lys Ala Val Gln Arg Arg
465                 470

<210> SEQ ID NO 49
<211> LENGTH: 1263
<212> TYPE: DNA
<213> ORGANISM: Mycobacterium tuberculosis

<400> SEQUENCE: 49
atggccgaga tcctggagat cttcaccgcg accgggcaac acccgctgaa gttcaccgcg 60
tatgacggca gcaccgcggg acaagacgac gccacactgg gcctggatct tcggacgccc 120
cgcggcgcca cctacttagc taccgctccc ggcgaactcg gcctggcccg cgcttatgtg 180
tcgggtgacc tacaggcaca cggagtacat cccggcgatc cgtacgaact gctcaaaacg 240
ctgaccgaaa gggtcgactt caaacggccg tcggcgcggg tgctggctaa tgtggtgcgc 300
tcgatcggcg ttgagcacat actgcccatc gcgccgccac cccaggaggc gcgacccccgg 360 tggcgtcgaa tggctaatgg cttgctgcac agcaagaccc gtgacgccga ggctatccat 420
caccactacg acgtctccaa caacttctac gagtgggtgc tcgggccatc gatgacctac 480
acgtgcgcgg tgtttccgaa cgctgaggct tcgctggagc aggcccaaga gaacaaatac 540
cgactcattt tcgaaaagct acggctagag ccgggtgacc ggctactcga cgtcggctgc 600
ggctggggcg gcatggtgcg ctacgccgcc cgacgcggtg tccgggtgat cggcgccacg 660
ctctcggccg agcaggccaa gtggggccag aaagcagtcg aggacgaggg attgagcgac 720
ctcgcgcagg tgcggcattc cgactaccgc gacgtagccg agaccggttt cgacgccgtt 780
tcttcgatcg ggctaaccga gcacatcggc gtcaagaatt acccgttcta cttcgggttt 840
ctcaagtcga agttgcgcac cggcggcttg ctgctcaatc actgcatcac ccgccacgac 900
aacaggtcga cgtcctttgc cggcgggttc accgaccgtt acgttttccc cgacggggag 960
ctgacgggct cgggacgtat taccaccgag atccagcagg tcggcttgga agtgctgcac 1020
gaggagaact tccgccatca ctacgcgatg acgctgcgcg actggtgcgg caacctcgtc 1080
gaacactggg acgacgcggt cgccgaggtc ggtctgccga ccgccaaggt gtggggcctg 1140
tacatggcgg cttcgcgggt ggccttcgaa cgaaacaacc tgcagctaca tcacgtattg 1200
gcgaccaagg tggacccccg gggcgacgac agcttgccac tgcggccctg gtggcagccc 1260
tag 1263

<210> SEQ ID NO 50
<211> LENGTH: 420
<212> TYPE: PRT
<213> ORGANISM: Mycobacterium tuberculosis

<400> SEQUENCE: 50

Met Ala Glu Ile Leu Glu Ile Phe Thr Ala Thr Gly Gln His Pro Leu
1               5                   10                  15

Lys Phe Thr Ala Tyr Asp Gly Ser Thr Ala Gly Gln Asp Asp Ala Thr
            20                  25                  30

Leu Gly Leu Asp Leu Arg Thr Pro Arg Gly Ala Thr Tyr Leu Ala Thr
        35                  40                  45

-continued

```
Ala Pro Gly Glu Leu Gly Leu Ala Arg Ala Tyr Val Ser Gly Asp Leu
    50                  55                  60

Gln Ala His Gly Val His Pro Gly Asp Pro Tyr Glu Leu Leu Lys Thr
65                  70                  75                  80

Leu Thr Glu Arg Val Asp Phe Lys Arg Pro Ser Ala Arg Val Leu Ala
                85                  90                  95

Asn Val Val Arg Ser Ile Gly Val Glu His Ile Leu Pro Ile Ala Pro
            100                 105                 110

Pro Pro Gln Glu Ala Arg Pro Arg Trp Arg Arg Met Ala Asn Gly Leu
        115                 120                 125

Leu His Ser Lys Thr Arg Asp Ala Glu Ala Ile His His His Tyr Asp
    130                 135                 140

Val Ser Asn Asn Phe Tyr Glu Trp Val Leu Gly Pro Ser Met Thr Tyr
145                 150                 155                 160

Thr Cys Ala Val Phe Pro Asn Ala Glu Ala Ser Leu Glu Gln Ala Gln
                165                 170                 175

Glu Asn Lys Tyr Arg Leu Ile Phe Glu Lys Leu Arg Leu Glu Pro Gly
            180                 185                 190

Asp Arg Leu Leu Asp Val Gly Cys Gly Trp Gly Gly Met Val Arg Tyr
        195                 200                 205

Ala Ala Arg Arg Gly Val Arg Val Ile Gly Ala Thr Leu Ser Ala Glu
    210                 215                 220

Gln Ala Lys Trp Gly Gln Lys Ala Val Glu Asp Glu Gly Leu Ser Asp
225                 230                 235                 240

Leu Ala Gln Val Arg His Ser Asp Tyr Arg Asp Val Ala Glu Thr Gly
                245                 250                 255

Phe Asp Ala Val Ser Ser Ile Gly Leu Thr Glu His Ile Gly Val Lys
            260                 265                 270

Asn Tyr Pro Phe Tyr Phe Gly Phe Leu Lys Ser Lys Leu Arg Thr Gly
        275                 280                 285

Gly Leu Leu Leu Asn His Cys Ile Thr Arg His Asp Asn Arg Ser Thr
    290                 295                 300

Ser Phe Ala Gly Gly Phe Thr Asp Arg Tyr Val Phe Pro Asp Gly Glu
305                 310                 315                 320

Leu Thr Gly Ser Gly Arg Ile Thr Thr Glu Ile Gln Gln Val Gly Leu
                325                 330                 335

Glu Val Leu His Glu Glu Asn Phe Arg His His Tyr Ala Met Thr Leu
            340                 345                 350

Arg Asp Trp Cys Gly Asn Leu Val Glu His Trp Asp Asp Ala Val Ala
        355                 360                 365

Glu Val Gly Leu Pro Thr Ala Lys Val Trp Gly Leu Tyr Met Ala Ala
    370                 375                 380

Ser Arg Val Ala Phe Glu Arg Asn Asn Leu Gln Leu His His Val Leu
385                 390                 395                 400

Ala Thr Lys Val Asp Pro Arg Gly Asp Asp Ser Leu Pro Leu Arg Pro
                405                 410                 415

Trp Trp Gln Pro
            420
```

<210> SEQ ID NO 51
<211> LENGTH: 1392
<212> TYPE: DNA
<213> ORGANISM: Unknown
<220> FEATURE:
<223> OTHER INFORMATION: Mycobacterium vanbaalenii

<400> SEQUENCE: 51

```
gtgtctgttc cttcgaccga cgcacgttct gctcacgccg acggcgtgca gcggcttctc     60
gccagctatc gggcgattcc ccaagacgcc acggtccggc tggccaaacc cacgtcgaac    120
ctcttccgtg cccgcgcgaa aaccaggacc aagggtctgg acacgtctgg gttgacgaac    180
gtgatcgcgg tcgacgcgga ggcacgcacc gccgatgtgg cagggatgtg cacctacgaa    240
gacctggtcg cggccacgct gccgcatgga ctttcgccgc tggtggtgcc gcagttgaag    300
acgatcaccc tcggcggggc ggtcaccgga ctcgggatcg agtccgcctc gttccgcaac    360
ggcctgccac acgaatcggt tctcgagatg gacgtcctca ccggcaccgg tgatgtcgtg    420
cgcgcctccc ccgacgagaa ccctgacctg tttcgggcgt ttccgaattc ctatggcacg    480
ttgggctatt cggttcggct caagatcgag ctggaaccgg tgaagccgtt cgtcgcgctg    540
cgccacctcc gtttccattc gctgtcggct ctcatcgagg cgatggaccg catcgtcgaa    600
accggcggcc tcaacggcga accggtggac tacctcgacg gcgtcgtgtt cagtgccgag    660
gagagttacc tgtgcgtggg gcagcgctcc gcgacaccgg gcccggtcag cgactacacg    720
ggcaagcaga tctactaccg ctcgattcag cacgacggcc cgaccgatgg cgccgagaag    780
cacgaccggc tgaccatcca cgactacctg tggcgctggg acaccgactg gttctggtgc    840
tcaagggcat tcggcgcgca gaacccgcgg atccggcgct ggtggccgcg ccggtaccgg    900
cgcagcagtg tgtactggaa gctgatcggc tacgaccggc gtttcggtat cgccgatcgc    960
atcgagaagc gcaacggccg acccccgcgc gagcgggtgg tccaggacat cgaggtgccc   1020
atcgagcgga ccgtcgagtt tctgcagtgg tttctcgaca ccgtgcccat cgaaccgatc   1080
tggttgtgcc cgttgcggct ccgcgacgac cgcgattggc ccctgtatcc gatccgaccc   1140
caccacacct acgtcaacgt gggtttctgg tcgtcggtgc cggtgggccc ggaggagggc   1200
tacaccaaca ggatgatcga acggaaagtc agcgacctcg acggtcacaa atcgctgtat   1260
tccgatgcgt actactcgcc ggaagagttt gattcgctct atggcgggga gacgtacaag   1320
acggtgaaga agacatacga cccagactct cgtttcctgg acctgtacgg caaagcagtg   1380
gggcggcaat ga                                                       1392
```

<210> SEQ ID NO 52
<211> LENGTH: 463
<212> TYPE: PRT
<213> ORGANISM: Unknown
<220> FEATURE:
<223> OTHER INFORMATION: Mycobacterium vanbaalenii

<400> SEQUENCE: 52

```
Val Ser Val Pro Ser Thr Asp Ala Arg Ser Ala His Ala Asp Gly Val
1               5                   10                  15

Gln Arg Leu Leu Ala Ser Tyr Arg Ala Ile Pro Gln Asp Ala Thr Val
            20                  25                  30

Arg Leu Ala Lys Pro Thr Ser Asn Leu Phe Arg Ala Arg Ala Lys Thr
        35                  40                  45

Arg Thr Lys Gly Leu Asp Thr Ser Gly Leu Thr Asn Val Ile Ala Val
    50                  55                  60

Asp Ala Glu Ala Arg Thr Ala Asp Val Ala Gly Met Cys Thr Tyr Glu
65                  70                  75                  80

Asp Leu Val Ala Ala Thr Leu Pro His Gly Leu Ser Pro Leu Val Val
                85                  90                  95
```

```
Pro Gln Leu Lys Thr Ile Thr Leu Gly Gly Ala Val Thr Gly Leu Gly
            100                 105                 110

Ile Glu Ser Ala Ser Phe Arg Asn Gly Leu Pro His Glu Ser Val Leu
        115                 120                 125

Glu Met Asp Val Leu Thr Gly Thr Gly Asp Val Val Arg Ala Ser Pro
    130                 135                 140

Asp Glu Asn Pro Asp Leu Phe Arg Ala Phe Pro Asn Ser Tyr Gly Thr
145                 150                 155                 160

Leu Gly Tyr Ser Val Arg Leu Lys Ile Glu Leu Glu Pro Val Lys Pro
                165                 170                 175

Phe Val Ala Leu Arg His Leu Arg Phe His Ser Leu Ser Ala Leu Ile
            180                 185                 190

Glu Ala Met Asp Arg Ile Val Glu Thr Gly Gly Leu Asn Gly Glu Pro
        195                 200                 205

Val Asp Tyr Leu Asp Gly Val Val Phe Ser Ala Glu Glu Ser Tyr Leu
    210                 215                 220

Cys Val Gly Gln Arg Ser Ala Thr Pro Gly Pro Val Ser Asp Tyr Thr
225                 230                 235                 240

Gly Lys Gln Ile Tyr Tyr Arg Ser Ile Gln His Asp Gly Pro Thr Asp
                245                 250                 255

Gly Ala Glu Lys His Asp Arg Leu Thr Ile His Asp Tyr Leu Trp Arg
            260                 265                 270

Trp Asp Thr Asp Trp Phe Trp Cys Ser Arg Ala Phe Gly Ala Gln Asn
        275                 280                 285

Pro Arg Ile Arg Arg Trp Trp Pro Arg Arg Tyr Arg Arg Ser Ser Val
    290                 295                 300

Tyr Trp Lys Leu Ile Gly Tyr Asp Arg Arg Phe Gly Ile Ala Asp Arg
305                 310                 315                 320

Ile Glu Lys Arg Asn Gly Arg Pro Pro Arg Glu Arg Val Val Gln Asp
                325                 330                 335

Ile Glu Val Pro Ile Glu Arg Thr Val Glu Phe Leu Gln Trp Phe Leu
            340                 345                 350

Asp Thr Val Pro Ile Glu Pro Ile Trp Leu Cys Pro Leu Arg Leu Arg
        355                 360                 365

Asp Asp Arg Asp Trp Pro Leu Tyr Pro Ile Arg Pro His His Thr Tyr
    370                 375                 380

Val Asn Val Gly Phe Trp Ser Ser Val Pro Val Gly Pro Glu Glu Gly
385                 390                 395                 400

Tyr Thr Asn Arg Met Ile Glu Arg Lys Val Ser Asp Leu Asp Gly His
                405                 410                 415

Lys Ser Leu Tyr Ser Asp Ala Tyr Tyr Ser Pro Glu Glu Phe Asp Ser
            420                 425                 430

Leu Tyr Gly Gly Glu Thr Tyr Lys Thr Val Lys Lys Thr Tyr Asp Pro
        435                 440                 445

Asp Ser Arg Phe Leu Asp Leu Tyr Gly Lys Ala Val Gly Arg Gln
    450                 455                 460
```

<210> SEQ ID NO 53
<211> LENGTH: 1323
<212> TYPE: DNA
<213> ORGANISM: Unknown
<220> FEATURE:
<223> OTHER INFORMATION: Mycobacterium vanbaalenii

<400> SEQUENCE: 53

-continued

```
ttgacgacat ttcgggacgg cgcggccgac accggcctgc acggagaccg caagctcacc     60

ctggcggagg tcttggaggt cttcgcctcg ggccgactgc ctctgaagtt cacggcgtac    120

gacggcagca gcgcgggccc ggacgacgcc acgctcgggc tggacctgct gaccccccgc    180

gggaccacgt acctcgcaac ggctcccggc gatctcggcc tggcccgggc ctacgtctcc    240

ggtgacctgc agttgcaggg ggtgcaccct ggcgacccgt acgacctgct caacgcactg    300

gtgcagaaac tggacttcaa gcgaccgtcc gcccgggtgc tggcgcaggt cgtccgatcg    360

atcgggatcg agcacctgaa accgatcgcg ccaccgccgc aggaggcgct gccgcggtgg    420

cggcgcatcg cagaaggact gcggcacagc aagacccgtg acgccgacgc gatccaccac    480

cattacgatg tctccaacac cttctacgag tgggtgctcg ggccgtcgat gacctacacc    540

tgcgcctgct acccgcatcc cgacgccacc ctcgaggagg cgcaggagaa caaatatcgg    600

ctggtgttcg agaaactgcg cctcaagccg ggcgaccgcc ttctcgacgt gggttgcggg    660

tggggcggaa tggtgcgcta cgcggcccgt cacggcgtca aggcgatcgg ggtgacgctg    720

tccagggagc aggcgcagtg ggcacgcgcc gccatcgaac gggacggcct gggtgacctc    780

gccgaggtcc gccacagcga ctaccgcgat gtgcgcgagt cccagttcga cgccgtgtct    840

tcgctggggc tcaccgagca catcggggtc gccaactatc cgtcgtactt ccggttcctc    900

aagtcgaagt tgcgcccggg cggcctactg ctcaaccact gcatcacccg gcacaacaat    960

cgcaccggcc ccgccgccgg gggattcatc gaccggtatg tgttcccgga cggggagctg   1020

accggatcgg gccggatcat caccgagatc caggacgtcg gtttggaggt gatgcacgaa   1080

gagaacctgc gccggcacta tgcgctgaca cttcgggact ggtgccggaa tctggtgcag   1140

cactgggacg aagcggtcgc agaggtcggc ctgcccaccg ccaaggtgtg ggtctgtac    1200

atggctgcct cgcgggtcgg cttcgagcag aacagcattc agctgcatca ggtactggcg   1260

gtgaagctcg acgaacgtgg cggggacggc ggtttgccgt tgcggccctg gtggaccgcg   1320

tag                                                                  1323
```

<210> SEQ ID NO 54
<211> LENGTH: 440
<212> TYPE: PRT
<213> ORGANISM: Unknown
<220> FEATURE:
<223> OTHER INFORMATION: Mycobacterium vanbaalenii

<400> SEQUENCE: 54

```
Leu Thr Thr Phe Arg Asp Gly Ala Ala Asp Thr Gly Leu His Gly Asp
1               5                   10                  15

Arg Lys Leu Thr Leu Ala Glu Val Leu Glu Val Phe Ala Ser Gly Arg
            20                  25                  30

Leu Pro Leu Lys Phe Thr Ala Tyr Asp Gly Ser Ser Ala Gly Pro Asp
        35                  40                  45

Asp Ala Thr Leu Gly Leu Asp Leu Leu Thr Pro Arg Gly Thr Thr Tyr
    50                  55                  60

Leu Ala Thr Ala Pro Gly Asp Leu Gly Leu Ala Arg Ala Tyr Val Ser
65                  70                  75                  80

Gly Asp Leu Gln Leu Gln Gly Val His Pro Gly Asp Pro Tyr Asp Leu
                85                  90                  95

Leu Asn Ala Leu Val Gln Lys Leu Asp Phe Lys Arg Pro Ser Ala Arg
            100                 105                 110

Val Leu Ala Gln Val Val Arg Ser Ile Gly Ile Glu His Leu Lys Pro
        115                 120                 125
```

```
Ile Ala Pro Pro Pro Gln Glu Ala Leu Pro Arg Trp Arg Arg Ile Ala
    130                 135                 140

Glu Gly Leu Arg His Ser Lys Thr Arg Asp Ala Asp Ala Ile His His
145                 150                 155                 160

His Tyr Asp Val Ser Asn Thr Phe Tyr Glu Trp Val Leu Gly Pro Ser
                165                 170                 175

Met Thr Tyr Thr Cys Ala Cys Tyr Pro His Pro Asp Ala Thr Leu Glu
            180                 185                 190

Glu Ala Gln Glu Asn Lys Tyr Arg Leu Val Phe Glu Lys Leu Arg Leu
        195                 200                 205

Lys Pro Gly Asp Arg Leu Leu Asp Val Gly Cys Gly Trp Gly Gly Met
    210                 215                 220

Val Arg Tyr Ala Ala Arg His Gly Val Lys Ala Ile Gly Val Thr Leu
225                 230                 235                 240

Ser Arg Glu Gln Ala Gln Trp Ala Arg Ala Ala Ile Glu Arg Asp Gly
                245                 250                 255

Leu Gly Asp Leu Ala Glu Val Arg His Ser Asp Tyr Arg Asp Val Arg
            260                 265                 270

Glu Ser Gln Phe Asp Ala Val Ser Ser Leu Gly Leu Thr Glu His Ile
        275                 280                 285

Gly Val Ala Asn Tyr Pro Ser Tyr Phe Arg Phe Leu Lys Ser Lys Leu
    290                 295                 300

Arg Pro Gly Gly Leu Leu Leu Asn His Cys Ile Thr Arg His Asn Asn
305                 310                 315                 320

Arg Thr Gly Pro Ala Ala Gly Gly Phe Ile Asp Arg Tyr Val Phe Pro
                325                 330                 335

Asp Gly Glu Leu Thr Gly Ser Gly Arg Ile Ile Thr Glu Ile Gln Asp
            340                 345                 350

Val Gly Leu Glu Val Met His Glu Glu Asn Leu Arg Arg His Tyr Ala
        355                 360                 365

Leu Thr Leu Arg Asp Trp Cys Arg Asn Leu Val Gln His Trp Asp Glu
    370                 375                 380

Ala Val Ala Glu Val Gly Leu Pro Thr Ala Lys Val Trp Gly Leu Tyr
385                 390                 395                 400

Met Ala Ala Ser Arg Val Gly Phe Glu Gln Asn Ser Ile Gln Leu His
                405                 410                 415

Gln Val Leu Ala Val Lys Leu Asp Glu Arg Gly Gly Asp Gly Gly Leu
            420                 425                 430

Pro Leu Arg Pro Trp Trp Thr Ala
        435                 440
```

<210> SEQ ID NO 55
<211> LENGTH: 381
<212> TYPE: DNA
<213> ORGANISM: Unknown
<220> FEATURE:
<223> OTHER INFORMATION: Mycobacterium vanbaalenii

<400> SEQUENCE: 55

```
gtgatccgct ttctgctgcg cgtcgcggtc tttctcggat cgtcggcgat cgggctactg      60

gtggccggct ggctggtgcc gggggtgtcg ctgtcggtgc tgggcttcgt caccgcggtg     120

gtgatcttca cggtggcaca agggattctg tcgccgttct tcctgaagat ggccagccgc     180

tacgcgtcgg ccttcctcgg cggcatcggc ctggtgtcca cgttcgtggc gctgctgctc     240
```

-continued gcgtcgctgc tgtccaacgg gctcagcatc cgcggcgtcg ggtcgtggat cgcggccacg 300
gtggtggtct ggctggtcac agccctggcg accgtcgtgc tgcccgttct ggtgctgcgg 360
gagaagaaga aagcagcctg a 381

<210> SEQ ID NO 56
<211> LENGTH: 126
<212> TYPE: PRT
<213> ORGANISM: Unknown
<220> FEATURE:
<223> OTHER INFORMATION: Mycobacterium vanbaalenii

<400> SEQUENCE: 56

```
Val Ile Arg Phe Leu Leu Arg Val Ala Val Phe Leu Gly Ser Ser Ala
1               5                   10                  15

Ile Gly Leu Leu Val Ala Gly Trp Leu Val Pro Gly Val Ser Leu Ser
            20                  25                  30

Val Leu Gly Phe Val Thr Ala Val Val Ile Phe Thr Val Ala Gln Gly
        35                  40                  45

Ile Leu Ser Pro Phe Phe Leu Lys Met Ala Ser Arg Tyr Ala Ser Ala
    50                  55                  60

Phe Leu Gly Gly Ile Gly Leu Val Ser Thr Phe Val Ala Leu Leu Leu
65                  70                  75                  80

Ala Ser Leu Leu Ser Asn Gly Leu Ser Ile Arg Gly Val Gly Ser Trp
                85                  90                  95

Ile Ala Ala Thr Val Val Val Trp Leu Val Thr Ala Leu Ala Thr Val
            100                 105                 110

Val Leu Pro Val Leu Val Leu Arg Glu Lys Lys Lys Ala Ala
        115                 120                 125
```

<210> SEQ ID NO 57
<211> LENGTH: 1452
<212> TYPE: DNA
<213> ORGANISM: Rhodococcus opacus

<400> SEQUENCE: 57
atgcgggagg gtggacgccc cttccgtgcg catcgcactc tgcccgtcac cgggatcgac 60
gctcaccgcg ccggcgtcga acggcttctc gcgtcctacc gcgcgattcc cacggacgcc 120
accgtgcgac tcgcgaagaa gacgtccaac ctgttccggg cgcgggccca gaccagcgca 180
cccggcctcg acgtctccgg gctcggcgga gtcatctcgg tcgacgagca ggaccggacc 240
gcggatgtcg ccggaatgtg cacgtacgaa gacctggtgg acgccaccct cccgtacggg 300
ctggcgccgc tggtggttcc gcaactcaag accatcacac tcggcggcgc ggtcaccggc 360
ctcggcatcg agtcgacgtc gttccgcaac gggctccccc acgaatcggt cctcgagatc 420
gacgtcctga ccggaagcgg cgacatcgtc accgcgagac cggaaggcga gaactccgac 480
ctgttctggg ggttccccaa ctcctacgga accctcggct actccacccg actgcgcatc 540
cagctcgaac ccgtcaaacg gtatgtggca ctgcgccatc tgcgtttcga ctccctggac 600
gagctgcagt cggcaatgga tcgcatcgtc accgagcgcg tccacgacgg catccccgtc 660
gactatctgg acggcgtcgt gttcaccgcg tccgagagtt acctgacact gggccatcag 720
accgacgagg gcggccccgt cagcgactac accgggcaga acatcttcta ccggtccatc 780
cagcacagtt ccgtgaacca ccccaaaacg gacaaactca ccatccgaga ctacctgtgg 840
cgctgggaca ccgactggtt ctggtgctcg cgcgccttcg gcgcccagaa ccccaccatc 900
cgccggctgt ggccgaagaa cctcctccgc agcagcttct actggaagct catcgccctc 960

-continued

```
gaccacaagt acgacatcgg cgaccgactc gagaagcgca agggcaaccc gccacgcgaa   1020

cgcgtcgtgc aggacgtcga agtgcccatc gagcgcaccg cggacttcgt ccgctggttc   1080

ctcgacgaaa tcccgatcga accgctgtgg ctgtgcccgt tgcggttgcg ggaacctgcc   1140

cccgccggcg cgtcctcgca acgcccctgg cccctgtacc ccctcgaacc gaaacgcacg   1200

tacgtgaaca tcggattctg gtcatcggtg cccatcgttc cgggccgacc cgaggggggcc  1260

gcgaatcggc tgatcgaaga caaggtcagt gacttcgacg gacacaagtc cctctactcc   1320

gattcgtact attcacgcga agatttcgaa cgcctctact acggcggcga tcgatacacg   1380

gaactgaaaa aacgctacga cccgaaatca cgattactgg accttttctc caaggcggtg   1440

caacgtcgat ga                                                       1452
```

<210> SEQ ID NO 58
<211> LENGTH: 483
<212> TYPE: PRT
<213> ORGANISM: Rhodococcus opacus

<400> SEQUENCE: 58

```
Met Arg Glu Gly Gly Arg Pro Phe Arg Ala His Arg Thr Leu Pro Val
1               5                   10                  15

Thr Gly Ile Asp Ala His Arg Ala Gly Val Glu Arg Leu Leu Ala Ser
            20                  25                  30

Tyr Arg Ala Ile Pro Thr Asp Ala Thr Val Arg Leu Ala Lys Lys Thr
        35                  40                  45

Ser Asn Leu Phe Arg Ala Arg Ala Gln Thr Ser Ala Pro Gly Leu Asp
    50                  55                  60

Val Ser Gly Leu Gly Gly Val Ile Ser Val Asp Glu Gln Asp Arg Thr
65                  70                  75                  80

Ala Asp Val Ala Gly Met Cys Thr Tyr Glu Asp Leu Val Asp Ala Thr
                85                  90                  95

Leu Pro Tyr Gly Leu Ala Pro Leu Val Val Pro Gln Leu Lys Thr Ile
            100                 105                 110

Thr Leu Gly Gly Ala Val Thr Gly Leu Gly Ile Glu Ser Thr Ser Phe
        115                 120                 125

Arg Asn Gly Leu Pro His Glu Ser Val Leu Glu Ile Asp Val Leu Thr
    130                 135                 140

Gly Ser Gly Asp Ile Val Thr Ala Arg Pro Glu Gly Glu Asn Ser Asp
145                 150                 155                 160

Leu Phe Trp Gly Phe Pro Asn Ser Tyr Gly Thr Leu Gly Tyr Ser Thr
                165                 170                 175

Arg Leu Arg Ile Gln Leu Glu Pro Val Lys Arg Tyr Val Ala Leu Arg
            180                 185                 190

His Leu Arg Phe Asp Ser Leu Asp Glu Leu Gln Ser Ala Met Asp Arg
        195                 200                 205

Ile Val Thr Glu Arg Val His Asp Gly Ile Pro Val Asp Tyr Leu Asp
    210                 215                 220

Gly Val Val Phe Thr Ala Ser Glu Ser Tyr Leu Thr Leu Gly His Gln
225                 230                 235                 240

Thr Asp Glu Gly Gly Pro Val Ser Asp Tyr Thr Gly Gln Asn Ile Phe
                245                 250                 255

Tyr Arg Ser Ile Gln His Ser Ser Val Asn His Pro Lys Thr Asp Lys
            260                 265                 270

Leu Thr Ile Arg Asp Tyr Leu Trp Arg Trp Asp Thr Asp Trp Phe Trp
```

```
        275                 280                 285

Cys Ser Arg Ala Phe Gly Ala Gln Asn Pro Thr Ile Arg Arg Leu Trp
    290                 295                 300

Pro Lys Asn Leu Leu Arg Ser Ser Phe Tyr Trp Lys Leu Ile Ala Leu
305                 310                 315                 320

Asp His Lys Tyr Asp Ile Gly Asp Arg Leu Glu Lys Arg Lys Gly Asn
                325                 330                 335

Pro Pro Arg Glu Arg Val Val Gln Asp Val Glu Val Pro Ile Glu Arg
            340                 345                 350

Thr Ala Asp Phe Val Arg Trp Phe Leu Asp Glu Ile Pro Ile Glu Pro
        355                 360                 365

Leu Trp Leu Cys Pro Leu Arg Leu Arg Glu Pro Ala Pro Ala Gly Ala
    370                 375                 380

Ser Ser Gln Arg Pro Trp Pro Leu Tyr Pro Leu Glu Pro Lys Arg Thr
385                 390                 395                 400

Tyr Val Asn Ile Gly Phe Trp Ser Ser Val Pro Ile Val Pro Gly Arg
                405                 410                 415

Pro Glu Gly Ala Ala Asn Arg Leu Ile Glu Asp Lys Val Ser Asp Phe
            420                 425                 430

Asp Gly His Lys Ser Leu Tyr Ser Asp Ser Tyr Tyr Ser Arg Glu Asp
        435                 440                 445

Phe Glu Arg Leu Tyr Tyr Gly Gly Asp Arg Tyr Thr Glu Leu Lys Lys
    450                 455                 460

Arg Tyr Asp Pro Lys Ser Arg Leu Leu Asp Leu Phe Ser Lys Ala Val
465                 470                 475                 480

Gln Arg Arg


<210> SEQ ID NO 59
<211> LENGTH: 1302
<212> TYPE: DNA
<213> ORGANISM: Rhodococcus opacus

<400> SEQUENCE: 59

atgacaactc tgaaagcttc acgctcccag gaccacaagc tgaccatcgc agagattctc      60

gaaactctgt ccgacggcat gctccccctg cggttctccg cctacgacgg cagcgccgcc     120

ggcccggagg acgcccccta cggtctccac ctcaagacga cccgaggcac cacctacctg     180

gcgaccgccc ccggcgacct cggcatggcc cgggcctacg tgtccggcga cctcgaggcc     240

cgcggcgtcc accccggcga cccgtacgag atcctccgcg tgatgggcga cgaactgcac     300

ttccgccgtc cgtccgcgct cacgctcgcc gccatcacgc gctcgctcgg ctgggatctg     360

ctgcgcccca tcgcccctcc cccgcaggag catctcccgc ggtggcgtcg agtcgcggaa     420

gggttgcggc actccaagtc ccgcgacgcc gaggtcatcc accaccacta cgacgtctcg     480

aacaccttct acgagtatgt cctcggcccg tccatgacgt acacgtgcgc ctgctacgag     540

aacgccgagc agaccctcga agaggcacag gacaacaagt accgcctcgt cttcgagaag     600

ctcggcctcc agcccggcga ccgactgctc gacatcggtt gcggctgggg atcgatggtc     660

cggtacgccg cccgccgcgg cgtcaaggtc atcggcgcca ccctgtcccg agagcaggcc     720

gaatgggcac agaaggccat cgccgaagaa ggactgtccg acctcgccga ggtccggttc     780

tccgactacc gtgacgtccc cgagaccgga ttcgacgcca tctcctcgat cggcctgacc     840

gagcacatcg gcgtcggcaa ctaccccgcc tacttcggac tgctgcagag caagctccgc     900

gagggcggcc ggctgctgaa ccactgcatc acccggcccg acaaccagag tcaggcacgc     960
```

gcgggcggct tcatcgaccg gtacgtcttc cccgacggcg aactcaccgg ctccggacgc 1020
atcatcaccg agatccagaa cgtcggactc gaggtgcggc acgaggagaa tctgcgcgag 1080
cactacgcac tcaccctcgc cggctggtgc cagaacctcg tcgacaactg ggacgcctgc 1140
gtcgccgagg tcggcgaagg caccgcacgt gtgtggggtc tctacatggc cgggtcgcga 1200
ctgggcttcg aacgcaacgt cgttcagctg caccaggtcc tcgccgtcaa gctcggaccc 1260
aagggcgagg cgcatgtgcc gctgcgtccg tggtggaagt ag 1302

<210> SEQ ID NO 60
<211> LENGTH: 433
<212> TYPE: PRT
<213> ORGANISM: Rhodococcus opacus

<400> SEQUENCE: 60

Met Thr Thr Leu Lys Ala Ser Arg Ser Gln Asp His Lys Leu Thr Ile
1 5 10 15

Ala Glu Ile Leu Glu Thr Leu Ser Asp Gly Met Leu Pro Leu Arg Phe
20 25 30

Ser Ala Tyr Asp Gly Ser Ala Ala Gly Pro Glu Asp Ala Pro Tyr Gly
35 40 45

Leu His Leu Lys Thr Thr Arg Gly Thr Thr Tyr Leu Ala Thr Ala Pro
50 55 60

Gly Asp Leu Gly Met Ala Arg Ala Tyr Val Ser Gly Asp Leu Glu Ala
65 70 75 80

Arg Gly Val His Pro Gly Asp Pro Tyr Glu Ile Leu Arg Val Met Gly
85 90 95

Asp Glu Leu His Phe Arg Arg Pro Ser Ala Leu Thr Leu Ala Ala Ile
100 105 110

Thr Arg Ser Leu Gly Trp Asp Leu Leu Arg Pro Ile Ala Pro Pro Pro
115 120 125

Gln Glu His Leu Pro Arg Trp Arg Arg Val Ala Glu Gly Leu Arg His
130 135 140

Ser Lys Ser Arg Asp Ala Glu Val Ile His His His Tyr Asp Val Ser
145 150 155 160

Asn Thr Phe Tyr Glu Tyr Val Leu Gly Pro Ser Met Thr Tyr Thr Cys
165 170 175

Ala Cys Tyr Glu Asn Ala Glu Gln Thr Leu Glu Glu Ala Gln Asp Asn
180 185 190

Lys Tyr Arg Leu Val Phe Glu Lys Leu Gly Leu Gln Pro Gly Asp Arg
195 200 205

Leu Leu Asp Ile Gly Cys Gly Trp Gly Ser Met Val Arg Tyr Ala Ala
210 215 220

Arg Arg Gly Val Lys Val Ile Gly Ala Thr Leu Ser Arg Glu Gln Ala
225 230 235 240

Glu Trp Ala Gln Lys Ala Ile Ala Glu Glu Gly Leu Ser Asp Leu Ala
245 250 255

Glu Val Arg Phe Ser Asp Tyr Arg Asp Val Pro Glu Thr Gly Phe Asp
260 265 270

Ala Ile Ser Ser Ile Gly Leu Thr Glu His Ile Gly Val Gly Asn Tyr
275 280 285

Pro Ala Tyr Phe Gly Leu Leu Gln Ser Lys Leu Arg Glu Gly Gly Arg
290 295 300

Leu Leu Asn His Cys Ile Thr Arg Pro Asp Asn Gln Ser Gln Ala Arg

-continued

```
305                 310                 315                 320

Ala Gly Gly Phe Ile Asp Arg Tyr Val Phe Pro Asp Gly Glu Leu Thr
                325                 330                 335

Gly Ser Gly Arg Ile Ile Thr Glu Ile Gln Asn Val Gly Leu Glu Val
            340                 345                 350

Arg His Glu Glu Asn Leu Arg Glu His Tyr Ala Leu Thr Leu Ala Gly
        355                 360                 365

Trp Cys Gln Asn Leu Val Asp Asn Trp Asp Ala Cys Val Ala Glu Val
    370                 375                 380

Gly Glu Gly Thr Ala Arg Val Trp Gly Leu Tyr Met Ala Gly Ser Arg
385                 390                 395                 400

Leu Gly Phe Glu Arg Asn Val Val Gln Leu His Gln Val Leu Ala Val
                405                 410                 415

Lys Leu Gly Pro Lys Gly Glu Ala His Val Pro Leu Arg Pro Trp Trp
            420                 425                 430

Lys
```

<210> SEQ ID NO 61
<211> LENGTH: 1428
<212> TYPE: DNA
<213> ORGANISM: Unknown
<220> FEATURE:
<223> OTHER INFORMATION: Streptomyces regnsis

<400> SEQUENCE: 61

```
atgatcacac tggcaggccg ggccggtgcg cgcgatcatg ggtgtatggc cttcggtgcc     60

gccatcccca cggggtcggg acacgccggg tacgccgagc gcgtcgcaac ccttcgcgcc    120

cacctggccg acctcccgga ggggacgccg gtccggctgg cgaagggcac ctcgaacctg    180

ttccggccgc ggtcccgcgc cacggcgggg ctcgacgtgt cggccttcga ccacgtgctg    240

tcgatcgatc cgcagaaccg gaccgccgac gtcgagggca tggtcaccta cgagcggctc    300

gtcgacgcga cgttgccgca cggcctgatg ccgctcgtcg ttccgcagct caagacgatc    360

acgctgggcg gggcggtcac gggactgggc atcgagtcgt cgtcgttccg cgagggcatg    420

ccccacgaat ccgtggtgga gatggacatc ctcacgggtg cgggagacgt ggtgaccgcg    480

accccggacg gcgagcacag cgacctgttc ttcgggttcc ccaactccta cggaacgctg    540

ggatacgcgc tgcgcctgcg gatcgaactc gcgccggtgc gcccgtacgt acgactcgaa    600

cacctgcgtt tctccgatcc ggcacgctac ttcgagcgcc tggcgcgtgc gtgccgcgac    660

cgggaggccg acttcgtcga cggcaccgtc ttcgctcccg acgagctgta cctgacgttg    720

gccacgttca gcggcgagcc cgacgaggtc agcgactaca cgtggatgga cgtctactac    780

cgctcgatca gggagaagac ggtcgaccat ctgccgatcc gcgactacct gtggcggtgg    840

gacaccgact ggttctggtg ttcgcgcgcg ctcggagcgc agaaccggct cgtgcggctg    900

ctcgcgggtc cacgtctgct gcgttccgat gtgtactgga agatcgtcgg tttcgaacgc    960

aggcaccggc tgtgggagcg tgcgagccgg ctgctgggca ggcccgagcg cgaagcggtg   1020

atgcaggaca tcgaggtgcc ggtgcaccgc gccgaggagt tcctgacgtt cctgcaccgg   1080

gagatcccca tcagtccggt gtggatctgc ccgctgagtg ggcgggacgc gcgccggtgg   1140

ccgctgtacg agctcgaccc ggacgagctg tacgtcaact tcggtttctg ggcacggtg    1200

ccgctcgagc caggcgaacc gcagggttcg cacaaccggc gggtggagaa cgtggttacc   1260

gaactcgacg gacggaaatc cctgtactcg gagagtttct acgaccgcga cacgttctgg   1320
```

-continued

```
cggttgtacg gagggaatca aggacagacg taccaggccc tgaagcatcg ctacgacccg   1380

aacgggagat tgctggacct gtacgccaag tgcgttcaag cgaggtga                1428


<210> SEQ ID NO 62
<211> LENGTH: 475
<212> TYPE: PRT
<213> ORGANISM: Unknown
<220> FEATURE:
<223> OTHER INFORMATION: Streptomyces regnsis

<400> SEQUENCE: 62

Met Ile Thr Leu Ala Gly Arg Ala Gly Ala Arg Asp His Gly Cys Met
1               5                   10                  15

Ala Phe Gly Ala Ala Ile Pro Thr Gly Ser Gly His Ala Gly Tyr Ala
            20                  25                  30

Glu Arg Val Ala Thr Leu Arg Ala His Leu Ala Asp Leu Pro Glu Gly
        35                  40                  45

Thr Pro Val Arg Leu Ala Lys Gly Thr Ser Asn Leu Phe Arg Pro Arg
    50                  55                  60

Ser Arg Ala Thr Ala Gly Leu Asp Val Ser Ala Phe Asp His Val Leu
65                  70                  75                  80

Ser Ile Asp Pro Gln Asn Arg Thr Ala Asp Val Glu Gly Met Val Thr
                85                  90                  95

Tyr Glu Arg Leu Val Asp Ala Thr Leu Pro His Gly Leu Met Pro Leu
            100                 105                 110

Val Val Pro Gln Leu Lys Thr Ile Thr Leu Gly Gly Ala Val Thr Gly
        115                 120                 125

Leu Gly Ile Glu Ser Ser Ser Phe Arg Glu Gly Met Pro His Glu Ser
    130                 135                 140

Val Val Glu Met Asp Ile Leu Thr Gly Ala Gly Asp Val Val Thr Ala
145                 150                 155                 160

Thr Pro Asp Gly Glu His Ser Asp Leu Phe Phe Gly Phe Pro Asn Ser
                165                 170                 175

Tyr Gly Thr Leu Gly Tyr Ala Leu Arg Leu Arg Ile Glu Leu Ala Pro
            180                 185                 190

Val Arg Pro Tyr Val Arg Leu Glu His Leu Arg Phe Ser Asp Pro Ala
        195                 200                 205

Arg Tyr Phe Glu Arg Leu Ala Arg Ala Cys Arg Asp Arg Glu Ala Asp
    210                 215                 220

Phe Val Asp Gly Thr Val Phe Ala Pro Asp Glu Leu Tyr Leu Thr Leu
225                 230                 235                 240

Ala Thr Phe Ser Gly Glu Pro Asp Glu Val Ser Asp Tyr Thr Trp Met
                245                 250                 255

Asp Val Tyr Tyr Arg Ser Ile Arg Glu Lys Thr Val Asp His Leu Pro
            260                 265                 270

Ile Arg Asp Tyr Leu Trp Arg Trp Asp Thr Asp Trp Phe Trp Cys Ser
        275                 280                 285

Arg Ala Leu Gly Ala Gln Asn Arg Leu Val Arg Leu Leu Ala Gly Pro
    290                 295                 300

Arg Leu Leu Arg Ser Asp Val Tyr Trp Lys Ile Val Gly Phe Glu Arg
305                 310                 315                 320

Arg His Arg Leu Trp Glu Arg Ala Ser Arg Leu Leu Gly Arg Pro Glu
                325                 330                 335

Arg Glu Ala Val Met Gln Asp Ile Glu Val Pro Val His Arg Ala Glu
            340                 345                 350
```

```
Glu Phe Leu Thr Phe Leu His Arg Glu Ile Pro Ile Ser Pro Val Trp
        355                 360                 365

Ile Cys Pro Leu Ser Gly Arg Asp Ala Arg Arg Trp Pro Leu Tyr Glu
    370                 375                 380

Leu Asp Pro Asp Glu Leu Tyr Val Asn Phe Gly Phe Trp Gly Thr Val
385                 390                 395                 400

Pro Leu Glu Pro Gly Glu Pro Gln Gly Ser His Asn Arg Arg Val Glu
                405                 410                 415

Asn Val Val Thr Glu Leu Asp Gly Arg Lys Ser Leu Tyr Ser Glu Ser
            420                 425                 430

Phe Tyr Asp Arg Asp Thr Phe Trp Arg Leu Tyr Gly Gly Asn Gln Gly
        435                 440                 445

Gln Thr Tyr Gln Ala Leu Lys His Arg Tyr Asp Pro Asn Gly Arg Leu
    450                 455                 460

Leu Asp Leu Tyr Ala Lys Cys Val Gln Ala Arg
465                 470                 475


<210> SEQ ID NO 63
<211> LENGTH: 1317
<212> TYPE: DNA
<213> ORGANISM: Unknown
<220> FEATURE:
<223> OTHER INFORMATION: Streptomyces regnsis

<400> SEQUENCE: 63

ttggcgtcgt cggggccacc gctgcccgcc agggcggggt cccgatcggc tgactcgacg      60

gcgttggacg cgatcctgcg ccgcgtgctc ggggacgacc cgcccgtggc cgtgaccgcg     120

ttcgacggca cggtggtcgg tgacccggac tcggcgctgc agctgcacat ccgcacgccg     180

acggccctga gctacgtgct caccgcgccc aacgaactcg ggttggcgcg ggcctacgtc     240

acgggacatc tcgacgtgac cggcgacgtc taccaggtgc tgcgcgcact gacgagcgtg     300

gccgagaacc tcacgacggc cgatcggatg tggctggccg gccgtctcgc acgggacttc     360

accgaccggc tgcggccggt gccgatcccc gtcgaggagg cgccgtcgcg gctccgcagg     420

accgcacgtg gcctccggca ttccaaggcg cgcgacagcg acgcgatctc ccggcactac     480

gacgtctcga accgcttcta cgagctggtg ctcggcccgt cgatggccta cacgtgcgcc     540

tgctacccgg aggatgcggc cacgctggag caggcacagt tccacaagtt cgacctcgtg     600

tgccgaaagc tcggtctgaa gccggggatg cgcctgctcg acgtgggctg cggttggggc     660

ggcatggtcg cccacgccgt ggagcactac ggggtgcggg cgatcggcgt caccctctcg     720

cgccagcagg cggagtgggg acagcgggac ctcgaggcca ggggcctggc cgatcgcggc     780

gagatccgcc atctggacta ccgcgacgtg cccgagaccg ggttcgacgc ggtgtcgtcc     840

atcgggctca ccgaacacat cggcgcgcgg aacctgccgt cgtacttccg cttcctgcac     900

tcgaagttgc gtcccggcgg acggttgctc aaccactgca tcgtgcgccc gcacacctac     960

gactcccatc ggacgggccc gttcatcgac cgctacgtct tcccggacgg cgaactcgag    1020

ggcgtcggga cgatcgtgtc ggcgatgcag gaccacgggt tcgaggtacg gcacgcggag    1080

aacctgcggg aacactacgg gcgcaccctc gcggcgtggt gcgccaatct cgacgcgcac    1140

tgggaggcgg cggtggccga ggcgggcgtg cagcgggcca gggtgtgggc gctgtacatg    1200

gcggcctccc ggctgtcgtt cgaacgtcat gagctcgagc tgcagcaggt gctcggcgtg    1260

aaacccgacg ccgcgggcgg gtcgtcgatg ccgcttcgcc cggactgggg ggtgtga       1317
```

<210> SEQ ID NO 64
<211> LENGTH: 438
<212> TYPE: PRT
<213> ORGANISM: Unknown
<220> FEATURE:
<223> OTHER INFORMATION: Streptomyces regnsis

<400> SEQUENCE: 64

```
Leu Ala Ser Ser Gly Pro Pro Leu Pro Ala Arg Ala Gly Ser Arg Ser
1               5                   10                  15

Ala Asp Ser Thr Ala Leu Asp Ala Ile Leu Arg Arg Val Leu Gly Asp
            20                  25                  30

Asp Pro Pro Val Ala Val Thr Ala Phe Asp Gly Thr Val Val Gly Asp
        35                  40                  45

Pro Asp Ser Ala Leu Gln Leu His Ile Arg Thr Pro Thr Ala Leu Ser
    50                  55                  60

Tyr Val Leu Thr Ala Pro Asn Glu Leu Gly Leu Ala Arg Ala Tyr Val
65                  70                  75                  80

Thr Gly His Leu Asp Val Thr Gly Asp Val Tyr Gln Val Leu Arg Ala
                85                  90                  95

Leu Thr Ser Val Ala Glu Asn Leu Thr Thr Ala Asp Arg Met Trp Leu
            100                 105                 110

Ala Gly Arg Leu Ala Arg Asp Phe Thr Asp Arg Leu Arg Pro Val Pro
        115                 120                 125

Ile Pro Val Glu Glu Ala Pro Ser Arg Leu Arg Arg Thr Ala Arg Gly
    130                 135                 140

Leu Arg His Ser Lys Ala Arg Asp Ser Asp Ala Ile Ser Arg His Tyr
145                 150                 155                 160

Asp Val Ser Asn Arg Phe Tyr Glu Leu Val Leu Gly Pro Ser Met Ala
                165                 170                 175

Tyr Thr Cys Ala Cys Tyr Pro Glu Asp Ala Ala Thr Leu Glu Gln Ala
            180                 185                 190

Gln Phe His Lys Phe Asp Leu Val Cys Arg Lys Leu Gly Leu Lys Pro
        195                 200                 205

Gly Met Arg Leu Leu Asp Val Gly Cys Gly Trp Gly Gly Met Val Ala
    210                 215                 220

His Ala Val Glu His Tyr Gly Val Arg Ala Ile Gly Val Thr Leu Ser
225                 230                 235                 240

Arg Gln Gln Ala Glu Trp Gly Gln Arg Asp Leu Glu Ala Arg Gly Leu
                245                 250                 255

Ala Asp Arg Gly Glu Ile Arg His Leu Asp Tyr Arg Asp Val Pro Glu
            260                 265                 270

Thr Gly Phe Asp Ala Val Ser Ser Ile Gly Leu Thr Glu His Ile Gly
        275                 280                 285

Ala Arg Asn Leu Pro Ser Tyr Phe Arg Phe Leu His Ser Lys Leu Arg
    290                 295                 300

Pro Gly Gly Arg Leu Leu Asn His Cys Ile Val Arg Pro His Thr Tyr
305                 310                 315                 320

Asp Ser His Arg Thr Gly Pro Phe Ile Asp Arg Tyr Val Phe Pro Asp
                325                 330                 335

Gly Glu Leu Glu Gly Val Gly Thr Ile Val Ser Ala Met Gln Asp His
            340                 345                 350

Gly Phe Glu Val Arg His Ala Glu Asn Leu Arg Glu His Tyr Gly Arg
        355                 360                 365
```

```
Thr Leu Ala Ala Trp Cys Ala Asn Leu Asp Ala His Trp Glu Ala Ala
    370                 375                 380

Val Ala Glu Ala Gly Val Gln Arg Ala Arg Val Trp Ala Leu Tyr Met
385                 390                 395                 400

Ala Ala Ser Arg Leu Ser Phe Glu Arg His Glu Leu Glu Leu Gln Gln
                405                 410                 415

Val Leu Gly Val Lys Pro Asp Ala Ala Gly Gly Ser Ser Met Pro Leu
            420                 425                 430

Arg Pro Asp Trp Gly Val
        435
```

<210> SEQ ID NO 65
<211> LENGTH: 501
<212> TYPE: DNA
<213> ORGANISM: Unknown
<220> FEATURE:
<223> OTHER INFORMATION: Streptomyces regnsis

<400> SEQUENCE: 65

```
gtgcgcgtgg caccgccccg catcggtgcc acacccggcg cggtgggcgc accggactac     60

gcctccgcct tccgcgtgcc gacggcggcg gcccgcaggc gttcgccgcg ggaatggacg    120

cgtgcggtgt tcgagggcgc gcccgcgccg ttggcgctgt tcgtgcgttg ggatggctg    180

gccgtgctcc ggttgcgcct cagtgaggac cccgaggcgg tggcgggctg gagacccacg    240

acgctcgacc ccggcacctc cgacgccccc gacacctctg agacagccgg aaactccgac    300

gctgccgcac tggaggccga atcgccgctg ctggaggcgt gcaacgtggc gttcgtcgac    360

gacgacggtg tcacgtgggc gacctacgtc cggttccgtg gtggcctcgg ccgcgcggtg    420

tgggcggtgg cggcgcggat ccaccacgtc gtcatcccct acctgctgcg gcgggcggtg    480

cggcgcacgg aacgggagtg a                                              501
```

<210> SEQ ID NO 66
<211> LENGTH: 166
<212> TYPE: PRT
<213> ORGANISM: Unknown
<220> FEATURE:
<223> OTHER INFORMATION: Streptomyces regnsis

<400> SEQUENCE: 66

```
Val Arg Val Ala Pro Pro Arg Ile Gly Ala Thr Pro Gly Ala Val Gly
1               5                   10                  15

Ala Pro Asp Tyr Ala Ser Ala Phe Arg Val Pro Thr Ala Ala Ala Arg
            20                  25                  30

Arg Arg Ser Pro Arg Glu Trp Thr Arg Ala Val Phe Glu Gly Ala Pro
        35                  40                  45

Ala Pro Leu Ala Leu Phe Val Arg Trp Gly Trp Leu Ala Val Leu Arg
    50                  55                  60

Leu Arg Leu Ser Glu Asp Pro Glu Ala Val Ala Gly Trp Arg Pro Thr
65                  70                  75                  80

Thr Leu Asp Pro Gly Thr Ser Asp Ala Pro Asp Thr Ser Glu Thr Ala
                85                  90                  95

Gly Asn Ser Asp Ala Ala Ala Leu Glu Ala Glu Ser Pro Leu Leu Glu
            100                 105                 110

Ala Cys Asn Val Ala Phe Val Asp Asp Asp Gly Val Thr Trp Ala Thr
        115                 120                 125

Tyr Val Arg Phe Arg Gly Gly Leu Gly Arg Ala Val Trp Ala Val Ala
    130                 135                 140
```

Ala Arg Ile His His Val Val Ile Pro Tyr Leu Leu Arg Arg Ala Val
145 150 155 160

Arg Arg Thr Glu Arg Glu
165

<210> SEQ ID NO 67
<211> LENGTH: 1413
<212> TYPE: DNA
<213> ORGANISM: Unknown
<220> FEATURE:
<223> OTHER INFORMATION: Thermobifida fusca

<400> SEQUENCE: 67
gtgaactgtc agtcttccgc gtccaacctc gccaaccaca tcaacgcggt gtacgagctg 60
cgccgcgcct atgcgcggct gtccgccgac aagccggtgc gcctggcgaa gaccacctcc 120
aacctcttcc gcttccgcag ccgggacgat gccgcgcgtc tcgacgtcag cgctttcacc 180
tcggtgatca gcatcgacac ggaggcgcgg gtcgcggagg tgggcggcat gaccacctac 240
gaggacctgg tcgccgccac cctgcggcat ggcctgatgc cgccggtggt tccgcaactg 300
cgcacgatca ccctgggcgg tgcggtcacc gggctgggga tcgaatcctc gtccttccgc 360
aacgggctcc cgcacgagtc agtggaagag atggagatcc tcaccggcag cggccaggtg 420
gtggtggccc ggcgcgacaa cgagcaccgc gacctgttct acggtttccc caactcgtac 480
ggcaccctcg gttacgcgct gcggctccgc atccagctcg aaccggtccg cccctacgtc 540
cacctgcggc acctgcggtt caccgatgcc gcagcggcca tggccgcgct ggagcagatc 600
tgcgcggacc gcacccacga cggggagacc gtcgacttcg tcgacggcgt cgtgttcgcc 660
cgcaacgagc tgtacctgac cttggggacg ttcaccgacc gggctccgtg gaccagcgac 720
tacaccggaa ccgacatcta ctaccggtcg atcccccgct acgcgggccc cggccccggc 780
gactacctca ccacgcacga ctacctgtgg cggtgggaca ccgactggtt ctggtgctcc 840
cgcgccttcg gactgcagca tcccgtggtg cgccgcctgt ggccgcgttc cttgaaacgc 900
tccgacgtct accgcaagct cgtcgcctgg gaccggcgca ctgacgcgag ccgcctgctc 960
gactactacc gcgggcgccc gcccaaggaa ccggtgatcc aggacatcga ggttgaggtg 1020
gggcgggctg ccgagttcct cgacttcttc cacaccgaga tcggcatgtc cccggtgtgg 1080
ctgtgcccgc tgcggctgcg agaagacaca gccgacgata cggaaccggt ctggccgctc 1140
taccccctca aaccccgccg cctctacgtc aacttcgggt tttggggcct cgttccgatc 1200
cgtcccggtg gaggcaggac ataccacaac cggctgatcg aaaaagaagt gacccggttg 1260
ggcgggcaca agtcgctcta ctcggacgcc ttctacgacg aggacgagtt ctgggagctc 1320
tacaacgggg agatctaccg caagctcaaa gctgcctacg accccgacgg tcgactgctc 1380
gacctgtaca ccaagtgcgt cggcggcggg tga 1413

<210> SEQ ID NO 68
<211> LENGTH: 470
<212> TYPE: PRT
<213> ORGANISM: Unknown
<220> FEATURE:
<223> OTHER INFORMATION: Thermobifida fusca

<400> SEQUENCE: 68

Val Asn Cys Gln Ser Ser Ala Ser Asn Leu Ala Asn His Ile Asn Ala
1 5 10 15

Val Tyr Glu Leu Arg Arg Ala Tyr Ala Arg Leu Ser Ala Asp Lys Pro

-continued

```
            20                  25                  30

Val Arg Leu Ala Lys Thr Thr Ser Asn Leu Phe Arg Phe Arg Ser Arg
        35                  40                  45

Asp Asp Ala Ala Arg Leu Asp Val Ser Ala Phe Thr Ser Val Ile Ser
    50                  55                  60

Ile Asp Thr Glu Ala Arg Val Ala Glu Val Gly Gly Met Thr Thr Tyr
65                  70                  75                  80

Glu Asp Leu Val Ala Ala Thr Leu Arg His Gly Leu Met Pro Pro Val
                85                  90                  95

Val Pro Gln Leu Arg Thr Ile Thr Leu Gly Gly Ala Val Thr Gly Leu
            100                 105                 110

Gly Ile Glu Ser Ser Ser Phe Arg Asn Gly Leu Pro His Glu Ser Val
        115                 120                 125

Glu Glu Met Glu Ile Leu Thr Gly Ser Gly Gln Val Val Val Ala Arg
    130                 135                 140

Arg Asp Asn Glu His Arg Asp Leu Phe Tyr Gly Phe Pro Asn Ser Tyr
145                 150                 155                 160

Gly Thr Leu Gly Tyr Ala Leu Arg Leu Arg Ile Gln Leu Glu Pro Val
                165                 170                 175

Arg Pro Tyr Val His Leu Arg His Leu Arg Phe Thr Asp Ala Ala Ala
            180                 185                 190

Ala Met Ala Ala Leu Glu Gln Ile Cys Ala Asp Arg Thr His Asp Gly
        195                 200                 205

Glu Thr Val Asp Phe Val Asp Gly Val Val Phe Ala Arg Asn Glu Leu
    210                 215                 220

Tyr Leu Thr Leu Gly Thr Phe Thr Asp Arg Ala Pro Trp Thr Ser Asp
225                 230                 235                 240

Tyr Thr Gly Thr Asp Ile Tyr Tyr Arg Ser Ile Pro Arg Tyr Ala Gly
                245                 250                 255

Pro Gly Pro Gly Asp Tyr Leu Thr Thr His Asp Tyr Leu Trp Arg Trp
            260                 265                 270

Asp Thr Asp Trp Phe Trp Cys Ser Arg Ala Phe Gly Leu Gln His Pro
        275                 280                 285

Val Val Arg Arg Leu Trp Pro Arg Ser Leu Lys Arg Ser Asp Val Tyr
    290                 295                 300

Arg Lys Leu Val Ala Trp Asp Arg Arg Thr Asp Ala Ser Arg Leu Leu
305                 310                 315                 320

Asp Tyr Tyr Arg Gly Arg Pro Pro Lys Glu Pro Val Ile Gln Asp Ile
                325                 330                 335

Glu Val Glu Val Gly Arg Ala Ala Glu Phe Leu Asp Phe Phe His Thr
            340                 345                 350

Glu Ile Gly Met Ser Pro Val Trp Leu Cys Pro Leu Arg Leu Arg Glu
        355                 360                 365

Asp Thr Ala Asp Asp Thr Glu Pro Val Trp Pro Leu Tyr Pro Leu Lys
    370                 375                 380

Pro Arg Arg Leu Tyr Val Asn Phe Gly Phe Trp Gly Leu Val Pro Ile
385                 390                 395                 400

Arg Pro Gly Gly Gly Arg Thr Tyr His Asn Arg Leu Ile Glu Lys Glu
                405                 410                 415

Val Thr Arg Leu Gly Gly His Lys Ser Leu Tyr Ser Asp Ala Phe Tyr
            420                 425                 430

Asp Glu Asp Glu Phe Trp Glu Leu Tyr Asn Gly Glu Ile Tyr Arg Lys
        435                 440                 445
```

Leu Lys Ala Ala Tyr Asp Pro Asp Gly Arg Leu Leu Asp Leu Tyr Thr
    450                 455                 460

Lys Cys Val Gly Gly Gly
465                 470

<210> SEQ ID NO 69
<211> LENGTH: 1272
<212> TYPE: DNA
<213> ORGANISM: Unknown
<220> FEATURE:
<223> OTHER INFORMATION: Thermobifida fusca

<400> SEQUENCE: 69
atgcgactgg cggaggtatt cgaacgtgtc gtcggacccg atgcgcccgt ccacttccgg 60
gcctacgacg gcagcactgc gggagatcca cgcagtgaag tcgctatcgt ggttcgccac 120
ccggcagccg tcaactacat cgtccaagcg ccgggagcac tcggtttgac ccgcgcctac 180
gtggcgggat acctcgacgt cgaaggggac atgtacaccg cgctgcgggc aatggccgac 240
gtggtgttcc aggaccggcc gcggctgtcc cccggggaac tgctgcggat catccgcggg 300
atcgggtggg tgaagttcgt caaccggctt ccaccgccgc cgcaggaggt gcgccagtcc 360
cgcctcgccg ccctgggctg gcgccactcc aagcagcgcg acgccgaagc catccagcac 420
cactacgacg tctccaacgc cttctacgcc ctggtcttgg gcgagtcgat gacctacacc 480
tgcgcggtct acccgaccga gcaggccacg ctggagcagg cacagttctt caagcacgag 540
ctgatcgccc gcaagctcgg tcttgcccct gggatacgac tgctggatgt ggggtgcggc 600
tggggcggca tggtcatcca cgcggcccgg gagcacgggg tcaaagccct gggggtgacc 660
ctgtccaaag agcaggctga gtgggcgcag aagcggatcg cccacgaggg cctgggcgac 720
ctggcagaag tccggcacat ggactaccgg gacctgcccg acggcgagta cgacgcgatc 780
agctcgatcg ggttgaccga gcacgtcggc aaaaagaacg tgcccgccta cttcgcgtcg 840
ctgtaccgca agctcgtccc gggaggccgc ctgctcaacc actgcatcac ccggccccgc 900
aacgacctgc cgcccttcaa acgcggcggg gtgatcaacc gctacgtctt ccccgatggg 960
gagctggaag ggcccggctg gctgcaggcg gcgatgaacg acgccgggtt cgaaatccgc 1020
caccaggaga acctgcggga gcactacgca cggaccctgc gggactggct ggccaacctg 1080
gaccgcaact gggatgccgc ggtgcgggaa gtgggggagg gcacggcccg agtgtggcgg 1140
ctctacatgg ccgggtgcgt gctcggcttc gaacgcaacg tggtgcaact gcaccagatc 1200
ctcggggtga agctcgacgg gaccgaggcg cggatgccgc tgcgccccga cttcgaaccg 1260
ccgctgcctt aa 1272

<210> SEQ ID NO 70
<211> LENGTH: 423
<212> TYPE: PRT
<213> ORGANISM: Unknown
<220> FEATURE:
<223> OTHER INFORMATION: Thermobifida fusca

<400> SEQUENCE: 70

Met Arg Leu Ala Glu Val Phe Glu Arg Val Val Gly Pro Asp Ala Pro
1               5                   10                  15

Val His Phe Arg Ala Tyr Asp Gly Ser Thr Ala Gly Asp Pro Arg Ser
            20                  25                  30

Glu Val Ala Ile Val Val Arg His Pro Ala Ala Val Asn Tyr Ile Val
        35                  40                  45

```
Gln Ala Pro Gly Ala Leu Gly Leu Thr Arg Ala Tyr Val Ala Gly Tyr
    50                  55                  60

Leu Asp Val Glu Gly Asp Met Tyr Thr Ala Leu Arg Ala Met Ala Asp
65                  70                  75                  80

Val Val Phe Gln Asp Arg Pro Arg Leu Ser Pro Gly Glu Leu Leu Arg
                85                  90                  95

Ile Ile Arg Gly Ile Gly Trp Val Lys Phe Val Asn Arg Leu Pro Pro
            100                 105                 110

Pro Pro Gln Glu Val Arg Gln Ser Arg Leu Ala Ala Leu Gly Trp Arg
        115                 120                 125

His Ser Lys Gln Arg Asp Ala Glu Ala Ile Gln His His Tyr Asp Val
    130                 135                 140

Ser Asn Ala Phe Tyr Ala Leu Val Leu Gly Glu Ser Met Thr Tyr Thr
145                 150                 155                 160

Cys Ala Val Tyr Pro Thr Glu Gln Ala Thr Leu Glu Gln Ala Gln Phe
                165                 170                 175

Phe Lys His Glu Leu Ile Ala Arg Lys Leu Gly Leu Ala Pro Gly Ile
            180                 185                 190

Arg Leu Leu Asp Val Gly Cys Gly Trp Gly Gly Met Val Ile His Ala
        195                 200                 205

Ala Arg Glu His Gly Val Lys Ala Leu Gly Val Thr Leu Ser Lys Glu
    210                 215                 220

Gln Ala Glu Trp Ala Gln Lys Arg Ile Ala His Glu Gly Leu Gly Asp
225                 230                 235                 240

Leu Ala Glu Val Arg His Met Asp Tyr Arg Asp Leu Pro Asp Gly Glu
                245                 250                 255

Tyr Asp Ala Ile Ser Ser Ile Gly Leu Thr Glu His Val Gly Lys Lys
            260                 265                 270

Asn Val Pro Ala Tyr Phe Ala Ser Leu Tyr Arg Lys Leu Val Pro Gly
        275                 280                 285

Gly Arg Leu Leu Asn His Cys Ile Thr Arg Pro Arg Asn Asp Leu Pro
    290                 295                 300

Pro Phe Lys Arg Gly Gly Val Ile Asn Arg Tyr Val Phe Pro Asp Gly
305                 310                 315                 320

Glu Leu Glu Gly Pro Gly Trp Leu Gln Ala Ala Met Asn Asp Ala Gly
                325                 330                 335

Phe Glu Ile Arg His Gln Glu Asn Leu Arg Glu His Tyr Ala Arg Thr
            340                 345                 350

Leu Arg Asp Trp Leu Ala Asn Leu Asp Arg Asn Trp Asp Ala Ala Val
        355                 360                 365

Arg Glu Val Gly Glu Gly Thr Ala Arg Val Trp Arg Leu Tyr Met Ala
    370                 375                 380

Gly Cys Val Leu Gly Phe Glu Arg Asn Val Val Gln Leu His Gln Ile
385                 390                 395                 400

Leu Gly Val Lys Leu Asp Gly Thr Glu Ala Arg Met Pro Leu Arg Pro
                405                 410                 415

Asp Phe Glu Pro Pro Leu Pro
            420
```

<210> SEQ ID NO 71
<211> LENGTH: 447
<212> TYPE: DNA
<213> ORGANISM: Unknown
<220> FEATURE:

<223> OTHER INFORMATION: Thermobifida fusca

<400> SEQUENCE: 71
atggctgcga ccgatgacga ccggcaccac accaccgtcg ccctcgacct catcgacgcg 60
tatgtgcgcg ccgaccgcag aatgatcggt gaacgttccg cggggatcag cgcggaggcg 120
ggggagcgga tcgtctccac cctgaaagtg tgcgcggcct tccttgcccg ccgggtccag 180
gagaccgggg tgccgtggcg cgccgcggac tcccgggaag cggtcgcccg caccgtcgcc 240
gacctgctgg aacccgaggt ggaattcgcg gtcgtctccg cctgggaggc gtacgcgatc 300
ggggagcacg aggccgcctg ggtccgggcg cacggcgatc cgctggtctt cgtccacatg 360
ctggccgcgt tctccgctgc tatcggcaca gcggtctacg gccgtgagga gctgctgccc 420
acgctgcgca gggtgacagc acgataa 447

<210> SEQ ID NO 72
<211> LENGTH: 148
<212> TYPE: PRT
<213> ORGANISM: Unknown
<220> FEATURE:
<223> OTHER INFORMATION: Thermobifida fusca

<400> SEQUENCE: 72

Met Ala Ala Thr Asp Asp Asp Arg His His Thr Thr Val Ala Leu Asp
1 5 10 15

Leu Ile Asp Ala Tyr Val Arg Ala Asp Arg Arg Met Ile Gly Glu Arg
20 25 30

Ser Ala Gly Ile Ser Ala Glu Ala Gly Glu Arg Ile Val Ser Thr Leu
35 40 45

Lys Val Cys Ala Ala Phe Leu Ala Arg Arg Val Gln Glu Thr Gly Val
50 55 60

Pro Trp Arg Ala Ala Asp Ser Arg Glu Ala Val Ala Arg Thr Val Ala
65 70 75 80

Asp Leu Leu Glu Pro Glu Val Glu Phe Ala Val Val Ser Ala Trp Glu
85 90 95

Ala Tyr Ala Ile Gly Glu His Glu Ala Ala Trp Val Arg Ala His Gly
100 105 110

Asp Pro Leu Val Phe Val His Met Leu Ala Ala Phe Ser Ala Ala Ile
115 120 125

Gly Thr Ala Val Tyr Gly Arg Glu Glu Leu Leu Pro Thr Leu Arg Arg
130 135 140

Val Thr Ala Arg
145

<210> SEQ ID NO 73
<211> LENGTH: 1368
<212> TYPE: DNA
<213> ORGANISM: Thermomonospora curvata

<400> SEQUENCE: 73
atgtcacagc tggcggtcac agaccaccac gagcgagcgg tcgaggcgct gcgcaggtcg 60
tatgcggcga tcccgccggg cacaccggtc cgcttggcca agcagacctc caacctgttc 120
cgcttccgcg agccgacggc cgcgcccggc ctggacgtgt ccggcttcaa ccgggtgctg 180
gcggtggacc cggatgcgcg caccgccgac gtgcagggca tgaccaccta cgaggacctg 240
gtcgacgcca ccctgccgca cgggctgatg ccgctggtgg tgccccagct caagacgatc 300
acgctgggcg gggcggtgac cggcctgggc atcgagtcca cctccttccg caacggcctg 360

```
ccgcacgagt cggtgctgga gatgcagatc atcaccggcg ccggcgaagt ggtcaccgcc    420

accccggacg gggagcactc cgacctgttc tggggcttcc ccaactccta cgggacgctg    480

gggtacgccc tgaagctgaa gatcgaactg gagccggtca agccgtacgt ccggctgcgg    540

cacctgcgct tcgacgacgc cggcgagtgc gccgccaagc tcgccgagct gagcgaaagc    600

cgcgagcacg agggcgatga ggtgcacttt ttggacggca ccttcttcgg gccgcgcgag    660

atgtacctga cgctcggcac gttcaccgac accgccccct atgtgtcgga ctacaccggg    720

cagcacatct actaccggtc gatccagcag cggtcgatcg actttttgac catccgcgac    780

tacctgtggc gctgggacac cgactggttc tggtgctcgc gcgccctggg cgtgcagaac    840

ccgctgatcc ggcgggtgtg gccgaagagc gccaagcggt cggatgtgta ccgcaagctg    900

gtggcctacg aaaagcgcta ccagttcaag gcgcgcatcg accggtggac gggcaagccg    960

ccgcgcgagg acgtcatcca ggacatcgag gtgccggcag aacgcctgcc ggagttcctg   1020

gagttcttcc acgacaagat cgggatgagc ccggtgtggc tgtgcccgct gcgggcgcgc   1080

caccgctggc cgctgtaccc gctcaagccc ggcgtcacct acgtcaacgc cggcttctgg   1140

gggacggtgc cgctgcagcc ggggcagatg cccgagtacc acaaccggct gatcgaacgg   1200

aaggtcgccc aactggacgg ccacaagtct ctgtactcga cggcgttcta ctcgcgtgag   1260

gagttctggc ggcactacga cggggaaacc taccggcgtc tgaaggacac ctacgacccc   1320

gacgcgcgcc tgctcgacct ctacgacaag tgcgtgcggg gacgctga                1368


<210> SEQ ID NO 74
<211> LENGTH: 455
<212> TYPE: PRT
<213> ORGANISM: Thermomonospora curvata

<400> SEQUENCE: 74

Met Ser Gln Leu Ala Val Thr Asp His His Glu Arg Ala Val Glu Ala
1               5                   10                  15

Leu Arg Arg Ser Tyr Ala Ala Ile Pro Pro Gly Thr Pro Val Arg Leu
            20                  25                  30

Ala Lys Gln Thr Ser Asn Leu Phe Arg Phe Arg Glu Pro Thr Ala Ala
        35                  40                  45

Pro Gly Leu Asp Val Ser Gly Phe Asn Arg Val Leu Ala Val Asp Pro
    50                  55                  60

Asp Ala Arg Thr Ala Asp Val Gln Gly Met Thr Thr Tyr Glu Asp Leu
65                  70                  75                  80

Val Asp Ala Thr Leu Pro His Gly Leu Met Pro Leu Val Val Pro Gln
                85                  90                  95

Leu Lys Thr Ile Thr Leu Gly Gly Ala Val Thr Gly Leu Gly Ile Glu
            100                 105                 110

Ser Thr Ser Phe Arg Asn Gly Leu Pro His Glu Ser Val Leu Glu Met
        115                 120                 125

Gln Ile Ile Thr Gly Ala Gly Glu Val Val Thr Ala Thr Pro Asp Gly
    130                 135                 140

Glu His Ser Asp Leu Phe Trp Gly Phe Pro Asn Ser Tyr Gly Thr Leu
145                 150                 155                 160

Gly Tyr Ala Leu Lys Leu Lys Ile Glu Leu Glu Pro Val Lys Pro Tyr
                165                 170                 175

Val Arg Leu Arg His Leu Arg Phe Asp Asp Ala Gly Glu Cys Ala Ala
            180                 185                 190
```

-continued

```
Lys Leu Ala Glu Leu Ser Glu Ser Arg Glu His Glu Gly Asp Glu Val
        195                 200                 205

His Phe Leu Asp Gly Thr Phe Phe Gly Pro Arg Glu Met Tyr Leu Thr
    210                 215                 220

Leu Gly Thr Phe Thr Asp Thr Ala Pro Tyr Val Ser Asp Tyr Thr Gly
225                 230                 235                 240

Gln His Ile Tyr Tyr Arg Ser Ile Gln Gln Arg Ser Ile Asp Phe Leu
                245                 250                 255

Thr Ile Arg Asp Tyr Leu Trp Arg Trp Asp Thr Asp Trp Phe Trp Cys
            260                 265                 270

Ser Arg Ala Leu Gly Val Gln Asn Pro Leu Ile Arg Arg Val Trp Pro
        275                 280                 285

Lys Ser Ala Lys Arg Ser Asp Val Tyr Arg Lys Leu Val Ala Tyr Glu
    290                 295                 300

Lys Arg Tyr Gln Phe Lys Ala Arg Ile Asp Arg Trp Thr Gly Lys Pro
305                 310                 315                 320

Pro Arg Glu Asp Val Ile Gln Asp Ile Glu Val Pro Ala Glu Arg Leu
                325                 330                 335

Pro Glu Phe Leu Glu Phe Phe His Asp Lys Ile Gly Met Ser Pro Val
            340                 345                 350

Trp Leu Cys Pro Leu Arg Ala Arg His Arg Trp Pro Leu Tyr Pro Leu
        355                 360                 365

Lys Pro Gly Val Thr Tyr Val Asn Ala Gly Phe Trp Gly Thr Val Pro
    370                 375                 380

Leu Gln Pro Gly Gln Met Pro Glu Tyr His Asn Arg Leu Ile Glu Arg
385                 390                 395                 400

Lys Val Ala Gln Leu Asp Gly His Lys Ser Leu Tyr Ser Thr Ala Phe
                405                 410                 415

Tyr Ser Arg Glu Glu Phe Trp Arg His Tyr Asp Gly Glu Thr Tyr Arg
            420                 425                 430

Arg Leu Lys Asp Thr Tyr Asp Pro Asp Ala Arg Leu Leu Asp Leu Tyr
        435                 440                 445

Asp Lys Cys Val Arg Gly Arg
    450                 455
```

<210> SEQ ID NO 75
<211> LENGTH: 1263
<212> TYPE: DNA
<213> ORGANISM: Thermomonospora curvata

<400> SEQUENCE: 75

```
atgacgctgg ccaaggtctt cgaggagctg gtcggggcgg acgcccctgt ggagctcacc      60

gcctacgacg gatcgagagc cggacgcctg ggcagtgatc tgcgggtcca cgtgaagtcg     120

ccgtacgcgg tgtcctacct ggtgcactcg ccgagcgcgc tcgggctggc ccgcgcgtac     180

gtggccgggc acctggacgc ctacggcgac atgtacacgc tgctgcggga gatgacgcag     240

ctgaccgagg cgctgacgcc caaggcccgg ctgcggctgc tggccggtgt cctgcaggat     300

ccgctgctgc gcgcggcggc cagccgccgt ctgccgcccc cgccgcagga ggtgcggacc     360

ggccgcacct cctggttccg gcacaccaag cggcgggacg ccaaggccat ctcccaccac     420

tacgacgtgt ccaacacctt ctatgagtgg gtgctgggcc cgtcgatgac ctacacctgc     480

gcctgtttcc ccaccgagga cgccaccttg gaggaggcgc agttccacaa gcacgacctg     540

gtcgccaaga agctcgggct gcggccgggc atgcggctgc tggacgtggg ctgcggctgg     600
```

-continued

```
ggcggcatgg tgatgcacgc cgccaagcac tacggggtgc gggcgctggg cgtcacgctg    660

tccaagcagc aggccgagtg ggcgcagaag gccatcgccg aggcgggcct gagcgacctg    720

gccgaggtcc gccaccagga ctaccgggac gtcaccgagg gcgacttcga cgccatcagc    780

tcgatcggcc tcaccgagca catcggcaag gccaacctgc cgtcctactt cggcttcctg    840

tacggcaagc tcaagccggg cgggcggctg ctcaaccact gcatcacccg gcccgacaac    900

acccagccgg ccatgaagaa ggacgggttc atcaaccggt acgtcttccc cgacggggag    960

ctggaggggc ccggctacct gcagacccag atgaacgacg ccggttttga gatccgccac   1020

caggagaacc tgcgcgagca ctacgcccgc accctggccg gatggtgccg caacctcgat   1080

gagcactggg acgaggcggt ggccgaggtc ggcgagggca ccgcgcgggt gtggcggctg   1140

tacatggccg gcagccggct cggtttcgag ctcaactgga tccagctgca ccagatcctg   1200

ggcgtcaagc tcggcgagcg cggcgagtcc cgcatgccgt tgcggcccga ctggggcgtg   1260

tga                                                                 1263
```

<210> SEQ ID NO 76
<211> LENGTH: 420
<212> TYPE: PRT
<213> ORGANISM: Thermomonospora curvata

<400> SEQUENCE: 76

```
Met Thr Leu Ala Lys Val Phe Glu Glu Leu Val Gly Ala Asp Ala Pro
1               5                   10                  15

Val Glu Leu Thr Ala Tyr Asp Gly Ser Arg Ala Gly Arg Leu Gly Ser
            20                  25                  30

Asp Leu Arg Val His Val Lys Ser Pro Tyr Ala Val Ser Tyr Leu Val
        35                  40                  45

His Ser Pro Ser Ala Leu Gly Leu Ala Arg Ala Tyr Val Ala Gly His
    50                  55                  60

Leu Asp Ala Tyr Gly Asp Met Tyr Thr Leu Leu Arg Glu Met Thr Gln
65                  70                  75                  80

Leu Thr Glu Ala Leu Thr Pro Lys Ala Arg Leu Arg Leu Leu Ala Gly
                85                  90                  95

Val Leu Gln Asp Pro Leu Leu Arg Ala Ala Ala Ser Arg Arg Leu Pro
            100                 105                 110

Pro Pro Pro Gln Glu Val Arg Thr Gly Arg Thr Ser Trp Phe Arg His
        115                 120                 125

Thr Lys Arg Arg Asp Ala Lys Ala Ile Ser His His Tyr Asp Val Ser
    130                 135                 140

Asn Thr Phe Tyr Glu Trp Val Leu Gly Pro Ser Met Thr Tyr Thr Cys
145                 150                 155                 160

Ala Cys Phe Pro Thr Glu Asp Ala Thr Leu Glu Glu Ala Gln Phe His
                165                 170                 175

Lys His Asp Leu Val Ala Lys Lys Leu Gly Leu Arg Pro Gly Met Arg
            180                 185                 190

Leu Leu Asp Val Gly Cys Gly Trp Gly Gly Met Val Met His Ala Ala
        195                 200                 205

Lys His Tyr Gly Val Arg Ala Leu Gly Val Thr Leu Ser Lys Gln Gln
    210                 215                 220

Ala Glu Trp Ala Gln Lys Ala Ile Ala Glu Ala Gly Leu Ser Asp Leu
225                 230                 235                 240

Ala Glu Val Arg His Gln Asp Tyr Arg Asp Val Thr Glu Gly Asp Phe
                245                 250                 255
```

```
Asp Ala Ile Ser Ser Ile Gly Leu Thr Glu His Ile Gly Lys Ala Asn
            260                 265                 270

Leu Pro Ser Tyr Phe Gly Phe Leu Tyr Gly Lys Leu Lys Pro Gly Gly
        275                 280                 285

Arg Leu Leu Asn His Cys Ile Thr Arg Pro Asp Asn Thr Gln Pro Ala
    290                 295                 300

Met Lys Lys Asp Gly Phe Ile Asn Arg Tyr Val Phe Pro Asp Gly Glu
305                 310                 315                 320

Leu Glu Gly Pro Gly Tyr Leu Gln Thr Gln Met Asn Asp Ala Gly Phe
                325                 330                 335

Glu Ile Arg His Gln Glu Asn Leu Arg Glu His Tyr Ala Arg Thr Leu
            340                 345                 350

Ala Gly Trp Cys Arg Asn Leu Asp Glu His Trp Asp Glu Ala Val Ala
        355                 360                 365

Glu Val Gly Glu Gly Thr Ala Arg Val Trp Arg Leu Tyr Met Ala Gly
    370                 375                 380

Ser Arg Leu Gly Phe Glu Leu Asn Trp Ile Gln Leu His Gln Ile Leu
385                 390                 395                 400

Gly Val Lys Leu Gly Glu Arg Gly Glu Ser Arg Met Pro Leu Arg Pro
                405                 410                 415

Asp Trp Gly Val
            420
```

<210> SEQ ID NO 77
<211> LENGTH: 7102
<212> TYPE: DNA
<213> ORGANISM: Artificial Sequence
<220> FEATURE:
<223> OTHER INFORMATION: Synthetic Nucleic Acid

<400> SEQUENCE: 77

```
gtttgtggaa gcggtattcg caatttaatt aaagctggtg acaattaatc atcggctcgt     60

ataatgtgtg gaattgaatc gatataagga ggttaatcat gtgtctgtgg ttactactga    120

cgcacaggct gcccatgccg ccggcgtctc gcgtcttctg gccagctacc gggcgatccc    180

gcccagcgcg acagtgcgcc ttgcgaaacc gacgtccaac ctgttccgcg cccgcgcccg    240

caccaatgtg aagggtctcg acgtctcggg cctgaccggt gtgatcggtg tcgacccgga    300

cgcgcgcacc gccgatgtgg cgggcatgtg cacctacgag gacctggtgg cggccacgct    360

tccgtacggc cttgccccac tggtggtgcc gcagctcaag accatcacgc tcggtggcgc    420

ggtcaccggt ctgggcatcg agtccacgtc gttccgcaac ggtctgccgc acgaaagtgt    480

cctggagatg gacatcttga ccggttcggg cgagatcgtc acggcctcac cggatcagca    540

ctcggatctg ttccatgcgt tccccaattc atatggaacc cttggttatt ccacccggct    600

gcgcatcgaa ctggagcccg tgcacccgtt tgtggcgttg cgccacctgc gctttcactc    660

gatcaccgat ctggtcgcgg cgatggaccg gatcatcgag accggcgggc tggacggtga    720

acccgtcgac tacctcgacg gcgtggtgtt cagcgcgact gagagttacc tgtgtgttgg    780

cttcaagacg aaaacgccgg ggccggtcag cgattacaca ggtcagcaga tcttctaccg    840

gtcgatccag catgacggcg acaccggcgc cgagaaacac gaccggctga ccatccacga    900

ctacctgtgg cgctgggaca ccgactggtt ctggtgctca cgggcattcg gcgctcagca    960

tccggtgatc cgcaggttct ggccgcggcg gctgcgccgc agcagcttct actggaagct   1020

ggtggcctac gaccagcggt acgacatcgc cgaccgtatc gagaagcgca acgggcgccc   1080
```

-continued

```
gccgcgcgag cgggtggtcc aggacgtcga ggtgcccatc gagcggtgcg cggacttcgt   1140
cgagtggttc ctgcagaatg tgccgatcga gccgatctgg ctgtgccccc tacggttgcg   1200
tgacagcgcc gacggcggtg cctcgtggcc cctgtatccg ctgaaggcgc accacaccta   1260
cgtcaacatc ggtttctggt catcagtgcc ggtgggcccc gaggagggcc acaccaaccg   1320
cctcatcgag aaaaaagtcg cggagctgga cgggcacaaa tctttgtact cggacgctta   1380
ttacacacgt gacgaattcg acgagctgta cggcggtgag gtctacaaca ccgtcaagaa   1440
gacgtacgac ccggattcac gtctgctaga cctgtattcg aaggcggtgc aaagacaatg   1500
accacattca aagaacgcga gacgtccaca gcggaccgca agctcaccct ggccgagatc   1560
ctcgagatct tcgccgcggg taaggagccg ctgaagttca ctgcgtacga cggcagctcg   1620
gccggtcccg aggacgccac gatgggtctg gacctcaaga ccccgcgtgg gaccacctat   1680
ctggccacgg cacccggcga tctgggcctg gcccgtgcgt atgtctccgg tgacctggag   1740
ccgcacggcg tgcatcccgg cgatccctac ccgctgctgc gcgccctggc cgaacgcatg   1800
gagttcaagc gcccgcctgc gcgtgtgctg gcgaacatcg tgcgctccat cggcatcgag   1860
cacctcaagc cgatcgcacc gccgccgcag gaggcgctgc cccggtggcg ccgcatcatg   1920
gagggcctgc ggcacagcaa gacccgcgac gccgaggcca tccaccacca ctacgacgtg   1980
tcgaacacgt tctacgagtg ggtgctgggc ccgtcgatga cctacacgtg cgcgtgctac   2040
cccaccgagg acgcgaccct cgaagaggcc caggacaaca agtaccgcct ggtgttcgag   2100
aagctgcgcc tgaagcccgg tgaccggttg ctcgacgtgg gctgcggctg gggcggcatg   2160
gtccgctacg cggcccgcca cggcgtcaag gcgctcggtg tcacgctcag ccgcgaacag   2220
gcgacgtggg cgcagaaggc catcgcccag gaaggtctca ccgatctggc cgaggtgcgt   2280
cacggtgatt accgcgacgt catcgaatcc gggttcgacg cggtgtcctc gatcgggctg   2340
accgagcaca tcggcgtgca caactacccg gcgtacttca acttcctcaa gtcgaagctg   2400
cgcaccggtg gcctgctgct caaccactgc atcacccgcc cggacaaccg gtcggcgcca   2460
tcggccggcg ggttcatcga caggtacgtg ttccccgacg gggagctcac cggctcgggc   2520
cgcatcatca ccgaggccca ggacgtgggc cttgaggtga tccacgagga gaacctacgc   2580
aatcactatg cgatgacgct gcgcgactgg tgccgcaacc tggtcgagca ctgggacgag   2640
gcggtcgaag aggtcgggct gcccaccgcg aaggtgtggg gcctgtacat ggccggctca   2700
cgtctgggct tcgagaccaa tgtggttcag ctgcaccagg ttctggcggt caagcttgac   2760
gatcagggca aggacggcgg actgccgttg cggccctggt ggtccgccta gcctcaaaat   2820
atattttccc tctatcttct cgttgcgctt aatttgacta attctcatta gcgaggcgcg   2880
cctttccata ggctccgccc ccctgacgag catcacaaaa atcgacgctc aagtcagagg   2940
tggcgaaacc cgacaggact ataaagatac caggcgtttc cccctggaag ctccctcgtg   3000
cgctctcctg ttccgaccct gccgcttacc ggatacctgt ccgcctttct cccttcggga   3060
agcgtggcgc tttctcatag ctcacgctgt aggtatctca gttcggtgta ggtcgttcgc   3120
tccaagctgg gctgtgtgca cgaacccccc gttcagcccg accgctgcgc cttatccggt   3180
aactatcgtc ttgagtccaa cccggtaaga cacgacttat cgccactggc agcagccact   3240
ggtaacagga ttagcagagc gaggtatgta ggcggtgcta cagagttctt gaagtggtgg   3300
cctaactacg gctacactag aagaacagta tttggtatct gcgctctgct gaagccagtt   3360
accttcggaa aaagagttgg tagctcttga tccggcaaac aaaccaccgc tggtagcggt   3420
```

-continued

```
ggttttttg tttgcaagca gcagattacg cgcagaaaaa aaggatctca agaagatcct   3480
ttgatctttt ctacggggtc tgacgctcag tggaacgaaa actcacgtta agggattttg   3540
gtcatgagat tatcaaaaag gatcttcacc tagatccttt taaattaaaa atgaagtttt   3600
aaatcaatct aaagtatata tgagtaaact tggtctgaca gttaccaatg cttaatcagt   3660
gaggcaccta tctcagcgat ctgtctattt cgttcatcca tagttgcctg actccccgtc   3720
gtgtagataa ctacgatacg ggagggctta ccatctggcc ccagtgctgc aatgataccg   3780
cgagacccac gctcaccggc tccagattta tcagcaataa accagccagc cggaagggcc   3840
gagcgcagaa gtggtcctgc aactttatcc gcctccatcc agtctattaa ttgttgccgg   3900
gaagctagag taagtagttc gccagttaat agtttgcgca acgttgttgc cattgctaca   3960
ggcatcgtgg tgtcacgctc gtcgtttggt atggcttcat tcagctccgg ttcccaacga   4020
tcaaggcgag ttacatgatc ccccatgttg tgcaaaaaag cggttagctc cttcggtcct   4080
ccgatcgttg tcagaagtaa gttggccgca gtgttatcac tcatggttat ggcagcactg   4140
cataattctc ttactgtcat gccatccgta agatgctttt ctgtgactgg tgagtactca   4200
accaagtcat tctgagaata gtgtatgcgg cgaccgagtt gctcttgccc ggcgtcaata   4260
cgggataata ccgcgccaca tagcagaact ttaaaagtgc tcatcattgg aaaacgttct   4320
tcggggcgaa aactctcaag gatcttaccg ctgttgagat ccagttcgat gtaacccact   4380
cgtgcaccca actgatcttc agcatctttt actttcacca gcgtttctgg gtgagcaaaa   4440
acaggaaggc aaaatgccgc aaaaaaggga ataagggcga cacggaaatg ttgaatactc   4500
atactcttcc tttttcaata ttattgaagc atttatcagg gttattgtct catgagcgga   4560
tacatatttg aatgtattta gaaaaataaa cagcgatcgc gcggccgcgg gtaataactg   4620
atataattaa attgaagctc taatttgtga gtttagtata catgcattta cttataatac   4680
agtttttag ttttgctggc cgcatcttct caaatatgct tcccagcctg cttttctgta   4740
acgttcaccc tctaccttag catcccttcc ctttgcaaat agtcctcttc caacaataat   4800
aatgtcagat cctgtagaga ccacatcatc cacggttcta tactgttgac ccaatgcgtc   4860
tcccttgtca tctaaaccca caccgggtgt cataatcaac caatcgtaac cttcatctct   4920
tccacccatg tctctttgag caataaagcc gataacaaaa tctttgtcgc tcttcgcaat   4980
gtcaacagta cccttagtat attctccagt agctagggag cccttgcatg acaattctgc   5040
taacatcaaa aggcctctag gttcctttgt tacttcttcc gccgcctgct tcaaaccgct   5100
aacaatacct gggcccacca caccgtgtgc attcgtaatg tctgcccatt ctgctattct   5160
gtatacaccc gcagagtact gcaatttgac tgtattacca atgtcagcaa attttctgtc   5220
ttcgaagagt aaaaaattgt acttggcgga taatgccttt agcggcttaa ctgtgccctc   5280
catggaaaaa tcagtcaaga tatccacatg tgtttttagt aaacaaattt tgggacctaa   5340
tgcttcaact aactccagta attccttggt ggtacgaaca tccaatgaag cacacaagtt   5400
tgtttgcttt tcgtgcatga tattaaatag cttggcagca acaggactag gatgagtagc   5460
agcacgttcc ttatatgtag ctttcgacat gatttatctt cgtttcctgc aggtttttgt   5520
tctgtgcagt tgggttaaga atactgggca atttcatgtt tcttcaacac cacatatgcg   5580
tatatatacc aatctaagtc tgtgctcctt ccttcgttct tccttctgct cggagattac   5640
cgaatcaaag ctagcttatc gatgataagc tgtcaaagat gagaattaat tccacggact   5700
atagactata ctagatactc cgtctactgt acgatacact tccgctcagg tccttgtcct   5760
ttaacgaggc cttaccactc ttttgttact ctattgatcc agctcagcaa aggcagtgtg   5820
```

```
atctaagatt ctatcttcgc gatgtagtaa aactagctag accgagaaag agactagaaa   5880
tgcaaaaggc acttctacaa tggctgccat cattattatc cgatgtgacg ctgcagcttc   5940
tcaatgatat tcgaatacgc tttgaggaga tacagcctaa tatccgacaa actgttttac   6000
agatttacga tcgtacttgt tacccatcat tgaattttga acatccgaac ctgggagttt   6060
tccctgaaac agatagtata tttgaacctg tataataata tatagtctag cgctttacgg   6120
aagacaatgt atgtatttcg gttcctggag aaactattgc atctattgca taggtaatct   6180
tgcacgtcgc atccccggtt cattttctgc gtttccatct tgcacttcaa tagcatatct   6240
ttgttaacga agcatctgtg cttcattttg tagaacaaaa atgcaacgcg agagcgctaa   6300
tttttcaaac aaagaatctg agctgcattt ttacagaaca gaaatgcaac gcgaaagcgc   6360
tattttacca acgaagaatc tgtgcttcat ttttgtaaaa caaaaatgca acgcgacgag   6420
agcgctaatt tttcaaacaa agaatctgag ctgcattttt acagaacaga aatgcaacgc   6480
gagagcgcta ttttaccaac aaagaatcta tacttctttt ttgttctaca aaaatgcatc   6540
ccgagagcgc tatttttcta acaaagcatc ttagattact ttttttctcc tttgtgcgct   6600
ctataatgca gtctcttgat aactttttgc actgtaggtc cgttaaggtt agaagaaggc   6660
tactttggtg tctattttct cttccataaa aaaagcctga ctccacttcc cgcgtttact   6720
gattactagc gaagctgcgg gtgcattttt tcaagataaa ggcatccccg attatattct   6780
ataccgatgt ggattgcgca tactttgtga acagaaagtg atagcgttga tgattcttca   6840
ttggtcagaa aattatgaac ggtttcttct attttgtctc tatatactac gtataggaaa   6900
tgtttacatt ttcgtattgt tttcgattca ctctatgaat agttcttact acaatttttt   6960
tgtctaaaga gtaatactag agataaacat aaaaaatgta gaggtcgagt ttagatgcaa   7020
gttcaaggag cgaaaggtgg atgggtaggt tatataggga tatagcacag agatatatag   7080
caaagagata cttttgagca at                                            7102
```

<210> SEQ ID NO 78
<211> LENGTH: 10766
<212> TYPE: DNA
<213> ORGANISM: Artificial Sequence
<220> FEATURE:
<223> OTHER INFORMATION: Synthetic Nucleic Acid

<400> SEQUENCE: 78

```
ttatcgatga taagctgtca aagatgagaa ttaattccac ggactataga ctatactaga     60
tactccgtct actgtacgat acacttccgc tcaggtcctt gtcctttaac gaggccttac    120
cactcttttg ttactctatt gatccagctc agcaaaggca gtgtgatcta agattctatc    180
ttcgcgatgt agtaaaacta gctagaccga gaaagagact agaaatgcaa aaggcacttc    240
tacaatggct gccatcatta ttatccgatg tgacgctgca gcttctcaat gatattcgaa    300
tacgctttga ggagatacag cctaatatcc gacaaactgt tttacagatt tacgatcgta    360
cttgttaccc atcattgaat tttgaacatc cgaacctggg agttttccct gaaacagata    420
gtatatttga acctgtataa taatatatag tctagcgctt tacggaagac aatgtatgta    480
tttcggttcc tggagaaact attgcatcta ttgcataggt aatcttgcac gtcgcatccc    540
cggttcattt tctgcgtttc catcttgcac ttcaatagca tatctttgtt aacgaagcat    600
ctgtgcttca ttttgtagaa caaaaatgca acgcgagagc gctaattttt caaacaaaga    660
atctgagctg catttttaca gaacagaaat gcaacgcgaa agcgctattt taccaacgaa    720
```

```
gaatctgtgc ttcatttttg taaaacaaaa atgcaacgcg acgagagcgc taatttttca    780
aacaaagaat ctgagctgca tttttacaga acagaaatgc aacgcgagag cgctatttta    840
ccaacaaaga atctatactt cttttttgtt ctacaaaaat gcatcccgag agcgctattt    900
ttctaacaaa gcatcttaga ttactttttt tctcctttgt gcgctctata atgcagtctc    960
ttgataactt tttgcactgt aggtccgtta aggttagaag aaggctactt tggtgtctat   1020
tttctcttcc ataaaaaaag cctgactcca cttcccgcgt ttactgatta ctagcgaagc   1080
tgcgggtgca tttttcaag ataaaggcat ccccgattat attctatacc gatgtggatt   1140
gcgcatactt tgtgaacaga aagtgatagc gttgatgatt cttcattggt cagaaaatta   1200
tgaacggttt cttctatttt gtctctatat actacgtata ggaaatgttt acattttcgt   1260
attgttttcg attcactcta tgaatagttc ttactacaat ttttttgtct aaagagtaat   1320
actagagata aacataaaaa atgtagaggt cgagtttaga tgcaagttca aggagcgaaa   1380
ggtggatggg taggttatat agggatatag cacagagata tatagcaaag agatactttt   1440
gagcaatgtt tgtggaagcg gtattcgcaa tgtttaaact gcgtcggaac gggatatgca   1500
ttcccctagt ttcgccgcag tgcagaatca ggcggtttct ttgcaccaca ccacatacgg   1560
aggatgacgg gcattattga tgttgaatag taacctgatc gtgactagta tgacggaacc   1620
caacagcaac agccgaccgt ttgtgagcgt ttttgcggcc ggtcaggcga gtttttccgg   1680
cctgccaatg gtccttccgt accctttacc ctgtacgctg tacctgccac ggataggccg   1740
tgctccacct gctcactatg gtgggtgcgg ggaaaacaac aggcaggctc aattgctctg   1800
caaatgggtt gagggggtga ttgatgtcac tggtacacca acaggggaat gctcggcgtt   1860
gattttgggc cacctctttt gtttgccaga gcttgtctct attgtcaaat ttaacggtct   1920
gcaactgttg cccaaaatgg gacaatgatc cgatgcctgc atagacaccc tgcttgaggg   1980
tgcgatcgcc ctaatacgag gcaaaccaag ttttccaatt gaccttcaat tgacgagcgg   2040
ttgttgcgac aggggactgg agtgctacct gtttagagtt caaatccgtc acccagcatt   2100
gaaagttttt ccccgcattg gatgattgca atgccgctaa cccgctcatc cgccaaagtt   2160
catagtccca ccctgcctcg acttatcgga ccacatgggg ctcccttatg cgcgcgcata   2220
tggcgcttga ttgcttttg gtcaacgttt gggacaaatt tcctttgtta aggcggaccc   2280
gccagcagat acgaaggtat aaatagggct cactttcacc atcttgtcca ttcaattgca   2340
agactcaaaa gtaataatga ccactctgga tgacaccgct taccgatacc gaacttccgt   2400
tcctggcgat gccgaggcta ttgaggctct ggatggatct ttcaccactg acaccgtttt   2460
ccgagtgacc gctactggcg acggcttcac cctgcgagag gtgcctgtcg accctcctct   2520
caccaaggtt ttccctgacg atgagtcgga cgatgagtct gacgctggag aggacggcga   2580
ccctgactct cgaactttcg tggcttacgg cgacgatgga gacctggccg gctttgtggt   2640
cgtttcttac tccggatgga accgacgact gaccgtggag gacatcgagg tcgctcctga   2700
gcaccgaggt catggtgtcg gacgagctct gatgggtctc gctactgagt tcgctcgaga   2760
gcgaggtgct ggccacctgt ggctcgaggt caccaacgtt aacgcccctg ctattcatgc   2820
ctaccgacga atgggtttta ccctgtgtgg cctcgatact gccctgtacg acggaaccgc   2880
ttccgatgga gagcaggccc tctacatgtc gatgccctgc ccttaaacag gcccctttc   2940
ctttgtcgat atcatgtaat tagttatgtc acgcttacat tcacgccctc ctcccacatc   3000
cgctctaacc gaaaaggaag gagttagaca acctgaagtc taggtcccta tttatttttt   3060
ttaatagtta tgttagtatt aagaacgtta tttatatttc aaatttttct ttttttctg    3120
```

```
tacaaacgcg tgtacgcatg taacattata ctgaaaacct tgcttgagaa ggttttggga   3180
cgctcgaagg ctttaatttg cagagaccgg gttggcggcg catttgtgtc ccaaaaaaca   3240
gccccaattg ccccaattga ccccaaattg acccagtagc gggcccaacc ccggcgagag   3300
ccccccttctc cccacatatc aaacctcccc cggttcccac acttgccgtt aagggcgtag   3360
ggtactgcag tctggaatct acgcttgttc agactttgta ctagtttctt tgtctggcca   3420
tccgggtaac ccatgccgga cgcaaaatag actactgaaa atttttttgc tttgtggttg   3480
ggactttagc caagggtata aaagaccacc gtccccgaat tacctttcct cttcttttct   3540
ctctctcctt gtcaactcac acccgaaatc gttaagcatt tccttctgag tataagaatc   3600
attcaaaatg tccgttgtta ccaccgatgc tcaagctgct catgctgctg gtgtttctag   3660
attattggct tcttatagag ccattccacc atctgctact gttagattgg ctaagccaac   3720
ttctaatttg ttcagagcta gagctagaac taacgttaag ggtttggatg tttctggttt   3780
gactggtgtt attggtgttg atccagatgc tagaactgct gatgttgctg gtatgtgtac   3840
ttacgaagat ttggttgctg ctactttgcc atatggtttg gctccattgg ttgttccaca   3900
attgaaaact attactttgg gtggtgctgt taccggtttg ggtattgaat ctacttcttt   3960
cagaaacggt ttgccacacg aatctgtttt ggaaatggat attttgaccg gttccggtga   4020
aatagttact gcttctccag atcaacactc cgatttgttt catgcttttc caaactctta   4080
cggtacattg ggttactcta ccagattgag aattgaattg gaaccagttc atccattcgt   4140
tgccttgaga catttgagat tccattccat tactgatttg gtcgcagcca tggatagaat   4200
tattgaaact ggtggtttag acggtgaacc agttgattat ttggatggtg ttgttttctc   4260
tgccaccgaa tcatatttgt gtgttggttt caaaactaag accccaggtc cagtttctga   4320
ttatactggt caacaaatct tctacagatc catccaacat gatggtgata ctggtgctga   4380
aaaacatgat agattgacca tccatgacta cttgtggaga tgggatactg attggttttg   4440
gtgttctaga gcttttggtg ctcaacatcc agttattaga agattctggc caagaagatt   4500
aagaagatcc tccttctact ggaaattggt tgcttacgat caaagatacg atatcgccga   4560
tagaatcgaa aagagaaatg gtagaccacc aagagaaaga gttgttcaag acgttgaagt   4620
tccaattgaa agatgcgctg atttcgttga atggttcttg caaaatgttc caatcgaacc   4680
tatttggttg tgcccattga gattgagaga ttctgctgat ggtggtgctt catggccatt   4740
atatccattg aaagctcatc acacctacgt caatattggt ttctggtcat ctgttccagt   4800
tggtccagaa gaaggtcata ccaatagatt gattgaaaaa aaggtcgccg aattggacgg   4860
tcacaaatca ttatattctg atgcctacta caccagagat gaattcgatg aattatacgg   4920
tggtgaagtt tacaacaccg tcaaaaaaac ttacgaccca gactcaagat tattagactt   4980
gtactctaag gccgtccaaa gacaatgagc tgcttgtacc tagtgcaacc ccagtttgtt   5040
aaaaattagt agtcaaaaac ttctgagtta gaaatttgtg agtgtagtga gattgtagag   5100
tatcatgtgt gtccgtaagt gaagtgttat tgactcttag ttagtttatc tagtactcgt   5160
ttagttgaca ctgatctagt attttacgag gcgtatgact ttagccaagt gttgtactta   5220
gtcttctctc caaacatgag agggctctgt cactcagtcg gcctatgggt gagatggctt   5280
ggtgagatct ttcgatagtc tcgtcaagat ggtaggatga tgggggaata cattactgct   5340
ctcgtcaagg aaaccacaat cagatcacac catcctccat ggtatccgat gactctcttc   5400
tccacagtcg cagtaggatg tcctgcacgg gtctttttgt ggggtgtgga gaaaggggtg   5460
```

-continued

```
cttggagatg gaagccggta gaaccgggct gcttgggggg atttggggcc gctgggctcc   5520
aaagaggggt aggcatttcg ttggggttac gtaattgcgg catttgggtc ctgcgcgcat   5580
gtcccattgg tcagaattag tccggatagg agacttatca gccaatcaca gcgccggatc   5640
cacctgtagg ttgggttggg tgggagcacc cctccacaga gtagagtcaa acagcagcag   5700
caacgtgata gttgggggtg tgcgtgttaa aggaaaaaaa aagaagcttg ggttatattc   5760
ccgctctatt tagaggttgc gggatagacg ccgacggagg gcaatggcgc catggaacct   5820
tgcggatatc gatacgccgc ggcggactgc gtccgaacca gctccagcag cgtttttttcc   5880
gggccattga gccgactgcg accccgccaa cgtgtcttgg cccacgcact catgtcatgt   5940
tggtgttggg aggccacttt ttaagtagca caaggcacct agctcgcggc agggtgtccg   6000
aaccaaagaa gcggctgcag tggtgcaaac ggggcggaaa cggcgggaaa aagccacggg   6060
ggcacgaatt gaggcacgcc ctcgaatttg agacgagtca cggccccatt cgcccgcgca   6120
atggctcgcc aacgcccggt cttttgcacc acatcaggtt accccaagcc aaacctttgt   6180
gttaaaaagc ttaacatatt ataccgaacg taggtttggg cgggcttgct ccgtctgtcc   6240
aaggcaacat ttatataagg gtctgcatcg ccggctcaat tgaatctttt ttcttcttct   6300
cttctctata ttcattcttg aattaaacac acatcaacaa tgaccacctt caaagaaaga   6360
gaaacttcta ccgctgatag aaagttgacc ttggctgaaa ttttggaaat tttcgctgct   6420
ggtaaagaac cattgaagtt cactgcttat gatggttctt ctgctggtcc tgaagatgct   6480
actatgggtt tggatttgaa aactccaaga ggtactactt acttggctac tgctccaggt   6540
gatttgggtt tggctagagc ttatgtttct ggtgacttgg aaccacatgg tgttcatcct   6600
ggtgatccat atccattatt gagagcttta gccgaaagaa tggaattcaa aagaccacca   6660
gctagagttt tggctaacat cgttagatcc attggtatcg aacatttgaa gccaattgct   6720
ccaccaccac aagaagcttt gccaagatgg agaagaatta tggaaggttt gagacactct   6780
aagaccagag atgctgaagc tattcatcat cactacgatg tttctaacac cttctacgaa   6840
tgggttttgg gtccatctat gacttatact tgtgcttgtt acccaacaga agatgccact   6900
ttggaagaag ctcaagataa caagtacaga ttggtctttg aaaagttgag attgaagcca   6960
ggtgacagat tattggatgt tggttgtggt tggggtggta tggttagata tgctgctaga   7020
catggtgtaa aagctttggg tgttactttg tctagagaac aagctacttg ggctcaaaaa   7080
gctattgctc aagaaggttt aaccgatttg gctgaagtta gacacggtga ttacagagat   7140
gttatcgaat ctggtttcga tgccgtttct tctattggtt tgactgaaca tatcggtgtt   7200
cataactatc cagcctactt caacttcttg aagtctaagt tgagaaccgg tggtttgttg   7260
ttgaaccatt gcattactag accagataac agatctgctc catctgctgg tggttttatt   7320
gatagatacg ttttcccaga tggtgaattg actggttccg gtagaattat tactgaagca   7380
caagatgtcg gtttggaagt tatccatgaa gaaaacttga gaaaccatta cgccatgact   7440
ttgagagatt ggtgtagaaa cttggttgaa cattgggatg aagccgttga agaagttggt   7500
ttgccaactg ctaaagtttg gggtttgtat atggctggtt ctagattagg ttttgaaact   7560
aacgttgtcc aattgcacca agttttggca gttaagttgg atgatcaagg taaagatggt   7620
ggtttgcctt taagaccatg gtggtctgct tgagcattag cgactactaa tatatatttg   7680
aatccatgga attataacaa acaagcatca aaacaagaat tagcgacatt atacttgaaa   7740
tcagcattag cgatactact aatatagttt attctatgta atgatccatg gaagttcgat   7800
tgatttgcca agttaatttg atagattatg catgccattt agtcgacgca ggtacgatct   7860
```

```
acagcgataa agaagaggtt gtgggtcatt caattttgca ccaattttgc accatcatag   7920
atcataatac atttacaagg cctacaattc ttacagggtc ttctcgagag caattcctta   7980
attaaggcgc gcctttccat aggctccgcc cccctgacga gcatcacaaa aatcgacgct   8040
caagtcagag gtggcgaaac ccgacaggac tataaagata ccaggcgttt ccccctggaa   8100
gctccctcgt gcgctctcct gttccgaccc tgccgcttac cggatacctg tccgcctttc   8160
tcccttcggg aagcgtggcg ctttctcata gctcacgctg taggtatctc agttcggtgt   8220
aggtcgttcg ctccaagctg ggctgtgtgc acgaaccccc cgttcagccc gaccgctgcg   8280
ccttatccgg taactatcgt cttgagtcca acccggtaag acacgactta tcgccactgg   8340
cagcagccac tggtaacagg attagcagag cgaggtatgt aggcggtgct acagagttct   8400
tgaagtggtg gcctaactac ggctacacta gaagaacagt atttggtatc tgcgctctgc   8460
tgaagccagt taccttcgga aaaagagttg gtagctcttg atccggcaaa caaaccaccg   8520
ctggtagcgg tggttttttt gtttgcaagc agcagattac gcgcagaaaa aaaggatctc   8580
aagaagatcc tttgatcttt tctacggggt ctgacgctca gtggaacgaa aactcacgtt   8640
aagggatttt ggtcatgaga ttatcaaaaa ggatcttcac ctagatcctt ttaaattaaa   8700
aatgaagttt taaatcaatc taaagtatat atgagtaaac ttggtctgac agttaccaat   8760
gcttaatcag tgaggcacct atctcagcga tctgtctatt tcgttcatcc atagttgcct   8820
gactccccgt cgtgtagata actacgatac gggagggctt accatctggc cccagtgctg   8880
caatgatacc gcgagaccca cgctcaccgg ctccagattt atcagcaata aaccagccag   8940
ccggaagggc cgagcgcaga agtggtcctg caactttatc cgcctccatc cagtctatta   9000
attgttgccg ggaagctaga gtaagtagtt cgccagttaa tagtttgcgc aacgttgttg   9060
ccattgctac aggcatcgtg gtgtcacgct cgtcgtttgg tatggcttca ttcagctccg   9120
gttcccaacg atcaaggcga gttacatgat cccccatgtt gtgcaaaaaa gcggttagct   9180
ccttcggtcc tccgatcgtt gtcagaagta agttggccgc agtgttatca ctcatggtta   9240
tggcagcact gcataattct cttactgtca tgccatccgt aagatgcttt tctgtgactg   9300
gtgagtactc aaccaagtca ttctgagaat agtgtatgcg gcgaccgagt tgctcttgcc   9360
cggcgtcaat acgggataat accgcgccac atagcagaac tttaaaagtg ctcatcattg   9420
gaaaacgttc ttcggggcga aaactctcaa ggatcttacc gctgttgaga tccagttcga   9480
tgtaacccac tcgtgcaccc aactgatctt cagcatcttt tactttcacc agcgtttctg   9540
ggtgagcaaa aacaggaagg caaaatgccg caaaaaaggg aataagggcg acacggaaat   9600
gttgaatact catactcttc ctttttcaat attattgaag catttatcag ggttattgtc   9660
tcatgagcgg atacatattt gaatgtattt agaaaaataa acagcgatcg cgcggccgcg   9720
ggtaataact gatataatta aattgaagct ctaatttgtg agtttagtat acatgcattt   9780
acttataata cagtttttta gttttgctgg ccgcatcttc tcaaatatgc ttcccagcct   9840
gcttttctgt aacgttcacc ctctacctta gcatcccttc cctttgcaaa tagtcctctt   9900
ccaacaataa taatgtcaga tcctgtagag accacatcat ccacggttct atactgttga   9960
cccaatgcgt ctcccttgtc atctaaaccc acaccgggtg tcataatcaa ccaatcgtaa  10020
ccttcatctc ttccacccat gtctctttga gcaataaagc cgataacaaa atctttgtcg  10080
ctcttcgcaa tgtcaacagt acccttagta tattctccag tagctaggga gcccttgcat  10140
gacaattctg ctaacatcaa aaggcctcta ggttcctttg ttacttcttc cgccgcctgc  10200
```

```
ttcaaaccgc taacaatacc tgggcccacc acaccgtgtg cattcgtaat gtctgcccat  10260

tctgctattc tgtatacacc cgcagagtac tgcaatttga ctgtattacc aatgtcagca  10320

aattttctgt cttcgaagag taaaaaattg tacttggcgg ataatgcctt tagcggctta  10380

actgtgccct ccatggaaaa atcagtcaag atatccacat gtgtttttag taaacaaatt  10440

ttgggaccta atgcttcaac taactccagt aattccttgg tggtacgaac atccaatgaa  10500

gcacacaagt ttgtttgctt ttcgtgcatg atattaaata gcttggcagc aacaggacta  10560

ggatgagtag cagcacgttc cttatatgta gctttcgaca tgatttatct tcgtttcctg  10620

caggtttttg ttctgtgcag ttgggttaag aatactgggc aatttcatgt ttcttcaaca  10680

ccacatatgc gtatatatac caatctaagt ctgtgctcct tccttcgttc ttccttctgc  10740

tcggagatta ccgaatcaaa gctagc                                       10766
```

<210> SEQ ID NO 79
<211> LENGTH: 10970
<212> TYPE: DNA
<213> ORGANISM: Artificial Sequence
<220> FEATURE:
<223> OTHER INFORMATION: Synthetic Nucleic Acid

<400> SEQUENCE: 79

```
ttatcgatga taagctgtca aagatgagaa ttaattccac ggactataga ctatactaga     60

tactccgtct actgtacgat acacttccgc tcaggtcctt gtcctttaac gaggccttac    120

cactcttttg ttactctatt gatccagctc agcaaaggca gtgtgatcta agattctatc    180

ttcgcgatgt agtaaaacta gctagaccga gaaagagact agaaatgcaa aaggcacttc    240

tacaatggct gccatcatta ttatccgatg tgacgctgca gcttctcaat gatattcgaa    300

tacgctttga ggagatacag cctaatatcc gacaaactgt tttacagatt tacgatcgta    360

cttgttaccc atcattgaat tttgaacatc cgaacctggg agttttccct gaaacagata    420

gtatatttga acctgtataa taatatatag tctagcgctt tacggaagac aatgtatgta    480

tttcggttcc tggagaaact attgcatcta ttgcataggt aatcttgcac gtcgcatccc    540

cggttcattt tctgcgtttc catcttgcac ttcaatagca tatctttgtt aacgaagcat    600

ctgtgcttca ttttgtagaa caaaaatgca acgcgagagc gctaattttt caaacaaaga    660

atctgagctg catttttaca gaacagaaat gcaacgcgaa agcgctattt taccaacgaa    720

gaatctgtgc ttcatttttg taaaacaaaa atgcaacgcg acgagagcgc taatttttca    780

aacaaagaat ctgagctgca tttttacaga acagaaatgc aacgcgagag cgctatttta    840

ccaacaaaga atctatactt cttttttgtt ctacaaaaat gcatcccgag agcgctattt    900

ttctaacaaa gcatcttaga ttactttttt tctcctttgt gcgctctata atgcagtctc    960

ttgataactt tttgcactgt aggtccgtta aggttagaag aaggctactt tggtgtctat   1020

tttctcttcc ataaaaaaag cctgactcca cttcccgcgt ttactgatta ctagcgaagc   1080

tgcgggtgca ttttttcaag ataaaggcat ccccgattat attctatacc gatgtggatt   1140

gcgcatactt tgtgaacaga aagtgatagc gttgatgatt cttcattggt cagaaaatta   1200

tgaacggttt cttctatttt gtctctatat actacgtata ggaaatgttt acattttcgt   1260

attgttttcg attcactcta tgaatagttc ttactacaat ttttttgtct aaagagtaat   1320

actagagata aacataaaaa atgtagaggt cgagtttaga tgcaagttca aggagcgaaa   1380

ggtggatggg taggttatat agggatatag cacagagata tatagcaaag agatactttt   1440

gagcaatgtt tgtggaagcg gtattcgcaa tgtttaaact gcgtcggaac gggatatgca   1500
```

-continued

```
ttcccctagt ttcgccgcag tgcagaatca ggcggtttct ttgcaccaca ccacatacgg   1560
aggatgacgg gcattattga tgttgaatag taacctgatc gtgactagta tgacggaacc   1620
caacagcaac agccgaccgt ttgtgagcgt ttttgcggcc ggtcaggcga gtttttccgg   1680
cctgccaatg gtccttccgt accctttacc ctgtacgctg tacctgccac ggataggccg   1740
tgctccacct gctcactatg gtgggtgcgg ggaaaacaac aggcaggctc aattgctctg   1800
caaatgggtt gagggggtga ttgatgtcac tggtacacca acaggggaat gctcggcgtt   1860
gattttgggc cacctctttt gtttgccaga gcttgtctct attgtcaaat ttaacggtct   1920
gcaactgttg cccaaaatgg gacaatgatc cgatgcctgc atagacaccc tgcttgaggg   1980
tgcgatcgcc ctaatacgag gcaaaccaag ttttccaatt gaccttcaat tgacgagcgg   2040
ttgttgcgac aggggactgg agtgctacct gtttagagtt caaatccgtc acccagcatt   2100
gaaagttttt ccccgcattg gatgattgca atgccgctaa cccgctcatc cgccaaagtt   2160
catagtccca ccctgcctcg acttatcgga ccacatgggg ctcccttatg cgcgcgcata   2220
tggcgcttga ttgcttttg gtcaacgttt gggacaaatt tcctttgtta aggcggaccc    2280
gccagcagat acgaaggtat aaatagggct cactttcacc atcttgtcca ttcaattgca   2340
agactcaaaa gtaataatga ccactctgga tgacaccgct taccgatacc gaacttccgt   2400
tcctggcgat gccgaggcta ttgaggctct ggatggatct ttcaccactg acaccgtttt   2460
ccgagtgacc gctactggcg acggcttcac cctgcgagag gtgcctgtcg accctcctct   2520
caccaaggtt ttccctgacg atgagtcgga cgatgagtct gacgctggag aggacggcga   2580
ccctgactct cgaactttcg tggcttacgg cgacgatgga gacctggccg gctttgtggt   2640
cgtttcttac tccggatgga accgacgact gaccgtggag gacatcgagg tcgctcctga   2700
gcaccgaggt catggtgtcg gacgagctct gatgggtctc gctactgagt tcgctcgaga   2760
gcgaggtgct ggccacctgt ggctcgaggt caccaacgtt aacgcccctg ctattcatgc   2820
ctaccgacga atgggtttta ccctgtgtgg cctcgatact gccctgtacg acggaaccgc   2880
ttccgatgga gagcaggccc tctacatgtc gatgccctgc ccttaaacag gcccctttc    2940
ctttgtcgat atcatgtaat tagttatgtc acgcttacat tcacgccctc ctcccacatc   3000
cgctctaacc gaaaaggaag gagttagaca acctgaagtc taggtcccta tttattttt    3060
ttaatagtta tgttagtatt aagaacgtta tttatatttc aaatttttct tttttttctg   3120
tacaaacgcg tgtacgcatg taacattata ctgaaaacct tgcttgagaa ggttttggga   3180
cgctcgaagg ctttaatttg cagagaccgg gttggcggcg catttgtgtc ccaaaaaaca   3240
gccccaattg ccccaattga ccccaaattg acccagtagc gggcccaacc ccggcgagag   3300
cccccttctc cccacatatc aaacctcccc cggttcccac acttgccgtt aagggcgtag   3360
ggtactgcag tctggaatct acgcttgttc agactttgta ctagtttctt tgtctggcca   3420
tccgggtaac ccatgccgga cgcaaaatag actactgaaa atttttttgc tttgtggttg   3480
ggactttagc caagggtata aaagaccacc gtccccgaat tacctttcct cttcttttct   3540
ctctctcctt gtcaactcac acccgaaatc gttaagcatt tccttctgag tataagaatc   3600
attcaaaatg aagttctcta tgccatcttg gggtgttgtt ttttacgctt tgttggtttg   3660
tttgttgcca ttcttgtcta aggctggtgt tcaagctatg tccgttgtta ccaccgatgc   3720
tcaagctgct catgctgctg gtgtttctag attattggct tcttatagag ccattccacc   3780
atctgctact gttagattgg ctaagccaac ttctaatttg ttcagagcta gagctagaac   3840
```

-continued

```
taacgttaag ggtttggatg tttctggttt gactggtgtt attggtgttg atccagatgc   3900
tagaactgct gatgttgctg gtatgtgtac ttacgaagat ttggttgctg ctactttgcc   3960
atatggtttg gctccattgg ttgttccaca attgaaaact attactttgg gtggtgctgt   4020
taccggtttg ggtattgaat ctacttcttt cagaaacggt ttgccacacg aatctgtttt   4080
ggaaatggat attttgaccg gttccggtga aatagttact gcttctccag atcaacactc   4140
cgatttgttt catgcttttc caaactctta cggtacattg ggttactcta ccagattgag   4200
aattgaattg gaaccagttc atccattcgt tgccttgaga catttgagat tccattccat   4260
tactgatttg gtcgcagcca tggatagaat tattgaaact ggtggtttag acggtgaacc   4320
agttgattat ttggatggtg ttgttttctc tgccaccgaa tcatatttgt gtgttggttt   4380
caaaactaag accccaggtc cagtttctga ttatactggt caacaaatct tctacagatc   4440
catccaacat gatggtgata ctggtgctga aaaacatgat agattgacca tccatgacta   4500
cttgtggaga tgggatactg attggttttg gtgttctaga gcttttggtg ctcaacatcc   4560
agttattaga agattctggc caagaagatt aagaagatcc tccttctact ggaaattggt   4620
tgcttacgat caaagatacg atatcgccga tagaatcgaa aagagaaatg gtagaccacc   4680
aagagaaaga gttgttcaag acgttgaagt tccaattgaa agatgcgctg atttcgttga   4740
atggttcttg caaaatgttc caatcgaacc tatttggttg tgcccattga gattgagaga   4800
ttctgctgat ggtggtgctt catggccatt atatccattg aaagctcatc acacctacgt   4860
caatattggt ttctggtcat ctgttccagt tggtccagaa gaaggtcata ccaatagatt   4920
gattgaaaaa aaggtcgccg aattggacgg tcacaaatca ttatattctg atgcctacta   4980
caccagagat gaattcgatg aattatacgg tggtgaagtt tacaacaccg tcaaaaaaac   5040
ttacgaccca gactcaagat tattagactt gtactctaag gccgtccaaa gacaacatga   5100
tgaattgtga gctgcttgta cctagtgcaa ccccagtttg ttaaaaatta gtagtcaaaa   5160
acttctgagt tagaaatttg tgagtgtagt gagattgtag agtatcatgt gtgtccgtaa   5220
gtgaagtgtt attgactctt agttagttta tctagtactc gtttagttga cactgatcta   5280
gtattttacg aggcgtatga ctttagccaa gtgttgtact tagtcttctc tccaaacatg   5340
agagggctct gtcactcagt cggcctatgg gtgagatggc ttggtgagat ctttcgatag   5400
tctcgtcaag atggtaggat gatgggggaa tacattactg ctctcgtcaa ggaaaccaca   5460
atcagatcac accatcctcc atggtatccg atgactctct tctccacagt cgcagtagga   5520
tgtcctgcac gggtcttttt gtggggtgtg gagaaagggg tgcttggaga tggaagccgg   5580
tagaaccggg ctgcttgggg ggatttgggg ccgctgggct ccaaagaggg gtaggcattt   5640
cgttggggtt acgtaattgc ggcatttggg tcctgcgcgc atgtcccatt ggtcagaatt   5700
agtccggata ggagacttat cagccaatca cagcgccgga tccacctgta ggttgggttg   5760
ggtgggagca cccctccaca gagtagagtc aaacagcagc agcaacgtga tagttggggg   5820
tgtgcgtgtt aaaggaaaaa aaaagaagct tgggttatat tcccgctcta tttagaggtt   5880
gcgggataga cgccgacgga gggcaatggc gccatggaac cttgcggata tcgatacgcc   5940
gcggcggact gcgtccgaac cagctccagc agcgtttttt ccgggccatt gagccgactg   6000
cgaccccgcc aacgtgtctt ggcccacgca ctcatgtcat gttggtgttg ggaggccact   6060
ttttaagtag cacaaggcac ctagctcgcg gcagggtgtc cgaaccaaag aagcggctgc   6120
agtggtgcaa acggggcgga aacggcggga aaaagccacg ggggcacgaa ttgaggcacg   6180
ccctcgaatt tgagacgagt cacggcccca ttcgcccgcg caatggctcg ccaacgcccg   6240
```

-continued

```
gtcttttgca ccacatcagg ttaccccaag ccaaaccttt gtgttaaaaa gcttaacata   6300
ttataccgaa cgtaggtttg ggcgggcttg ctccgtctgt ccaaggcaac atttatataa   6360
gggtctgcat cgccggctca attgaatctt ttttcttctt ctcttctcta tattcattct   6420
tgaattaaac acacatcaac aatgaagttc tctatgccat cttggggtgt tgttttttac   6480
gctttgttgg tttgtttgtt gccattcttg tctaaggctg gtgttcaagc tatgaccacc   6540
ttcaaagaaa gagaaacttc taccgctgat agaaagttga ccttggctga aattttggaa   6600
attttcgctg ctggtaaaga accattgaag ttcactgctt atgatggttc ttctgctggt   6660
cctgaagatg ctactatggg tttggatttg aaaactccaa gaggtactac ttacttggct   6720
actgctccag gtgatttggg tttggctaga gcttatgttt ctggtgactt ggaaccacat   6780
ggtgttcatc ctggtgatcc atatccatta ttgagagctt tagccgaaag aatggaattc   6840
aaaagaccac cagctagagt tttggctaac atcgttagat ccattggtat cgaacatttg   6900
aagccaattg ctccaccacc acaagaagct ttgccaagat ggagaagaat tatggaaggt   6960
ttgagacact ctaagaccag agatgctgaa gctattcatc atcactacga tgtttctaac   7020
accttctacg aatgggtttt gggtccatct atgacttata cttgtgcttg ttacccaaca   7080
gaagatgcca ctttggaaga agctcaagat aacaagtaca gattggtctt tgaaaagttg   7140
agattgaagc caggtgacag attattggat gttggttgtg gttggggtgg tatggttaga   7200
tatgctgcta gacatggtgt aaaagctttg ggtgttactt tgtctagaga acaagctact   7260
tgggctcaaa aagctattgc tcaagaaggt ttaaccgatt tggctgaagt tagacacggt   7320
gattacagag atgttatcga atctggtttc gatgccgttt cttctattgg tttgactgaa   7380
catatcggtg ttcataacta tccagcctac ttcaacttct tgaagtctaa gttgagaacc   7440
ggtggtttgt tgttgaacca ttgcattact agaccagata acagatctgc tccatctgct   7500
ggtggtttta ttgatagata cgttttccca gatggtgaat tgactggttc cggtagaatt   7560
attactgaag cacaagatgt cggtttggaa gttatccatg aagaaaactt gagaaaccat   7620
tacgccatga ctttgagaga ttggtgtaga aacttggttg aacattggga tgaagccgtt   7680
gaagaagttg gtttgccaac tgctaaagtt tggggtttgt atatggctgg ttctagatta   7740
ggttttgaaa ctaacgttgt ccaattgcac caagttttgg cagttaagtt ggatgatcaa   7800
ggtaaagatg gtggtttgcc tttaagacca tggtggtctg ctcatgatga attgtgagca   7860
ttagcgacta ctaatatata tttgaatcca tggaattata acaaacaagc atcaaaacaa   7920
gaattagcga cattatactt gaaatcagca ttagcgatac tactaatata gtttattcta   7980
tgtaatgatc catggaagtt cgattgattt gccaagttaa tttgatagat tatgcatgcc   8040
atttagtcga cgcaggtacg atctacagcg ataaagaaga ggttgtgggt cattcaattt   8100
tgcaccaatt ttgcaccatc atagatcata atacatttac aaggcctaca attcttacag   8160
ggtcttctcg agagcaattc cttaattaag gcgcgccttt ccataggctc cgcccccctg   8220
acgagcatca caaaaatcga cgctcaagtc agaggtggcg aaacccgaca ggactataaa   8280
gataccaggc gtttccccct ggaagctccc tcgtgcgctc tcctgttccg accctgccgc   8340
ttaccggata cctgtccgcc tttctccctt cgggaagcgt ggcgctttct catagctcac   8400
gctgtaggta tctcagttcg gtgtaggtcg ttcgctccaa gctgggctgt gtgcacgaac   8460
cccccgttca gcccgaccgc tgcgccttat ccggtaacta tcgtcttgag tccaacccgg   8520
taagacacga cttatcgcca ctggcagcag ccactggtaa caggattagc agagcgaggt   8580
```

```
atgtaggcgg tgctacagag ttcttgaagt ggtggcctaa ctacggctac actagaagaa   8640
cagtatttgg tatctgcgct ctgctgaagc cagttacctt cggaaaaaga gttggtagct   8700
cttgatccgg caaacaaacc accgctggta gcggtggttt ttttgtttgc aagcagcaga   8760
ttacgcgcag aaaaaaagga tctcaagaag atcctttgat cttttctacg gggtctgacg   8820
ctcagtggaa cgaaaactca cgttaaggga ttttggtcat gagattatca aaaaggatct   8880
tcacctagat ccttttaaat taaaaatgaa gttttaaatc aatctaaagt atatatgagt   8940
aaacttggtc tgacagttac caatgcttaa tcagtgaggc acctatctca gcgatctgtc   9000
tatttcgttc atccatagtt gcctgactcc ccgtcgtgta gataactacg atacgggagg   9060
gcttaccatc tggccccagt gctgcaatga taccgcgaga cccacgctca ccggctccag   9120
atttatcagc aataaaccag ccagccggaa gggccgagcg cagaagtggt cctgcaactt   9180
tatccgcctc catccagtct attaattgtt gccgggaagc tagagtaagt agttcgccag   9240
ttaatagttt gcgcaacgtt gttgccattg ctacaggcat cgtggtgtca cgctcgtcgt   9300
ttggtatggc ttcattcagc tccggttccc aacgatcaag gcgagttaca tgatccccca   9360
tgttgtgcaa aaaagcggtt agctccttcg gtcctccgat cgttgtcaga agtaagttgg   9420
ccgcagtgtt atcactcatg gttatggcag cactgcataa ttctcttact gtcatgccat   9480
ccgtaagatg cttttctgtg actggtgagt actcaaccaa gtcattctga gaatagtgta   9540
tgcggcgacc gagttgctct tgcccggcgt caatacggga taataccgcg ccacatagca   9600
gaactttaaa agtgctcatc attggaaaac gttcttcggg gcgaaaactc tcaaggatct   9660
taccgctgtt gagatccagt tcgatgtaac ccactcgtgc acccaactga tcttcagcat   9720
cttttacttt caccagcgtt tctgggtgag caaaaacagg aaggcaaaat gccgcaaaaa   9780
agggaataag ggcgacacgg aaatgttgaa tactcatact cttccttttt caatattatt   9840
gaagcattta tcagggttat tgtctcatga gcggatacat atttgaatgt atttagaaaa   9900
ataaacagcg atcgcgcggc cgcgggtaat aactgatata attaaattga agctctaatt   9960
tgtgagttta gtatacatgc atttacttat aatacagttt tttagttttg ctggccgcat  10020
cttctcaaat atgcttccca gcctgctttt ctgtaacgtt caccctctac cttagcatcc  10080
cttccctttg caaatagtcc tcttccaaca ataataatgt cagatcctgt agagaccaca  10140
tcatccacgg ttctatactg ttgacccaat gcgtctccct tgtcatctaa acccacaccg  10200
ggtgtcataa tcaaccaatc gtaaccttca tctcttccac ccatgtctct ttgagcaata  10260
aagccgataa caaaatcttt gtcgctcttc gcaatgtcaa cagtaccctt agtatattct  10320
ccagtagcta gggagccctt gcatgacaat tctgctaaca tcaaaaggcc tctaggttcc  10380
tttgttactt cttccgccgc ctgcttcaaa ccgctaacaa tacctgggcc caccacaccg  10440
tgtgcattcg taatgtctgc ccattctgct attctgtata cacccgcaga gtactgcaat  10500
ttgactgtat taccaatgtc agcaaatttt ctgtcttcga agagtaaaaa attgtacttg  10560
gcggataatg cctttagcgg cttaactgtg ccctccatgg aaaaatcagt caagatatcc  10620
acatgtgttt ttagtaaaca aattttggga cctaatgctt caactaactc cagtaattcc  10680
ttggtggtac gaacatccaa tgaagcacac aagtttgttt gcttttcgtg catgatatta  10740
aatagcttgg cagcaacagg actaggatga gtagcagcac gttccttata tgtagctttc  10800
gacatgattt atcttcgttt cctgcaggtt tttgttctgt gcagttgggt taagaatact  10860
gggcaatttc atgtttcttc aacaccacat atgcgtatat ataccaatct aagtctgtgc  10920
tccttccttc gttcttcctt ctgctcggag attaccgaat caaagctagc             10970
```

<210> SEQ ID NO 80
<211> LENGTH: 1410
<212> TYPE: DNA
<213> ORGANISM: Artificial Sequence
<220> FEATURE:
<223> OTHER INFORMATION: Synthetic Nucleic Acid

<400> SEQUENCE: 80
atgtccgttg ttaccaccga tgctcaagct gctcatgctg ctggtgtttc tagattattg 60
gcttcttata gagccattcc accatctgct actgttagat tggctaagcc aacttctaat 120
ttgttcagag ctagagctag aactaacgtt aagggtttgg atgtttctgg tttgactggt 180
gttattggtg ttgatccaga tgctagaact gctgatgttg ctggtatgtg tacttacgaa 240
gatttggttg ctgctacttt gccatatggt ttggctccat tggttgttcc acaattgaaa 300
actattactt tgggtggtgc tgttaccggt ttgggtattg aatctacttc tttcagaaac 360
ggtttgccac acgaatctgt tttggaaatg gatattttga ccggttccgg tgaaatagtt 420
actgcttctc cagatcaaca ctccgatttg tttcatgctt ttccaaactc ttacggtaca 480
ttgggttact ctaccagatt gagaattgaa ttggaaccag ttcatccatt cgttgccttg 540
agacatttga gattccattc cattactgat ttggtcgcag ccatggatag aattattgaa 600
actggtggtt tagacggtga accagttgat tatttggatg gtgttgtttt ctctgccacc 660
gaatcatatt tgtgtgttgg tttcaaaact aagaccccag gtccagtttc tgattatact 720
ggtcaacaaa tcttctacag atccatccaa catgatggtg atactggtgc tgaaaaacat 780
gatagattga ccatccatga ctacttgtgg agatgggata ctgattggtt ttggtgttct 840
agagcttttg gtgctcaaca tccagttatt agaagattct ggccaagaag attaagaaga 900
tcctccttct actggaaatt ggttgcttac gatcaaagat acgatatcgc cgatagaatc 960
gaaaagagaa atggtagacc accaagagaa agagttgttc aagacgttga agttccaatt 1020
gaaagatgcg ctgatttcgt tgaatggttc ttgcaaaatg ttccaatcga acctatttgg 1080
ttgtgcccat tgagattgag agattctgct gatggtggtg cttcatggcc attatatcca 1140
ttgaaagctc atcacaccta cgtcaatatt ggtttctggt catctgttcc agttggtcca 1200
gaagaaggtc ataccaatag attgattgaa aaaaaggtcg ccgaattgga cggtcacaaa 1260
tcattatatt ctgatgccta ctacaccaga gatgaattcg atgaattata cggtggtgaa 1320
gtttacaaca ccgtcaaaaa aacttacgac ccagactcaa gattattaga cttgtactct 1380
aaggccgtcc aaagacaaca tgatgaattg 1410

<210> SEQ ID NO 81
<211> LENGTH: 1311
<212> TYPE: DNA
<213> ORGANISM: Artificial Sequence
<220> FEATURE:
<223> OTHER INFORMATION: Synthetic Nucleic Acid

<400> SEQUENCE: 81
atgaccacct tcaaagaaag agaaacttct accgctgata gaaagttgac cttggctgaa 60
attttggaaa ttttcgctgc tggtaaagaa ccattgaagt tcactgctta tgatggttct 120
tctgctggtc ctgaagatgc tactatgggt ttggatttga aaactccaag aggtactact 180
tacttggcta ctgctccagg tgatttgggt ttggctagag cttatgtttc tggtgacttg 240
gaaccacatg gtgttcatcc tggtgatcca tatccattat tgagagcttt agccgaaaga 300
atggaattca aaagaccacc agctagagtt ttggctaaca tcgttagatc cattggtatc 360
gaacatttga agccaattgc tccaccacca caagaagctt tgccaagatg gagaagaatt 420
atggaaggtt tgagacactc taagaccaga gatgctgaag ctattcatca tcactacgat 480
gtttctaaca ccttctacga atgggttttg ggtccatcta tgacttatac ttgtgcttgt 540
tacccaacag aagatgccac tttggaagaa gctcaagata acaagtacag attggtcttt 600
gaaaagttga gattgaagcc aggtgacaga ttattggatg ttggttgtgg ttggggtggt 660
atggttagat atgctgctag acatggtgta aaagctttgg gtgttacttt gtctagagaa 720
caagctactt gggctcaaaa agctattgct caagaaggtt taaccgattt ggctgaagtt 780
agacacggtg attacagaga tgttatcgaa tctggtttcg atgccgtttc ttctattggt 840
ttgactgaac atatcggtgt tcataactat ccagcctact tcaacttctt gaagtctaag 900
ttgagaaccg gtggtttgtt gttgaaccat tgcattacta gaccagataa cagatctgct 960
ccatctgctg gtggttttat tgatagatac gttttcccag atggtgaatt gactggttcc 1020
ggtagaatta ttactgaagc acaagatgtc ggtttggaag ttatccatga agaaaacttg 1080
agaaaccatt acgccatgac tttgagagat tggtgtagaa acttggttga acattgggat 1140
gaagccgttg aagaagttgg tttgccaact gctaaagttt ggggtttgta tatggctggt 1200
tctagattag gttttgaaac taacgttgtc caattgcacc aagttttggc agttaagttg 1260
gatgatcaag gtaaagatgg tggtttgcct ttaagaccat ggtggtctgc t 1311

<210> SEQ ID NO 82
<211> LENGTH: 4399
<212> TYPE: DNA
<213> ORGANISM: Artificial Sequence
<220> FEATURE:
<223> OTHER INFORMATION: Synthetic Nucleic Acid

<400> SEQUENCE: 82
tgggtaggtt atatagggat atagcacaga gatatatagc aaagagatac ttttgagcaa 60
tgtttgtgga agcggtattc gcaatttaat taaagctggt gacaattaat catcggctcg 120
tataatgtgt ggaattgaat cgatataagg aggttaatca tgtttaaacc ctcaaaatat 180
attttccctc tatcttctcg ttgcgcttaa tttgactaat tctcattagc gaggcgcgcc 240
tttccatagg ctccgccccc ctgacgagca tcacaaaaat cgacgctcaa gtcagaggtg 300
gcgaaacccg acaggactat aaagatacca ggcgtttccc cctggaagct ccctcgtgcg 360
ctctcctgtt ccgaccctgc cgcttaccgg atacctgtcc gcctttctcc cttcgggaag 420
cgtggcgctt tctcatagct cacgctgtag gtatctcagt tcggtgtagg tcgttcgctc 480
caagctgggc tgtgtgcacg aaccccccgt tcagcccgac cgctgcgcct tatccggtaa 540
ctatcgtctt gagtccaacc cggtaagaca cgacttatcg ccactggcag cagccactgg 600
taacaggatt agcagagcga ggtatgtagg cggtgctaca gagttcttga agtggtggcc 660
taactacggc tacactagaa gaacagtatt tggtatctgc gctctgctga agccagttac 720
cttcggaaaa agagttggta gctcttgatc cggcaaacaa accaccgctg gtagcggtgg 780
tttttttgtt tgcaagcagc agattacgcg cagaaaaaaa ggatctcaag aagatccttt 840
gatcttttct acggggtctg acgctcagtg gaacgaaaac tcacgttaag ggattttggt 900
catgagatta tcaaaaagga tcttcaccta gatcctttta aattaaaaat gaagttttaa 960
atcaatctaa agtatatatg agtaaacttg gtctgacagt taccaatgct taatcagtga 1020
ggcacctatc tcagcgatct gtctatttcg ttcatccata gttgcctgac tccccgtcgt 1080

-continued

```
gtagataact acgatacggg agggcttacc atctggcccc agtgctgcaa tgataccgcg   1140
agacccacgc tcaccggctc cagatttatc agcaataaac cagccagccg gaagggccga   1200
gcgcagaagt ggtcctgcaa ctttatccgc ctccatccag tctattaatt gttgccggga   1260
agctagagta agtagttcgc cagttaatag tttgcgcaac gttgttgcca ttgctacagg   1320
catcgtggtg tcacgctcgt cgtttggtat ggcttcattc agctccggtt cccaacgatc   1380
aaggcgagtt acatgatccc ccatgttgtg caaaaaagcg gttagctcct tcggtcctcc   1440
gatcgttgtc agaagtaagt tggccgcagt gttatcactc atggttatgg cagcactgca   1500
taattctctt actgtcatgc catccgtaag atgcttttct gtgactggtg agtactcaac   1560
caagtcattc tgagaatagt gtatgcggcg accgagttgc tcttgcccgg cgtcaatacg   1620
ggataatacc gcgccacata gcagaacttt aaaagtgctc atcattggaa aacgttcttc   1680
ggggcgaaaa ctctcaagga tcttaccgct gttgagatcc agttcgatgt aacccactcg   1740
tgcacccaac tgatcttcag catcttttac tttcaccagc gtttctgggt gagcaaaaac   1800
aggaaggcaa aatgccgcaa aaaagggaat aagggcgaca cggaaatgtt gaatactcat   1860
actcttcctt tttcaatatt attgaagcat ttatcagggt tattgtctca tgagcggata   1920
catatttgaa tgtatttaga aaaataaaca gcgatcgcgc ggccgcgggt aataactgat   1980
ataattaaat tgaagctcta atttgtgagt ttagtataca tgcatttact tataatacag   2040
tttttagtt ttgctggccg catcttctca aatatgcttc ccagcctgct tttctgtaac   2100
gttcaccctc taccttagca tcccttccct ttgcaaatag tcctcttcca acaataataa   2160
tgtcagatcc tgtagagacc acatcatcca cggttctata ctgttgaccc aatgcgtctc   2220
ccttgtcatc taaacccaca ccgggtgtca taatcaacca atcgtaacct tcatctcttc   2280
cacccatgtc tctttgagca ataaagccga taacaaaatc tttgtcgctc ttcgcaatgt   2340
caacagtacc cttagtatat tctccagtag ctagggagcc cttgcatgac aattctgcta   2400
acatcaaaag gcctctaggt tcctttgtta cttcttccgc cgcctgcttc aaaccgctaa   2460
caatacctgg gcccaccaca ccgtgtgcat tcgtaatgtc tgcccattct gctattctgt   2520
atacacccgc agagtactgc aatttgactg tattaccaat gtcagcaaat tttctgtctt   2580
cgaagagtaa aaaattgtac ttggcggata atgcctttag cggcttaact gtgccctcca   2640
tggaaaaatc agtcaagata tccacatgtg tttttagtaa acaaattttg ggacctaatg   2700
cttcaactaa ctccagtaat tccttggtgg tacgaacatc caatgaagca cacaagtttg   2760
tttgcttttc gtgcatgata ttaaatagct tggcagcaac aggactagga tgagtagcag   2820
cacgttcctt atatgtagct ttcgacatga tttatcttcg tttcctgcag gtttttgttc   2880
tgtgcagttg ggttaagaat actgggcaat ttcatgtttc ttcaacacca catatgcgta   2940
tatataccaa tctaagtctg tgctccttcc ttcgttcttc cttctgctcg gagattaccg   3000
aatcaaagct agcttatcga tgataagctg tcaaagatga gaattaattc cacggactat   3060
agactatact agatactccg tctactgtac gatacacttc cgctcaggtc cttgtccttt   3120
aacgaggcct taccactctt ttgttactct attgatccag ctcagcaaag gcagtgtgat   3180
ctaagattct atcttcgcga tgtagtaaaa ctagctagac cgagaaagag actagaaatg   3240
caaaaggcac ttctacaatg gctgccatca ttattatccg atgtgacgct gcagcttctc   3300
aatgatattc gaatacgctt tgaggagata cagcctaata tccgacaaac tgttttacag   3360
atttacgatc gtacttgtta cccatcattg aattttgaac atccgaacct gggagttttc   3420
```

-continued

```
cctgaaacag atagtatatt tgaacctgta taataatata tagtctagcg ctttacggaa   3480

gacaatgtat gtatttcggt tcctggagaa actattgcat ctattgcata ggtaatcttg   3540

cacgtcgcat ccccggttca ttttctgcgt ttccatcttg cacttcaata gcatatcttt   3600

gttaacgaag catctgtgct tcattttgta gaacaaaaat gcaacgcgag agcgctaatt   3660

tttcaaacaa agaatctgag ctgcattttt acagaacaga aatgcaacgc gaaagcgcta   3720

ttttaccaac gaagaatctg tgcttcattt ttgtaaaaca aaaatgcaac gcgacgagag   3780

cgctaatttt tcaaacaaag aatctgagct gcatttttac agaacagaaa tgcaacgcga   3840

gagcgctatt ttaccaacaa agaatctata cttctttttt gttctacaaa aatgcatccc   3900

gagagcgcta tttttctaac aaagcatctt agattacttt ttttctcctt tgtgcgctct   3960

ataatgcagt ctcttgataa ctttttgcac tgtaggtccg ttaaggttag aagaaggcta   4020

ctttggtgtc tattttctct tccataaaaa aagcctgact ccacttcccg cgtttactga   4080

ttactagcga agctgcgggt gcattttttc aagataaagg catccccgat tatattctat   4140

accgatgtgg attgcgcata ctttgtgaac agaaagtgat agcgttgatg attcttcatt   4200

ggtcagaaaa ttatgaacgg tttcttctat tttgtctcta tatactacgt ataggaaatg   4260

tttacatttt cgtattgttt tcgattcact ctatgaatag ttcttactac aatttttttg   4320

tctaaagagt aatactagag ataaacataa aaaatgtaga ggtcgagttt agatgcaagt   4380

tcaaggagcg aaaggtgga                                                4399
```

<210> SEQ ID NO 83
<211> LENGTH: 7531
<212> TYPE: DNA
<213> ORGANISM: Artificial Sequence
<220> FEATURE:
<223> OTHER INFORMATION: Synthetic Nucleic Acid

<400> SEQUENCE: 83

```
gtttgtggaa gcggtattcg caatttaatt aaagctggtg acaattaatc atcggctcgt     60

ataatgtgtg gaattgaatc gatataagga ggttaatcat gtgtctgttc cttcgaccga    120

cgcacgttct gctcacgccg acggcgtgca gcggcttctc gccagctatc gggcgattcc    180

ccaagacgcc acggtccggc tggccaaacc cacgtcgaac ctcttccgtg cccgcgcgaa    240

aaccaggacc aagggtctgg acacgtctgg gttgacgaac gtgatcgcgg tcgacgcgga    300

ggcacgcacc gccgatgtgg cagggatgtg cacctacgaa gacctggtcg cggccacgct    360

gccgcatgga ctttcgccgc tggtggtgcc gcagttgaag acgatcaccc tcggcggggc    420

ggtcaccgga ctcgggatcg agtccgcctc gttccgcaac ggcctgccac acgaatcggt    480

tctcgagatg gacgtcctca ccggcaccgg tgatgtcgtg cgcgcctccc ccgacgagaa    540

ccctgacctg tttcgggcgt ttccgaattc ctatggcacg ttgggctatt cggttcggct    600

caagatcgag ctggaaccgg tgaagccgtt cgtcgcgctg cgccacctcc gtttccattc    660

gctgtcggct ctcatcgagg cgatggaccg catcgtcgaa accggcggcc tcaacggcga    720

accggtggac tacctcgacg gcgtcgtgtt cagtgccgag gagagttacc tgtgcgtggg    780

gcagcgctcc gcgacaccgg gcccggtcag cgactacacg ggcaagcaga tctactaccg    840

ctcgattcag cacgacggcc cgaccgatgg cgccgagaag cacgaccggc tgaccatcca    900

cgactacctg tggcgctggg acaccgactg gttctggtgc tcaagggcat tcggcgcgca    960

gaacccgcgg atccggcgct ggtggccgcg ccggtaccgg cgcagcagtg tgtactggaa   1020

gctgatcggc tacgaccggc gtttcggtat cgccgatcgc atcgagaagc gcaacggccg   1080
```

-continued

```
acccccgcgc gagcgggtgg tccaggacat cgaggtgccc atcgagcgga ccgtcgagtt   1140
tctgcagtgg tttctcgaca ccgtgcccat cgaaccgatc tggttgtgcc cgttgcggct   1200
ccgcgacgac cgcgattggc ccctgtatcc gatccgaccc caccacacct acgtcaacgt   1260
gggtttctgg tcgtcggtgc cggtgggccc ggaggagggc tacaccaaca ggatgatcga   1320
acggaaagtc agcgacctcg acggtcacaa atcgctgtat tccgatgcgt actactcgcc   1380
ggaagagttt gattcgctct atggcgggga gacgtacaag acggtgaaga agacatacga   1440
cccagactct cgtttcctgg acctgtacgg caaagcagtg gggcggcaat gagcgttgac   1500
gcgaagaacg gaggccacag ttgacgacat ttcgggacgg cgcggccgac accggcctgc   1560
acggagaccg caagctcacc ctggcggagg tcttggaggt cttcgcctcg ggccgactgc   1620
ctctgaagtt cacggcgtac gacggcagca gcgcgggccc ggacgacgcc acgctcgggc   1680
tggacctgct gaccccccgc gggaccacgt acctcgcaac ggctcccggc gatctcggcc   1740
tggcccgggc ctacgtctcc ggtgacctgc agttgcaggg ggtgcaccct ggcgacccgt   1800
acgacctgct caacgcactg gtgcagaaac tggacttcaa gcgaccgtcc gcccgggtgc   1860
tggcgcaggt cgtccgatcg atcgggatcg agcacctgaa accgatcgcg ccaccgccgc   1920
aggaggcgct gccgcggtgg cggcgcatcg cagaaggact gcggcacagc aagacccgtg   1980
acgccgacgc gatccaccac cattacgatg tctccaacac cttctacgag tgggtgctcg   2040
ggccgtcgat gacctacacc tgcgcctgct acccgcatcc cgacgccacc ctcgaggagg   2100
cgcaggagaa caaatatcgg ctggtgttcg agaaactgcg cctcaagccg ggcgaccgcc   2160
ttctcgacgt gggttgcggg tggggcggaa tggtgcgcta cgcggcccgt cacggcgtca   2220
aggcgatcgg ggtgacgctg tccagggagc aggcgcagtg ggcacgcgcc gccatcgaac   2280
gggacggcct gggtgacctc gccgaggtcc gccacagcga ctaccgcgat gtgcgcgagt   2340
cccagttcga cgccgtgtct tcgctggggc tcaccgagca catcggggtc gccaactatc   2400
cgtcgtactt ccggttcctc aagtcgaagt tgcgcccggg cggcctactg ctcaaccact   2460
gcatcacccg gcacaacaat cgcaccggcc ccgccgccgg gggattcatc gaccggtatg   2520
tgttcccgga cggggagctg accggatcgg gccggatcat caccgagatc caggacgtcg   2580
gtttggaggt gatgcacgaa gagaacctgc gccggcacta tgcgctgaca cttcgggact   2640
ggtgccggaa tctggtgcag cactgggacg aagcggtcgc agaggtcggc ctgcccaccg   2700
ccaaggtgtg ggtctgtac atggctgcct cgcgggtcgg cttcgagcag aacagcattc   2760
agctgcatca ggtactggcg gtgaagctcg acgaacgtgg cggggacggc ggtttgccgt   2820
tgcggccctg gtggaccgcg tagcaactat gctcaccgtg tgatccgctt tctgctgcgc   2880
gtcgcggtct ttctcggatc gtcggcgatc gggctactgg tggccggctg gctggtgccg   2940
ggggtgtcgc tgtcggtgct gggcttcgtc accgcggtgg tgatcttcac ggtggcacaa   3000
gggattctgt cgccgttctt cctgaagatg gccagccgct acgcgtcggc cttcctcggc   3060
ggcatcggcc tggtgtccac gttcgtggcg ctgctgctcg cgtcgctgct gtccaacggg   3120
ctcagcatcc gcggcgtcgg gtcgtggatc gcggccacgg tggtggtctg gctggtcaca   3180
gccctggcga ccgtcgtgct gcccgttctg gtgctgcggg agaagaagaa agcagcctga   3240
cctcaaaata tattttccct ctatcttctc gttgcgctta atttgactaa ttctcattag   3300
cgaggcgcgc ctttccatag gctccgcccc cctgacgagc atcacaaaaa tcgacgctca   3360
agtcagaggt ggcgaaaccc gacaggacta taaagatacc aggcgtttcc ccctggaagc   3420
```

tccctcgtgc gctctcctgt tccgaccctg ccgcttaccg gatacctgtc cgcctttctc 3480
ccttcgggaa gcgtggcgct ttctcatagc tcacgctgta ggtatctcag ttcggtgtag 3540
gtcgttcgct ccaagctggg ctgtgtgcac gaaccccccg ttcagcccga ccgctgcgcc 3600
ttatccggta actatcgtct tgagtccaac ccggtaagac acgacttatc gccactggca 3660
gcagccactg gtaacaggat tagcagagcg aggtatgtag gcggtgctac agagttcttg 3720
aagtggtggc ctaactacgg ctacactaga agaacagtat ttggtatctg cgctctgctg 3780
aagccagtta ccttcggaaa aagagttggt agctcttgat ccggcaaaca aaccaccgct 3840
ggtagcggtg gtttttttgt ttgcaagcag cagattacgc gcagaaaaaa aggatctcaa 3900
gaagatcctt tgatcttttc tacggggtct gacgctcagt ggaacgaaaa ctcacgttaa 3960
gggattttgg tcatgagatt atcaaaaagg atcttcacct agatcctttt aaattaaaaa 4020
tgaagtttta aatcaatcta aagtatatat gagtaaactt ggtctgacag ttaccaatgc 4080
ttaatcagtg aggcacctat ctcagcgatc tgtctatttc gttcatccat agttgcctga 4140
ctccccgtcg tgtagataac tacgatacgg gagggcttac catctggccc cagtgctgca 4200
atgataccgc gagacccacg ctcaccggct ccagatttat cagcaataaa ccagccagcc 4260
ggaagggccg agcgcagaag tggtcctgca actttatccg cctccatcca gtctattaat 4320
tgttgccggg aagctagagt aagtagttcg ccagttaata gtttgcgcaa cgttgttgcc 4380
attgctacag gcatcgtggt gtcacgctcg tcgtttggta tggcttcatt cagctccggt 4440
tcccaacgat caaggcgagt tacatgatcc cccatgttgt gcaaaaaagc ggttagctcc 4500
ttcggtcctc cgatcgttgt cagaagtaag ttggccgcag tgttatcact catggttatg 4560
gcagcactgc ataattctct tactgtcatg ccatccgtaa gatgcttttc tgtgactggt 4620
gagtactcaa ccaagtcatt ctgagaatag tgtatgcggc gaccgagttg ctcttgcccg 4680
gcgtcaatac gggataatac cgcgccacat agcagaactt taaaagtgct catcattgga 4740
aaacgttctt cggggcgaaa actctcaagg atcttaccgc tgttgagatc cagttcgatg 4800
taacccactc gtgcacccaa ctgatcttca gcatctttta ctttcaccag cgtttctggg 4860
tgagcaaaaa caggaaggca aaatgccgca aaaaagggaa taagggcgac acggaaatgt 4920
tgaatactca tactcttcct ttttcaatat tattgaagca tttatcaggg ttattgtctc 4980
atgagcggat acatatttga atgtatttag aaaaataaac agcgatcgcg cggccgcggg 5040
taataactga tataattaaa ttgaagctct aatttgtgag tttagtatac atgcatttac 5100
ttataataca gtttttagt tttgctggcc gcatcttctc aaatatgctt cccagcctgc 5160
ttttctgtaa cgttcaccct ctaccttagc atcccttccc tttgcaaata gtcctcttcc 5220
aacaataata atgtcagatc ctgtagagac cacatcatcc acggttctat actgttgacc 5280
caatgcgtct cccttgtcat ctaaacccac accgggtgtc ataatcaacc aatcgtaacc 5340
ttcatctctt ccacccatgt ctctttgagc aataaagccg ataacaaaat ctttgtcgct 5400
cttcgcaatg tcaacagtac ccttagtata ttctccagta gctagggagc ccttgcatga 5460
caattctgct aacatcaaaa ggcctctagg ttcctttgtt acttcttccg ccgcctgctt 5520
caaaccgcta acaatacctg ggcccaccac accgtgtgca ttcgtaatgt ctgcccattc 5580
tgctattctg tatacacccg cagagtactg caatttgact gtattaccaa tgtcagcaaa 5640
ttttctgtct tcgaagagta aaaaattgta cttggcggat aatgccttta gcggcttaac 5700
tgtgccctcc atggaaaaat cagtcaagat atccacatgt gtttttagta aacaaatttt 5760
gggacctaat gcttcaacta actccagtaa ttccttggtg gtacgaacat ccaatgaagc 5820
acacaagttt gtttgctttt cgtgcatgat attaaatagc ttggcagcaa caggactagg 5880
atgagtagca gcacgttcct tatatgtagc tttcgacatg atttatcttc gtttcctgca 5940
ggtttttgtt ctgtgcagtt gggttaagaa tactgggcaa tttcatgttt cttcaacacc 6000
acatatgcgt atatatacca atctaagtct gtgctccttc cttcgttctt ccttctgctc 6060
ggagattacc gaatcaaagc tagcttatcg atgataagct gtcaaagatg agaattaatt 6120
ccacggacta tagactatac tagatactcc gtctactgta cgatacactt ccgctcaggt 6180
ccttgtcctt taacgaggcc ttaccactct tttgttactc tattgatcca gctcagcaaa 6240
ggcagtgtga tctaagattc tatcttcgcg atgtagtaaa actagctaga ccgagaaaga 6300
gactagaaat gcaaaaggca cttctacaat ggctgccatc attattatcc gatgtgacgc 6360
tgcagcttct caatgatatt cgaatacgct ttgaggagat acagcctaat atccgacaaa 6420
ctgttttaca gatttacgat cgtacttgtt acccatcatt gaattttgaa catccgaacc 6480
tgggagtttt ccctgaaaca gatagtatat ttgaacctgt ataataatat atagtctagc 6540
gctttacgga agacaatgta tgtatttcgg ttcctggaga aactattgca tctattgcat 6600
aggtaatctt gcacgtcgca tccccggttc attttctgcg tttccatctt gcacttcaat 6660
agcatatctt tgttaacgaa gcatctgtgc ttcattttgt agaacaaaaa tgcaacgcga 6720
gagcgctaat tttcaaaca aagaatctga gctgcatttt tacagaacag aaatgcaacg 6780
cgaaagcgct attttaccaa cgaagaatct gtgcttcatt tttgtaaaac aaaaatgcaa 6840
cgcgacgaga gcgctaattt ttcaaacaaa gaatctgagc tgcattttta cagaacagaa 6900
atgcaacgcg agagcgctat tttaccaaca aagaatctat acttcttttt tgttctacaa 6960
aaatgcatcc cgagagcgct atttttctaa caaagcatct tagattactt tttttctcct 7020
ttgtgcgctc tataatgcag tctcttgata actttttgca ctgtaggtcc gttaaggtta 7080
gaagaaggct actttggtgt ctattttctc ttccataaaa aaagcctgac tccacttccc 7140
gcgtttactg attactagcg aagctgcggg tgcatttttt caagataaag gcatccccga 7200
ttatattcta taccgatgtg gattgcgcat actttgtgaa cagaaagtga tagcgttgat 7260
gattcttcat tggtcagaaa attatgaacg gtttcttcta ttttgtctct atatactacg 7320
tataggaaat gtttacattt tcgtattgtt ttcgattcac tctatgaata gttcttacta 7380
caattttttt gtctaaagag taatactaga gataaacata aaaaatgtag aggtcgagtt 7440
tagatgcaag ttcaaggagc gaaaggtgga tgggtaggtt atatagggat atagcacaga 7500
gatatatagc aaagagatac ttttgagcaa t 7531

<210> SEQ ID NO 84
<211> LENGTH: 7126
<212> TYPE: DNA
<213> ORGANISM: Artificial Sequence
<220> FEATURE:
<223> OTHER INFORMATION: Synthetic Nucleic Acid

<400> SEQUENCE: 84
gtttgtggaa gcggtattcg caatttaatt aaagctggtg acaattaatc atcggctcgt 60
ataatgtgtg gaattgaatc gatataagga ggttaatcat atgacgcctg aagctagtgc 120
ggcggcgcac gccgctgcgg tggatcgcct catccatagc tatcgggcga ttcctgatga 180
cgcgccggtg cggctggcga agaagacgtc aaacctattc cgccacaggg aaaagacttc 240
tgctcctggg cttgacgtat ccggcctggc tcgcgtgatt gggatcgact cagacactcg 300

-continued

```
cactgccgac gttggcggca tgtgcacata cgaggacctt gtcgcggcga cgctcgaata    360
cgatctggtc cccctggtcg tcccgcaact caaaacgatc actctcggcg gcgcggtgac    420
gggcctggga attgagtcca cctcgttccg caatgggctt ccccatgaat ctgttctcga    480
aatggatatc ctgacgggcg ccggggaggt cgtcacggcc ggcccggaag gcccccatag    540
cgatttgtac tgggggtttc cgaattcgta cggcacgctc ggctatgcga cgcgcctgcg    600
catcgaacta gaaccggtcg agccgtacgt cgaactcagg cacctgcggt tcactagcct    660
cgatgagctt caggagacac ttgacaccgt ttcgtacgaa cacacgtatg acggggaacc    720
cgttcattac gtcgatggag tcatgttctc agccacggaa agctacctca cgcttggccg    780
tcagacgagc gaacccggcc cggtcagcga ctacaccgga aaccagatct actaccgttc    840
aatacagcac ggtggcgctg aaactcccgt cgtcgaccgg atgaccattc atgactatct    900
atggcgctgg gatactgact ggttctggtg ctcgcgtgcc ttcggaacgc aacacccagt    960
ggtccggaga ttctggccac gccgctatcg ccgcagcagc ttctactgga agctgatcgc   1020
gcttgaccgc caggttgggc tcgcggactt catcgaacaa cggaagggca acctcccccg   1080
ggaacgcgta gtccaggaca tcgaggtccc gatcgagaac actgcgagct tcttgcggtg   1140
gttcttggcg aacgtgccga tcgagccggt atggctatgc ccgctgcgcc tgcgaaaaac   1200
acgcagcccc ggcctgcctt cgccgacgtc cccggcttca cgcccatggc ccctctatcc   1260
gctcgagcct cagcgcacat acgtcaatgt tggcttctgg tcagcggtgc cggtcgtggc   1320
cggccagccc gaggggcaca ccaaccggat gatcgagaac gaagtcgatc gccttgacgg   1380
tcacaaatcg ctgtactcag atgcgtttta cgagcgaaaa gagtttgacg cgctgtacgg   1440
cggcgatacc tatagagaac tcaaagagac ctacgaccca aacagccggt tacttgatct   1500
ctatgcaaag gcggtgcaag gacgatgaag gcagtgttga cggcgtttac ggctccccaa   1560
ctcgaaagga tgaacgtcgc tgagatactc agcgcggtac tcgggcgaga tttcccgatc   1620
cggttcactg cgtacgacgg cagcgcgctc ggccccgaaa ccgcccgcta cggcttgcac   1680
ctcacgacgc cgcgcgggct gacctacctc gctaccgcgc ccggtgatct cgggctcgca   1740
cgcgcgtacg tgtccggcga cctcgaggtc agtggggttc atcagggtga cccgtacgag   1800
ataatgaaga tcctcgcgca tgacgtccgg gtgcggcggc cctcgccagc aacgatcgct   1860
tcgatcatgc ggtccctcgg ctgggaacgc ttgcgaccgg tcgcgccgcc cccgcaagag   1920
aacatgcccc gttggcgccg gatggccctt ggcctgctgc actcgaagag ccgtgatgct   1980
gcggcaatcc accatcatta cgacgtgtcg aacgagtttt acgagcacat cctcggcccg   2040
tcgatgacgt acacatgcgc ggcctacccc agcgcagaca gttccctgga ggaagcacag   2100
gacaacaagt accgactcgt cttcgagaaa cttggcctga aagccgggga tcgcctgctt   2160
gacgtcgggt gcgggtgggg cggcatggtg cggttcgccg ctaagcgcgg cgttcatgtc   2220
atcggtgcga cattgtcccg caaacaggcg gaatgggctc agaagatgat tgcccatgaa   2280
ggattgggcg atctggcgga agtccgtttc tgcgactacc gcgatgtcac agaggcgggc   2340
ttcgacgcag tgtcgtcgat cggcctcact gaacacatcg gtttggcgaa ctacccgtcg   2400
tacttcggct tcctgaagga caagttgcgg ccaggcggac gactgctgaa ccattgcatc   2460
actcgcccga acaaccttca aagcaaccgc gcaggtgact tcattgaccg gtacgttttc   2520
cctgacggag agctcgccgg acctggcttc atcatttcag ctgtccacga cgccggtttc   2580
gaggtgcggc acgaagagaa cctccgcgag cactacgcac tgacgctgcg ggactggaac   2640
cgcaacctcg ctcgcgactg ggacgcgtgt gtgcacgcct ccgacgaggg caccgcccgc   2700
```

```
gtctggggac tgtacatttc cggttcacga gtcgcgtttg aaacgaactc gattcagctg   2760
caccaggtcc tggcggtcaa aaccgcgcgg aatggcgaag cgcaggtccc gttgggtcag   2820
tggtggaccc gctgacctca aaatatattt tccctctatc ttctcgttgc gcttaatttg   2880
actaattctc attagcgagg cgcgcctttc cataggctcc gcccccctga cgagcatcac   2940
aaaaatcgac gctcaagtca gaggtggcga aacccgacag gactataaag ataccaggcg   3000
tttccccctg gaagctccct cgtgcgctct cctgttccga ccctgccgct taccggatac   3060
ctgtccgcct ttctcccttc gggaagcgtg gcgctttctc atagctcacg ctgtaggtat   3120
ctcagttcgg tgtaggtcgt tcgctccaag ctgggctgtg tgcacgaacc ccccgttcag   3180
cccgaccgct gcgccttatc cggtaactat cgtcttgagt ccaacccggt aagacacgac   3240
ttatcgccac tggcagcagc cactggtaac aggattagca gagcgaggta tgtaggcggt   3300
gctacagagt tcttgaagtg gtggcctaac tacggctaca ctagaagaac agtatttggt   3360
atctgcgctc tgctgaagcc agttaccttc ggaaaaagag ttggtagctc ttgatccggc   3420
aaacaaacca ccgctggtag cggtggtttt tttgtttgca agcagcagat tacgcgcaga   3480
aaaaaaggat ctcaagaaga tcctttgatc ttttctacgg ggtctgacgc tcagtggaac   3540
gaaaactcac gttaagggat tttggtcatg agattatcaa aaaggatctt cacctagatc   3600
cttttaaatt aaaaatgaag ttttaaatca atctaaagta tatatgagta aacttggtct   3660
gacagttacc aatgcttaat cagtgaggca cctatctcag cgatctgtct atttcgttca   3720
tccatagttg cctgactccc cgtcgtgtag ataactacga tacgggaggg cttaccatct   3780
ggccccagtg ctgcaatgat accgcgagac ccacgctcac cggctccaga tttatcagca   3840
ataaaccagc cagccggaag ggccgagcgc agaagtggtc ctgcaacttt atccgcctcc   3900
atccagtcta ttaattgttg ccgggaagct agagtaagta gttcgccagt taatagtttg   3960
cgcaacgttg ttgccattgc tacaggcatc gtggtgtcac gctcgtcgtt tggtatggct   4020
tcattcagct ccggttccca acgatcaagg cgagttacat gatcccccat gttgtgcaaa   4080
aaagcggtta gctccttcgg tcctccgatc gttgtcagaa gtaagttggc cgcagtgtta   4140
tcactcatgg ttatggcagc actgcataat tctcttactg tcatgccatc cgtaagatgc   4200
ttttctgtga ctggtgagta ctcaaccaag tcattctgag aatagtgtat gcggcgaccg   4260
agttgctctt gcccggcgtc aatacgggat aataccgcgc cacatagcag aactttaaaa   4320
gtgctcatca ttggaaaacg ttcttcgggg cgaaaactct caaggatctt accgctgttg   4380
agatccagtt cgatgtaacc cactcgtgca cccaactgat cttcagcatc ttttactttc   4440
accagcgttt ctgggtgagc aaaaacagga aggcaaaatg ccgcaaaaaa gggaataagg   4500
gcgacacgga aatgttgaat actcatactc ttcctttttc aatattattg aagcatttat   4560
cagggttatt gtctcatgag cggatacata tttgaatgta tttagaaaaa taaacagcga   4620
tcgcgcggcc gcgggtaata actgatataa ttaaattgaa gctctaattt gtgagtttag   4680
tatacatgca tttacttata atacagtttt ttagttttgc tggccgcatc ttctcaaata   4740
tgcttcccag cctgcttttc tgtaacgttc accctctacc ttagcatccc ttccctttgc   4800
aaatagtcct cttccaacaa taataatgtc agatcctgta gagaccacat catccacggt   4860
tctatactgt tgacccaatg cgtctccctt gtcatctaaa cccacaccgg gtgtcataat   4920
caaccaatcg taaccttcat ctcttccacc catgtctctt tgagcaataa agccgataac   4980
aaaatctttg tcgctcttcg caatgtcaac agtaccctta gtatattctc cagtagctag   5040
```

ggagcccttg catgacaatt ctgctaacat caaaaggcct ctaggttcct ttgttacttc 5100
ttccgccgcc tgcttcaaac cgctaacaat acctgggccc accacaccgt gtgcattcgt 5160
aatgtctgcc cattctgcta ttctgtatac acccgcagag tactgcaatt tgactgtatt 5220
accaatgtca gcaaattttc tgtcttcgaa gagtaaaaaa ttgtacttgg cggataatgc 5280
ctttagcggc ttaactgtgc cctccatgga aaaatcagtc aagatatcca catgtgtttt 5340
tagtaaacaa attttgggac ctaatgcttc aactaactcc agtaattcct tggtggtacg 5400
aacatccaat gaagcacaca agtttgtttg cttttcgtgc atgatattaa atagcttggc 5460
agcaacagga ctaggatgag tagcagcacg ttccttatat gtagctttcg acatgattta 5520
tcttcgtttc ctgcaggttt ttgttctgtg cagttgggtt aagaatactg ggcaatttca 5580
tgtttcttca acaccacata tgcgtatata taccaatcta agtctgtgct ccttccttcg 5640
ttcttccttc tgctcggaga ttaccgaatc aaagctagct tatcgatgat aagctgtcaa 5700
agatgagaat taattccacg gactatagac tatactagat actccgtcta ctgtacgata 5760
cacttccgct caggtccttg tcctttaacg aggccttacc actcttttgt tactctattg 5820
atccagctca gcaaaggcag tgtgatctaa gattctatct tcgcgatgta gtaaaactag 5880
ctagaccgag aaagagacta gaaatgcaaa aggcacttct acaatggctg ccatcattat 5940
tatccgatgt gacgctgcag cttctcaatg atattcgaat acgctttgag gagatacagc 6000
ctaatatccg acaaactgtt ttacagattt acgatcgtac ttgttaccca tcattgaatt 6060
ttgaacatcc gaacctggga gttttccctg aaacagatag tatatttgaa cctgtataat 6120
aatatatagt ctagcgcttt acggaagaca atgtatgtat ttcggttcct ggagaaacta 6180
ttgcatctat tgcataggta atcttgcacg tcgcatcccc ggttcatttt ctgcgtttcc 6240
atcttgcact tcaatagcat atctttgtta acgaagcatc tgtgcttcat tttgtagaac 6300
aaaaatgcaa cgcgagagcg ctaatttttc aaacaaagaa tctgagctgc atttttacag 6360
aacagaaatg caacgcgaaa gcgctatttt accaacgaag aatctgtgct tcatttttgt 6420
aaaacaaaaa tgcaacgcga cgagagcgct aatttttcaa acaaagaatc tgagctgcat 6480
ttttacagaa cagaaatgca acgcgagagc gctattttac caacaaagaa tctatacttc 6540
tttttgttc tacaaaaatg catcccgaga gcgctatttt tctaacaaag catcttagat 6600
tactttttt ctcctttgtg cgctctataa tgcagtctct tgataacttt ttgcactgta 6660
ggtccgttaa ggttagaaga aggctacttt ggtgtctatt ttctcttcca taaaaaaagc 6720
ctgactccac ttcccgcgtt tactgattac tagcgaagct gcgggtgcat tttttcaaga 6780
taaaggcatc cccgattata ttctataccg atgtggattg cgcatacttt gtgaacagaa 6840
agtgatagcg ttgatgattc ttcattggtc agaaaattat gaacggtttc ttctattttg 6900
tctctatata ctacgtatag gaaatgttta cattttcgta ttgttttcga ttcactctat 6960
gaatagttct tactacaatt tttttgtcta aagagtaata ctagagataa acataaaaaa 7020
tgtagaggtc gagtttagat gcaagttcaa ggagcgaaag gtggatgggt aggttatata 7080
gggatatagc acagagatat atagcaaaga gatacttttg agcaat 7126

<210> SEQ ID NO 85
<211> LENGTH: 7925
<212> TYPE: DNA
<213> ORGANISM: Artificial Sequence
<220> FEATURE:
<223> OTHER INFORMATION: Synthetic Nucleic Acid

<400> SEQUENCE: 85

-continued

```
gtttgtggaa gcggtattcg caatttaatt aaagctggtg acaattaatc atcggctcgt     60
ataatgtgtg gaattgaatc gatataagga ggttaatcat gtgaccgtcg ccggcaggat    120
cactgacgcg gtacgcatag gaaatggact tgaccagcga gatctagccc ccgtcgggtg    180
gtacgcacac gaacaggccg tggcgcgact gaaggccagt ttcgacgcgg tccccgccgg    240
gcgtcgcgtg cggctggcga agaagacgtc caaccttttc cgcgggcgtt ccggcgaggc    300
agtcgggctc gacgtgtcgg ggctgcacgg cgtcatcgcc gtcgaccccg ttgagggcac    360
cgctgacgtc cagggcatgt gcacgtacga ggacctggtg gacgtcctgc tgccctacgg    420
tctggcgccc accgtcgttc cgcagctgaa gaccatcact ctcggcggtg cggtgaccgg    480
catgggggtg gaatccacct ccttccgcaa cggcctgccg cacgaagccg tcctggaaat    540
ggatgtgctc accggtaccg gagacatcct cacctgttcg ccgacccaga acaccgacct    600
ctaccgcggc ttccccaact cctacggttc cctgggatac agcgtgcggc tgaaggtgcg    660
gtgcgaacgg gtggaaccct acgtcgacct gcggcatgta cgcttcgatg acgttcagtc    720
gctcaccgac gccctcgaca acatcgtcgt ggacaaggag tacgagggtg aacgggtcga    780
ctatctcgac ggtgtggtct tcagcctgga ggagagctac ctcgtcctgg gacgggcgac    840
cagcgaggcc ggccccgtta gcgactacac ccgcgagcgc agttactacc gttctctgca    900
gcatccgtcg gggtcctgc gcgacaagtt gaccatccgc gactacctct ggcggtggga    960
cgtcgactgg ttctggtgca accgggcctt cggtacccag aaccccacca tccgtactct   1020
gtggccgcgg gatctcctgc ggtcgagctt ctactggaag atcatcggct gggaccgacg   1080
cttcgacatc gcggaccgga tcgaggcaca caacgggcgc cccgcacgcg agcgcgtcgt   1140
ccaggacatc gaggtcaccc ccgacaacct gccggagttc ctcacgtggt tcttcaccca   1200
ctgcgagatc gagccggtgt ggctgtgccc cattcgactg gccgacgact cgggcgagcg   1260
gacaccgtgg cccctgtacc cgctgtcacc cggcgacacc tgggtcaacg tgggattctg   1320
gagctcggtg cccgccgacc tgatggggaa ggacgccccg accggagcct tcaaccggga   1380
ggtggagaga gtcgtctcgg acctcggcgg acacaagtcg ttgtactccg aggcattcta   1440
ttctgaggaa cagttcgccg ccctctacgg cggtgaacgt cccgcacaac tcaaggcggt   1500
cttcgacccg gatgaccggt tccccgggtt gtacgagaag accgtgggcg gcgtctgacg   1560
acacgcacga cgacgcacac cgagcacgat gacgcacgac aagcacgatg acgcatgatg   1620
accaagagga gagagatgag caggggattc acgccgctga cggtgggaca gatcgtggac   1680
aaggtcatca caccgccggc accgttccgg gtgaccgctt tcgacggatc caccgcgggg   1740
ccggcagacg cggaactggc actggagatc acatcgccgg acgccctggc ctatatcgtg   1800
accgcgccgg gcgacctcgg actggcacgc gcctacatca ccggaagcct ccgcgtcacc   1860
ggtgacgagc ccggccaccc gtacctcgtc tttgaccacc tccagcacct ttacgaccag   1920
atccgacgcc cctcggcgaa ggacctgctg gatatcgccc gctcgctgaa ggccatgggg   1980
gcgatcaagg tgcagccggc accggagcag gagaccctcc cgggctggaa gagggccata   2040
ctcgaggggc tgtcccggca ctctccggaa cgggacaagg aggtcgtgag ccgccactac   2100
gacgtgggca atgacttcta cgagctcttc ctcggcgatt ccatggccta cacctgtgcc   2160
tactatcccg agtttgacgg tgagaaccag gtcaccggtc ccaccggcgg gtggcggtac   2220
gacgactggg agaaagggcc gaccgccaac gggccgttga cccaggcgca ggacaacaag   2280
catcgcctgg tcttcgacaa gctgcgactc aacccgggtg accggttgtt ggacgtcggc   2340
```

-continued

```
tgcgggtggg gcggtatggt gcggtacgcc gcccgccacg gcgtgaaggc catcggtgtc   2400
acgctgtccc gagagcagta cgagtggggt aaggcgaaga tcgaggagga gggtctgcag   2460
gacctcgccg aggtccggtg tatggactac cgtgacgtgc cggagtccga cttcgacgcg   2520
gtcagtgcca tcggcatcct cgagcacatc ggcgtgccca actacgagga ctacttcacc   2580
cgcctgttcg ccaagctgcg cccgggcggt cggatgctga accactgcat cacccgtccg   2640
cacaaccgga agacgaagac cggccagttc atcgaccgct acatcttccc cgacggtgag   2700
ctgaccggct cgggccggat catcacgatc atgcaggaca ccggattcga cgtcgtccac   2760
gaggagaatc tgcgaccgca ctaccagcgc acgttgcatg actggtgtga actgttggcc   2820
accaactggg accaggccgt ccatctcgtg ggcgaggaga cggctcgtct gttcggcctg   2880
tacatggcgg ggtcggaatg gggtttcgaa cacaacgtga tccagctcca ccaggttctc   2940
ggcgtgaagc cggacgcggc aggcagttcc ggggtgccgg tccgccagtg gtggaggtcc   3000
tgacggtaac gtcgggacga tgagacggat caccagaggc gctgcggtgg cggtgctgtg   3060
cacaccgttg ctgctcggag cctgcaccat cggcgacgcg ggaccggggg acgagaccac   3120
ggaccctgtc gtggacactg aagcaccgcc cgataaaccg gtgccggact ctgcggcgga   3180
atccggcgct gaagacggac ctgattctga ggtgccggac gaccccgacc agcctgatgc   3240
tgagccggtg gagactgatc ccgacgcccc gggggcccgg ggactggcga tcggtgactg   3300
cgtcgccgac atggaccagc tcgacggcac cggcgacatc gacgtcgtcg actgcgccgg   3360
cccccatgcc ggcgaggtgt acgcacaggc ggatatcgca ggtaagaacc tgttccccgg   3420
caacgagccg ttggggcagg aggcgggagc gatctgcggg ggtgactcct tcaccggcta   3480
tgtcggcatc ggattccccg agtcctcgct ggacgtcgtc acgatgatgc cgtccaagga   3540
gagctgggcg caggaggacc ggacggtgac ctgtgtggtc accgacccga acctcgagca   3600
gatcgccggc acgctcgagc agagctggcg ttagcctcaa aatatatttt ccctctatct   3660
tctcgttgcg cttaatttga ctaattctca ttagcgaggc gcgcctttcc ataggctccg   3720
ccccccctgac gagcatcaca aaaatcgacg ctcaagtcag aggtggcgaa acccgacagg   3780
actataaaga taccaggcgt ttccccctgg aagctccctc gtgcgctctc ctgttccgac   3840
cctgccgctt accggatacc tgtccgcctt tctcccttcg ggaagcgtgg cgctttctca   3900
tagctcacgc tgtaggtatc tcagttcggt gtaggtcgtt cgctccaagc tgggctgtgt   3960
gcacgaaccc cccgttcagc ccgaccgctg cgccttatcc ggtaactatc gtcttgagtc   4020
caacccggta agacacgact tatcgccact ggcagcagcc actggtaaca ggattagcag   4080
agcgaggtat gtaggcggtg ctacagagtt cttgaagtgg tggcctaact acggctacac   4140
tagaagaaca gtatttggta tctgcgctct gctgaagcca gttaccttcg gaaaaagagt   4200
tggtagctct tgatccggca aacaaaccac cgctggtagc ggtggttttt ttgtttgcaa   4260
gcagcagatt acgcgcagaa aaaaaggatc tcaagaagat cctttgatct tttctacggg   4320
gtctgacgct cagtggaacg aaaactcacg ttaagggatt ttggtcatga gattatcaaa   4380
aaggatcttc acctagatcc ttttaaatta aaaatgaagt tttaaatcaa tctaaagtat   4440
atatgagtaa acttggtctg acagttacca atgcttaatc agtgaggcac ctatctcagc   4500
gatctgtcta tttcgttcat ccatagttgc ctgactcccc gtcgtgtaga taactacgat   4560
acgggagggc ttaccatctg gccccagtgc tgcaatgata ccgcgagacc cacgctcacc   4620
ggctccagat ttatcagcaa taaaccagcc agccggaagg gccgagcgca gaagtggtcc   4680
tgcaacttta tccgcctcca tccagtctat taattgttgc cgggaagcta gagtaagtag   4740
```

```
ttcgccagtt aatagtttgc gcaacgttgt tgccattgct acaggcatcg tggtgtcacg   4800
ctcgtcgttt ggtatggctt cattcagctc cggttcccaa cgatcaaggc gagttacatg   4860
atcccccatg ttgtgcaaaa aagcggttag ctccttcggt cctccgatcg ttgtcagaag   4920
taagttggcc gcagtgttat cactcatggt tatggcagca ctgcataatt ctcttactgt   4980
catgccatcc gtaagatgct tttctgtgac tggtgagtac tcaaccaagt cattctgaga   5040
atagtgtatg cggcgaccga gttgctcttg cccggcgtca atacgggata ataccgcgcc   5100
acatagcaga actttaaaag tgctcatcat tggaaaacgt tcttcggggc gaaaactctc   5160
aaggatctta ccgctgttga gatccagttc gatgtaaccc actcgtgcac ccaactgatc   5220
ttcagcatct tttactttca ccagcgtttc tgggtgagca aaaacaggaa ggcaaaatgc   5280
cgcaaaaaag ggaataaggg cgacacggaa atgttgaata ctcatactct tcctttttca   5340
atattattga agcatttatc agggttattg tctcatgagc ggatacatat ttgaatgtat   5400
ttagaaaaat aaacagcgat cgcgcggccg cgggtaataa ctgatataat taaattgaag   5460
ctctaatttg tgagtttagt atacatgcat ttacttataa tacagttttt tagttttgct   5520
ggccgcatct tctcaaatat gcttcccagc ctgcttttct gtaacgttca ccctctacct   5580
tagcatccct tccctttgca aatagtcctc ttccaacaat aataatgtca gatcctgtag   5640
agaccacatc atccacggtt ctatactgtt gacccaatgc gtctcccttg tcatctaaac   5700
ccacaccggg tgtcataatc aaccaatcgt aaccttcatc tcttccaccc atgtctcttt   5760
gagcaataaa gccgataaca aaatctttgt cgctcttcgc aatgtcaaca gtacccttag   5820
tatattctcc agtagctagg gagcccttgc atgacaattc tgctaacatc aaaaggcctc   5880
taggttcctt tgttacttct tccgccgcct gcttcaaacc gctaacaata cctgggccca   5940
ccacaccgtg tgcattcgta atgtctgccc attctgctat tctgtataca cccgcagagt   6000
actgcaattt gactgtatta ccaatgtcag caaattttct gtcttcgaag agtaaaaaat   6060
tgtacttggc ggataatgcc tttagcggct taactgtgcc ctccatggaa aaatcagtca   6120
agatatccac atgtgttttt agtaaacaaa ttttgggacc taatgcttca actaactcca   6180
gtaattcctt ggtggtacga acatccaatg aagcacacaa gtttgtttgc ttttcgtgca   6240
tgatattaaa tagcttggca gcaacaggac taggatgagt agcagcacgt tccttatatg   6300
tagctttcga catgatttat cttcgtttcc tgcaggtttt tgttctgtgc agttgggtta   6360
agaatactgg gcaatttcat gtttcttcaa caccacatat gcgtatatat accaatctaa   6420
gtctgtgctc cttccttcgt tcttccttct gctcggagat taccgaatca aagctagctt   6480
atcgatgata agctgtcaaa gatgagaatt aattccacgg actatagact atactagata   6540
ctccgtctac tgtacgatac acttccgctc aggtccttgt cctttaacga ggccttacca   6600
ctcttttgtt actctattga tccagctcag caaaggcagt gtgatctaag attctatctt   6660
cgcgatgtag taaaactagc tagaccgaga aagagactag aaatgcaaaa ggcacttcta   6720
caatggctgc catcattatt atccgatgtg acgctgcagc ttctcaatga tattcgaata   6780
cgctttgagg agatacagcc taatatccga caaactgttt tacagattta cgatcgtact   6840
tgttacccat cattgaattt tgaacatccg aacctgggag ttttccctga aacagatagt   6900
atatttgaac ctgtataata atatatagtc tagcgcttta cggaagacaa tgtatgtatt   6960
tcggttcctg gagaaactat tgcatctatt gcataggtaa tcttgcacgt cgcatccccg   7020
gttcattttc tgcgtttcca tcttgcactt caatagcata tctttgttaa cgaagcatct   7080
```

```
gtgcttcatt ttgtagaaca aaaatgcaac gcgagagcgc taatttttca aacaaagaat   7140
ctgagctgca tttttacaga acagaaatgc aacgcgaaag cgctatttta ccaacgaaga   7200
atctgtgctt catttttgta aaacaaaaat gcaacgcgac gagagcgcta atttttcaaa   7260
caaagaatct gagctgcatt tttacagaac agaaatgcaa cgcgagagcg ctattttacc   7320
aacaaagaat ctatacttct tttttgttct acaaaaatgc atcccgagag cgctattttt   7380
ctaacaaagc atcttagatt actttttttc tcctttgtgc gctctataat gcagtctctt   7440
gataactttt tgcactgtag gtccgttaag gttagaagaa ggctactttg gtgtctattt   7500
tctcttccat aaaaaaagcc tgactccact tcccgcgttt actgattact agcgaagctg   7560
cgggtgcatt ttttcaagat aaaggcatcc ccgattatat tctataccga tgtggattgc   7620
gcatactttg tgaacagaaa gtgatagcgt tgatgattct tcattggtca gaaaattatg   7680
aacggtttct tctattttgt ctctatatac tacgtatagg aaatgtttac attttcgtat   7740
tgttttcgat tcactctatg aatagttctt actacaattt ttttgtctaa agagtaatac   7800
tagagataaa cataaaaaat gtagaggtcg agtttagatg caagttcaag gagcgaaagg   7860
tggatgggta ggttatatag ggatatagca cagagatata tagcaaagag atacttttga   7920
gcaat                                                               7925

<210> SEQ ID NO 86
<211> LENGTH: 7141
<212> TYPE: DNA
<213> ORGANISM: Artificial Sequence
<220> FEATURE:
<223> OTHER INFORMATION: Synthetic Nucleic Acid

<400> SEQUENCE: 86

gtttgtggaa gcggtattcg caatttaatt aaagctggtg acaattaatc atcggctcgt     60
ataatgtgtg gaattgaatc gatataagga ggttaatcat atgcgggagg gtggacgccc    120
cttccgtgcg catcgcactc tgcccgtcac cgggatcgac gctcaccgcg ccggcgtcga    180
acggcttctc gcgtcctacc gcgcgattcc cacggacgcc accgtgcgac tcgcgaagaa    240
gacgtccaac ctgttccggg cgcgggccca gaccagcgca cccggcctcg acgtctccgg    300
gctcggcgga gtcatctcgg tcgacgagca ggaccggacc gcggatgtcg ccggaatgtg    360
cacgtacgaa gacctggtgg acgccaccct cccgtacggg ctggcgccgc tggtggttcc    420
gcaactcaag accatcacac tcggcggcgc ggtcaccggc ctcggcatcg agtcgacgtc    480
gttccgcaac gggctccccc acgaatcggt cctcgagatc gacgtcctga ccggaagcgg    540
cgacatcgtc accgcgagac cggaaggcga gaactccgac ctgttctggg ggttccccaa    600
ctcctacgga accctcggct actccacccg actgcgcatc cagctcgaac ccgtcaaacg    660
gtatgtggca ctgcgccatc tgcgtttcga ctccctggac gagctgcagt cggcaatgga    720
tcgcatcgtc accgagcgcg tccacgacgg catccccgtc gactatctgg acggcgtcgt    780
gttcaccgcg tccgagagtt acctgacact gggccatcag accgacgagg gcggccccgt    840
cagcgactac accgggcaga acatcttcta ccggtccatc cagcacagtt ccgtgaacca    900
ccccaaaacg gacaaactca ccatccgaga ctacctgtgg cgctgggaca ccgactggtt    960
ctggtgctcg cgcgccttcg gcgcccagaa ccccaccatc cgccggctgt ggccgaagaa   1020
cctcctccgc agcagcttct actggaagct catcgccctc gaccacaagt acgacatcgg   1080
cgaccgactc gagaagcgca agggcaaccc gccacgcgaa cgcgtcgtgc aggacgtcga   1140
agtgcccatc gagcgcaccg cggacttcgt ccgctggttc ctcgacgaaa tcccgatcga   1200
```

```
accgctgtgg ctgtgcccgt tgcggttgcg ggaacctgcc cccgccggcg cgtcctcgca   1260
acgcccctgg cccctgtacc ccctcgaacc gaaacgcacg tacgtgaaca tcggattctg   1320
gtcatcggtg cccatcgttc cgggccgacc cgagggggcc gcgaatcggc tgatcgaaga   1380
caaggtcagt gacttcgacg gacacaagtc cctctactcc gattcgtact attcacgcga   1440
agatttcgaa cgcctctact acggcggcga tcgatacacg gaactgaaaa aacgctacga   1500
cccgaaatca cgattactgg accttttctc caaggcggtg caacgtcgat gacaactctg   1560
aaagcttcac gctcccagga ccacaagctg accatcgcag agattctcga aactctgtcc   1620
gacggcatgc tccccctgcg gttctccgcc tacgacggca gcgccgccgg cccggaggac   1680
gcccccctacg gtctccacct caagacgacc cgaggcacca cctacctggc gaccgccccc   1740
ggcgacctcg gcatggcccg ggcctacgtg tccggcgacc tcgaggcccg cggcgtccac   1800
cccggcgacc cgtacgagat cctccgcgtg atgggcgacg aactgcactt ccgccgtccg   1860
tccgcgctca cgctcgccgc catcacgcgc tcgctcggct gggatctgct gcgccccatc   1920
gcccctcccc cgcaggagca tctcccgcgg tggcgtcgag tcgcggaagg gttgcggcac   1980
tccaagtccc gcgacgccga ggtcatccac caccactacg acgtctcgaa caccttctac   2040
gagtatgtcc tcggcccgtc catgacgtac acgtgcgcct gctacgagaa cgccgagcag   2100
accctcgaag aggcacagga caacaagtac cgcctcgtct tcgagaagct cggcctccag   2160
cccggcgacc gactgctcga catcggttgc ggctggggat cgatggtccg gtacgccgcc   2220
cgccgcggcg tcaaggtcat cggcgccacc ctgtcccgag agcaggccga atgggcacag   2280
aaggccatcg ccgaagaagg actgtccgac ctcgccgagg tccggttctc cgactaccgt   2340
gacgtccccg agaccggatt cgacgccatc tcctcgatcg gcctgaccga gcacatcggc   2400
gtcggcaact accccgccta cttcggactg ctgcagagca agctccgcga gggcggccgg   2460
ctgctgaacc actgcatcac ccggcccgac aaccagagtc aggcacgcgc gggcggcttc   2520
atcgaccggt acgtcttccc cgacggcgaa ctcaccggct ccggacgcat catcaccgag   2580
atccagaacg tcggactcga ggtgcggcac gaggagaatc tgcgcgagca ctacgcactc   2640
accctcgccg gctggtgcca gaacctcgtc gacaactggg acgcctgcgt cgccgaggtc   2700
ggcgaaggca ccgcacgtgt gtggggtctc tacatggccg ggtcgcgact gggcttcgaa   2760
cgcaacgtcg ttcagctgca ccaggtcctc gccgtcaagc tcggacccaa gggcgaggcg   2820
catgtgccgc tgcgtccgtg gtggaagtag cctcaaaata tattttccct ctatcttctc   2880
gttgcgctta atttgactaa ttctcattag cgaggcgcgc ctttccatag gctccgcccc   2940
cctgacgagc atcacaaaaa tcgacgctca agtcagaggt ggcgaaaccc gacaggacta   3000
taaagatacc aggcgtttcc ccctggaagc tccctcgtgc gctctcctgt tccgaccctg   3060
ccgcttaccg gatacctgtc cgcctttctc ccttcgggaa gcgtggcgct ttctcatagc   3120
tcacgctgta ggtatctcag ttcggtgtag gtcgttcgct ccaagctggg ctgtgtgcac   3180
gaaccccccg ttcagcccga ccgctgcgcc ttatccggta actatcgtct tgagtccaac   3240
ccggtaagac acgacttatc gccactggca gcagccactg gtaacaggat tagcagagcg   3300
aggtatgtag gcggtgctac agagttcttg aagtggtggc ctaactacgg ctacactaga   3360
agaacagtat ttggtatctg cgctctgctg aagccagtta ccttcggaaa aagagttggt   3420
agctcttgat ccggcaaaca aaccaccgct ggtagcggtg gtttttttgt ttgcaagcag   3480
cagattacgc gcagaaaaaa aggatctcaa gaagatcctt tgatcttttc tacggggtct   3540
```

-continued

```
gacgctcagt ggaacgaaaa ctcacgttaa gggattttgg tcatgagatt atcaaaaagg   3600
atcttcacct agatcctttt aaattaaaaa tgaagtttta aatcaatcta aagtatatat   3660
gagtaaactt ggtctgacag ttaccaatgc ttaatcagtg aggcacctat ctcagcgatc   3720
tgtctatttc gttcatccat agttgcctga ctccccgtcg tgtagataac tacgatacgg   3780
gagggcttac catctggccc cagtgctgca atgataccgc gagacccacg ctcaccggct   3840
ccagatttat cagcaataaa ccagccagcc ggaagggccg agcgcagaag tggtcctgca   3900
actttatccg cctccatcca gtctattaat tgttgccggg aagctagagt aagtagttcg   3960
ccagttaata gtttgcgcaa cgttgttgcc attgctacag gcatcgtggt gtcacgctcg   4020
tcgtttggta tggcttcatt cagctccggt tcccaacgat caaggcgagt tacatgatcc   4080
cccatgttgt gcaaaaaagc ggttagctcc ttcggtcctc cgatcgttgt cagaagtaag   4140
ttggccgcag tgttatcact catggttatg gcagcactgc ataattctct tactgtcatg   4200
ccatccgtaa gatgcttttc tgtgactggt gagtactcaa ccaagtcatt ctgagaatag   4260
tgtatgcggc gaccgagttg ctcttgcccg gcgtcaatac gggataatac cgcgccacat   4320
agcagaactt taaaagtgct catcattgga aaacgttctt cggggcgaaa actctcaagg   4380
atcttaccgc tgttgagatc cagttcgatg taacccactc gtgcacccaa ctgatcttca   4440
gcatctttta ctttcaccag cgtttctggg tgagcaaaaa caggaaggca aaatgccgca   4500
aaaaagggaa taagggcgac acggaaatgt tgaatactca tactcttcct ttttcaatat   4560
tattgaagca tttatcaggg ttattgtctc atgagcggat acatatttga atgtatttag   4620
aaaaataaac agcgatcgcg cggccgcggg taataactga tataattaaa ttgaagctct   4680
aatttgtgag tttagtatac atgcatttac ttataataca gtttttttagt tttgctggcc   4740
gcatcttctc aaatatgctt cccagcctgc ttttctgtaa cgttcaccct ctaccttagc   4800
atcccttccc tttgcaaata gtcctcttcc aacaataata atgtcagatc ctgtagagac   4860
cacatcatcc acggttctat actgttgacc caatgcgtct ccccttgtcat ctaaacccac   4920
accgggtgtc ataatcaacc aatcgtaacc ttcatctctt ccacccatgt ctctttgagc   4980
aataaagccg ataacaaaat ctttgtcgct cttcgcaatg tcaacagtac ccttagtata   5040
ttctccagta gctagggagc ccttgcatga caattctgct aacatcaaaa ggcctctagg   5100
ttcctttgtt acttcttccg ccgcctgctt caaaccgcta acaatacctg ggcccaccac   5160
accgtgtgca ttcgtaatgt ctgcccattc tgctattctg tatacacccg cagagtactg   5220
caatttgact gtattaccaa tgtcagcaaa ttttctgtct tcgaagagta aaaaattgta   5280
cttggcggat aatgccttta gcggcttaac tgtgccctcc atggaaaaat cagtcaagat   5340
atccacatgt gtttttagta aacaaatttt gggacctaat gcttcaacta actccagtaa   5400
ttccttggtg gtacgaacat ccaatgaagc acacaagttt gtttgctttt cgtgcatgat   5460
attaaatagc ttggcagcaa caggactagg atgagtagca gcacgttcct tatatgtagc   5520
tttcgacatg atttatcttc gtttcctgca ggtttttgtt ctgtgcagtt gggttaagaa   5580
tactgggcaa tttcatgttt cttcaacacc acatatgcgt atatatacca atctaagtct   5640
gtgctccttc cttcgttctt ccttctgctc ggagattacc gaatcaaagc tagcttatcg   5700
atgataagct gtcaaagatg agaattaatt ccacggacta tagactatac tagatactcc   5760
gtctactgta cgatacactt ccgctcaggt ccttgtcctt taacgaggcc ttaccactct   5820
tttgttactc tattgatcca gctcagcaaa ggcagtgtga tctaagattc tatcttcgcg   5880
atgtagtaaa actagctaga ccgagaaaga gactagaaat gcaaaaggca cttctacaat   5940
```

ggctgccatc attattatcc gatgtgacgc tgcagcttct caatgatatt cgaatacgct 6000
ttgaggagat acagcctaat atccgacaaa ctgttttaca gatttacgat cgtacttgtt 6060
acccatcatt gaattttgaa catccgaacc tgggagtttt ccctgaaaca gatagtatat 6120
ttgaacctgt ataataatat atagtctagc gctttacgga agacaatgta tgtatttcgg 6180
ttcctggaga aactattgca tctattgcat aggtaatctt gcacgtcgca tccccggttc 6240
attttctgcg tttccatctt gcacttcaat agcatatctt tgttaacgaa gcatctgtgc 6300
ttcattttgt agaacaaaaa tgcaacgcga gagcgctaat tttcaaaca aagaatctga 6360 gctgcatttt tacagaacag aaatgcaacg cgaaagcgct attttaccaa cgaagaatct 6420
gtgcttcatt tttgtaaaac aaaaatgcaa cgcgacgaga gcgctaattt ttcaaacaaa 6480
gaatctgagc tgcattttta cagaacagaa atgcaacgcg agagcgctat tttaccaaca 6540
aagaatctat acttcttttt tgttctacaa aaatgcatcc cgagagcgct atttttctaa 6600
caaagcatct tagattactt tttttctcct ttgtgcgctc tataatgcag tctcttgata 6660
actttttgca ctgtaggtcc gttaaggtta gaagaaggct actttggtgt ctattttctc 6720
ttccataaaa aaagcctgac tccacttccc gcgtttactg attactagcg aagctgcggg 6780
tgcatttttt caagataaag gcatccccga ttatattcta taccgatgtg gattgcgcat 6840
actttgtgaa cagaaagtga tagcgttgat gattcttcat tggtcagaaa attatgaacg 6900
gtttcttcta ttttgtctct atatactacg tataggaaat gtttacattt tcgtattgtt 6960
ttcgattcac tctatgaata gttcttacta caattttttt gtctaaagag taatactaga 7020
gataaacata aaaaatgtag aggtcgagtt tagatgcaag ttcaaggagc gaaaggtgga 7080
tgggtaggtt atatagggat atagcacaga gatatatagc aaagagatac ttttgagcaa 7140
t 7141

<210> SEQ ID NO 87
<211> LENGTH: 7588
<212> TYPE: DNA
<213> ORGANISM: Artificial Sequence
<220> FEATURE:
<223> OTHER INFORMATION: Synthetic Nucleic Acid

<400> SEQUENCE: 87
gtttgtggaa gcggtattcg caatttaatt aaagctggtg acaattaatc atcggctcgt 60
ataatgtgtg gaattgaatc gatataagga ggttaatcat gtgaactgtc agtcttccgc 120
gtccaacctc gccaaccaca tcaacgcggt gtacgagctg cgccgcgcct atgcgcggct 180
gtccgccgac aagccggtgc gcctggcgaa gaccacctcc aacctcttcc gcttccgcag 240
ccgggacgat gccgcgcgtc tcgacgtcag cgctttcacc tcggtgatca gcatcgacac 300
ggaggcgcgg gtcgcggagg tgggcggcat gaccacctac gaggacctgg tcgccgccac 360
cctgcggcat ggcctgatgc cgccggtggt tccgcaactg cgcacgatca ccctgggcgg 420
tgcggtcacc gggctgggga tcgaatcctc gtccttccgc aacgggctcc cgcacgagtc 480
agtggaagag atggagatcc tcaccggcag cggccaggtg gtggtggccc ggcgcgacaa 540
cgagcaccgc gacctgttct acggtttccc caactcgtac ggcaccctcg gttacgcgct 600
gcggctccgc atccagctcg aaccggtccg cccctacgtc cacctgcggc acctgcggtt 660
caccgatgcc gcagcggcca tggccgcgct ggagcagatc tgcgcggacc gcacccacga 720
cggggagacc gtcgacttcg tcgacggcgt cgtgttcgcc cgcaacgagc tgtacctgac 780

-continued

```
cttggggacg ttcaccgacc gggctccgtg gaccagcgac tacaccggaa ccgacatcta    840
ctaccggtcg atcccccgct acgcgggccc cggccccggc gactacctca ccacgcacga    900
ctacctgtgg cggtgggaca ccgactggtt ctggtgctcc cgcgccttcg gactgcagca    960
tcccgtggtg cgccgcctgt ggccgcgttc cttgaaacgc tccgacgtct accgcaagct   1020
cgtcgcctgg gaccggcgca ctgacgcgag ccgcctgctc gactactacc gcgggcgccc   1080
gcccaaggaa ccggtgatcc aggacatcga ggttgaggtg gggcgggctg ccgagttcct   1140
cgacttcttc cacaccgaga tcggcatgtc cccggtgtgg ctgtgcccgc tgcggctgcg   1200
agaagacaca gccgacgata cggaaccggt ctggccgctc taccccctca aaccccgccg   1260
cctctacgtc aacttcgggt tttggggcct cgttccgatc cgtcccggtg gaggcaggac   1320
ataccacaac cggctgatcg aaaaagaagt gacccggttg ggcgggcaca agtcgctcta   1380
ctcggacgcc ttctacgacg aggacgagtt ctgggagctc tacaacgggg agatctaccg   1440
caagctcaaa gctgcctacg accccgacgg tcgactgctc gacctgtaca ccaagtgcgt   1500
cggcggcggg tgagaaagga tgagggatgc gactggcgga ggtattcgaa cgtgtcgtcg   1560
gacccgatgc gcccgtccac ttccgggcct acgacggcag cactgcggga gatccacgca   1620
gtgaagtcgc tatcgtggtt cgccacccgg cagccgtcaa ctacatcgtc caagcgccgg   1680
gagcactcgg tttgacccgc gcctacgtgg cgggatacct cgacgtcgaa ggggacatgt   1740
acaccgcgct gcgggcaatg gccgacgtgg tgttccagga ccggccgcgg ctgtccccccg   1800
gggaactgct gcggatcatc cgcgggatcg ggtgggtgaa gttcgtcaac cggcttccac   1860
cgccgccgca ggaggtgcgc cagtcccgcc tcgccgccct gggctggcgc cactccaagc   1920
agcgcgacgc cgaagccatc cagcaccact acgacgtctc caacgccttc tacgccctgg   1980
tcttgggcga gtcgatgacc tacacctgcg cggtctaccc gaccgagcag gccacgctgg   2040
agcaggcaca gttcttcaag cacgagctga tcgcccgcaa gctcggtctt gcccctggga   2100
tacgactgct ggatgtgggg tgcggctggg gcggcatggt catccacgcg gcccgggagc   2160
acggggtcaa agccctgggg gtgaccctgt ccaaagagca ggctgagtgg gcgcagaagc   2220
ggatcgccca cgagggcctg ggcgacctgg cagaagtccg gcacatggac taccgggacc   2280
tgcccgacgg cgagtacgac gcgatcagct cgatcgggtt gaccgagcac gtcggcaaaa   2340
agaacgtgcc cgcctacttc gcgtcgctgt accgcaagct cgtcccggga ggccgcctgc   2400
tcaaccactg catcacccgg ccccgcaacg acctgccgcc cttcaaacgc ggcggggtga   2460
tcaaccgcta cgtcttcccc gatggggagc tggaagggcc cggctggctg caggcggcga   2520
tgaacgacgc cgggttcgaa atccgccacc aggagaacct gcgggagcac tacgcacgga   2580
ccctgcggga ctggctggcc aacctggacc gcaactggga tgccgcggtg cgggaagtgg   2640
gggagggcac ggcccgagtg tggcggctct acatggccgg gtgcgtgctc ggcttcgaac   2700
gcaacgtggt gcaactgcac cagatcctcg gggtgaagct cgacgggacc gaggcgcgga   2760
tgccgctgcg ccccgacttc gaaccgccgc tgccttaacc gcggtgcaca gccgggggat   2820
atcagtcgcg gaaccgggca tgatgagccc atggctgcga ccgatgacga ccggcaccac   2880
accaccgtcg ccctcgacct catcgacgcg tatgtgcgcg ccgaccgcag aatgatcggt   2940
gaacgttccg cggggatcag cgcggaggcg ggggagcgga tcgtctccac cctgaaagtg   3000
tgcgcggcct tccttgcccg ccgggtccag gagaccgggg tgccgtggcg cgcagcggac   3060
tcccgggaag cggtcgcccg caccgtcgcc gacctgctgg aacccgaggt ggaattcgcg   3120
gtcgtctccg cctgggaggc gtacgcgatc ggggagcacg aggccgcctg ggtccgggcg   3180
```

```
cacggcgatc cgctggtctt cgtccacatg ctggccgcgt tctccgctgc tatcggcaca   3240
gcggtctacg gccgtgagga gctgctgccc acgctgcgca gggtgacagc acgataacct   3300
caaaatatat tttccctcta tcttctcgtt gcgcttaatt tgactaattc tcattagcga   3360
ggcgcgcctt tccataggct ccgccccct gacgagcatc acaaaaatcg acgctcaagt   3420
cagaggtggc gaaacccgac aggactataa agataccagg cgtttccccc tggaagctcc   3480
ctcgtgcgct ctcctgttcc gaccctgccg cttaccggat acctgtccgc ctttctccct   3540
tcgggaagcg tggcgctttc tcatagctca cgctgtaggt atctcagttc ggtgtaggtc   3600
gttcgctcca agctgggctg tgtgcacgaa ccccccgttc agcccgaccg ctgcgcctta   3660
tccggtaact atcgtcttga gtccaacccg gtaagacacg acttatcgcc actggcagca   3720
gccactggta acaggattag cagagcgagg tatgtaggcg gtgctacaga gttcttgaag   3780
tggtggccta actacggcta cactagaaga acagtatttg gtatctgcgc tctgctgaag   3840
ccagttacct tcggaaaaag agttggtagc tcttgatccg gcaaacaaac caccgctggt   3900
agcggtggtt tttttgtttg caagcagcag attacgcgca gaaaaaaagg atctcaagaa   3960
gatcctttga tcttttctac ggggtctgac gctcagtgga acgaaaactc acgttaaggg   4020
attttggtca tgagattatc aaaaaggatc ttcacctaga tccttttaaa ttaaaaatga   4080
agttttaaat caatctaaag tatatatgag taaacttggt ctgacagtta ccaatgctta   4140
atcagtgagg cacctatctc agcgatctgt ctatttcgtt catccatagt tgcctgactc   4200
cccgtcgtgt agataactac gatacgggag ggcttaccat ctggccccag tgctgcaatg   4260
ataccgcgag acccacgctc accggctcca gatttatcag caataaacca gccagccgga   4320
agggccgagc gcagaagtgg tcctgcaact ttatccgcct ccatccagtc tattaattgt   4380
tgccgggaag ctagagtaag tagttcgcca gttaatagtt tgcgcaacgt tgttgccatt   4440
gctacaggca tcgtggtgtc acgctcgtcg tttggtatgg cttcattcag ctccggttcc   4500
caacgatcaa ggcgagttac atgatccccc atgttgtgca aaaaagcggt tagctccttc   4560
ggtcctccga tcgttgtcag aagtaagttg gccgcagtgt tatcactcat ggttatggca   4620
gcactgcata attctcttac tgtcatgcca tccgtaagat gcttttctgt gactggtgag   4680
tactcaacca agtcattctg agaatagtgt atgcggcgac cgagttgctc ttgcccggcg   4740
tcaatacggg ataataccgc gccacatagc agaactttaa aagtgctcat cattggaaaa   4800
cgttcttcgg ggcgaaaact ctcaaggatc ttaccgctgt tgagatccag ttcgatgtaa   4860
cccactcgtg cacccaactg atcttcagca tcttttactt tcaccagcgt ttctgggtga   4920
gcaaaaacag gaaggcaaaa tgccgcaaaa aagggaataa gggcgacacg gaaatgttga   4980
atactcatac tcttcctttt tcaatattat tgaagcattt atcagggtta ttgtctcatg   5040
agcggataca tatttgaatg tatttagaaa aataaacagc gatcgcgcgg ccgcgggtaa   5100
taactgatat aattaaattg aagctctaat ttgtgagttt agtatacatg catttactta   5160
taatacagtt ttttagtttt gctggccgca tcttctcaaa tatgcttccc agcctgcttt   5220
tctgtaacgt tcaccctcta ccttagcatc ccttcccttt gcaaatagtc ctcttccaac   5280
aataataatg tcagatcctg tagagaccac atcatccacg gttctatact gttgacccaa   5340
tgcgtctccc ttgtcatcta aacccacacc gggtgtcata atcaaccaat cgtaaccttc   5400
atctcttcca cccatgtctc tttgagcaat aaagccgata acaaaatctt tgtcgctctt   5460
cgcaatgtca acagtaccct tagtatattc tccagtagct agggagccct tgcatgacaa   5520
```

```
ttctgctaac atcaaaaggc ctctaggttc ctttgttact tcttccgccg cctgcttcaa   5580

accgctaaca atacctgggc ccaccacacc gtgtgcattc gtaatgtctg cccattctgc   5640

tattctgtat acacccgcag agtactgcaa tttgactgta ttaccaatgt cagcaaattt   5700

tctgtcttcg aagagtaaaa aattgtactt ggcggataat gcctttagcg gcttaactgt   5760

gccctccatg gaaaaatcag tcaagatatc cacatgtgtt tttagtaaac aaattttggg   5820

acctaatgct tcaactaact ccagtaattc cttggtggta cgaacatcca atgaagcaca   5880

caagtttgtt tgcttttcgt gcatgatatt aaatagcttg gcagcaacag gactaggatg   5940

agtagcagca cgttccttat atgtagcttt cgacatgatt tatcttcgtt tcctgcaggt   6000

ttttgttctg tgcagttggg ttaagaatac tgggcaattt catgtttctt caacaccaca   6060

tatgcgtata tataccaatc taagtctgtg ctccttcctt cgttcttcct tctgctcgga   6120

gattaccgaa tcaaagctag cttatcgatg ataagctgtc aaagatgaga attaattcca   6180

cggactatag actatactag atactccgtc tactgtacga tacacttccg ctcaggtcct   6240

tgtcctttaa cgaggcctta ccactctttt gttactctat tgatccagct cagcaaaggc   6300

agtgtgatct aagattctat cttcgcgatg tagtaaaact agctagaccg agaaagagac   6360

tagaaatgca aaaggcactt ctacaatggc tgccatcatt attatccgat gtgacgctgc   6420

agcttctcaa tgatattcga atacgctttg aggagataca gcctaatatc cgacaaactg   6480

ttttacagat ttacgatcgt acttgttacc catcattgaa ttttgaacat ccgaacctgg   6540

gagttttccc tgaaacagat agtatatttg aacctgtata ataatatata gtctagcgct   6600

ttacggaaga caatgtatgt atttcggttc ctggagaaac tattgcatct attgcatagg   6660

taatcttgca cgtcgcatcc ccggttcatt ttctgcgttt ccatcttgca cttcaatagc   6720

atatctttgt taacgaagca tctgtgcttc attttgtaga acaaaaatgc aacgcgagag   6780

cgctaatttt tcaaacaaag aatctgagct gcatttttac agaacagaaa tgcaacgcga   6840

aagcgctatt ttaccaacga agaatctgtg cttcattttt gtaaaacaaa aatgcaacgc   6900

gacgagagcg ctaatttttc aaacaaagaa tctgagctgc atttttacag aacagaaatg   6960

caacgcgaga gcgctatttt accaacaaag aatctatact tctttttgt tctacaaaaa   7020

tgcatcccga gagcgctatt tttctaacaa agcatcttag attacttttt ttctcctttg   7080

tgcgctctat aatgcagtct cttgataact tttgcactg taggtccgtt aaggttagaa   7140

gaaggctact ttggtgtcta ttttctcttc cataaaaaaa gcctgactcc acttcccgcg   7200

tttactgatt actagcgaag ctgcgggtgc attttttcaa gataaaggca tccccgatta   7260

tattctatac cgatgtggat tgcgcatact ttgtgaacag aaagtgatag cgttgatgat   7320

tcttcattgg tcagaaaatt atgaacggtt tcttctattt tgtctctata tactacgtat   7380

aggaaatgtt tacattttcg tattgttttc gattcactct atgaatagtt cttactacaa   7440

ttttttttgtc taaagagtaa tactagagat aaacataaaa aatgtagagg tcgagtttag   7500

atgcaagttc aaggagcgaa aggtggatgg gtaggttata tagggatata gcacagagat   7560

atatagcaaa gagatacttt tgagcaat                                      7588
```

<210> SEQ ID NO 88
<211> LENGTH: 7074
<212> TYPE: DNA
<213> ORGANISM: Artificial Sequence
<220> FEATURE:
<223> OTHER INFORMATION: Synthetic Nucleic Acid

<400> SEQUENCE: 88

-continued

```
gtttgtggaa gcggtattcg caatttaatt aaagctggtg acaattaatc atcggctcgt     60
ataatgtgtg gaattgaatc gatataagga ggttaatcat atgtcacagc tggcggtcac    120
agaccaccac gagcgagcgg tcgaggcgct gcgcaggtcg tatgcggcga tcccgccggg    180
cacaccggtc cgcttggcca agcagacctc caacctgttc cgcttccgcg agccgacggc    240
cgcgcccggc ctggacgtgt ccggcttcaa ccgggtgctg gcggtggacc cggatgcgcg    300
caccgccgac gtgcagggca tgaccaccta cgaggacctg gtcgacgcca ccctgccgca    360
cgggctgatg ccgctggtgg tgccccagct caagacgatc acgctgggcg gggcggtgac    420
cggcctgggc atcgagtcca cctccttccg caacggcctg ccgcacgagt cggtgctgga    480
gatgcagatc atcaccggcg ccggcgaagt ggtcaccgcc accccggacg gggagcactc    540
cgacctgttc tggggcttcc ccaactccta cgggacgctg ggtacgccc tgaagctgaa    600
gatcgaactg gagccggtca agccgtacgt ccggctgcgg cacctgcgct tcgacgacgc    660
cggcgagtgc gccgccaagc tcgccgagct gagcgaaagc cgcgagcacg agggcgatga    720
ggtgcacttt ttggacggca ccttcttcgg gccgcgcgag atgtacctga cgctcggcac    780
gttcaccgac accgccccct atgtgtcgga ctacaccggg cagcacatct actaccggtc    840
gatccagcag cggtcgatcg actttttgac catccgcgac tacctgtggc gctgggacac    900
cgactggttc tggtgctcgc gcgccctggg cgtgcagaac ccgctgatcc ggcgggtgtg    960
gccgaagagc gccaagcggt cggatgtgta ccgcaagctg gtggcctacg aaaagcgcta   1020
ccagttcaag gcgcgcatcg accggtggac gggcaagccg ccgcgcgagg acgtcatcca   1080
ggacatcgag gtgccggcag aacgcctgcc ggagttcctg gagttcttcc acgacaagat   1140
cgggatgagc ccggtgtggc tgtgcccgct gcgggcgcgc caccgctggc cgctgtaccc   1200
gctcaagccc ggcgtcacct acgtcaacgc cggcttctgg gggacggtgc cgctgcagcc   1260
ggggcagatg cccgagtacc acaaccggct gatcgaacgg aaggtcgccc aactggacgg   1320
ccacaagtct ctgtactcga cggcgttcta ctcgcgtgag gagttctggc ggcactacga   1380
cggggaaacc taccggcgtc tgaaggacac ctacgacccc gacgcgcgcc tgctcgacct   1440
ctacgacaag tgcgtgcggg gacgctgacc ggggcggcgg cgatgaagac ccgcggggcg   1500
ggacggacag gagggaagcg atgacgctgg ccaaggtctt cgaggagctg gtcggggcgg   1560
acgcccctgt ggagctcacc gcctacgacg gatcgagagc cggacgcctg ggcagtgatc   1620
tgcgggtcca cgtgaagtcg ccgtacgcgg tgtcctacct ggtgcactcg ccgagcgcgc   1680
tcgggctggc ccgcgcgtac gtggccgggc acctggacgc ctacggcgac atgtacacgc   1740
tgctgcggga gatgacgcag ctgaccgagg cgctgacgcc caaggcccgg ctgcggctgc   1800
tggccggtgt cctgcaggat ccgctgctgc gcgcggcggc cagccgccgt ctgccgcccc   1860
cgccgcagga ggtgcggacc ggccgcacct cctggttccg gcacaccaag cggcgggacg   1920
ccaaggccat ctcccaccac tacgacgtgt ccaacacctt ctatgagtgg gtgctgggcc   1980
cgtcgatgac ctacacctgc gcctgtttcc ccaccgagga cgccaccttg gaggaggcgc   2040
agttccacaa gcacgacctg gtcgccaaga agctcgggct gcggccgggc atgcggctgc   2100
tggacgtggg ctgcggctgg ggcggcatgg tgatgcacgc cgccaagcac tacggggtgc   2160
gggcgctggg cgtcacgctg tccaagcagc aggccgagtg ggcgcagaag gccatcgccg   2220
aggcgggcct gagcgacctg gccgaggtcc gccaccagga ctaccgggac gtcaccgagg   2280
gcgacttcga cgccatcagc tcgatcggcc tcaccgagca catcggcaag gccaacctgc   2340
```

-continued

```
cgtcctactt cggcttcctg tacggcaagc tcaagccggg cgggcggctg ctcaaccact   2400
gcatcacccg gcccgacaac acccagccgg ccatgaagaa ggacgggttc atcaaccggt   2460
acgtcttccc cgacggggag ctggaggggc ccggctacct gcagacccag atgaacgacg   2520
ccggttttga gatccgccac caggagaacc tgcgcgagca ctacgcccgc accctggccg   2580
gatggtgccg caacctcgat gagcactggg acgaggcggt ggccgaggtc ggcgagggca   2640
ccgcgcgggt gtggcggctg tacatggccg gcagccggct cggtttcgag ctcaactgga   2700
tccagctgca ccagatcctg ggcgtcaagc tcggcgagcg cggcgagtcc cgcatgccgt   2760
tgcggcccga ctggggcgtg tgacctcaaa atatattttc cctctatctt ctcgttgcgc   2820
ttaatttgac taattctcat tagcgaggcg cgcctttcca taggctccgc ccccctgacg   2880
agcatcacaa aaatcgacgc tcaagtcaga ggtggcgaaa cccgacagga ctataaagat   2940
accaggcgtt tccccctgga agctccctcg tgcgctctcc tgttccgacc ctgccgctta   3000
ccggatacct gtccgccttt ctcccttcgg gaagcgtggc gctttctcat agctcacgct   3060
gtaggtatct cagttcggtg taggtcgttc gctccaagct gggctgtgtg cacgaacccc   3120
ccgttcagcc cgaccgctgc gccttatccg gtaactatcg tcttgagtcc aacccggtaa   3180
gacacgactt atcgccactg gcagcagcca ctggtaacag gattagcaga gcgaggtatg   3240
taggcggtgc tacagagttc ttgaagtggt ggcctaacta cggctacact agaagaacag   3300
tatttggtat ctgcgctctg ctgaagccag ttaccttcgg aaaaagagtt ggtagctctt   3360
gatccggcaa acaaaccacc gctggtagcg gtggtttttt tgtttgcaag cagcagatta   3420
cgcgcagaaa aaaaggatct caagaagatc ctttgatctt ttctacgggg tctgacgctc   3480
agtggaacga aaactcacgt taagggattt tggtcatgag attatcaaaa aggatcttca   3540
cctagatcct tttaaattaa aaatgaagtt ttaaatcaat ctaaagtata tatgagtaaa   3600
cttggtctga cagttaccaa tgcttaatca gtgaggcacc tatctcagcg atctgtctat   3660
ttcgttcatc catagttgcc tgactccccg tcgtgtagat aactacgata cgggagggct   3720
taccatctgg ccccagtgct gcaatgatac cgcgagaccc acgctcaccg gctccagatt   3780
tatcagcaat aaaccagcca gccggaaggg ccgagcgcag aagtggtcct gcaactttat   3840
ccgcctccat ccagtctatt aattgttgcc gggaagctag agtaagtagt tcgccagtta   3900
atagtttgcg caacgttgtt gccattgcta caggcatcgt ggtgtcacgc tcgtcgtttg   3960
gtatggcttc attcagctcc ggttcccaac gatcaaggcg agttacatga tcccccatgt   4020
tgtgcaaaaa agcggttagc tccttcggtc ctccgatcgt tgtcagaagt aagttggccg   4080
cagtgttatc actcatggtt atggcagcac tgcataattc tcttactgtc atgccatccg   4140
taagatgctt ttctgtgact ggtgagtact caaccaagtc attctgagaa tagtgtatgc   4200
ggcgaccgag ttgctcttgc ccggcgtcaa tacgggataa taccgcgcca catagcagaa   4260
ctttaaaagt gctcatcatt ggaaaacgtt cttcggggcg aaaactctca aggatcttac   4320
cgctgttgag atccagttcg atgtaaccca ctcgtgcacc caactgatct tcagcatctt   4380
ttactttcac cagcgtttct gggtgagcaa aaacaggaag gcaaaatgcc gcaaaaaagg   4440
gaataagggc gacacggaaa tgttgaatac tcatactctt cctttttcaa tattattgaa   4500
gcatttatca gggttattgt ctcatgagcg gatacatatt tgaatgtatt tagaaaaata   4560
aacagcgatc gcgcggccgc gggtaataac tgatataatt aaattgaagc tctaatttgt   4620
gagtttagta tacatgcatt tacttataat acagtttttt agttttgctg gccgcatctt   4680
ctcaaatatg cttcccagcc tgcttttctg taacgttcac cctctacctt agcatccctt   4740
```

```
ccctttgcaa atagtcctct tccaacaata ataatgtcag atcctgtaga gaccacatca   4800
tccacggttc tatactgttg acccaatgcg tctcccttgt catctaaacc cacaccgggt   4860
gtcataatca accaatcgta accttcatct cttccaccca tgtctctttg agcaataaag   4920
ccgataacaa aatctttgtc gctcttcgca atgtcaacag tacccttagt atattctcca   4980
gtagctaggg agcccttgca tgacaattct gctaacatca aaaggcctct aggttccttt   5040
gttacttctt ccgccgcctg cttcaaaccg ctaacaatac ctgggcccac cacaccgtgt   5100
gcattcgtaa tgtctgccca ttctgctatt ctgtatacac ccgcagagta ctgcaatttg   5160
actgtattac caatgtcagc aaattttctg tcttcgaaga gtaaaaaatt gtacttggcg   5220
gataatgcct ttagcggctt aactgtgccc tccatggaaa aatcagtcaa gatatccaca   5280
tgtgttttta gtaaacaaat tttgggacct aatgcttcaa ctaactccag taattccttg   5340
gtggtacgaa catccaatga agcacacaag tttgtttgct tttcgtgcat gatattaaat   5400
agcttggcag caacaggact aggatgagta gcagcacgtt ccttatatgt agctttcgac   5460
atgatttatc ttcgtttcct gcaggttttt gttctgtgca gttgggttaa gaatactggg   5520
caatttcatg tttcttcaac accacatatg cgtatatata ccaatctaag tctgtgctcc   5580
ttccttcgtt cttccttctg ctcggagatt accgaatcaa agctagctta tcgatgataa   5640
gctgtcaaag atgagaatta attccacgga ctatagacta tactagatac tccgtctact   5700
gtacgataca cttccgctca ggtccttgtc ctttaacgag gccttaccac tcttttgtta   5760
ctctattgat ccagctcagc aaaggcagtg tgatctaaga ttctatcttc gcgatgtagt   5820
aaaactagct agaccgagaa agagactaga aatgcaaaag gcacttctac aatggctgcc   5880
atcattatta tccgatgtga cgctgcagct tctcaatgat attcgaatac gctttgagga   5940
gatacagcct aatatccgac aaactgtttt acagatttac gatcgtactt gttacccatc   6000
attgaatttt gaacatccga acctgggagt ttccctgaa acagatagta tatttgaacc   6060
tgtataataa tatatagtct agcgctttac ggaagacaat gtatgtattt cggttcctgg   6120
agaaactatt gcatctattg cataggtaat cttgcacgtc gcatccccgg ttcattttct   6180
gcgtttccat cttgcacttc aatagcatat ctttgttaac gaagcatctg tgcttcattt   6240
tgtagaacaa aaatgcaacg cgagagcgct aatttttcaa acaaagaatc tgagctgcat   6300
ttttacagaa cagaaatgca acgcgaaagc gctattttac caacgaagaa tctgtgcttc   6360
atttttgtaa aacaaaaatg caacgcgacg agagcgctaa tttttcaaac aaagaatctg   6420
agctgcattt ttacagaaca gaaatgcaac gcgagagcgc tattttacca acaaagaatc   6480
tatacttctt ttttgttcta caaaaatgca tcccgagagc gctatttttc taacaaagca   6540
tcttagatta cttttttctt cctttgtgcg ctctataatg cagtctcttg ataacttttt   6600
gcactgtagg tccgttaagg ttagaagaag gctactttgg tgtctatttt ctcttccata   6660
aaaaaagcct gactccactt cccgcgttta ctgattacta gcgaagctgc gggtgcattt   6720
tttcaagata aaggcatccc cgattatatt ctataccgat gtggattgcg catactttgt   6780
gaacagaaag tgatagcgtt gatgattctt cattggtcag aaaattatga acggtttctt   6840
ctattttgtc tctatatact acgtatagga aatgtttaca ttttcgtatt gttttcgatt   6900
cactctatga atagttctta ctacaatttt tttgtctaaa gagtaatact agagataaac   6960
ataaaaaatg tagaggtcga gtttagatgc aagttcaagg agcgaaaggt ggatgggtag   7020
gttatatagg gatatagcac agagatatat agcaaagaga tacttttgag caat         7074
```

<210> SEQ ID NO 89
<211> LENGTH: 7331
<212> TYPE: DNA
<213> ORGANISM: Artificial Sequence
<220> FEATURE:
<223> OTHER INFORMATION: Synthetic Nucleic Acid

<400> SEQUENCE: 89
gtttgtggaa gcggtattcg caatttaatt aaagctggtg acaattaatc atcggctcgt 60
ataatgtgtg gaattgaatc gatataagga ggttaatcat atgagcggat tagttgaccc 120
ggatagtact tttttaaaga ccatcggaaa actgagcaac agcttgtcca ttggtcgtgg 180
agtagatcaa aaagaggtaa tccccaaagg ctggaacgcc cattgggagg caattacaaa 240
gcttaagaga agctttgacg cgattcctgc tggggagcgg gtgcgtttag ctaagaaaac 300
ctccaacctg ttccgtggac gctccgatgc aggtcacggc ctagatgtgg cagcgcttgg 360
gggagtgatt gccattgatc cggtcaatgc caccgccgat gtacagggca tgtgcacgta 420
tgaagacctg gtagatgcca ctttaagtta tggtctgatg ccgttggttg tgcctcaact 480
gaaaaccatc acgcttggtg gcgcagtgac cggaatgggc gtggaatcca catccttccg 540
caacggtttg ccacacgaat cagtgctgga gatggatatt tttaccggca ctggtgagat 600
cgtgacttgc tcgcccacag aaaatgtcga cctttacaga ggttttccca actcttatgg 660
ttcgctggga tacgcggtgc ggctaaaaat tgagctggaa ccagtgcaag attacgtcca 720
gctgcgccac gtgcgcttca acgatttaga gtctttgacc aaagcgattg aggaagtcgc 780
gtcttctctg gagtttgata accaacccgt cgattacctt gacggcgtgg tgttttcacc 840
cacggaagcc tacttagttc ttggcacgca aacctcacaa cctggcccca ccagcgatta 900
caccagggat ttaagctact accgctccct gcaacaccca gagggcatca cctatgaccg 960
cctgacaatc cgcgattaca tctggcgctg ggacaccgac tggttctggt gttcacgcgc 1020
attcggcacc caaaaccccg tggtgcgcaa actctggccc agggatctgc tgcgctcgag 1080
tttctattgg aagatcatcg gctgggatcg aaaatactcc atcgctgatc gcctggaaga 1140
gcgcaaaggc cgcccggcta gggaacgggt ggtccaagac gtggaagtta cgattgataa 1200
actgccagaa tttttgaaat ggttctttga aagcagcgac atcgagccgc tgtggctgtg 1260
cccgatcaag cttcgggagg taccaggtag ttcggttggt gctggagaaa ttttgagctc 1320
cgctgaagca atcgactccg gtgctgctga acacccttgg ccgctgtatc ccttgaagaa 1380
ggacgtgctg tgggtcaaca tcggattctg gtcctcagtg ccggttgatc tgatgggctc 1440
cgatgcacca gagggagcat ttaacagaga aatcgaacgc gtcatggcag agctaggcgg 1500
acataaatcg ctgtactccg aagcgttcta caccagggaa gactttgaaa aactttatgg 1560
cggaaccatc ccggcgctgc taaaaaagca gtgggatccc cacagccgat tccccggttt 1620
gtatgaaaag acagtaaaag gcgcctagga tcgctcactg taggtagagg cttgtggtca 1680
ctacttgtgg ccacatttta aaaaaatgca caagaagaga aagcaaagca ttatgagtaa 1740
cgccgtagcg caggacctca tgaccatcgc cgacatcgtc gaggccacga ccactgcacc 1800
catcccattc cacatcactg ccttcgatgg aagcttcact ggccctgaag atgctcccta 1860
ccagctgttt gttgccaaca cggatgcagt atcctacatc gcaacagcgc caggagattt 1920
gggtttggca cgtgcctacc tcatgggaga cctcatcgtg gaaggtgagc atcccggcca 1980
tccttatggg atctttgatg cgttgaagga gttctaccgc tgcttcaaac gcccagatgc 2040
atccaccacc ttgcagatca tgtggactct gcggaaaatg aatgccttaa aattccagga 2100

-continued

```
aattccacca atggaacaag cccctgcatg gcgtaaagca ctgatcaacg ggctagcatc   2160
caggcactcg aaatcccgcg acaagaaagc cattagctac cactacgacg tgggcaatga   2220
gttctactcc ctgtttttag atgattccat gacctatacc tgcgcgtatt atccaacgcc   2280
agaatcaagt ttggaagaag cccaagaaaa caaataccgc ctcatctttg aaaaactgcg   2340
tctgaaagaa ggcgatcgcc tcctagacgt gggatgcggt tggggaggca tggtccgcta   2400
cgccgccaaa cacggtgtga aagccatcgg agttacgctg tctgaacagc aatatgagtg   2460
ggtcaagca gagatcaaac gccaaggttt ggaagacctc gcggaaattc gcttcatgga   2520
ttaccgcgat gttccagaaa ctggattcga tgcgatctca gcaatcggca tcattgaaca   2580
catcggtgtg aacaactatc ccgactactt tgaattgctc agcagcaaac tcaaaacagg   2640
cggactgatg ctcaaccaca gcatcaccta cccagacaac cgcccccgcc acgcaggtgc   2700
atttattgat cgctacattt tccccgacgg tgaactcact ggctctggca ccctgatcaa   2760
gcacatgcag gacaacggtt tcgaagtgct gcacgaagaa aacctccgct ttgattacca   2820
acgcaccctg cacgcgtggt gcgaaaacct caaagaaaat tgggaggaag cagttgaact   2880
cgccggtgaa cccactgcac gactctttgg cctgtacatg gcaggttcgg aatggggatt   2940
tgcccacaac atcgtccagc tgcaccaagt actgggtgtg aaactcgatg agcagggaag   3000
tcgcggagaa gttcctgaaa gaatgtggtg gactatctaa cctcaaaata tattttccct   3060
ctatcttctc gttgcgctta atttgactaa ttctcattag cgaggcgcgc ctttccatag   3120
gctccgcccc cctgacgagc atcacaaaaa tcgacgctca agtcagaggt ggcgaaaccc   3180
gacaggacta taaagatacc aggcgtttcc ccctggaagc tccctcgtgc gctctcctgt   3240
tccgaccctg ccgcttaccg gatacctgtc cgcctttctc ccttcgggaa gcgtggcgct   3300
ttctcatagc tcacgctgta ggtatctcag ttcggtgtag gtcgttcgct ccaagctggg   3360
ctgtgtgcac gaaccccccg ttcagcccga ccgctgcgcc ttatccggta actatcgtct   3420
tgagtccaac ccggtaagac acgacttatc gccactggca gcagccactg gtaacaggat   3480
tagcagagcg aggtatgtag gcggtgctac agagttcttg aagtggtggc ctaactacgg   3540
ctacactaga agaacagtat ttggtatctg cgctctgctg aagccagtta ccttcggaaa   3600
aagagttggt agctcttgat ccggcaaaca aaccaccgct ggtagcggtg gtttttttgt   3660
ttgcaagcag cagattacgc gcagaaaaaa aggatctcaa gaagatcctt tgatcttttc   3720
tacggggtct gacgctcagt ggaacgaaaa ctcacgttaa gggattttgg tcatgagatt   3780
atcaaaaagg atcttcacct agatcctttt aaattaaaaa tgaagtttta aatcaatcta   3840
aagtatatat gagtaaactt ggtctgacag ttaccaatgc ttaatcagtg aggcacctat   3900
ctcagcgatc tgtctatttc gttcatccat agttgcctga ctccccgtcg tgtagataac   3960
tacgatacgg gagggcttac catctggccc cagtgctgca atgataccgc gagacccacg   4020
ctcaccggct ccagatttat cagcaataaa ccagccagcc ggaagggccg agcgcagaag   4080
tggtcctgca actttatccg cctccatcca gtctattaat tgttgccggg aagctagagt   4140
aagtagttcg ccagttaata gtttgcgcaa cgttgttgcc attgctacag gcatcgtggt   4200
gtcacgctcg tcgtttggta tggcttcatt cagctccggt tcccaacgat caaggcgagt   4260
tacatgatcc cccatgttgt gcaaaaaagc ggttagctcc ttcggtcctc cgatcgttgt   4320
cagaagtaag ttggccgcag tgttatcact catggttatg gcagcactgc ataattctct   4380
tactgtcatg ccatccgtaa gatgcttttc tgtgactggt gagtactcaa ccaagtcatt   4440
```

-continued

```
ctgagaatag tgtatgcggc gaccgagttg ctcttgcccg gcgtcaatac gggataatac   4500
cgcgccacat agcagaactt taaaagtgct catcattgga aaacgttctt cggggcgaaa   4560
actctcaagg atcttaccgc tgttgagatc cagttcgatg taacccactc gtgcacccaa   4620
ctgatcttca gcatctttta ctttcaccag cgtttctggg tgagcaaaaa caggaaggca   4680
aaatgccgca aaaaagggaa taagggcgac acggaaatgt tgaatactca tactcttcct   4740
ttttcaatat tattgaagca tttatcaggg ttattgtctc atgagcggat acatatttga   4800
atgtatttag aaaaataaac agcgatcgcg cggccgcggg taataactga tataattaaa   4860
ttgaagctct aatttgtgag tttagtatac atgcatttac ttataataca gtttttagt    4920
tttgctggcc gcatcttctc aaatatgctt cccagcctgc ttttctgtaa cgttcaccct   4980
ctaccttagc atcccttccc tttgcaaata gtcctcttcc aacaataata atgtcagatc   5040
ctgtagagac cacatcatcc acggttctat actgttgacc caatgcgtct cccttgtcat   5100
ctaaacccac accgggtgtc ataatcaacc aatcgtaacc ttcatctctt ccacccatgt   5160
ctctttgagc aataaagccg ataacaaaat ctttgtcgct cttcgcaatg tcaacagtac   5220
ccttagtata ttctccagta gctagggagc ccttgcatga caattctgct aacatcaaaa   5280
ggcctctagg ttcctttgtt acttcttccg ccgcctgctt caaaccgcta acaatacctg   5340
ggcccaccac accgtgtgca ttcgtaatgt ctgcccattc tgctattctg tatacacccg   5400
cagagtactg caatttgact gtattaccaa tgtcagcaaa ttttctgtct tcgaagagta   5460
aaaaattgta cttggcggat aatgccttta gcggcttaac tgtgccctcc atggaaaaat   5520
cagtcaagat atccacatgt gtttttagta aacaaatttt gggacctaat gcttcaacta   5580
actccagtaa ttccttggtg gtacgaacat ccaatgaagc acacaagttt gtttgctttt   5640
cgtgcatgat attaaatagc ttggcagcaa caggactagg atgagtagca gcacgttcct   5700
tatatgtagc tttcgacatg atttatcttc gtttcctgca ggtttttgtt ctgtgcagtt   5760
gggttaagaa tactgggcaa tttcatgttt cttcaacacc acatatgcgt atatatacca   5820
atctaagtct gtgctccttc cttcgttctt ccttctgctc ggagattacc gaatcaaagc   5880
tagcttatcg atgataagct gtcaaagatg agaattaatt ccacggacta tagactatac   5940
tagatactcc gtctactgta cgatacactt ccgctcaggt ccttgtcctt taacgaggcc   6000
ttaccactct tttgttactc tattgatcca gctcagcaaa ggcagtgtga tctaagattc   6060
tatcttcgcg atgtagtaaa actagctaga ccgagaaaga gactagaaat gcaaaaggca   6120
cttctacaat ggctgccatc attattatcc gatgtgacgc tgcagcttct caatgatatt   6180
cgaatacgct ttgaggagat acagcctaat atccgacaaa ctgttttaca gatttacgat   6240
cgtacttgtt acccatcatt gaattttgaa catccgaacc tgggagtttt ccctgaaaca   6300
gatagtatat ttgaacctgt ataataatat atagtctagc gctttacgga agacaatgta   6360
tgtatttcgg ttcctggaga aactattgca tctattgcat aggtaatctt gcacgtcgca   6420
tccccggttc attttctgcg tttccatctt gcacttcaat agcatatctt tgttaacgaa   6480
gcatctgtgc ttcattttgt agaacaaaaa tgcaacgcga gagcgctaat ttttcaaaca   6540
aagaatctga gctgcatttt tacagaacag aaatgcaacg cgaaagcgct attttaccaa   6600
cgaagaatct gtgcttcatt tttgtaaaac aaaaatgcaa cgcgacgaga gcgctaattt   6660
ttcaaacaaa gaatctgagc tgcattttta cagaacagaa atgcaacgcg agagcgctat   6720
tttaccaaca aagaatctat acttcttttt tgttctacaa aaatgcatcc cgagagcgct   6780
atttttctaa caaagcatct tagattactt tttttctcct ttgtgcgctc tataatgcag   6840
```

```
tctcttgata actttttgca ctgtaggtcc gttaaggtta gaagaaggct actttggtgt   6900

ctattttctc ttccataaaa aaagcctgac tccacttccc gcgtttactg attactagcg   6960

aagctgcggg tgcatttttt caagataaag gcatccccga ttatattcta taccgatgtg   7020

gattgcgcat actttgtgaa cagaaagtga tagcgttgat gattcttcat tggtcagaaa   7080

attatgaacg gtttcttcta ttttgtctct atatactacg tataggaaat gtttacattt   7140

tcgtattgtt ttcgattcac tctatgaata gttcttacta caattttttt gtctaaagag   7200

taatactaga gataaacata aaaaatgtag aggtcgagtt tagatgcaag ttcaaggagc   7260

gaaaggtgga tgggtaggtt atatagggat atagcacaga gatatatagc aaagagatac   7320

ttttgagcaa t                                                        7331
```

```
<210> SEQ ID NO 90
<211> LENGTH: 7126
<212> TYPE: DNA
<213> ORGANISM: Artificial Sequence
<220> FEATURE:
<223> OTHER INFORMATION: Synthetic Nucleic Acid

<400> SEQUENCE: 90

gtttgtggaa gcggtattcg caatttaatt aaagctggtg acaattaatc atcggctcgt     60

ataatgtgtg gaattgaatc gatataagga ggttaatcat gtgtccgctc ctgcgaccga    120

tgcacgaacc gcccacgccg acggcgtgga gcgattgctc gagagttatc gggcggtgcc    180

ggcggccgca tcggtgcggc tcgccaagcg cacctcgaac ctcttccggt cccgagcggc    240

gacggatgcc cctggcctcg acacctccgg cctgacccac gtcatcgcgg tcgacccggg    300

ggcgcgcacg gccgacgtcg ccggcatgtg cacctacgac gacctcgtcg ccgcgacact    360

gccgcatggg ctcgcgccac tcgtggtgcc gcaactgaag accatcaccc tcgggggcgc    420

cgtaacggga ctcggcatcg agtcgacgtc gttccgcaac ggtctgccgc acgagtcggt    480

gctcgagatc gacgtgctca ccggcgcagg cgagatcatc acggcgtcgc cgatcgagca    540

cgcagagctg ttccgcgcct tccccaactc gtacggcacc ctcggctacg ccgtgcgcct    600

gcgcatcgag ctcgagccgg tcgagccgtt cgtcgcactc acgcaccttc ggttccatgc    660

gctcaccgac ctcatcgagg caatggagcg catcatcgag accggtcgac tcgacggggt    720

tgccgtcgat tccctcgacg gcgtggtgtt cagcgctgaa gagagctacc tgtgcgtcgg    780

cacgcagacc gcggcatccg gcccggtcag cgactacacc cgccagcaga tcttctatcg    840

ctccatccag catgacgacg gtgcgaagca cgaccggctc accatgcacg actacctgtg    900

gcgctgggac gccgactggt tctggtgctc gcaggcgttc ggcgcgcagc atccgctgat    960

tcgccggttc tggccgcggc gataccggcg cagccgctcg tactcgacgc tcatgcgcct   1020

cgaacggcga ttcgacctcg gcgatcgcct cgagaagctc aagggccggc cggcgcgcga   1080

acgcgtgatc caagacgtcg aggtgccgat cgggcgcacc gtcggcttcc tcgaatggtt   1140

cctcgcgaac gtgccgatcg agccgatctg gttgtgcccg ctgcgcctgc ggggcgaccg   1200

cggctggcct ctctacccga tccggccgca gcagacctac gtcaacatcg gcttctggtc   1260

gacggttccg gtgggcggct ccgagggcga gacgaaccgc tcgatcgagc gcgccgtgag   1320

cgagttcgac ggacacaagt cgctgtactc cgactcgtac tactcgcgcg aggagttcga   1380

ggagctctac ggcggcgagg cgtaccgggc cgtgaagcgg cgatacgacc ccgactctcg   1440

actgctcgac ctctatgcga aggcggtgca acggcgatga ccacgaccaa acgccaggcg   1500
```

-continued

```
acagcggggc aggctgagac cgcgccgacg acggatgcgg cggccgcacc cgactcgtcg   1560
gcgaagctca ccctcgccga gatcctcgag atcgtcgtcg ccggtcggct gccgctgagg   1620
ttcaccgcct acgacgggag ctcggcgggg ccgcctgacg ccctgttcgg cctcgacctg   1680
aagactccgc gaggaacgac ctatctcgcc accggccgcg gcgatctcgg cctcgcccgc   1740
gcctacatcg cgggcgacct cgagatacag ggggtgcacc ccggagaccc ctacgagctg   1800
ctcaaggcac tcgccgacag cctggtcttc aagctgccac cgccgcgggt gatgacccag   1860
atcatccgtt cgatcggcgt cgaacatctg cggccgatcg cgccgccgcc gcaagaggtg   1920
ccgccccggt ggcgccgcat cgccgagggg ctccgacaca gcaagggccg cgacgccgaa   1980
gcgatccacc accactacga cgtgtcgaac accttctacg aatgggtgct cgggccgtcg   2040
atgacctaca cgtgcgcgtg ctacccgggc ctcgacgcat ccctcgacga ggcgcagcag   2100
aacaagtacc ggctcgtgtt cgagaagctg cggctgaagc cgggcgaccg actgctcgac   2160
gtcggctgcg ggtggggcgg catggtgcgc tacgccgcgc gccacggcgt gcaggcgttg   2220
ggcgtgaccc tgtcgcgaga gcagacggcg tgggcgcagc aggcgatcgc cgtcgagggc   2280
ctcgccgacc tcgccgaggt gcgctacggc gactaccgcg acatcgccga agacggcttc   2340
gatgcggtgt catcgatcgg gctgctcgag cacatcggcg tgcgcaacta cgcttcgtat   2400
ttcggctttc tgcagtcgcg cttgcggccc gggggactct tgctcaacca ctgcatcacc   2460
cggcccgaca atcgctccga gccgtcggcg cgcggcttca tcgaccggta cgtgttcccc   2520
gacggagagc tcaccggctc gggccgcatc atcaccgagg cgcaggatgt cggcttcgaa   2580
gtgctgcacg aagagaacct gcgtcagcat tatgcactga cactgcgcga ttggtgcgcc   2640
aacctcgtcg cgcactggga agaggcggtc gccgaggtcg ggctgccgac cgcgaaggtg   2700
tggggcctct acatggccgg gtcacggctc gcgttcgaga gcggcggcat ccagttgcac   2760
caggtgctgg cggtcagacc agacgatcgc agcgacgccg cccagctgcc gctgcggccg   2820
tggtggacgc catagcctca aaatatattt tccctctatc ttctcgttgc gcttaatttg   2880
actaattctc attagcgagg cgcgcctttc cataggctcc gcccccctga cgagcatcac   2940
aaaaatcgac gctcaagtca gaggtggcga aacccgacag gactataaag ataccaggcg   3000
tttccccctg gaagctccct cgtgcgctct cctgttccga ccctgccgct taccggatac   3060
ctgtccgcct ttctcccttc gggaagcgtg gcgctttctc atagctcacg ctgtaggtat   3120
ctcagttcgg tgtaggtcgt tcgctccaag ctgggctgtg tgcacgaacc ccccgttcag   3180
cccgaccgct gcgccttatc cggtaactat cgtcttgagt ccaacccggt aagacacgac   3240
ttatcgccac tggcagcagc cactggtaac aggattagca gagcgaggta tgtaggcggt   3300
gctacagagt tcttgaagtg gtggcctaac tacggctaca ctagaagaac agtatttggt   3360
atctgcgctc tgctgaagcc agttaccttc ggaaaaagag ttggtagctc ttgatccggc   3420
aaacaaacca ccgctggtag cggtggtttt tttgtttgca agcagcagat tacgcgcaga   3480
aaaaaaggat ctcaagaaga tcctttgatc ttttctacgg ggtctgacgc tcagtggaac   3540
gaaaactcac gttaagggat tttggtcatg agattatcaa aaaggatctt cacctagatc   3600
cttttaaatt aaaaatgaag ttttaaatca atctaaagta tatatgagta aacttggtct   3660
gacagttacc aatgcttaat cagtgaggca cctatctcag cgatctgtct atttcgttca   3720
tccatagttg cctgactccc cgtcgtgtag ataactacga tacgggaggg cttaccatct   3780
ggccccagtg ctgcaatgat accgcgagac ccacgctcac cggctccaga tttatcagca   3840
ataaaccagc cagccggaag ggccgagcgc agaagtggtc ctgcaacttt atccgcctcc   3900
```

-continued

```
atccagtcta ttaattgttg ccgggaagct agagtaagta gttcgccagt taatagtttg   3960
cgcaacgttg ttgccattgc tacaggcatc gtggtgtcac gctcgtcgtt tggtatggct   4020
tcattcagct ccggttccca acgatcaagg cgagttacat gatcccccat gttgtgcaaa   4080
aaagcggtta gctccttcgg tcctccgatc gttgtcagaa gtaagttggc cgcagtgtta   4140
tcactcatgg ttatggcagc actgcataat tctcttactg tcatgccatc cgtaagatgc   4200
ttttctgtga ctggtgagta ctcaaccaag tcattctgag aatagtgtat gcggcgaccg   4260
agttgctctt gcccggcgtc aatacgggat aataccgcgc cacatagcag aactttaaaa   4320
gtgctcatca ttggaaaacg ttcttcgggg cgaaaactct caaggatctt accgctgttg   4380
agatccagtt cgatgtaacc cactcgtgca cccaactgat cttcagcatc ttttactttc   4440
accagcgttt ctgggtgagc aaaaacagga aggcaaaatg ccgcaaaaaa gggaataagg   4500
gcgacacgga aatgttgaat actcatactc ttcctttttc aatattattg aagcatttat   4560
cagggttatt gtctcatgag cggatacata tttgaatgta tttagaaaaa taaacagcga   4620
tcgcgcggcc gcgggtaata actgatataa ttaaattgaa gctctaattt gtgagtttag   4680
tatacatgca tttacttata atacagtttt ttagttttgc tggccgcatc ttctcaaata   4740
tgcttcccag cctgcttttc tgtaacgttc accctctacc ttagcatccc ttccctttgc   4800
aaatagtcct cttccaacaa taataatgtc agatcctgta gagaccacat catccacggt   4860
tctatactgt tgacccaatg cgtctccctt gtcatctaaa cccacaccgg gtgtcataat   4920
caaccaatcg taaccttcat ctcttccacc catgtctctt tgagcaataa agccgataac   4980
aaaatctttg tcgctcttcg caatgtcaac agtaccctta gtatattctc cagtagctag   5040
ggagcccttg catgacaatt ctgctaacat caaaaggcct ctaggttcct ttgttacttc   5100
ttccgccgcc tgcttcaaac cgctaacaat acctgggccc accacaccgt gtgcattcgt   5160
aatgtctgcc cattctgcta ttctgtatac acccgcagag tactgcaatt tgactgtatt   5220
accaatgtca gcaaattttc tgtcttcgaa gagtaaaaaa ttgtacttgg cggataatgc   5280
ctttagcggc ttaactgtgc cctccatgga aaaatcagtc aagatatcca catgtgtttt   5340
tagtaaacaa attttgggac ctaatgcttc aactaactcc agtaattcct tggtggtacg   5400
aacatccaat gaagcacaca agtttgtttg cttttcgtgc atgatattaa atagcttggc   5460
agcaacagga ctaggatgag tagcagcacg ttccttatat gtagctttcg acatgattta   5520
tcttcgtttc ctgcaggttt ttgttctgtg cagttgggtt aagaatactg ggcaatttca   5580
tgtttcttca acaccacata tgcgtatata taccaatcta agtctgtgct ccttccttcg   5640
ttcttccttc tgctcggaga ttaccgaatc aaagctagct tatcgatgat aagctgtcaa   5700
agatgagaat taattccacg gactatagac tatactagat actccgtcta ctgtacgata   5760
cacttccgct caggtccttg tcctttaacg aggccttacc actcttttgt tactctattg   5820
atccagctca gcaaaggcag tgtgatctaa gattctatct tcgcgatgta gtaaaactag   5880
ctagaccgag aaagagacta gaaatgcaaa aggcacttct acaatggctg ccatcattat   5940
tatccgatgt gacgctgcag cttctcaatg atattcgaat acgctttgag gagatacagc   6000
ctaatatccg acaaactgtt ttacagattt acgatcgtac ttgttaccca tcattgaatt   6060
ttgaacatcc gaacctggga gtttccctg aaacagatag tatatttgaa cctgtataat   6120
aatatatagt ctagcgcttt acggaagaca atgtatgtat ttcggttcct ggagaaacta   6180
ttgcatctat tgcataggta atcttgcacg tcgcatcccc ggttcatttt ctgcgtttcc   6240
```

-continued

```
atcttgcact tcaatagcat atctttgtta acgaagcatc tgtgcttcat tttgtagaac   6300
aaaaatgcaa cgcgagagcg ctaatttttc aaacaaagaa tctgagctgc atttttacag   6360
aacagaaatg caacgcgaaa gcgctatttt accaacgaag aatctgtgct tcatttttgt   6420
aaaacaaaaa tgcaacgcga cgagagcgct aatttttcaa acaaagaatc tgagctgcat   6480
ttttacagaa cagaaatgca acgcgagagc gctattttac caacaaagaa tctatacttc   6540
tttttgttc tacaaaaatg catcccgaga gcgctatttt tctaacaaag catcttagat   6600
tactttttt ctcctttgtg cgctctataa tgcagtctct tgataacttt ttgcactgta   6660
ggtccgttaa ggttagaaga aggctacttt ggtgtctatt ttctcttcca taaaaaaagc   6720
ctgactccac ttcccgcgtt tactgattac tagcgaagct gcgggtgcat tttttcaaga   6780
taaaggcatc cccgattata ttctataccg atgtggattg cgcatacttt gtgaacagaa   6840
agtgatagcg ttgatgattc ttcattggtc agaaaattat gaacggtttc ttctattttg   6900
tctctatata ctacgtatag gaaatgttta cattttcgta ttgttttcga ttcactctat   6960
gaatagttct tactacaatt tttttgtcta aagagtaata ctagagataa acataaaaaa   7020
tgtagaggtc gagtttagat gcaagttcaa ggagcgaaag gtggatgggt aggttatata   7080
gggatatagc acagagatat atagcaaaga gatacttttg agcaat                   7126
```

```
<210> SEQ ID NO 91
<211> LENGTH: 7505
<212> TYPE: DNA
<213> ORGANISM: Artificial Sequence
<220> FEATURE:
<223> OTHER INFORMATION: Synthetic Nucleic Acid

<400> SEQUENCE: 91
```

```
gtttgtggaa gcggtattcg caatttaatt aaagctggtg acaattaatc atcggctcgt     60
ataatgtgtg gaattgaatc gatataagga ggttaatcat gtgtctgttg ccgtaaccga    120
cgcacgatcc gcctacgccc acggcgtgca gcggctggtc gcgagttacc gcgccatccc    180
cgccggcgcc accgtccgcc tggccaaacc cacgtccaac ctgttccgcg ccagggcgaa    240
gagcaccgcg gcgggcctcg acacctccgg cctgacacat gtgatcgccg tggaccccga    300
gacgcgcacc gccgaggtcg cggggatgtg cacctacgag gacctggtgg cggcgacgct    360
gccccacggg ctttcaccgc tggtggtccc gcaactcaag acgatcaccc tcggcggcgc    420
cgtcaccggg ctcggcatcg agtcggcgtc gttccgcaac ggccttccgc acgaatcggt    480
cctggagatg gacatcctca ccgggaccgg cgacatcgtg cgcgccgcgc ccgacgagaa    540
tcccgacctt ttccgcacct tcccgaattc ttatggaacg ctgggttact cggttcggct    600
gaagatcgag ctggagccgg tgaagccgtt cgtggcgtta cgccatctcc gcttccactc    660
actgtcgaca ctcatcgcga cgatggaccg catcgtcgac accgggagtc tcgacggtga    720
gcaggtcgac tatctcgacg gagtggtgtt cagcgccgag gagagctacc tgtgcgtcgg    780
aacacgttcc gcgacaccgg gtcctgtcag cgactacacc ggcgagcaca tcttctaccg    840
gtcgatccag cacgattgcc cgaccgaagg cggacagaag cacgaccggc tgacggcgca    900
cgactacttc tggcgctggg acaccgactg gttctggtgc tcaagggcat tcggcgcgca    960
gaacccgaag gtccgtcggt ggtggccccg acggctccgg cgcagcagct tctactggaa   1020
gctcgtcggc tacgaccagc gtttcggcat cgccgaccgg atcgagaaac accacggccg   1080
gccaccgcgc gaacgcgtcg tccaggacgt cgaggtcccc atcgagcgca ccgtcgaatt   1140
cctgcagtgg ttcctcgaca cgatcccgat agagccgctc tggttgtgcc cgttgcgact   1200
```

-continued

```
tcgcgatgac aacagctggt cgctgtaccc gctccggccc catcgcacgt atgtcaacgt   1260
gggattctgg tcgtcggtgc ccgtcgggcc ggaggagggt cacaccaaca agctgatcga   1320
acgcaggatc agcgagctgg agggacacaa gtcgctgtac tccgacgcct tctattcggc   1380
cgacgagttc gacgcgctgt acggcggcga gatctaccgg accgtgaaga agacctacga   1440
cccagattct cgtttcctcg acctctatgc gaaggcggtg cgacggcaat gacgactttt   1500
cgggaacata ccgacagttc ggcgtccgac ccggatcgga aactcacttt ggcagaggtg   1560
ttggagatct tcgccgcggg tcgccgtccg ctgaagttca ccgcctatga cggaagtagt   1620
tgcgggcctg aggatgcgac actgggcctc gacctgctga ccccgcgggg cacgacctac   1680
ctggccacgg cgccgggtga tctcggcctg gcgcgggcct acatcgccgg cgatctgcgc   1740
ctcagtggtg tgcatcccgg cgatccccat gacctgctca cggcgctgac ggaacgcctg   1800
gagtacaggc gtccgccggt gcgagtgctg gccaatgttc tgcgctccat cgggatcgag   1860
cacctcaagc ccgtcgcgcc gccaccccag gagcacctgc cgcggtggcg gcggatcgca   1920
gaggggttgc ggcacagcaa gacccgtgac gctgaggcca tccagcacca ctacgacgtc   1980
tcgaacacgt tctactcatg ggtcctgggt ccgtcgatga cctacacctg cgcctgctat   2040
ccacacccgg atgccacgct ggaggaggcg caggagaaca agtaccggct ggtgttcgag   2100
aagcttcgac tcaagcccgg tgaccggctg ctcgacgtcg gttgcggctg gggcggaatg   2160
gtccgctacg ccgcccggca cggggtcaag gtcctggggg tgacgctgtc gaaggagcag   2220
gcgcagtggg cggccgacgc agtcgagcgg gacggcctgg gtgagttggc cgaggtccgc   2280
cacggcgact accgcgacgt gcgcgagtcg cacttcgacg cagtgtcctc gctcgggctc   2340
accgagcaca tcggcgtcgc gaactacccg tcgtacttcc gcttcctgaa gtcgaaactg   2400
cggccgggtg gcctgctgct caaccactgc atcacccgaa acaacaaccg gagtcacgcc   2460
accgcaggcg gattcatcga tcgctatgtc tttcccgacg gggagctgac ggggtcgggg   2520
cgaatcatca ccgaaatgca ggacgtcgga ctcgaggtcg tgcacgagga gaatctgcgt   2580
caccactacg cgctgacgct gcgcgactgg agccgcaacc tggtcgcgca ctgggacgac   2640
gcggtgaccg aggtcggtct gccgactgcc aaggtgtggg gcctctacat cgccgcgtcg   2700
cgagtcggct tcgagcagaa cgccattcag ctgcaccagg tgctgtcggt caagctcgac   2760
gagcgtggct cggacggcgg actgccgtta cgaccctggt ggaacgccta gccactatgc   2820
tctgcccatg atccggttcc tgctgcgcat cgcggtcttt ctgggctcat cagcgatcgg   2880
gctcctcgtc gccggatggc tggtgcccgg ggtgtcgctg tcggtgtggg gcttcgtcac   2940
ggcagtggtg atcttcaccg tggcgcaggc gatcctgtcc ccgttcttcc tcaagatggc   3000
cagccgctac gcctcggcgt tcctcggcgg gatcggtctg gtgtcgacgt ttgccgcgct   3060
gctgctcgtc tcgctgctgt ccaacggtct gagcatccgc ggcatcggat cctggatcgc   3120
cgcaaccgtg gtggtctggt tggtgaccgc cctggcgacg ctggtgctgc cgatgttggt   3180
gctgcgcgag aagaaaaccg cgtcgcgcgt ctgacctcaa aatatatttt ccctctatct   3240
tctcgttgcg cttaatttga ctaattctca ttagcgaggc gcgcctttcc ataggctccg   3300
ccccccctgac gagcatcaca aaaatcgacg ctcaagtcag aggtggcgaa acccgacagg   3360
actataaaga taccaggcgt ttccccctgg aagctccctc gtgcgctctc ctgttccgac   3420
cctgccgctt accggatacc tgtccgcctt tctcccttcg ggaagcgtgg cgctttctca   3480
tagctcacgc tgtaggtatc tcagttcggt gtaggtcgtt cgctccaagc tgggctgtgt   3540
```

-continued

```
gcacgaaccc cccgttcagc ccgaccgctg cgccttatcc ggtaactatc gtcttgagtc   3600
caacccggta agacacgact tatcgccact ggcagcagcc actggtaaca ggattagcag   3660
agcgaggtat gtaggcggtg ctacagagtt cttgaagtgg tggcctaact acggctacac   3720
tagaagaaca gtatttggta tctgcgctct gctgaagcca gttaccttcg gaaaaagagt   3780
tggtagctct tgatccggca aacaaaccac cgctggtagc ggtggttttt ttgtttgcaa   3840
gcagcagatt acgcgcagaa aaaaaggatc tcaagaagat cctttgatct tttctacggg   3900
gtctgacgct cagtggaacg aaaactcacg ttaagggatt ttggtcatga gattatcaaa   3960
aaggatcttc acctagatcc ttttaaatta aaaatgaagt tttaaatcaa tctaaagtat   4020
atatgagtaa acttggtctg acagttacca atgcttaatc agtgaggcac ctatctcagc   4080
gatctgtcta tttcgttcat ccatagttgc ctgactcccc gtcgtgtaga taactacgat   4140
acgggagggc ttaccatctg gccccagtgc tgcaatgata ccgcgagacc cacgctcacc   4200
ggctccagat ttatcagcaa taaaccagcc agccggaagg gccgagcgca gaagtggtcc   4260
tgcaacttta tccgcctcca tccagtctat taattgttgc cgggaagcta gagtaagtag   4320
ttcgccagtt aatagtttgc gcaacgttgt tgccattgct acaggcatcg tggtgtcacg   4380
ctcgtcgttt ggtatggctt cattcagctc cggttcccaa cgatcaaggc gagttacatg   4440
atcccccatg ttgtgcaaaa aagcggttag ctccttcggt cctccgatcg ttgtcagaag   4500
taagttggcc gcagtgttat cactcatggt tatggcagca ctgcataatt ctcttactgt   4560
catgccatcc gtaagatgct tttctgtgac tggtgagtac tcaaccaagt cattctgaga   4620
atagtgtatg cggcgaccga gttgctcttg cccggcgtca atacgggata ataccgcgcc   4680
acatagcaga actttaaaag tgctcatcat tggaaaacgt tcttcggggc gaaaactctc   4740
aaggatctta ccgctgttga gatccagttc gatgtaaccc actcgtgcac ccaactgatc   4800
ttcagcatct tttactttca ccagcgtttc tgggtgagca aaaacaggaa ggcaaaatgc   4860
cgcaaaaaag ggaataaggg cgacacggaa atgttgaata ctcatactct tcctttttca   4920
atattattga agcatttatc agggttattg tctcatgagc ggatacatat ttgaatgtat   4980
ttagaaaaat aaacagcgat cgcgcggccg cgggtaataa ctgatataat taaattgaag   5040
ctctaatttg tgagtttagt atacatgcat ttacttataa tacagttttt tagttttgct   5100
ggccgcatct tctcaaatat gcttcccagc ctgcttttct gtaacgttca ccctctacct   5160
tagcatccct tccctttgca aatagtcctc ttccaacaat aataatgtca gatcctgtag   5220
agaccacatc atccacggtt ctatactgtt gacccaatgc gtctcccttg tcatctaaac   5280
ccacaccggg tgtcataatc aaccaatcgt aaccttcatc tcttccaccc atgtctcttt   5340
gagcaataaa gccgataaca aaatctttgt cgctcttcgc aatgtcaaca gtacccttag   5400
tatattctcc agtagctagg gagcccttgc atgacaattc tgctaacatc aaaaggcctc   5460
taggttcctt tgttacttct tccgccgcct gcttcaaacc gctaacaata cctgggccca   5520
ccacaccgtg tgcattcgta atgtctgccc attctgctat tctgtataca cccgcagagt   5580
actgcaattt gactgtatta ccaatgtcag caaattttct gtcttcgaag agtaaaaaat   5640
tgtacttggc ggataatgcc tttagcggct taactgtgcc ctccatggaa aaatcagtca   5700
agatatccac atgtgttttt agtaaacaaa ttttgggacc taatgcttca actaactcca   5760
gtaattcctt ggtggtacga acatccaatg aagcacacaa gtttgtttgc ttttcgtgca   5820
tgatattaaa tagcttggca gcaacaggac taggatgagt agcagcacgt tccttatatg   5880
tagctttcga catgatttat cttcgtttcc tgcaggtttt tgttctgtgc agttgggtta   5940
```

agaatactgg gcaatttcat gtttcttcaa caccacatat gcgtatatat accaatctaa 6000
gtctgtgctc cttccttcgt tcttccttct gctcggagat taccgaatca aagctagctt 6060
atcgatgata agctgtcaaa gatgagaatt aattccacgg actatagact atactagata 6120
ctccgtctac tgtacgatac acttccgctc aggtccttgt cctttaacga ggccttacca 6180
ctcttttgtt actctattga tccagctcag caaaggcagt gtgatctaag attctatctt 6240
cgcgatgtag taaaactagc tagaccgaga aagagactag aaatgcaaaa ggcacttcta 6300
caatggctgc catcattatt atccgatgtg acgctgcagc ttctcaatga tattcgaata 6360
cgctttgagg agatacagcc taatatccga caaactgttt tacagattta cgatcgtact 6420
tgttacccat cattgaattt tgaacatccg aacctgggag ttttccctga aacagatagt 6480
atatttgaac ctgtataata atatatagtc tagcgcttta cggaagacaa tgtatgtatt 6540
tcggttcctg gagaaactat tgcatctatt gcataggtaa tcttgcacgt cgcatccccg 6600
gttcattttc tgcgtttcca tcttgcactt caatagcata tctttgttaa cgaagcatct 6660
gtgcttcatt ttgtagaaca aaaatgcaac gcgagagcgc taatttttca aacaaagaat 6720
ctgagctgca tttttacaga acagaaatgc aacgcgaaag cgctatttta ccaacgaaga 6780
atctgtgctt catttttgta aaacaaaaat gcaacgcgac gagagcgcta atttttcaaa 6840
caaagaatct gagctgcatt tttacagaac agaaatgcaa cgcgagagcg ctattttacc 6900
aacaaagaat ctatacttct tttttgttct acaaaaatgc atcccgagag cgctattttt 6960
ctaacaaagc atcttagatt actttttttc tcctttgtgc gctctataat gcagtctctt 7020
gataactttt tgcactgtag gtccgttaag gttagaagaa ggctactttg gtgtctattt 7080
tctcttccat aaaaaaagcc tgactccact tcccgcgttt actgattact agcgaagctg 7140
cgggtgcatt ttttcaagat aaaggcatcc ccgattatat tctataccga tgtggattgc 7200
gcatactttg tgaacagaaa gtgatagcgt tgatgattct tcattggtca gaaaattatg 7260
aacggtttct tctattttgt ctctatatac tacgtatagg aaatgtttac attttcgtat 7320
tgttttcgat tcactctatg aatagttctt actacaattt ttttgtctaa agagtaatac 7380
tagagataaa cataaaaaat gtagaggtcg agtttagatg caagttcaag gagcgaaagg 7440
tggatgggta ggttatatag ggatatagca cagagatata tagcaaagag atacttttga 7500
gcaat 7505

<210> SEQ ID NO 92
<211> LENGTH: 7123
<212> TYPE: DNA
<213> ORGANISM: Artificial Sequence
<220> FEATURE:
<223> OTHER INFORMATION: Synthetic Nucleic Acid

<400> SEQUENCE: 92
gtttgtggaa gcggtattcg caatttaatt aaagctggtg acaattaatc atcggctcgt 60
ataatgtgtg gaattgaatc gatataagga ggttaatcat atgcacgggc tgttgtcgaa 120
gactagggta tatgtggtgc ctgtccttgg atctgcactc tcggcccaca agtcgggcgt 180
tgaccggctg ctggcaagct atcgatccat tcccgcaacg tccgcggtcc ggctggccaa 240
accgacgtca aacctgttcc gcgcccgcac caaacgtgac gcgcccggct tggacacctc 300
ggggctgacc ggcgtcctga gcgtggatcc cgaaacccgc accgcggacg tcgccggcat 360
gtgcacctac gcggacctgg tggccgcaac gctgccctac ggcctgtcgc cgctggtcgt 420

```
cccgcagctg aagaccatca ccctcggcgg ggcggtcagc ggcctgggga tcgagtcggc    480
gtcgtttcgc aacgggctgc cgcacgaatc ggtgctggag atggatatcc tcaccggcgc    540
tggcgatttg ctcaccgcat cacgtaccca gcacccggac ctgttccgcg ccttcccgaa    600
ttcctatggg acactggggt attcgacccg gcttcggatc gagctggaac ccgtcgcacc    660
gttcgtcgcg ctgcgccaca tccgcttccg ctcgctgccc gcgctgatcg ccgcggccga    720
acgcatcgtc gacaccggcg ggcagggcgg aaccccggtc gactacctcg acggggtggt    780
cttcagcgcc gacgaaagct acctgtgcgt gggccggcgg accaccaccc ccggcccggt    840
cagcgactac accggcaagg acatctacta ccagtccatc cggcacgacg ccccgggcct    900
ggaggcgacc aaggatgacc ggctgaccat gcacgactac ttctggcgct gggacaccga    960
ttggttctgg tgctcgcgcg cgttcggcgt gcaggacccg cgggtgcgac gcttctggcc   1020
gcgccgttat cggcgcagca gcttctactg gaagctgatt tccctggacc ggcgcttcgg   1080
gatctccgac cgcatcgagg cgcgcaacgg gcggccccca cgcgaacggg tggtgcaaga   1140
catcgagatt ccaatcgaac ggacctgcga cttcctggag tggttcctgg acaacgtgcc   1200
aatcacgccg atctggttgt gcccgttgcg ccttcgcgac cgcgacggct ggccgttgta   1260
cccgatgcgg ccggatcaca cgtacgtcaa cgtcggcttc tggtcgtcgg tgccgggggg   1320
cgcgaccgag ggcgccgcca accggatgat cgaagaaaag gtgagcgaac tcgacgggca   1380
caagtccctg tactccgatt ccttctactc ccgcgaggac ttcgacgagc tgtacggcgg   1440
cgagacctac aacaccgtca agaaaaccta cgaccccgat tctcgtttac tcgacctcta   1500
cgcaaaggcg gtgcaacggc gatgacgact accaaggaac cccaccgcac gtcgcacggg   1560
aaactgagca tggccgagat cctggaggtc ttcgccgcca ccggccgaca tccgctgaag   1620
ttcaccgcct acgacggcag catcgccggc aacgaggacg ccgaactggg cctggacctt   1680
cgcagccccc gcggcgccac ctatctggcg accgcccccg gcgaactcgg cctcgcccgc   1740
gcctacgtgt cgggcgacct gcaggcctac ggcgtccatc ccggcgaccc gtaccaactg   1800
ctcaagacgc tcaccgatcg ggtggaattc aagcggcccc cggtgcgggt gctggccaac   1860
gtcgtgcggt cgctggggtt cgagcggttg ctgccggtcg cgccgccccc gcaggaggcg   1920
ctgccccggt ggcggcgcat cgccgacggg ctgatgcaca cgaggacccg cgacgccgag   1980
gccatccacc accactacga cgtgtccaac accttctacg aattggtgtt ggggccgtcg   2040
atgacctaca cctgcgcggt gtatcccgat gccgacgcga cactcgaaca ggcgcaggag   2100
aacaagtacc ggctgatctt cgagaagctg cggctgaagg cgggcgaccg gctgctcgac   2160
gtcggctgcg gctggggcgg catggtgcgc tacgcggccc ggcgcggcgt ccgggccacc   2220
ggcgccaccc tgtcggccga acaggcgaag tgggcgcaga aggcgatcgc cgaggaaggc   2280
cttgcggacc tggccgaggt gcgccacacc gactatcggg acgtgggcga ggcggcgttc   2340
gacgccgtgt cctcgatcgg gctgaccgag cacatcggcg tcaagaatta ccccgcctac   2400
ttcggcttct tgaagtcgaa gctgcgcacc ggcggcctgc tgctcaatca ctgcatcacc   2460
cgccacgaca acacgtcgac gtcgttcgcg ggcggattca ccgatcgcta tgtcttcccg   2520
gacggggagc tgaccggctc gggccgcatc acctgcgacg tccaggactg cggcttcgag   2580
gtgctgcacg cggagaactt ccgccaccac tacgcgatga cgctgcgcga ctggtgccgc   2640
aatctggtcg agaactggga cgccgcggtc agcgaggtcg gcctaccgac cgcgaaggtc   2700
tggggcctgt acatggcggc gtcacgggtt gcgttcgagc agaacaacct tcagctgcat   2760
cacgtgctgg cggccaagac cgacgcgcgg ggcgacgacg acctgccgct gcggccgtgg   2820
```

-continued

```
tggacggcct gacctcaaaa tatattttcc ctctatcttc tcgttgcgct taatttgact   2880
aattctcatt agcgaggcgc gcctttccat aggctccgcc cccctgacga gcatcacaaa   2940
aatcgacgct caagtcagag gtggcgaaac ccgacaggac tataaagata ccaggcgttt   3000
ccccctggaa gctccctcgt gcgctctcct gttccgaccc tgccgcttac cggatacctg   3060
tccgcctttc tcccttcggg aagcgtggcg ctttctcata gctcacgctg taggtatctc   3120
agttcggtgt aggtcgttcg ctccaagctg ggctgtgtgc acgaaccccc cgttcagccc   3180
gaccgctgcg ccttatccgg taactatcgt cttgagtcca acccggtaag acacgactta   3240
tcgccactgg cagcagccac tggtaacagg attagcagag cgaggtatgt aggcggtgct   3300
acagagttct tgaagtggtg gcctaactac ggctacacta gaagaacagt atttggtatc   3360
tgcgctctgc tgaagccagt taccttcgga aaaagagttg gtagctcttg atccggcaaa   3420
caaaccaccg ctggtagcgg tggttttttt gtttgcaagc agcagattac gcgcagaaaa   3480
aaaggatctc aagaagatcc tttgatcttt tctacggggt ctgacgctca gtggaacgaa   3540
aactcacgtt aagggatttt ggtcatgaga ttatcaaaaa ggatcttcac ctagatcctt   3600
ttaaattaaa aatgaagttt taaatcaatc taaagtatat atgagtaaac ttggtctgac   3660
agttaccaat gcttaatcag tgaggcacct atctcagcga tctgtctatt tcgttcatcc   3720
atagttgcct gactccccgt cgtgtagata actacgatac gggagggctt accatctggc   3780
cccagtgctg caatgatacc gcgagaccca cgctcaccgg ctccagattt atcagcaata   3840
aaccagccag ccggaagggc cgagcgcaga agtggtcctg caactttatc cgcctccatc   3900
cagtctatta attgttgccg ggaagctaga gtaagtagtt cgccagttaa tagtttgcgc   3960
aacgttgttg ccattgctac aggcatcgtg gtgtcacgct cgtcgtttgg tatggcttca   4020
ttcagctccg gttcccaacg atcaaggcga gttacatgat cccccatgtt gtgcaaaaaa   4080
gcggttagct ccttcggtcc tccgatcgtt gtcagaagta agttggccgc agtgttatca   4140
ctcatggtta tggcagcact gcataattct cttactgtca tgccatccgt aagatgcttt   4200
tctgtgactg gtgagtactc aaccaagtca ttctgagaat agtgtatgcg gcgaccgagt   4260
tgctcttgcc cggcgtcaat acgggataat accgcgccac atagcagaac tttaaaagtg   4320
ctcatcattg gaaaacgttc ttcggggcga aaactctcaa ggatcttacc gctgttgaga   4380
tccagttcga tgtaacccac tcgtgcaccc aactgatctt cagcatcttt tactttcacc   4440
agcgtttctg ggtgagcaaa aacaggaagg caaaatgccg caaaaaaggg aataagggcg   4500
acacggaaat gttgaatact catactcttc ctttttcaat attattgaag catttatcag   4560
ggttattgtc tcatgagcgg atacatattt gaatgtattt agaaaaataa acagcgatcg   4620
cgcggccgcg ggtaataact gatataatta aattgaagct ctaatttgtg agtttagtat   4680
acatgcattt acttataata cagtttttta gttttgctgg ccgcatcttc tcaaatatgc   4740
ttcccagcct gcttttctgt aacgttcacc ctctacctta gcatcccttc cctttgcaaa   4800
tagtcctctt ccaacaataa taatgtcaga tcctgtagag accacatcat ccacggttct   4860
atactgttga cccaatgcgt ctcccttgtc atctaaaccc acaccgggtg tcataatcaa   4920
ccaatcgtaa ccttcatctc ttccacccat gtctctttga gcaataaagc cgataacaaa   4980
atctttgtcg ctcttcgcaa tgtcaacagt acccttagta tattctccag tagctaggga   5040
gcccttgcat gacaattctg ctaacatcaa aaggcctcta ggttcctttg ttacttcttc   5100
cgccgcctgc ttcaaaccgc taacaatacc tgggcccacc acaccgtgtg cattcgtaat   5160
```

gtctgcccat tctgctattc tgtatacacc cgcagagtac tgcaatttga ctgtattacc 5220
aatgtcagca aattttctgt cttcgaagag taaaaaattg tacttggcgg ataatgcctt 5280
tagcggctta actgtgccct ccatggaaaa atcagtcaag atatccacat gtgtttttag 5340
taaacaaatt ttgggaccta atgcttcaac taactccagt aattccttgg tggtacgaac 5400
atccaatgaa gcacacaagt ttgtttgctt ttcgtgcatg atattaaata gcttggcagc 5460
aacaggacta ggatgagtag cagcacgttc cttatatgta gctttcgaca tgatttatct 5520
tcgtttcctg caggtttttg ttctgtgcag ttgggttaag aatactgggc aatttcatgt 5580
ttcttcaaca ccacatatgc gtatatatac caatctaagt ctgtgctcct tccttcgttc 5640
ttccttctgc tcggagatta ccgaatcaaa gctagcttat cgatgataag ctgtcaaaga 5700
tgagaattaa ttccacggac tatagactat actagatact ccgtctactg tacgatacac 5760
ttccgctcag gtccttgtcc tttaacgagg ccttaccact cttttgttac tctattgatc 5820
cagctcagca aaggcagtgt gatctaagat tctatcttcg cgatgtagta aaactagcta 5880
gaccgagaaa gagactagaa atgcaaaagg cacttctaca atggctgcca tcattattat 5940
ccgatgtgac gctgcagctt ctcaatgata ttcgaatacg ctttgaggag atacagccta 6000
atatccgaca aactgtttta cagatttacg atcgtacttg ttacccatca ttgaattttg 6060
aacatccgaa cctgggagtt ttccctgaaa cagatagtat atttgaacct gtataataat 6120
atatagtcta gcgctttacg gaagacaatg tatgtatttc ggttcctgga gaaactattg 6180
catctattgc ataggtaatc ttgcacgtcg catccccggt tcattttctg cgtttccatc 6240
ttgcacttca atagcatatc tttgttaacg aagcatctgt gcttcatttt gtagaacaaa 6300
aatgcaacgc gagagcgcta atttttcaaa caaagaatct gagctgcatt tttacagaac 6360
agaaatgcaa cgcgaaagcg ctattttacc aacgaagaat ctgtgcttca tttttgtaaa 6420
acaaaaatgc aacgcgacga gagcgctaat ttttcaaaca aagaatctga gctgcatttt 6480
tacagaacag aaatgcaacg cgagagcgct attttaccaa caaagaatct atacttcttt 6540
tttgttctac aaaaatgcat cccgagagcg ctatttttct aacaaagcat cttagattac 6600
tttttttctc ctttgtgcgc tctataatgc agtctcttga taactttttg cactgtaggt 6660
ccgttaaggt tagaagaagg ctactttggt gtctattttc tcttccataa aaaaagcctg 6720
actccacttc ccgcgtttac tgattactag cgaagctgcg ggtgcatttt ttcaagataa 6780
aggcatcccc gattatattc tataccgatg tggattgcgc atactttgtg aacagaaagt 6840
gatagcgttg atgattcttc attggtcaga aaattatgaa cggtttcttc tattttgtct 6900
ctatatacta cgtataggaa atgtttacat tttcgtattg ttttcgattc actctatgaa 6960
tagttcttac tacaattttt ttgtctaaag agtaatacta gagataaaca taaaaaatgt 7020
agaggtcgag tttagatgca agttcaagga gcgaaaggtg gatgggtagg ttatataggg 7080
atatagcaca gagatatata gcaaagagat acttttgagc aat 7123

<210> SEQ ID NO 93
<211> LENGTH: 9807
<212> TYPE: DNA
<213> ORGANISM: Artificial Sequence
<220> FEATURE:
<223> OTHER INFORMATION: Synthetic Nucleic Acid

<400> SEQUENCE: 93
ggttatatag ggatatagca cagagatata tagcaaagag atacttttga gcaatgtttg 60
tggaagcggt attcgcaatt taattaacgc ttaccttggc cgttagacat catggtaaat 120

-continued

```
ctgcgcagac agccctgtgc agctgaaacg cggttacgta tagcttgcca tatgtctagc    180
catacgtaac cgcaggtaaa aggcatattt ttcgcgtgtc atggctagta aataacaccg    240
gtgtcattta gagtcaggga aagacaatga aaaacgaaga aagccaccgg gcggcaaccc    300
gatgactttc gcttatcacc cagcacacac ctgggagaaa tcacggtcat gagtttacag    360
actcatgcgc agaatgcgca cactaaaaca cctacccgcg tcgagcgcga ccgtggtgga    420
ctggacaaca ccccagcatc tgccagtgac cgcgaccttt tacgcgatca tctaggccgc    480
gatgtactcc acggttcagt cacacgagac tttaaaaagg cctatcgacg caacgctgac    540
ggcacgaact cgccgcgtat gtatcgcttc gagactgatg ctttaggacg gtgcgagtac    600
gccatgctca ccaccaagca gtacgccgcc gtcctggtcg tagacgttga ccaagtaggt    660
accgcaggcg gtgaccccgc agacttaaac ccgtacgtcc gcgacgtggt gcgctcactg    720
attactcata gcgtcgggcc agcctgggtg ggtattaacc caactaacgg caaagcccag    780
ttcatatggc ttattgaccc tgtctacgct gaccgtaacg gtaaatctgc gcagatgaag    840
cttcttgcag caaccacgcg tgtgctgggt gagcttttag accatgaccc gcacttttcc    900
caccgcttta gccgcaaccc gttctacaca ggcaaagccc ctaccgctta tcgttggtat    960
aggcagcaca accgggtgat gcgccttgga gacttgataa agcaggtaag ggatatggca   1020
ggacacgacc agttcaaccc caccccacgc cagcaattca gctctggccg cgaacttatc   1080
aacgcggtca agacccgccg tgaagaagcc caagcattca aagcactcgc ccaggacgta   1140
gacgcggaaa tcgccggtgg tctcgaccag tatgacccgg aacttatcga cggtgtgcgt   1200
gtgctctgga ttgtccaagg aaccgcagca cgcgacgaaa cagcctttag acatgcgctt   1260
aagactggcc accgcttgcg ccagcaaggc caacgcctga cagacgcagc aatcatcgac   1320
gcctatgagc acgcctacaa cgtcgcacac acccacggcg gtgcaggccg cgacaacgag   1380
atgccaccca tgcgcgaccg ccaaaccatg gcaaggcgcg tgcgcgggta tgtcgcccaa   1440
tccaagagcg agacctacag cggctctaac gcaccaggta aagccaccag cagcgagcgg   1500
aaagccttgg ccacgatggg acgcagaggc ggacaaaaag ccgcacaacg ctggaaaaca   1560
gaccccgagg gcaaatatgc gcaagcacaa aggtcgaagc ttgaaaagac gcaccgtaag   1620
aaaaaggctc aaggacgatc tacgaagtcc cgtattagcc aaatggtgaa cgatcagtat   1680
ttccagacag ggacagttcc cacgtgggct gaaatagggg cagaggtagg agtctctcgc   1740
gccacggttg ctaggcatgt cgcggagcta aagaagagcg gtgactatcc ggacgtttaa   1800
ggggtctcat accgtaagca atatacggtt cccctgccgt taggcagtta gataaaacct   1860
cacttgaaga aaaccttgag ggcagggca gcttatatgc ttcaaagcat gacttcctct    1920
gttctcctag acctcgcaac cctccgccat aacctcaccc tgctctgcga ggctggccgg   1980
ctaccgccgg cgtaacagat gagggcaagc ggatggctga tgaaaccaag ccgcggccgg   2040
gaagccgatc tcggcttgaa cgaattgtta ggtggcggta cttgggtcga tatcaaagtg   2100
catcacttct tcccgtatgc ccaactttgt atagagagcc actgcgggat cgtcaccgta   2160
atctgcttgc acgtagatca cataagcacc aagcgcgttg gcctcatgct tgaggagatt   2220
gatgagcgcg gtggcaatgc cctgcctccg gtgctcgccg gagactgcga gatcatagat   2280
atagatctca ctacgcggct gctcaaactt gggcagaacg taagccgcga gagcgccaac   2340
aaccgcttct tggtcgaagg cagcaagcgc gatgaatgtc ttactacgga gcaagttccc   2400
gaggtaatcg gagtccggct gatgttggga gtaggtggct acgtctccga actcacgacc   2460
```

-continued

```
gaaaagatca agagcagccc gcatggattt gacttggtca gggccgagcc tacatgtgcg   2520
aatgatgccc atacttgagc cacctaactt tgttttaggg cgactgccct gctgcgtaac   2580
atcgttgctg ctccataaca tcaaacatcg acccacggcg taacgcgctt gctgcttgga   2640
tgcccgaggc atagactgta caaaaaaaca gtcataacaa gccatgaaaa ccgccactgc   2700
gccgttacca ccgctgcgtt cggtcaaggt tctggaccag ttgcgtgagc gcatacgcta   2760
cttgcattac agtttacgaa ccgagtttaa acagctggtg acaattaatc atcggctcgt   2820
ataatgtgtg gaattgaatc gatataagga ggttaatcat gtgtctgtgg ttactactga   2880
cgcacaggct gcccatgccg ccggcgtctc gcgtcttctg gccagctacc gggcgatccc   2940
gcccagcgcg acagtgcgcc ttgcgaaacc gacgtccaac ctgttccgcg cccgcgcccg   3000
caccaatgtg aagggtctcg acgtctcggg cctgaccggt gtgatcggtg tcgacccgga   3060
cgcgcgcacc gccgatgtgg cgggcatgtg cacctacgag gacctggtgg cggccacgct   3120
tccgtacggc cttgccccac tggtggtgcc gcagctcaag accatcacgc tcggtggcgc   3180
ggtcaccggt ctgggcatcg agtccacgtc gttccgcaac ggtctgccgc acgaaagtgt   3240
cctggagatg gacatcttga ccggttcggg cgagatcgtc acggcctcac cggatcagca   3300
ctcggatctg ttccatgcgt tccccaattc atatggaacc cttggttatt ccacccggct   3360
gcgcatcgaa ctggagcccg tgcacccgtt tgtggcgttg cgccacctgc gctttcactc   3420
gatcaccgat ctggtcgcgg cgatggaccg gatcatcgag accggcgggc tggacggtga   3480
acccgtcgac tacctcgacg gcgtggtgtt cagcgcgact gagagttacc tgtgtgttgg   3540
cttcaagacg aaaacgccgg ggccggtcag cgattacaca ggtcagcaga tcttctaccg   3600
gtcgatccag catgacggcg acaccggcgc cgagaaacac gaccggctga ccatccacga   3660
ctacctgtgg cgctgggaca ccgactggtt ctggtgctca cgggcattcg gcgctcagca   3720
tccggtgatc cgcaggttct ggccgcggcg gctgcgccgc agcagcttct actggaagct   3780
ggtggcctac gaccagcggt acgacatcgc cgaccgtatc gagaagcgca acgggcgccc   3840
gccgcgcgag cgggtggtcc aggacgtcga ggtgcccatc gagcggtgcg cggacttcgt   3900
cgagtggttc ctgcagaatg tgccgatcga gccgatctgg ctgtgccccc tacggttgcg   3960
tgacagcgcc gacggcggtg cctcgtggcc cctgtatccg ctgaaggcgc accacaccta   4020
cgtcaacatc ggtttctggt catcagtgcc ggtgggcccc gaggagggcc acaccaaccg   4080
cctcatcgag aaaaaagtcg cggagctgga cgggcacaaa tctttgtact cggacgctta   4140
ttacacacgt gacgaattcg acgagctgta cggcggtgag gtctacaaca ccgtcaagaa   4200
gacgtacgac ccggattcac gtctgctaga cctgtattcg aaggcggtgc aaagacaatg   4260
accacattca aagaacgcga gacgtccaca gcggaccgca agctcaccct ggccgagatc   4320
ctcgagatct tcgccgcggg taaggagccg ctgaagttca ctgcgtacga cggcagctcg   4380
gccggtcccg aggacgccac gatgggtctg gacctcaaga ccccgcgtgg gaccacctat   4440
ctggccacgg cacccggcga tctgggcctg gcccgtgcgt atgtctccgg tgacctggag   4500
ccgcacggcg tgcatcccgg cgatccctac ccgctgctgc gcgccctggc cgaacgcatg   4560
gagttcaagc gcccgcctgc gcgtgtgctg gcgaacatcg tgcgctccat cggcatcgag   4620
cacctcaagc cgatcgcacc gccgccgcag gaggcgctgc cccggtggcg ccgcatcatg   4680
gagggcctgc ggcacagcaa gacccgcgac gccgaggcca tccaccacca ctacgacgtg   4740
tcgaacacgt tctacgagtg ggtgctgggc ccgtcgatga cctacacgtg cgcgtgctac   4800
cccaccgagg acgcgaccct cgaagaggcc caggacaaca agtaccgcct ggtgttcgag   4860
```

-continued aagctgcgcc tgaagcccgg tgaccggttg ctcgacgtgg gctgcggctg gggcggcatg 4920
gtccgctacg cggcccgcca cggcgtcaag gcgctcggtg tcacgctcag ccgcgaacag 4980
gcgacgtggg cgcagaaggc catcgcccag gaaggtctca ccgatctggc cgaggtgcgt 5040
cacggtgatt accgcgacgt catcgaatcc gggttcgacg cggtgtcctc gatcgggctg 5100
accgagcaca tcggcgtgca caactacccg gcgtacttca acttcctcaa gtcgaagctg 5160
cgcaccggtg gcctgctgct caaccactgc atcacccgcc cggacaaccg gtcggcgcca 5220
tcggccggcg ggttcatcga caggtacgtg ttccccgacg gggagctcac cggctcgggc 5280
cgcatcatca ccgaggccca ggacgtgggc cttgaggtga tccacgagga gaacctacgc 5340
aatcactatg cgatgacgct gcgcgactgg tgccgcaacc tggtcgagca ctgggacgag 5400
gcggtcgaag aggtcgggct gcccaccgcg aaggtgtggg gcctgtacat ggccggctca 5460
cgtctgggct tcgagaccaa tgtggttcag ctgcaccagg ttctggcggt caagcttgac 5520
gatcagggca aggacggcgg actgccgttg cggccctggt ggtccgccta gcctcaaaat 5580
atattttccc tctatcttct cgttgcgctt aatttgacta attctcatta gcgaggcgcg 5640
cctttccata ggctccgccc ccctgacgag catcacaaaa atcgacgctc aagtcagagg 5700
tggcgaaacc cgacaggact ataaagatac caggcgtttc cccctggaag ctccctcgtg 5760
cgctctcctg ttccgaccct gccgcttacc ggatacctgt ccgcctttct cccttcggga 5820
agcgtggcgc tttctcatag ctcacgctgt aggtatctca gttcggtgta ggtcgttcgc 5880
tccaagctgg gctgtgtgca cgaacccccc gttcagcccg accgctgcgc cttatccggt 5940
aactatcgtc ttgagtccaa cccggtaaga cacgacttat cgccactggc agcagccact 6000
ggtaacagga ttagcagagc gaggtatgta ggcggtgcta cagagttctt gaagtggtgg 6060
cctaactacg gctacactag aagaacagta tttggtatct gcgctctgct gaagccagtt 6120
accttcggaa aaagagttgg tagctcttga tccggcaaac aaaccaccgc tggtagcggt 6180
ggtttttttg tttgcaagca gcagattacg cgcagaaaaa aaggatctca agaagatcct 6240
ttgatctttt ctacggggtc tgacgctcag tggaacgaaa actcacgtta agggattttg 6300
gtcatgagat tatcaaaaag gatcttcacc tagatccttt taaattaaaa atgaagtttt 6360
aaatcaatct aaagtatata tgagtaaact tggtctgaca gttaccaatg cttaatcagt 6420
gaggcaccta tctcagcgat ctgtctattt cgttcatcca tagttgcctg actccccgtc 6480
gtgtagataa ctacgatacg ggagggctta ccatctggcc ccagtgctgc aatgataccg 6540
cgagacccac gctcaccggc tccagattta tcagcaataa accagccagc cggaagggcc 6600
gagcgcagaa gtggtcctgc aactttatcc gcctccatcc agtctattaa ttgttgccgg 6660
gaagctagag taagtagttc gccagttaat agtttgcgca acgttgttgc cattgctaca 6720
ggcatcgtgg tgtcacgctc gtcgtttggt atggcttcat tcagctccgg ttcccaacga 6780
tcaaggcgag ttacatgatc ccccatgttg tgcaaaaaag cggttagctc cttcggtcct 6840
ccgatcgttg tcagaagtaa gttggccgca gtgttatcac tcatggttat ggcagcactg 6900
cataattctc ttactgtcat gccatccgta agatgctttt ctgtgactgg tgagtactca 6960
accaagtcat tctgagaata gtgtatgcgg cgaccgagtt gctcttgccc ggcgtcaata 7020
cgggataata ccgcgccaca tagcagaact ttaaaagtgc tcatcattgg aaaacgttct 7080
tcggggcgaa aactctcaag gatcttaccg ctgttgagat ccagttcgat gtaacccact 7140
cgtgcaccca actgatcttc agcatctttt actttcacca gcgtttctgg gtgagcaaaa 7200

-continued acaggaaggc aaaatgccgc aaaaaaggga ataagggcga cacggaaatg ttgaatactc 7260
atactcttcc tttttcaata ttattgaagc atttatcagg gttattgtct catgagcgga 7320
tacatatttg aatgtattta gaaaaataaa cagcgatcgc gcggccgcgg gtaataactg 7380
atataattaa attgaagctc taatttgtga gtttagtata catgcattta cttataatac 7440
agttttttag ttttgctggc cgcatcttct caaatatgct tcccagcctg cttttctgta 7500
acgttcaccc tctaccttag catcccttcc ctttgcaaat agtcctcttc caacaataat 7560
aatgtcagat cctgtagaga ccacatcatc cacggttcta tactgttgac ccaatgcgtc 7620
tcccttgtca tctaaaccca caccgggtgt cataatcaac caatcgtaac cttcatctct 7680
tccacccatg tctctttgag caataaagcc gataacaaaa tctttgtcgc tcttcgcaat 7740
gtcaacagta cccttagtat attctccagt agctagggag cccttgcatg acaattctgc 7800
taacatcaaa aggcctctag gttcctttgt tacttcttcc gccgcctgct tcaaaccgct 7860
aacaatacct gggcccacca caccgtgtgc attcgtaatg tctgcccatt ctgctattct 7920
gtatacaccc gcagagtact gcaatttgac tgtattacca atgtcagcaa attttctgtc 7980
ttcgaagagt aaaaaattgt acttggcgga taatgccttt agcggcttaa ctgtgccctc 8040
catggaaaaa tcagtcaaga tatccacatg tgtttttagt aaacaaattt tgggacctaa 8100
tgcttcaact aactccagta attccttggt ggtacgaaca tccaatgaag cacacaagtt 8160
tgtttgcttt tcgtgcatga tattaaatag cttggcagca acaggactag gatgagtagc 8220
agcacgttcc ttatatgtag ctttcgacat gatttatctt cgtttcctgc aggtttttgt 8280
tctgtgcagt tgggttaaga atactgggca atttcatgtt tcttcaacac cacatatgcg 8340
tatatatacc aatctaagtc tgtgctcctt ccttcgttct tccttctgct cggagattac 8400
cgaatcaaag ctagcttatc gatgataagc tgtcaaagat gagaattaat tccacggact 8460
atagactata ctagatactc cgtctactgt acgatacact tccgctcagg tccttgtcct 8520
ttaacgaggc cttaccactc ttttgttact ctattgatcc agctcagcaa aggcagtgtg 8580
atctaagatt ctatcttcgc gatgtagtaa aactagctag accgagaaag agactagaaa 8640
tgcaaaaggc acttctacaa tggctgccat cattattatc cgatgtgacg ctgcagcttc 8700
tcaatgatat tcgaatacgc tttgaggaga tacagcctaa tatccgacaa actgttttac 8760
agatttacga tcgtacttgt tacccatcat tgaattttga acatccgaac ctgggagttt 8820
tccctgaaac agatagtata tttgaacctg tataataata tatagtctag cgctttacgg 8880
aagacaatgt atgtatttcg gttcctggag aaactattgc atctattgca taggtaatct 8940
tgcacgtcgc atccccggtt cattttctgc gtttccatct tgcacttcaa tagcatatct 9000
ttgttaacga agcatctgtg cttcattttg tagaacaaaa atgcaacgcg agagcgctaa 9060
tttttcaaac aaagaatctg agctgcattt ttacagaaca gaaatgcaac gcgaaagcgc 9120
tattttacca acgaagaatc tgtgcttcat ttttgtaaaa caaaaatgca acgcgacgag 9180
agcgctaatt tttcaaacaa agaatctgag ctgcattttt acagaacaga aatgcaacgc 9240
gagagcgcta ttttaccaac aaagaatcta tacttctttt ttgttctaca aaaatgcatc 9300
ccgagagcgc tatttttcta acaaagcatc ttagattact ttttttctcc tttgtgcgct 9360
ctataatgca gtctcttgat aactttttgc actgtaggtc cgttaaggtt agaagaaggc 9420
tactttggtg tctattttct cttccataaa aaaagcctga ctccacttcc cgcgtttact 9480
gattactagc gaagctgcgg gtgcattttt tcaagataaa ggcatccccg attatattct 9540
ataccgatgt ggattgcgca tactttgtga acagaaagtg atagcgttga tgattcttca 9600

```
ttggtcagaa aattatgaac ggtttcttct attttgtctc tatatactac gtataggaaa   9660

tgtttacatt ttcgtattgt tttcgattca ctctatgaat agttcttact acaatttttt   9720

tgtctaaaga gtaatactag agataaacat aaaaaatgta gaggtcgagt ttagatgcaa   9780

gttcaaggag cgaaaggtgg atgggta                                       9807


<210> SEQ ID NO 94
<211> LENGTH: 10293
<212> TYPE: DNA
<213> ORGANISM: Artificial Sequence
<220> FEATURE:
<223> OTHER INFORMATION: Synthetic Nucleic Acid

<400> SEQUENCE: 94

gtttgtggaa gcggtattcg caatttaatt aacgcttacc ttggccgtta gacatcatgg     60

taaatctgcg cagacagccc tgtgcagctg aaacgcggtt acgtatagct tgccatatgt    120

ctagccatac gtaaccgcag gtaaaaggca tatttttcgc gtgtcatggc tagtaaataa    180

caccggtgtc atttagagtc agggaaagac aatgaaaaac gaagaaagcc accgggcggc    240

aacccgatga ctttcgctta tcacccagca cacacctggg agaaatcacg gtcatgagtt    300

tacagactca tgcgcagaat gcgcacacta aaacacctac ccgcgtcgag cgcgaccgtg    360

gtggactgga caacacccca gcatctgcca gtgaccgcga ccttttacgc gatcatctag    420

gccgcgatgt actccacggt tcagtcacac gagactttaa aaaggcctat cgacgcaacg    480

ctgacggcac gaactcgccg cgtatgtatc gcttcgagac tgatgcttta ggacggtgcg    540

agtacgccat gctcaccacc aagcagtacg ccgccgtcct ggtcgtagac gttgaccaag    600

taggtaccgc aggcggtgac cccgcagact taaacccgta cgtccgcgac gtggtgcgct    660

cactgattac tcatagcgtc gggccagcct gggtgggtat taacccaact aacggcaaag    720

cccagttcat atggcttatt gaccctgtct acgctgaccg taacggtaaa tctgcgcaga    780

tgaagcttct tgcagcaacc acgcgtgtgc tgggtgagct tttagaccat gacccgcact    840

tttcccaccg ctttagccgc aacccgttct acacaggcaa agcccctacc gcttatcgtt    900

ggtataggca gcacaaccgg gtgatgcgcc ttggagactt gataaagcag gtaagggata    960

tggcaggaca cgaccagttc aaccccaccc cacgccagca attcagctct ggccgcgaac   1020

ttatcaacgc ggtcaagacc cgccgtgaag aagcccaagc attcaaagca ctcgcccagg   1080

acgtagacgc ggaaatcgcc ggtggtctcg accagtatga cccggaactt atcgacggtg   1140

tgcgtgtgct ctggattgtc caaggaaccg cagcacgcga cgaaacagcc tttagacatg   1200

cgcttaagac tggccaccgc ttgcgccagc aaggccaacg cctgacagac gcagcaatca   1260

tcgacgccta tgagcacgcc tacaacgtcg cacacaccca cggcggtgca ggccgcgaca   1320

acgagatgcc acccatgcgc gaccgccaaa ccatggcaag gcgcgtgcgc gggtatgtcg   1380

cccaatccaa gagcgagacc tacagcggct ctaacgcacc aggtaaagcc accagcagcg   1440

agcggaaagc cttggccacg atgggacgca gaggcggaca aaaagccgca caacgctgga   1500

aacagacccc cgagggcaaa tatgcgcaag cacaaaggtc gaagcttgaa aagacgcacc   1560

gtaagaaaaa ggctcaagga cgatctacga agtcccgtat tagccaaatg gtgaacgatc   1620

agtatttcca gacagggaca gttcccacgt gggctgaaat aggggcagag gtaggagtct   1680

ctcgcgccac ggttgctagg catgtcgcgg agctaaagaa gagcggtgac tatccggacg   1740

tttaaggggt ctcataccgt aagcaatata cggttcccct gccgttaggc agttagataa   1800
```

-continued

```
aacctcactt gaagaaaacc ttgaggggca gggcagctta tatgcttcaa agcatgactt   1860
cctctgttct cctagacctc gcaaccctcc gccataacct caccctgctc tgcgaggctg   1920
gccggctacc gccggcgtaa cagatgaggg caagcggatg gctgatgaaa ccaagccgcg   1980
gccgggaagc cgatctcggc ttgaacgaat tgttaggtgg cggtacttgg gtcgatatca   2040
aagtgcatca cttcttcccg tatgcccaac tttgtataga gagccactgc gggatcgtca   2100
ccgtaatctg cttgcacgta gatcacataa gcaccaagcg cgttggcctc atgcttgagg   2160
agattgatga gcgcggtggc aatgccctgc ctccggtgct cgccggagac tgcgagatca   2220
tagatataga tctcactacg cggctgctca aacttgggca gaacgtaagc cgcgagagcg   2280
ccaacaaccg cttcttggtc gaaggcagca agcgcgatga atgtcttact acggagcaag   2340
ttcccgaggt aatcggagtc cggctgatgt tgggagtagg tggctacgtc tccgaactca   2400
cgaccgaaaa gatcaagagc agcccgcatg gatttgactt ggtcagggcc gagcctacat   2460
gtgcgaatga tgcccatact tgagccacct aactttgttt tagggcgact gccctgctgc   2520
gtaacatcgt tgctgctcca taacatcaaa catcgaccca cggcgtaacg cgcttgctgc   2580
ttggatgccc gaggcataga ctgtacaaaa aaacagtcat aacaagccat gaaaaccgcc   2640
actgcgccgt taccaccgct gcgttcggtc aaggttctgg accagttgcg tgagcgcata   2700
cgctacttgc attacagttt acgaaccgag tttaaacagc tggtgacaat taatcatcgg   2760
ctcgtataat gtgtggaatt gaatcgatat aaggaggtta atcatgtgaa ctgtcagtct   2820
tccgcgtcca acctcgccaa ccacatcaac gcggtgtacg agctgcgccg cgcctatgcg   2880
cggctgtccg ccgacaagcc ggtgcgcctg gcgaagacca cctccaacct cttccgcttc   2940
cgcagccggg acgatgccgc gcgtctcgac gtcagcgctt tcacctcggt gatcagcatc   3000
gacacggagg cgcgggtcgc ggaggtgggc ggcatgacca cctacgagga cctggtcgcc   3060
gccaccctgc ggcatggcct gatgccgccg gtggttccgc aactgcgcac gatcaccctg   3120
ggcggtgcgg tcaccgggct ggggatcgaa tcctcgtcct tccgcaacgg gctcccgcac   3180
gagtcagtgg aagagatgga gatcctcacc ggcagcggcc aggtggtggt ggcccggcgc   3240
gacaacgagc accgcgacct gttctacggt ttccccaact cgtacggcac cctcggttac   3300
gcgctgcggc tccgcatcca gctcgaaccg gtccgcccct acgtccacct gcggcacctg   3360
cggttcaccg atgccgcagc ggccatggcc gcgctggagc agatctgcgc ggaccgcacc   3420
cacgacgggg agaccgtcga cttcgtcgac ggcgtcgtgt tcgcccgcaa cgagctgtac   3480
ctgaccttgg ggacgttcac cgaccgggct ccgtggacca gcgactacac cggaaccgac   3540
atctactacc ggtcgatccc ccgctacgcg ggcccccggcc ccggcgacta cctcaccacg   3600
cacgactacc tgtggcggtg ggacaccgac tggttctggt gctcccgcgc cttcggactg   3660
cagcatcccg tggtgcgccg cctgtggccg cgttccttga aacgctccga cgtctaccgc   3720
aagctcgtcg cctgggaccg gcgcactgac gcgagccgcc tgctcgacta ctaccgcggg   3780
cgcccgccca aggaaccggt gatccaggac atcgaggttg aggtggggcg ggctgccgag   3840
ttcctcgact tcttccacac cgagatcggc atgtccccgg tgtggctgtg cccgctgcgg   3900
ctgcgagaag acacagccga cgatacggaa ccggtctggc cgctctaccc cctcaaaccc   3960
cgccgcctct acgtcaactt cgggttttgg ggcctcgttc cgatccgtcc cggtggaggc   4020
aggacatacc acaaccggct gatcgaaaaa gaagtgaccc ggttgggcgg gcacaagtcg   4080
ctctactcgg acgccttcta cgacgaggac gagttctggg agctctacaa cggggagatc   4140
taccgcaagc tcaaagctgc ctacgacccc gacggtcgac tgctcgacct gtacaccaag   4200
```

```
tgcgtcggcg gcgggtgaga aaggatgagg gatgcgactg gcggaggtat tcgaacgtgt   4260
cgtcggaccc gatgcgcccg tccacttccg ggcctacgac ggcagcactg cgggagatcc   4320
acgcagtgaa gtcgctatcg tggttcgcca cccggcagcc gtcaactaca tcgtccaagc   4380
gccgggagca ctcggtttga cccgcgccta cgtggcggga tacctcgacg tcgaagggga   4440
catgtacacc gcgctgcggg caatggccga cgtggtgttc caggaccggc cgcggctgtc   4500
ccccggggaa ctgctgcgga tcatccgcgg gatcgggtgg gtgaagttcg tcaaccggct   4560
tccaccgccg ccgcaggagg tgcgccagtc ccgcctcgcc gccctgggct ggcgccactc   4620
caagcagcgc gacgccgaag ccatccagca ccactacgac gtctccaacg ccttctacgc   4680
cctggtcttg ggcgagtcga tgacctacac ctgcgcggtc tacccgaccg agcaggccac   4740
gctggagcag gcacagttct tcaagcacga gctgatcgcc cgcaagctcg gtcttgcccc   4800
tgggatacga ctgctggatg tggggtgcgg ctggggcggc atggtcatcc acgcggcccg   4860
ggagcacggg gtcaaagccc tgggggtgac cctgtccaaa gagcaggctg agtgggcgca   4920
gaagcggatc gcccacgagg gcctgggcga cctggcagaa gtccggcaca tggactaccg   4980
ggacctgccc gacggcgagt acgacgcgat cagctcgatc gggttgaccg agcacgtcgg   5040
caaaaagaac gtgcccgcct acttcgcgtc gctgtaccgc aagctcgtcc cgggaggccg   5100
cctgctcaac cactgcatca cccggccccg caacgacctg ccgcccttca aacgcggcgg   5160
ggtgatcaac cgctacgtct tccccgatgg ggagctggaa gggcccggct ggctgcaggc   5220
ggcgatgaac gacgccgggt tcgaaatccg ccaccaggag aacctgcggg agcactacgc   5280
acggaccctg cgggactggc tggccaacct ggaccgcaac tgggatgccg cggtgcggga   5340
agtgggggag ggcacggccc gagtgtggcg gctctacatg gccgggtgcg tgctcggctt   5400
cgaacgcaac gtggtgcaac tgcaccagat cctcggggtg aagctcgacg ggaccgaggc   5460
gcggatgccg ctgcgccccg acttcgaacc gccgctgcct taaccgcggt gcacagccgg   5520
gggatatcag tcgcggaacc gggcatgatg agcccatggc tgcgaccgat gacgaccggc   5580
accacaccac cgtcgccctc gacctcatcg acgcgtatgt gcgcgccgac cgcagaatga   5640
tcggtgaacg ttccgcgggg atcagcgcgg aggcggggga gcggatcgtc tccaccctga   5700
aagtgtgcgc ggccttcctt gcccgccggg tccaggagac cggggtgccg tggcgcgcag   5760
cggactcccg ggaagcggtc gcccgcaccg tcgccgacct gctggaaccc gaggtggaat   5820
tcgcggtcgt ctccgcctgg gaggcgtacg cgatcgggga gcacgaggcc gcctgggtcc   5880
gggcgcacgg cgatccgctg gtcttcgtcc acatgctggc cgcgttctcc gctgctatcg   5940
gcacagcggt ctacggccgt gaggagctgc tgcccacgct gcgcagggtg acagcacgat   6000
aacctcaaaa tatattttcc ctctatcttc tcgttgcgct taatttgact aattctcatt   6060
agcgaggcgc gcctttccat aggctccgcc cccctgacga gcatcacaaa aatcgacgct   6120
caagtcagag gtggcgaaac ccgacaggac tataaagata ccaggcgttt ccccctggaa   6180
gctccctcgt gcgctctcct gttccgaccc tgccgcttac cggatacctg tccgcctttc   6240
tcccttcggg aagcgtggcg ctttctcata gctcacgctg taggtatctc agttcggtgt   6300
aggtcgttcg ctccaagctg ggctgtgtgc acgaaccccc cgttcagccc gaccgctgcg   6360
ccttatccgg taactatcgt cttgagtcca acccggtaag acacgactta tcgccactgg   6420
cagcagccac tggtaacagg attagcagag cgaggtatgt aggcggtgct acagagttct   6480
tgaagtggtg gcctaactac ggctacacta gaagaacagt atttggtatc tgcgctctgc   6540
```

-continued

```
tgaagccagt taccttcgga aaaagagttg gtagctcttg atccggcaaa caaaccaccg   6600
ctggtagcgg tggttttttt gtttgcaagc agcagattac gcgcagaaaa aaaggatctc   6660
aagaagatcc tttgatcttt tctacggggt ctgacgctca gtggaacgaa aactcacgtt   6720
aagggatttt ggtcatgaga ttatcaaaaa ggatcttcac ctagatcctt ttaaattaaa   6780
aatgaagttt taaatcaatc taaagtatat atgagtaaac ttggtctgac agttaccaat   6840
gcttaatcag tgaggcacct atctcagcga tctgtctatt tcgttcatcc atagttgcct   6900
gactccccgt cgtgtagata actacgatac gggagggctt accatctggc cccagtgctg   6960
caatgatacc gcgagaccca cgctcaccgg ctccagattt atcagcaata aaccagccag   7020
ccggaagggc cgagcgcaga agtggtcctg caactttatc cgcctccatc cagtctatta   7080
attgttgccg ggaagctaga gtaagtagtt cgccagttaa tagtttgcgc aacgttgttg   7140
ccattgctac aggcatcgtg gtgtcacgct cgtcgtttgg tatggcttca ttcagctccg   7200
gttcccaacg atcaaggcga gttacatgat cccccatgtt gtgcaaaaaa gcggttagct   7260
ccttcggtcc tccgatcgtt gtcagaagta agttggccgc agtgttatca ctcatggtta   7320
tggcagcact gcataattct cttactgtca tgccatccgt aagatgcttt tctgtgactg   7380
gtgagtactc aaccaagtca ttctgagaat agtgtatgcg gcgaccgagt tgctcttgcc   7440
cggcgtcaat acgggataat accgcgccac atagcagaac tttaaaagtg ctcatcattg   7500
gaaaacgttc ttcggggcga aaactctcaa ggatcttacc gctgttgaga tccagttcga   7560
tgtaacccac tcgtgcaccc aactgatctt cagcatcttt tactttcacc agcgtttctg   7620
ggtgagcaaa aacaggaagg caaaatgccg caaaaaaggg aataagggcg acacggaaat   7680
gttgaatact catactcttc ctttttcaat attattgaag catttatcag ggttattgtc   7740
tcatgagcgg atacatattt gaatgtattt agaaaaataa acagcgatcg cgcggccgcg   7800
ggtaataact gatataatta aattgaagct ctaatttgtg agtttagtat acatgcattt   7860
acttataata cagtttttta gttttgctgg ccgcatcttc tcaaatatgc ttcccagcct   7920
gcttttctgt aacgttcacc ctctacctta gcatcccttc cctttgcaaa tagtcctctt   7980
ccaacaataa taatgtcaga tcctgtagag accacatcat ccacggttct atactgttga   8040
cccaatgcgt ctcccttgtc atctaaaccc acaccgggtg tcataatcaa ccaatcgtaa   8100
ccttcatctc ttccacccat gtctctttga gcaataaagc cgataacaaa atctttgtcg   8160
ctcttcgcaa tgtcaacagt acccttagta tattctccag tagctaggga gcccttgcat   8220
gacaattctg ctaacatcaa aaggcctcta ggttcctttg ttacttcttc cgccgcctgc   8280
ttcaaaccgc taacaatacc tgggcccacc acaccgtgtg cattcgtaat gtctgcccat   8340
tctgctattc tgtatacacc cgcagagtac tgcaatttga ctgtattacc aatgtcagca   8400
aattttctgt cttcgaagag taaaaaattg tacttggcgg ataatgcctt tagcggctta   8460
actgtgccct ccatggaaaa atcagtcaag atatccacat gtgtttttag taaacaaatt   8520
ttgggaccta atgcttcaac taactccagt aattccttgg tggtacgaac atccaatgaa   8580
gcacacaagt ttgtttgctt ttcgtgcatg atattaaata gcttggcagc aacaggacta   8640
ggatgagtag cagcacgttc cttatatgta gctttcgaca tgatttatct tcgtttcctg   8700
caggtttttg ttctgtgcag ttgggttaag aatactgggc aatttcatgt ttcttcaaca   8760
ccacatatgc gtatatatac caatctaagt ctgtgctcct tccttcgttc ttccttctgc   8820
tcggagatta ccgaatcaaa gctagcttat cgatgataag ctgtcaaaga tgagaattaa   8880
ttccacggac tatagactat actagatact ccgtctactg tacgatacac ttccgctcag   8940
```

```
gtccttgtcc tttaacgagg ccttaccact cttttgttac tctattgatc cagctcagca   9000

aaggcagtgt gatctaagat tctatcttcg cgatgtagta aaactagcta gaccgagaaa   9060

gagactagaa atgcaaaagg cacttctaca atggctgcca tcattattat ccgatgtgac   9120

gctgcagctt ctcaatgata ttcgaatacg ctttgaggag atacagccta atatccgaca   9180

aactgtttta cagatttacg atcgtacttg ttacccatca ttgaattttg aacatccgaa   9240

cctgggagtt ttccctgaaa cagatagtat atttgaacct gtataataat atatagtcta   9300

gcgctttacg gaagacaatg tatgtatttc ggttcctgga gaaactattg catctattgc   9360

ataggtaatc ttgcacgtcg catccccggt tcattttctg cgtttccatc ttgcacttca   9420

atagcatatc tttgttaacg aagcatctgt gcttcatttt gtagaacaaa aatgcaacgc   9480

gagagcgcta atttttcaaa caaagaatct gagctgcatt tttacagaac agaaatgcaa   9540

cgcgaaagcg ctattttacc aacgaagaat ctgtgcttca tttttgtaaa acaaaaatgc   9600

aacgcgacga gagcgctaat tttcaaaca aagaatctga gctgcatttt tacagaacag   9660

aaatgcaacg cgagagcgct attttaccaa caaagaatct atacttcttt tttgttctac   9720

aaaaatgcat cccgagagcg ctatttttct aacaaagcat cttagattac ttttttttctc   9780

ctttgtgcgc tctataatgc agtctcttga taacttttg cactgtaggt ccgttaaggt   9840

tagaagaagg ctactttggt gtctattttc tcttccataa aaaaagcctg actccacttc   9900

ccgcgtttac tgattactag cgaagctgcg ggtgcatttt ttcaagataa aggcatcccc   9960

gattatattc tataccgatg tggattgcgc atactttgtg aacagaaagt gatagcgttg  10020

atgattcttc attggtcaga aaattatgaa cggtttcttc tattttgtct ctatatacta  10080

cgtataggaa atgtttacat tttcgtattg ttttcgattc actctatgaa tagttcttac  10140

tacaattttt ttgtctaaag agtaatacta gagataaaca taaaaaatgt agaggtcgag  10200

tttagatgca agttcaagga gcgaaaggtg gatgggtagg ttatataggg atatagcaca  10260

gagatatata gcaaagagat acttttgagc aat                              10293
```

<210> SEQ ID NO 95
<211> LENGTH: 5654
<212> TYPE: DNA
<213> ORGANISM: Artificial Sequence
<220> FEATURE:
<223> OTHER INFORMATION: Synthetic Nucleic Acid

<400> SEQUENCE: 95

```
tgggtaggtt atatagggat atagcacaga gatatatagc aaagagatac ttttgagcaa     60

tgtttgtgga agcggtattc gcaatttaat taaagctggt gacaattaat catcggctcg    120

tataatgtgt ggaattgaat cgatataagg aggttaatca tatgacgctg gccaaggtct    180

tcgaggagct ggtcggggcg gacgcccctg tggagctcac cgcctacgac ggatcgagag    240

ccggacgcct gggcagtgat ctgcgggtcc acgtgaagtc gccgtacgcg gtgtcctacc    300

tggtgcactc gccgagcgcg ctcgggctgg cccgcgcgta cgtggccggg cacctggacg    360

cctacggcga catgtacacg ctgctgcggg agatgacgca gctgaccgag gcgctgacgc    420

ccaaggcccg gctgcggctg ctggccggtg tcctgcagga tccgctgctg cgcgcggcgg    480

ccagccgccg tctgccgccc ccgccgcagg aggtgcggac cggccgcacc tcctggttcc    540

ggcacaccaa gcggcgggac gccaaggcca tctcccacca ctacgacgtg tccaacacct    600

tctatgagtg ggtgctgggc ccgtcgatga cctacacctg cgcctgtttc cccaccgagg    660
```

-continued

```
acgccacctt ggaggaggcg cagttccaca agcacgacct ggtcgccaag aagctcgggc    720
tgcggccggg catgcggctg ctggacgtgg gctgcggctg gggcggcatg gtgatgcacg    780
ccgccaagca ctacggggtg cgggcgctgg gcgtcacgct gtccaagcag caggccgagt    840
gggcgcagaa ggccatcgcc gaggcgggcc tgagcgacct ggccgaggtc cgccaccagg    900
actaccggga cgtcaccgag ggcgacttcg acgccatcag ctcgatcggc ctcaccgagc    960
acatcggcaa ggccaacctg ccgtcctact tcggcttcct gtacggcaag ctcaagccgg   1020
gcgggcggct gctcaaccac tgcatcaccc ggcccgacaa cacccagccg gccatgaaga   1080
aggacgggtt catcaaccgg tacgtcttcc ccgacgggga gctggagggg cccggctacc   1140
tgcagaccca gatgaacgac gccggttttg agatccgcca ccaggagaac ctgcgcgagc   1200
actacgcccg caccctggcc ggatggtgcc gcaacctcga tgagcactgg gacgaggcgg   1260
tggccgaggt cggcgagggc accgcgcggg tgtggcggct gtacatggcc ggcagccggc   1320
tcggtttcga gctcaactgg atccagctgc accagatcct gggcgtcaag ctcggcgagc   1380
gcggcgagtc ccgcatgccg ttgcggcccg actggggcgt gtgacctcaa aatatatttt   1440
ccctctatct tctcgttgcg cttaatttga ctaattctca ttagcgaggc gcgcctttcc   1500
ataggctccg cccccctgac gagcatcaca aaaatcgacg ctcaagtcag aggtggcgaa   1560
acccgacagg actataaaga taccaggcgt ttccccctgg aagctccctc gtgcgctctc   1620
ctgttccgac cctgccgctt accggatacc tgtccgcctt tctcccttcg ggaagcgtgg   1680
cgctttctca tagctcacgc tgtaggtatc tcagttcggt gtaggtcgtt cgctccaagc   1740
tgggctgtgt gcacgaaccc cccgttcagc ccgaccgctg cgccttatcc ggtaactatc   1800
gtcttgagtc caacccggta agacacgact tatcgccact ggcagcagcc actggtaaca   1860
ggattagcag agcgaggtat gtaggcggtg ctacagagtt cttgaagtgg tggcctaact   1920
acggctacac tagaagaaca gtatttggta tctgcgctct gctgaagcca gttaccttcg   1980
gaaaaagagt tggtagctct tgatccggca aacaaaccac cgctggtagc ggtggttttt   2040
ttgtttgcaa gcagcagatt acgcgcagaa aaaaaggatc tcaagaagat cctttgatct   2100
tttctacggg gtctgacgct cagtggaacg aaaactcacg ttaagggatt ttggtcatga   2160
gattatcaaa aaggatcttc acctagatcc ttttaaatta aaaatgaagt tttaaatcaa   2220
tctaaagtat atatgagtaa acttggtctg acagttacca atgcttaatc agtgaggcac   2280
ctatctcagc gatctgtcta tttcgttcat ccatagttgc ctgactcccc gtcgtgtaga   2340
taactacgat acgggagggc ttaccatctg gccccagtgc tgcaatgata ccgcgagacc   2400
cacgctcacc ggctccagat ttatcagcaa taaaccagcc agccggaagg gccgagcgca   2460
gaagtggtcc tgcaacttta tccgcctcca tccagtctat taattgttgc cgggaagcta   2520
gagtaagtag ttcgccagtt aatagtttgc gcaacgttgt tgccattgct acaggcatcg   2580
tggtgtcacg ctcgtcgttt ggtatggctt cattcagctc cggttcccaa cgatcaaggc   2640
gagttacatg atcccccatg ttgtgcaaaa aagcggttag ctccttcggt cctccgatcg   2700
ttgtcagaag taagttggcc gcagtgttat cactcatggt tatggcagca ctgcataatt   2760
ctcttactgt catgccatcc gtaagatgct tttctgtgac tggtgagtac tcaaccaagt   2820
cattctgaga atagtgtatg cggcgaccga gttgctcttg cccggcgtca atacgggata   2880
ataccgcgcc acatagcaga actttaaaag tgctcatcat tggaaaacgt tcttcggggc   2940
gaaaactctc aaggatctta ccgctgttga gatccagttc gatgtaaccc actcgtgcac   3000
ccaactgatc ttcagcatct tttactttca ccagcgtttc tgggtgagca aaaacaggaa   3060
```

```
ggcaaaatgc cgcaaaaaag ggaataaggg cgacacggaa atgttgaata ctcatactct   3120
tcctttttca atattattga agcatttatc agggttattg tctcatgagc ggatacatat   3180
ttgaatgtat ttagaaaaat aaacagcgat cgcgcggccg cgggtaataa ctgatataat   3240
taaattgaag ctctaatttg tgagtttagt atacatgcat ttacttataa tacagttttt   3300
tagttttgct ggccgcatct tctcaaatat gcttcccagc ctgcttttct gtaacgttca   3360
ccctctacct tagcatccct tccctttgca aatagtcctc ttccaacaat aataatgtca   3420
gatcctgtag agaccacatc atccacggtt ctatactgtt gacccaatgc gtctcccttg   3480
tcatctaaac ccacaccggg tgtcataatc aaccaatcgt aaccttcatc tcttccaccc   3540
atgtctcttt gagcaataaa gccgataaca aaatctttgt cgctcttcgc aatgtcaaca   3600
gtacccttag tatattctcc agtagctagg gagcccttgc atgacaattc tgctaacatc   3660
aaaaggcctc taggttcctt tgttacttct tccgccgcct gcttcaaacc gctaacaata   3720
cctgggccca ccacaccgtg tgcattcgta atgtctgccc attctgctat tctgtataca   3780
cccgcagagt actgcaattt gactgtatta ccaatgtcag caaattttct gtcttcgaag   3840
agtaaaaaat tgtacttggc ggataatgcc tttagcggct taactgtgcc ctccatggaa   3900
aaatcagtca agatatccac atgtgttttt agtaaacaaa ttttgggacc taatgcttca   3960
actaactcca gtaattcctt ggtggtacga acatccaatg aagcacacaa gtttgtttgc   4020
ttttcgtgca tgatattaaa tagcttggca gcaacaggac taggatgagt agcagcacgt   4080
tccttatatg tagctttcga catgatttat cttcgtttcc tgcaggtttt tgttctgtgc   4140
agttgggtta agaatactgg gcaatttcat gtttcttcaa caccacatat gcgtatatat   4200
accaatctaa gtctgtgctc cttccttcgt tcttccttct gctcggagat taccgaatca   4260
aagctagctt atcgatgata agctgtcaaa gatgagaatt aattccacgg actatagact   4320
atactagata ctccgtctac tgtacgatac acttccgctc aggtccttgt cctttaacga   4380
ggccttacca ctcttttgtt actctattga tccagctcag caaaggcagt gtgatctaag   4440
attctatctt cgcgatgtag taaaactagc tagaccgaga aagagactag aaatgcaaaa   4500
ggcacttcta caatggctgc catcattatt atccgatgtg acgctgcagc ttctcaatga   4560
tattcgaata cgctttgagg agatacagcc taatatccga caaactgttt tacagattta   4620
cgatcgtact tgttacccat cattgaattt tgaacatccg aacctgggag ttttccctga   4680
aacagatagt atatttgaac ctgtataata atatatagtc tagcgcttta cggaagacaa   4740
tgtatgtatt tcggttcctg gagaaactat tgcatctatt gcataggtaa tcttgcacgt   4800
cgcatccccg gttcattttc tgcgtttcca tcttgcactt caatagcata tctttgttaa   4860
cgaagcatct gtgcttcatt ttgtagaaca aaaatgcaac gcgagagcgc taatttttca   4920
aacaaagaat ctgagctgca tttttacaga acagaaatgc aacgcgaaag cgctatttta   4980
ccaacgaaga atctgtgctt catttttgta aaacaaaaat gcaacgcgac gagagcgcta   5040
atttttcaaa caaagaatct gagctgcatt tttacagaac agaaatgcaa cgcgagagcg   5100
ctattttacc aacaaagaat ctatacttct tttttgttct acaaaaatgc atcccgagag   5160
cgctattttt ctaacaaagc atcttagatt actttttttc tcctttgtgc gctctataat   5220
gcagtctctt gataactttt tgcactgtag gtccgttaag gttagaagaa ggctactttg   5280
gtgtctattt tctcttccat aaaaaaagcc tgactccact tcccgcgttt actgattact   5340
agcgaagctg cgggtgcatt ttttcaagat aaaggcatcc ccgattatat tctataccga   5400
```

tgtggattgc gcatactttg tgaacagaaa gtgatagcgt tgatgattct tcattggtca 5460
gaaaattatg aacggtttct tctattttgt ctctatatac tacgtatagg aaatgtttac 5520
attttcgtat tgttttcgat tcactctatg aatagttctt actacaattt ttttgtctaa 5580
agagtaatac tagagataaa cataaaaaat gtagaggtcg agtttagatg caagttcaag 5640
gagcgaaagg tgga 5654

<210> SEQ ID NO 96
<211> LENGTH: 5759
<212> TYPE: DNA
<213> ORGANISM: Artificial Sequence
<220> FEATURE:
<223> OTHER INFORMATION: Synthetic Nucleic Acid

<400> SEQUENCE: 96
tgggtaggtt atatagggat atagcacaga gatatatagc aaagagatac ttttgagcaa 60
tgtttgtgga agcggtattc gcaatttaat taaagctggt gacaattaat catcggctcg 120
tataatgtgt ggaattgaat cgatataagg aggttaatca tatgtcacag ctggcggtca 180
cagaccacca cgagcgagcg gtcgaggcgc tgcgcaggtc gtatgcggcg atcccgccgg 240
gcacaccggt ccgcttggcc aagcagacct ccaacctgtt ccgcttccgc gagccgacgg 300
ccgcgcccgg cctggacgtg tccggcttca accgggtgct ggcggtggac ccggatgcgc 360
gcaccgccga cgtgcagggc atgaccacct acgaggacct ggtcgacgcc accctgccgc 420
acgggctgat gccgctggtg gtgccccagc tcaagacgat cacgctgggc ggggcggtga 480
ccggcctggg catcgagtcc acctccttcc gcaacggcct gccgcacgag tcggtgctgg 540
agatgcagat catcaccggc gccggcgaag tggtcaccgc caccccggac ggggagcact 600
ccgacctgtt ctggggcttc cccaactcct acgggacgct ggggtacgcc ctgaagctga 660
agatcgaact ggagccggtc aagccgtacg tccggctgcg gcacctgcgc ttcgacgacg 720
ccggcgagtg cgccgccaag ctcgccgagc tgagcgaaag ccgcgagcac gagggcgatg 780
aggtgcactt tttggacggc accttcttcg ggccgcgcga gatgtacctg acgctcggca 840
cgttcaccga caccgccccc tatgtgtcgg actacaccgg gcagcacatc tactaccggt 900
cgatccagca gcggtcgatc gactttttga ccatccgcga ctacctgtgg cgctgggaca 960
ccgactggtt ctggtgctcg cgcgccctgg gcgtgcagaa cccgctgatc cggcgggtgt 1020
ggccgaagag cgccaagcgg tcggatgtgt accgcaagct ggtggcctac gaaaagcgct 1080
accagttcaa ggcgcgcatc gaccggtgga cgggcaagcc gccgcgcgag gacgtcatcc 1140
aggacatcga ggtgccggca gaacgcctgc cggagttcct ggagttcttc cacgacaaga 1200
tcgggatgag cccggtgtgg ctgtgcccgc tgcgggcgcg ccaccgctgg ccgctgtacc 1260
cgctcaagcc cggcgtcacc tacgtcaacg ccggcttctg gggacggtg ccgctgcagc 1320 cggggcagat gcccgagtac cacaaccggc tgatcgaacg gaaggtcgcc caactggacg 1380
gccacaagtc tctgtactcg acggcgttct actcgcgtga ggagttctgg cggcactacg 1440
acggggaaac ctaccggcgt ctgaaggaca cctacgaccc cgacgcgcgc ctgctcgacc 1500
tctacgacaa gtgcgtgcgg ggacgctgac ctcaaaatat attttccctc tatcttctcg 1560
ttgcgcttaa tttgactaat tctcattagc gaggcgcgcc tttccatagg ctccgccccc 1620
ctgacgagca tcacaaaaat cgacgctcaa gtcagaggtg gcgaaacccg acaggactat 1680
aaagatacca ggcgtttccc cctggaagct ccctcgtgcg ctctcctgtt ccgaccctgc 1740
cgcttaccgg atacctgtcc gcctttctcc cttcgggaag cgtggcgctt tctcatagct 1800

-continued

```
cacgctgtag gtatctcagt tcggtgtagg tcgttcgctc caagctgggc tgtgtgcacg   1860
aaccccccgt tcagcccgac cgctgcgcct tatccggtaa ctatcgtctt gagtccaacc   1920
cggtaagaca cgacttatcg ccactggcag cagccactgg taacaggatt agcagagcga   1980
ggtatgtagg cggtgctaca gagttcttga agtggtggcc taactacggc tacactagaa   2040
gaacagtatt tggtatctgc gctctgctga agccagttac cttcggaaaa agagttggta   2100
gctcttgatc cggcaaacaa accaccgctg gtagcggtgg tttttttgtt tgcaagcagc   2160
agattacgcg cagaaaaaaa ggatctcaag aagatccttt gatcttttct acggggtctg   2220
acgctcagtg gaacgaaaac tcacgttaag ggattttggt catgagatta tcaaaaagga   2280
tcttcaccta gatcctttta aattaaaaat gaagttttaa atcaatctaa agtatatatg   2340
agtaaacttg gtctgacagt taccaatgct taatcagtga ggcacctatc tcagcgatct   2400
gtctatttcg ttcatccata gttgcctgac tccccgtcgt gtagataact acgatacggg   2460
agggcttacc atctggcccc agtgctgcaa tgataccgcg agacccacgc tcaccggctc   2520
cagatttatc agcaataaac cagccagccg gaagggccga gcgcagaagt ggtcctgcaa   2580
ctttatccgc ctccatccag tctattaatt gttgccggga agctagagta agtagttcgc   2640
cagttaatag tttgcgcaac gttgttgcca ttgctacagg catcgtggtg tcacgctcgt   2700
cgtttggtat ggcttcattc agctccggtt cccaacgatc aaggcgagtt acatgatccc   2760
ccatgttgtg caaaaaagcg gttagctcct tcggtcctcc gatcgttgtc agaagtaagt   2820
tggccgcagt gttatcactc atggttatgg cagcactgca taattctctt actgtcatgc   2880
catccgtaag atgcttttct gtgactggtg agtactcaac caagtcattc tgagaatagt   2940
gtatgcggcg accgagttgc tcttgcccgg cgtcaatacg ggataatacc gcgccacata   3000
gcagaacttt aaaagtgctc atcattggaa aacgttcttc ggggcgaaaa ctctcaagga   3060
tcttaccgct gttgagatcc agttcgatgt aacccactcg tgcacccaac tgatcttcag   3120
catcttttac tttcaccagc gtttctgggt gagcaaaaac aggaaggcaa aatgccgcaa   3180
aaaagggaat aagggcgaca cggaaatgtt gaatactcat actcttcctt tttcaatatt   3240
attgaagcat ttatcagggt tattgtctca tgagcggata catatttgaa tgtatttaga   3300
aaaataaaca gcgatcgcgc ggccgcgggt aataactgat ataattaaat tgaagctcta   3360
atttgtgagt ttagtataca tgcatttact tataatacag tttttagtt ttgctggccg   3420
catcttctca aatatgcttc ccagcctgct tttctgtaac gttcaccctc taccttagca   3480
tcccttccct ttgcaaatag tcctcttcca acaataataa tgtcagatcc tgtagagacc   3540
acatcatcca cggttctata ctgttgaccc aatgcgtctc ccttgtcatc taaacccaca   3600
ccgggtgtca taatcaacca atcgtaacct tcatctcttc cacccatgtc tctttgagca   3660
ataaagccga taacaaaatc tttgtcgctc ttcgcaatgt caacagtacc cttagtatat   3720
tctccagtag ctagggagcc cttgcatgac aattctgcta acatcaaaag gcctctaggt   3780
tcctttgtta cttcttccgc cgcctgcttc aaaccgctaa caatacctgg gcccaccaca   3840
ccgtgtgcat tcgtaatgtc tgcccattct gctattctgt atacacccgc agagtactgc   3900
aatttgactg tattaccaat gtcagcaaat tttctgtctt cgaagagtaa aaaattgtac   3960
ttggcggata atgcctttag cggcttaact gtgccctcca tggaaaaatc agtcaagata   4020
tccacatgtg tttttagtaa acaaattttg ggacctaatg cttcaactaa ctccagtaat   4080
tccttggtgg tacgaacatc caatgaagca cacaagtttg tttgcttttc gtgcatgata   4140
```

-continued ttaaatagct tggcagcaac aggactagga tgagtagcag cacgttcctt atatgtagct 4200
ttcgacatga tttatcttcg tttcctgcag gtttttgttc tgtgcagttg ggttaagaat 4260
actgggcaat ttcatgtttc ttcaacacca catatgcgta tatataccaa tctaagtctg 4320
tgctccttcc ttcgttcttc cttctgctcg gagattaccg aatcaaagct agcttatcga 4380
tgataagctg tcaaagatga gaattaattc cacggactat agactatact agatactccg 4440
tctactgtac gatacacttc cgctcaggtc cttgtccttt aacgaggcct taccactctt 4500
ttgttactct attgatccag ctcagcaaag gcagtgtgat ctaagattct atcttcgcga 4560
tgtagtaaaa ctagctagac cgagaaagag actagaaatg caaaaggcac ttctacaatg 4620
gctgccatca ttattatccg atgtgacgct gcagcttctc aatgatattc gaatacgctt 4680
tgaggagata cagcctaata tccgacaaac tgttttacag atttacgatc gtacttgtta 4740
cccatcattg aattttgaac atccgaacct gggagttttc cctgaaacag atagtatatt 4800
tgaacctgta taataatata tagtctagcg ctttacggaa gacaatgtat gtatttcggt 4860
tcctggagaa actattgcat ctattgcata ggtaatcttg cacgtcgcat ccccggttca 4920
ttttctgcgt ttccatcttg cacttcaata gcatatcttt gttaacgaag catctgtgct 4980
tcattttgta gaacaaaaat gcaacgcgag agcgctaatt tttcaaacaa agaatctgag 5040
ctgcattttt acagaacaga aatgcaacgc gaaagcgcta ttttaccaac gaagaatctg 5100
tgcttcattt ttgtaaaaca aaaatgcaac gcgacgagag cgctaatttt tcaaacaaag 5160
aatctgagct gcatttttac agaacagaaa tgcaacgcga gagcgctatt ttaccaacaa 5220
agaatctata cttctttttt gttctacaaa aatgcatccc gagagcgcta tttttctaac 5280
aaagcatctt agattacttt ttttctcctt tgtgcgctct ataatgcagt ctcttgataa 5340
ctttttgcac tgtaggtccg ttaaggttag aagaaggcta ctttggtgtc tattttctct 5400
tccataaaaa aagcctgact ccacttcccg cgtttactga ttactagcga agctgcgggt 5460 gcatttttttc aagataaagg catccccgat tatattctat accgatgtgg attgcgcata 5520
ctttgtgaac agaaagtgat agcgttgatg attcttcatt ggtcagaaaa ttatgaacgg 5580
tttcttctat tttgtctcta tatactacgt ataggaaatg tttacatttt cgtattgttt 5640
tcgattcact ctatgaatag ttcttactac aatttttttg tctaaagagt aatactagag 5700
ataaacataa aaaatgtaga ggtcgagttt agatgcaagt tcaaggagcg aaaggtgga 5759

<210> SEQ ID NO 97
<211> LENGTH: 2664
<212> TYPE: DNA
<213> ORGANISM: Thermomonospora curvata

<400> SEQUENCE: 97
atgtcacagc tggcggtcac agaccaccac gagcgagcgg tcgaggcgct gcgcaggtcg 60
tatgcggcga tcccgccggg cacaccggtc cgcttggcca agcagacctc caacctgttc 120
cgcttccgcg agccgacggc cgcgcccggc ctggacgtgt ccggcttcaa ccgggtgctg 180
gcggtggacc cggatgcgcg caccgccgac gtgcagggca tgaccaccta cgaggacctg 240
gtcgacgcca ccctgccgca cgggctgatg ccgctggtgg tgccccagct caagacgatc 300
acgctgggcg gggcggtgac cggcctgggc atcgagtcca cctccttccg caacggcctg 360
ccgcacgagt cggtgctgga gatgcagatc atcaccggcg ccggcgaagt ggtcaccgcc 420
accccggacg gggagcactc cgacctgttc tggggcttcc ccaactccta cgggacgctg 480
gggtacgccc tgaagctgaa gatcgaactg gagccggtca agccgtacgt ccggctgcgg 540

```
cacctgcgct tcgacgacgc cggcgagtgc gccgccaagc tcgccgagct gagcgaaagc    600
cgcgagcacg agggcgatga ggtgcacttt ttggacggca ccttcttcgg gccgcgcgag    660
atgtacctga cgctcggcac gttcaccgac accgcccccct atgtgtcgga ctacaccggg    720
cagcacatct actaccggtc gatccagcag cggtcgatcg actttttgac catccgcgac    780
tacctgtggc gctgggacac cgactggttc tggtgctcgc gcgccctggg cgtgcagaac    840
ccgctgatcc ggcgggtgtg gccgaagagc gccaagcggt cggatgtgta ccgcaagctg    900
gtggcctacg aaaagcgcta ccagttcaag gcgcgcatcg accggtggac gggcaagccg    960
ccgcgcgagg acgtcatcca ggacatcgag gtgccggcag aacgcctgcc ggagttcctg   1020
gagttcttcc acgacaagat cgggatgagc ccggtgtggc tgtgcccgct gcgggcgcgc   1080
caccgctggc cgctgtaccc gctcaagccc ggcgtcacct acgtcaacgc cggcttctgg   1140
gggacggtgc cgctgcagcc ggggcagatg cccgagtacc acaaccggct gatcgaacgg   1200
aaggtcgccc aactggacgg ccacaagtct ctgtactcga cggcgttcta ctcgcgtgag   1260
gagttctggc ggcactacga cggggaaacc taccggcgtc tgaaggacac ctacgacccc   1320
gacgcgcgcc tgctcgacct ctacgacaag tgcgtgcggg gacgcgctgg tggtgccgag   1380
ggtggcaatg gcggtggcgc catgacgctg gccaaggtct tcgaggagct ggtcggggcg   1440
gacgcccctg tggagctcac cgcctacgac ggatcgagag ccggacgcct gggcagtgat   1500
ctgcgggtcc acgtgaagtc gccgtacgcg gtgtcctacc tggtgcactc gccgagcgcg   1560
ctcgggctgg cccgcgcgta cgtggccggg cacctggacg cctacggcga catgtacacg   1620
ctgctgcggg agatgacgca gctgaccgag gcgctgacgc ccaaggcccg gctgcggctg   1680
ctggccggtg tcctgcagga tccgctgctg cgcgcggcgg ccagccgccg tctgccgccc   1740
ccgccgcagg aggtgcggac cggccgcacc tcctggttcc ggcacaccaa gcggcgggac   1800
gccaaggcca tctcccacca ctacgacgtg tccaacacct tctatgagtg ggtgctgggc   1860
ccgtcgatga cctacacctg cgcctgtttc ccccaccgagg acgccacctt ggaggaggcg   1920
cagttccaca agcacgacct ggtcgccaag aagctcgggc tgcggccggg catgcggctg   1980
ctggacgtgg gctgcggctg gggcggcatg gtgatgcacg ccgccaagca ctacggggtg   2040
cgggcgctgg gcgtcacgct gtccaagcag caggccgagt gggcgcagaa ggccatcgcc   2100
gaggcgggcc tgagcgacct ggccgaggtc cgccaccagg actaccggga cgtcaccgag   2160
ggcgacttcg acgccatcag ctcgatcggc ctcaccgagc acatcggcaa ggccaacctg   2220
ccgtcctact tcggcttcct gtacggcaag ctcaagccgg gcgggcggct gctcaaccac   2280
tgcatcaccc ggcccgacaa cacccagccg gccatgaaga aggacgggtt catcaaccgg   2340
tacgtcttcc ccgacgggga gctggagggg cccggctacc tgcagaccca gatgaacgac   2400
gccggttttg agatccgcca ccaggagaac ctgcgcgagc actacgcccg caccctggcc   2460
ggatggtgcc gcaacctcga tgagcactgg gacgaggcgg tggccgaggt cggcgagggc   2520
accgcgcggg tgtggcggct gtacatggcc ggcagccggc tcggtttcga gctcaactgg   2580
atccagctgc accagatcct gggcgtcaag ctcggcgagc gcggcgagtc ccgcatgccg   2640
ttgcggcccg actggggcgt gtga                                          2664
```

<210> SEQ ID NO 98
<211> LENGTH: 2664
<212> TYPE: DNA
<213> ORGANISM: Thermomonospora curvata

<400> SEQUENCE: 98
atgacgctgg ccaaggtctt cgaggagctg gtcggggcgg acgcccctgt ggagctcacc 60
gcctacgacg gatcgagagc cggacgcctg ggcagtgatc tgcgggtcca cgtgaagtcg 120
ccgtacgcgg tgtcctacct ggtgcactcg ccgagcgcgc tcgggctggc ccgcgcgtac 180
gtggccgggc acctggacgc ctacggcgac atgtacacgc tgctgcggga gatgacgcag 240
ctgaccgagg cgctgacgcc caaggcccgg ctgcggctgc tggccggtgt cctgcaggat 300
ccgctgctgc gcgcggcggc cagccgccgt ctgccgcccc cgccgcagga ggtgcggacc 360
ggccgcacct cctggttccg gcacaccaag cggcgggacg ccaaggccat ctcccaccac 420
tacgacgtgt ccaacacctt ctatgagtgg gtgctgggcc cgtcgatgac ctacacctgc 480
gcctgtttcc ccaccgagga cgccaccttg gaggaggcgc agttccacaa gcacgacctg 540
gtcgccaaga agctcgggct gcggccgggc atgcggctgc tggacgtggg ctgcggctgg 600
ggcggcatgg tgatgcacgc cgccaagcac tacggggtgc gggcgctggg cgtcacgctg 660
tccaagcagc aggccgagtg ggcgcagaag gccatcgccg aggcgggcct gagcgacctg 720
gccgaggtcc gccaccagga ctaccgggac gtcaccgagg gcgacttcga cgccatcagc 780
tcgatcggcc tcaccgagca catcggcaag gccaacctgc cgtcctactt cggcttcctg 840
tacggcaagc tcaagccggg cgggcggctg ctcaaccact gcatcacccg gcccgacaac 900
acccagccgg ccatgaagaa ggacgggttc atcaaccggt acgtcttccc cgacggggag 960
ctggaggggc ccggctacct gcagacccag atgaacgacg ccggttttga gatccgccac 1020
caggagaacc tgcgcgagca ctacgcccgc accctggccg gatggtgccg caacctcgat 1080
gagcactggg acgaggcggt ggccgaggtc ggcgagggca ccgcgcgggt gtggcggctg 1140
tacatggccg gcagccggct cggtttcgag ctcaactgga tccagctgca ccagatcctg 1200
ggcgtcaagc tcggcgagcg cggcgagtcc cgcatgccgt tgcggcccga ctggggcgtg 1260
gctggtggtg ccgagggtgg caatggcggt ggcgccatgt cacagctggc ggtcacagac 1320
caccacgagc gagcggtcga ggcgctgcgc aggtcgtatg cggcgatccc gccgggcaca 1380
ccggtccgct tggccaagca gacctccaac ctgttccgct tccgcgagcc gacggccgcg 1440
cccggcctgg acgtgtccgg cttcaaccgg gtgctggcgg tggacccgga tgcgcgcacc 1500
gccgacgtgc agggcatgac cacctacgag gacctggtcg acgccaccct gccgcacggg 1560
ctgatgccgc tggtggtgcc ccagctcaag acgatcacgc tgggcggggc ggtgaccggc 1620
ctgggcatcg agtccacctc cttccgcaac ggcctgccgc acgagtcggt gctggagatg 1680
cagatcatca ccggcgccgg cgaagtggtc accgccaccc cggacgggga gcactccgac 1740
ctgttctggg gcttccccaa ctcctacggg acgctggggt acgccctgaa gctgaagatc 1800
gaactggagc cggtcaagcc gtacgtccgg ctgcggcacc tgcgcttcga cgacgccggc 1860
gagtgcgccg ccaagctcgc cgagctgagc gaaagccgcg agcacgaggg cgatgaggtg 1920
cactttttgg acggcacctt cttcgggccg cgcgagatgt acctgacgct cggcacgttc 1980
accgacaccg ccccctatgt gtcggactac accgggcagc acatctacta ccggtcgatc 2040
cagcagcggt cgatcgactt tttgaccatc cgcgactacc tgtggcgctg ggacaccgac 2100
tggttctggt gctcgcgcgc cctgggcgtg cagaacccgc tgatccggcg ggtgtggccg 2160
aagagcgcca agcggtcgga tgtgtaccgc aagctggtgg cctacgaaaa gcgctaccag 2220
ttcaaggcgc gcatcgaccg gtggacgggc aagccgccgc gcgaggacgt catccaggac 2280
atcgaggtgc cggcagaacg cctgccggag ttcctggagt tcttccacga caagatcggg 2340

```
atgagcccgg tgtggctgtg cccgctgcgg gcgcgccacc gctggccgct gtacccgctc    2400

aagcccggcg tcacctacgt caacgccggc ttctggggga cggtgccgct gcagccgggg    2460

cagatgcccg agtaccacaa ccggctgatc gaacggaagg tcgcccaact ggacggccac    2520

aagtctctgt actcgacggc gttctactcg cgtgaggagt tctggcggca ctacgacggg    2580

gaaacctacc ggcgtctgaa ggacacctac gaccccgacg cgcgcctgct cgacctctac    2640

gacaagtgcg tgcggggacg ctga                                           2664
```

HETEROLOGOUS PRODUCTION OF 10-METHYLSTEARIC ACID

CROSS REFERENCE TO RELATED APPLICATIONS

This application claims priority to U.S. Provisional Patent Application Ser. No. 62/396,870, filed Sep. 20, 2016, which is incorporated by reference herein in its entirety.

BACKGROUND

Fatty acids derived from agricultural plant and animal oils find use as industrial lubricants, hydraulic fluids, greases, and other specialty fluids in addition to oleochemical feedstocks for processing. The physical and chemical properties of these fatty acids result in large part from their carbon chain length and number of unsaturated double bonds. Fatty acids are typically 16:0 (sixteen carbons, zero double bonds), 16:1 (sixteen carbons, 1 double bond), 18:0, 18:1, 18:2, or 18:3. Importantly, fatty acids with no double bonds (saturated) have high oxidative stability, but they solidify at low temperature. Double bonds improve low-temperature fluidity, but decrease oxidative stability. This trade-off poses challenges for lubricant and other specialty-fluid formulations because consistent long term performance (high oxidative stability) over a wide range of operating temperatures is desirable. High 18:1 (oleic) fatty acid oils provide low temperature fluidity with relatively good oxidative stability. Accordingly, several commercial products, such as high oleic soybean oil, high oleic sunflower oil, and high oleic algal oil, have been developed with high oleic compositions. Oleic acid is an alkene, however, and subject to oxidative degradation.

SUMMARY

The nucleic acids, cells, and methods described herein are generally useful for the production of branched (methyl) lipids, such as 10-methylstearic acid, and compositions that include such lipids. Saturated branched (methyl)lipids like 10-methylstearic acid have favorable low-temperature fluidity and favorable oxidative stability, which are desirable properties for lubricants and specialty fluids.

Various aspects relate to nucleic acids comprising a recombinant tmsB gene encoding a methyltransferase protein, a recombinant tmsA gene encoding a reductase protein, and/or a recombinant tmsC gene encoding a tmsC protein. The methyltransferase protein, reductase protein, and/or tmsC protein may be proteins expressed by species of Actinobacteria, and the recombinant tmsB gene, recombinant tmsA gene, and/or recombinant tmsC gene may be codon-optimized for expression in a different phylum of bacteria (e.g., Proteobacterium) or in eukaryotes (e.g., yeast, such as *Arxula adeninivorans* (also known as *Blastobotrys adeninivorans* or *Trichosporon adeninivorans*), *Saccharomyces cerevisiae*, or *Yarrowia lipolytica*). The recombinant tmsB gene, recombinant tmsA gene, or recombinant tmsC gene may be operably-linked to a promoter capable of driving expression in a phylum of bacteria other than Actinobacteria (e.g., Proteobacterium) or in eukaryotes (e.g., yeast). The nucleic acid may be a plasmid or a chromosome.

Some aspects relate to a cell comprising a nucleic acid as described herein. The cell may comprise a branched (methyl)lipid, such as 10-methylstearic acid, and/or an exomethylene-substituted lipid, such as 10-methylenestearic acid. The cell may be a eukaryotic cell, such as an algae cell, yeast cell, or plant cell.

Some aspects relate to a composition produced by cultivating a cell culture comprising cells as described herein. The oil composition may comprise a branched (methyl)lipid, such as 10-methylstearic acid, and or an exomethylene-substituted lipid, such as 10-methylenestearic acid.

BRIEF DESCRIPTION OF THE DRAWINGS

FIG. 3 depicts prokaryotic operons encoding enzymes that catalyze the transfer of methyl groups to alkyl chains from sixteen different species of bacteria, labeled A-P. The tmsA and tmsB genes are particularly important for methylating alkyl chains. The tmsC gene may also be important for methylating alkyl chains. The nucleotide sequences of these genes and the amino acid sequences that they encode are shown in SEQ ID NO:1-76.

*Saccharomyces cerevisiae*, and *Yarrowia lipolytica*. The nucleotide sequence of plasmid BS-10MS_ER is set forth in SEQ ID NO:79.

Figure 7A:
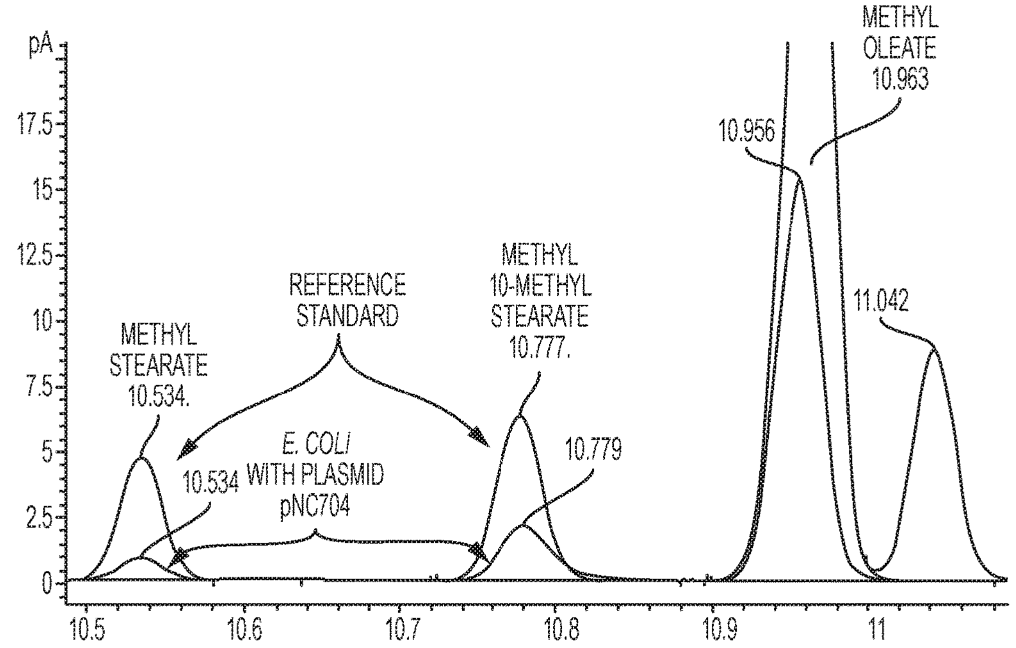
Figure 7B:
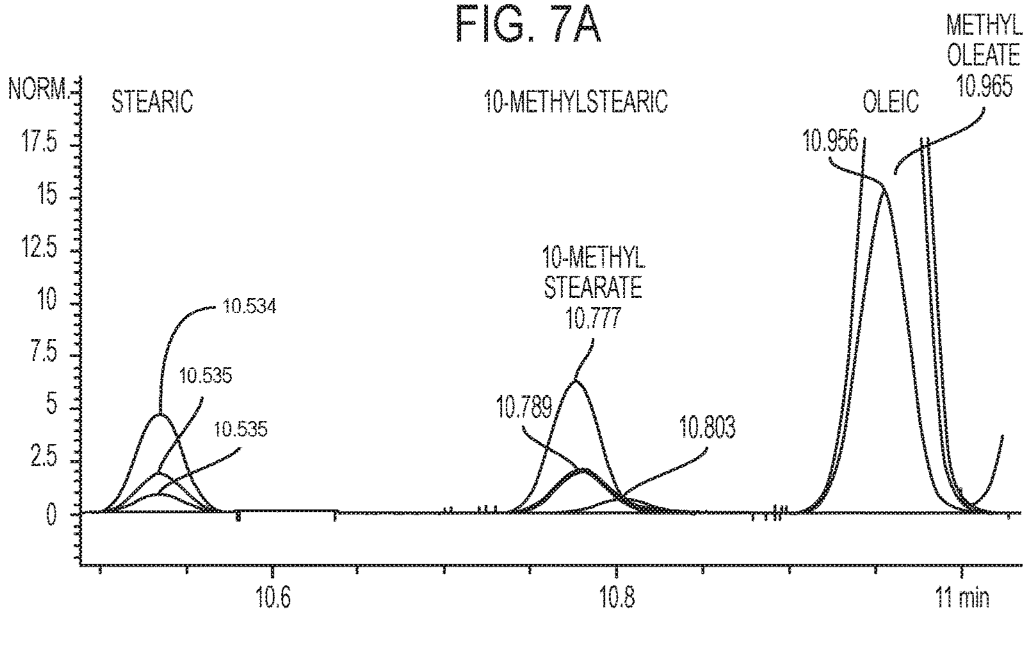

FIGS. 7A and 7B consist of overlaid gas chromatography (GC) traces of various fatty acid standards and lipids extracted from various samples. The standards were stearic acid, 10-methylstearic acid, and oleic acid. Each sample and standard was transesterified into fatty acid methyl esters (FAMEs) prior to analysis. FIG. 7A depicts the GC trace of FAMEs prepared from *E. coli* that express the tmsA and tmsB genes from *Mycobacterium smegmatis* as well as the GC traces of each standard. The tmsA/tmsB sample displayed a peak at about 10.777 minutes, corresponding to the 10-methylstearic acid standard. FIG. 7B depicts each trace of FIG. 7A and two additional traces. The first additional trace corresponds to FAMEs prepared from *E. coli* that express the ufa gene from *Mycobacterium tuberculosis*. This sample displayed a peak at about 10.777 minutes, corresponding to the 10-methylstearic acid standard. The second additional trace corresponds to FAMEs prepared from *E. coli* that had been transfected with an empty vector. This control did not display a peak at 10.777 minutes, suggesting that the tmsA and tmsB genes synthesized 10-methylstearic acid in the transformed *E. coli*.

Figure 8A:
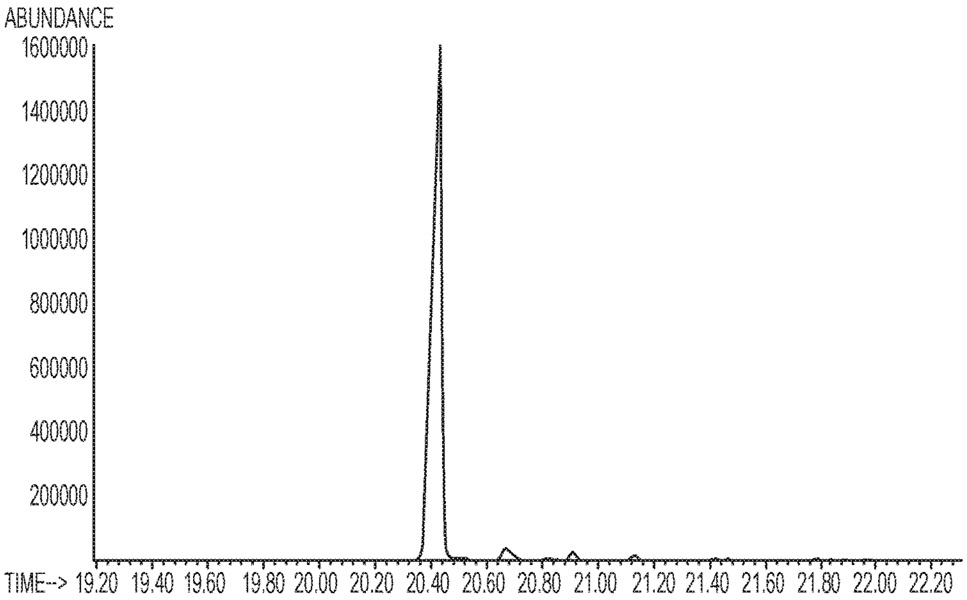
Figure 8B:
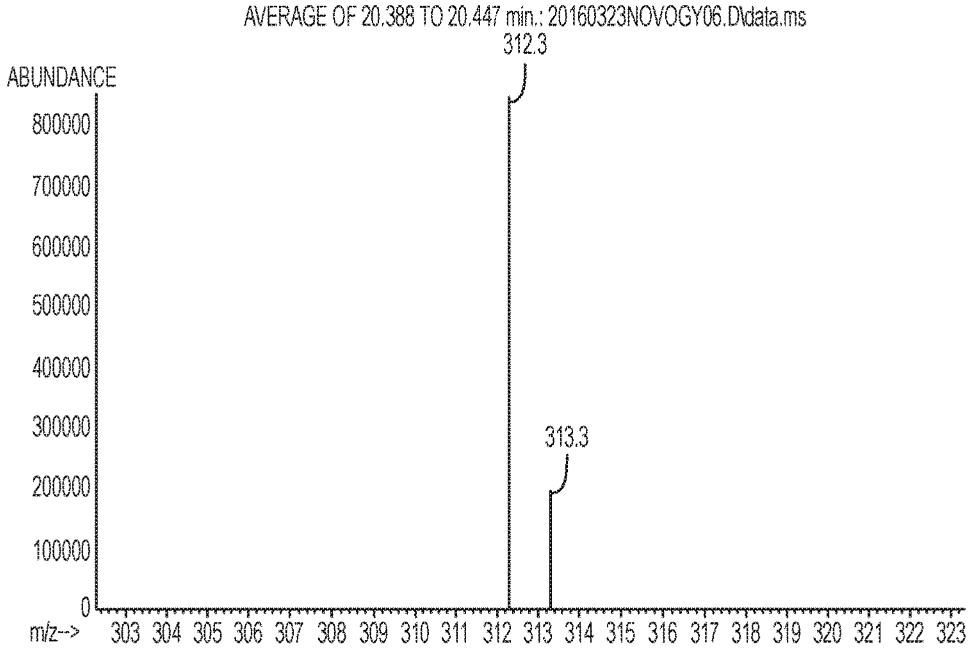
Figure 9A:
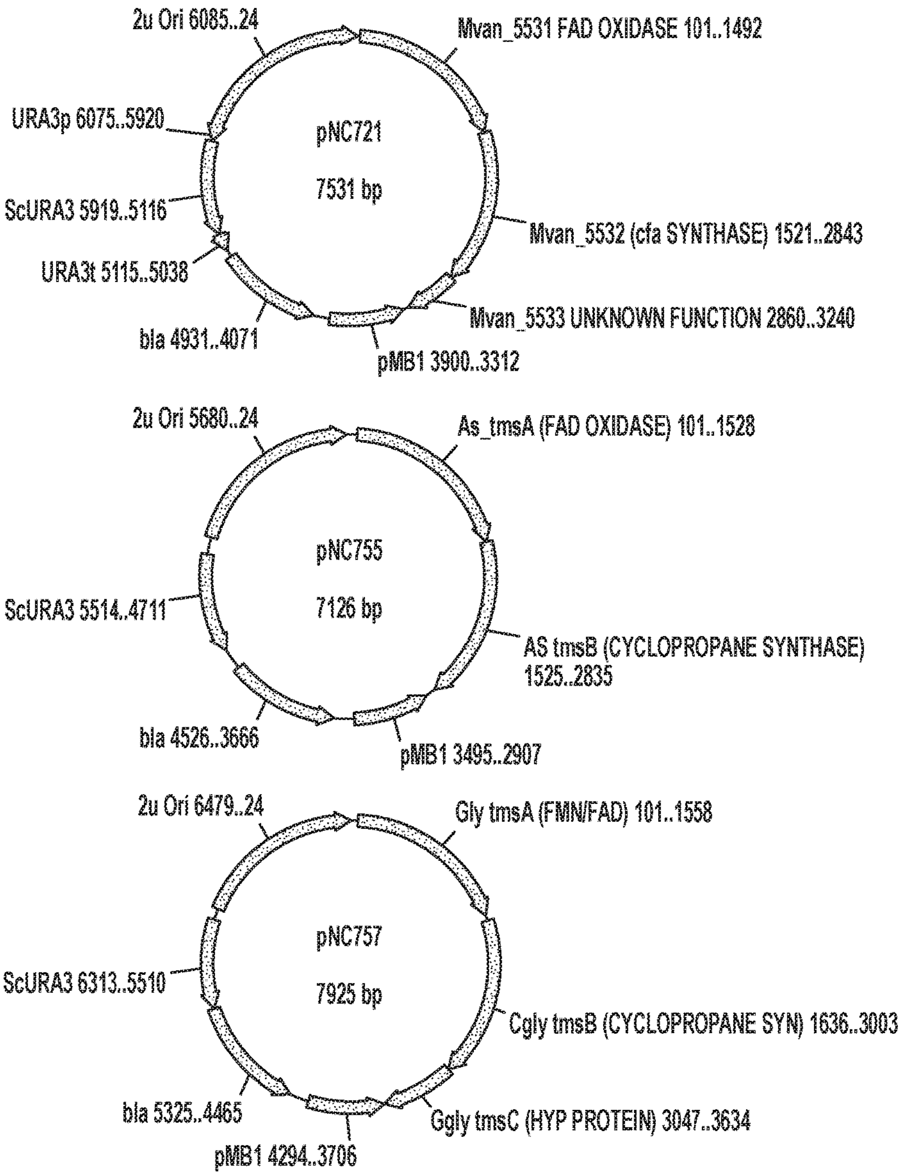
Figure 9B:
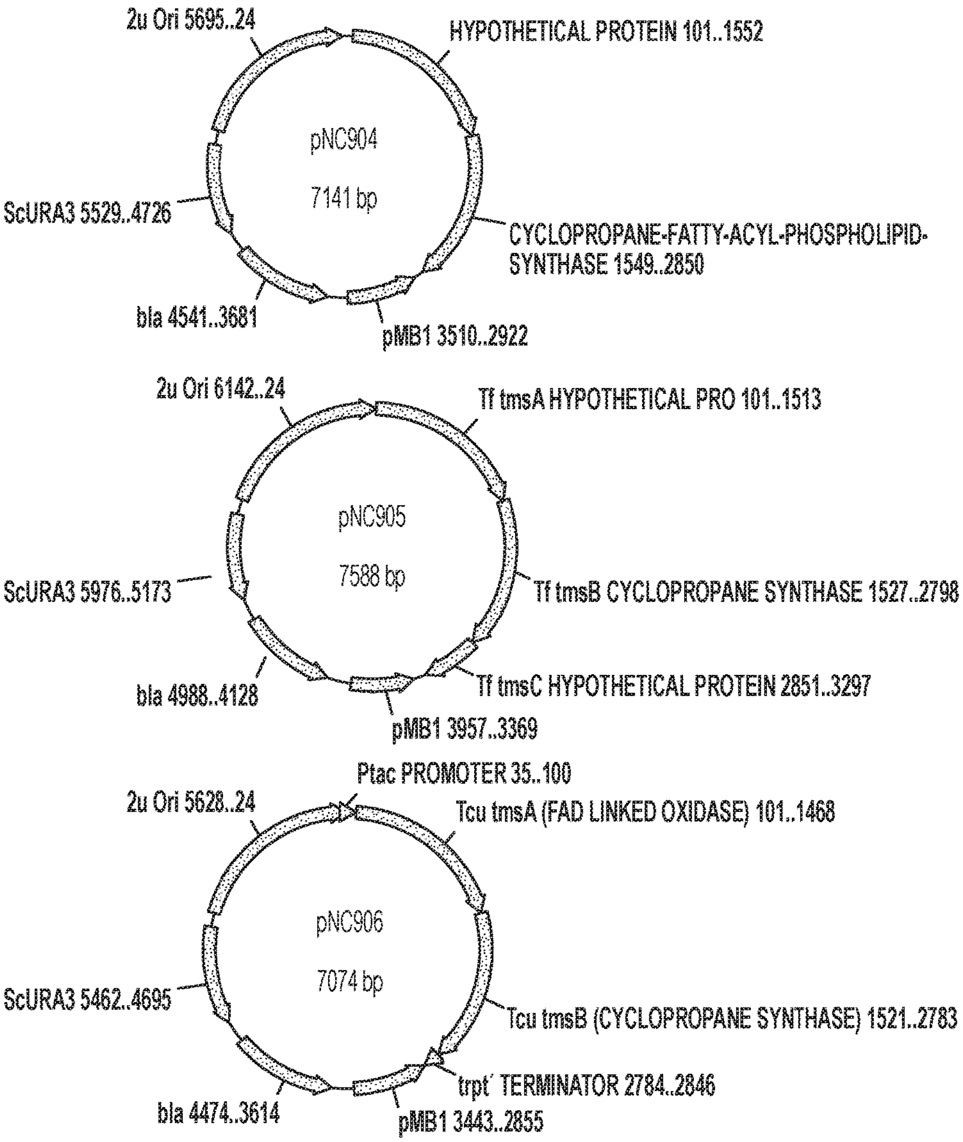
Figure 9C:
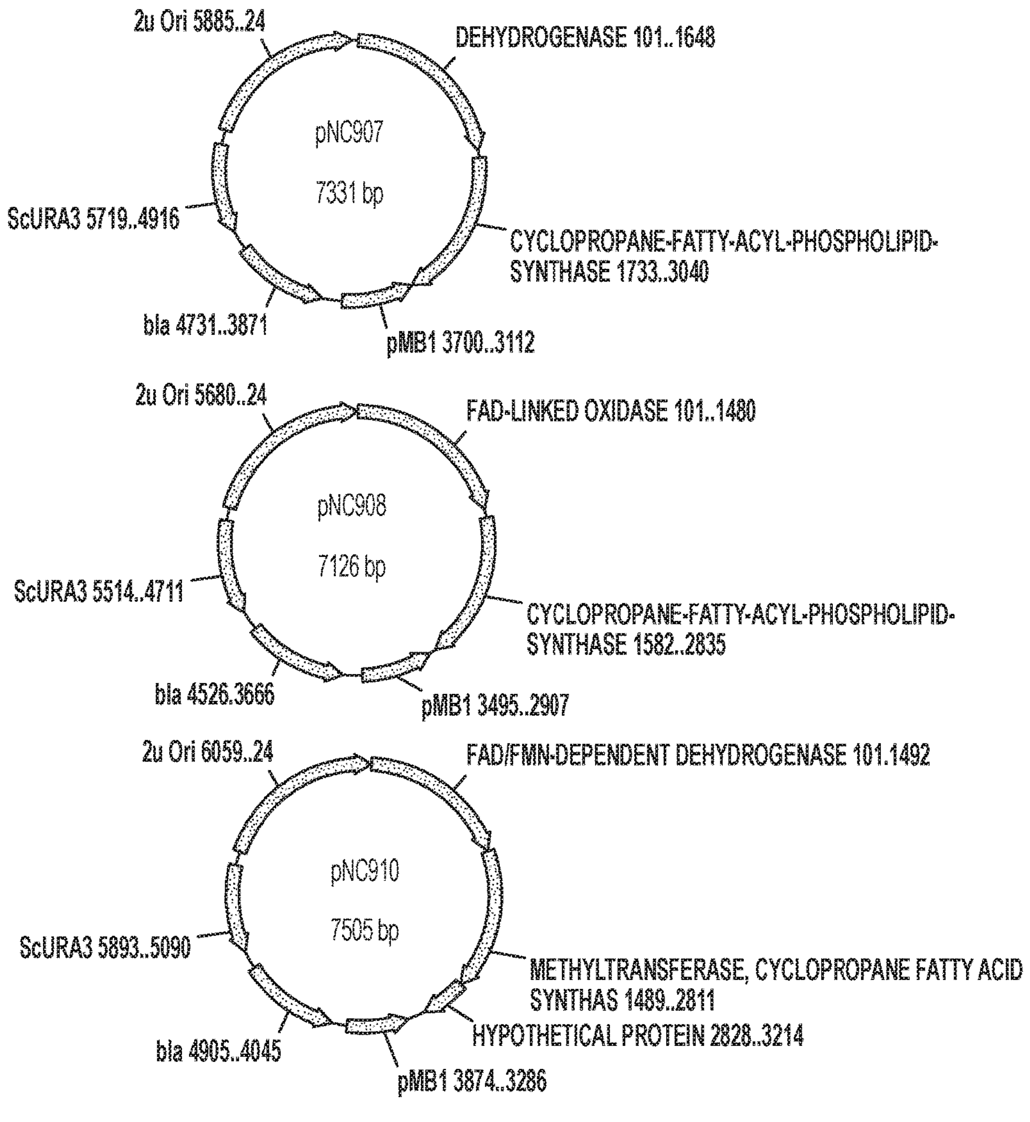
Figure 9D:
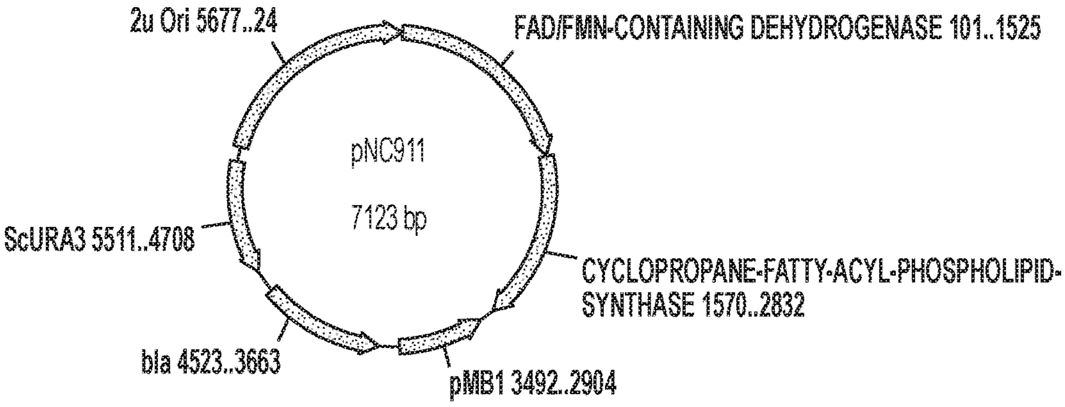

FIGS. 8A and 8B depict GC-MS result. FIG. 8A is a gas chromatography (GC) trace of lipids eluting from a GC column. The lipids were purified from *E. coli* that had been transfected with pNC704 encoding *Mycobacterium smegmatis* genes tmsA and tmsB, and the lipids were converted into fatty acid methyl esters. FIG. 8B is a mass spectroscopy spectrum of the lipids eluted during the GC run of panel A from 20.388 to 20.447 minutes. The mass spectrum is gated for the 10-methylstearate fatty acid methyl ester, which has a molecular weight of 312. The spectrum also displays a peak at 313 m/z corresponding to 10-methylstearate methyl esters comprising natural-abundance isotopes (e.g., a single $^{13}C$).

FIGS. 9A-9D depict maps of the following vectors, which can be used to express the tmsA and tmsB genes of the indicated species: pNC721 (*Mycobacterium vanbaaleni*) (SEQ ID NO:83), pNC755 (*Amycolicicoccus subflavus*) (SEQ ID NO:84), pNC757 (*Corynebacterium glyciniphilum*) (SEQ ID NO:85), pNC 904 (*Rhodococcus opacus*) (SEQ ID NO:86), pNC905 (*Thermobifida fusca*) (SEQ ID NO:87), pNC906 (*Thermomonospora curvata*) (SEQ ID NO:88), pNC907 (*Corynebacterium glutamicum*) (SEQ ID NO:89), pNC908 (*Agromycies subbeticus*) (SEQ ID NO:90), pNC910 (*Mycobacterium gilvum*) (SEQ ID NO:91), pNC911 (*Mycobacterium* sp. *indicus*) (SEQ ID NO:92).

Figure 10:
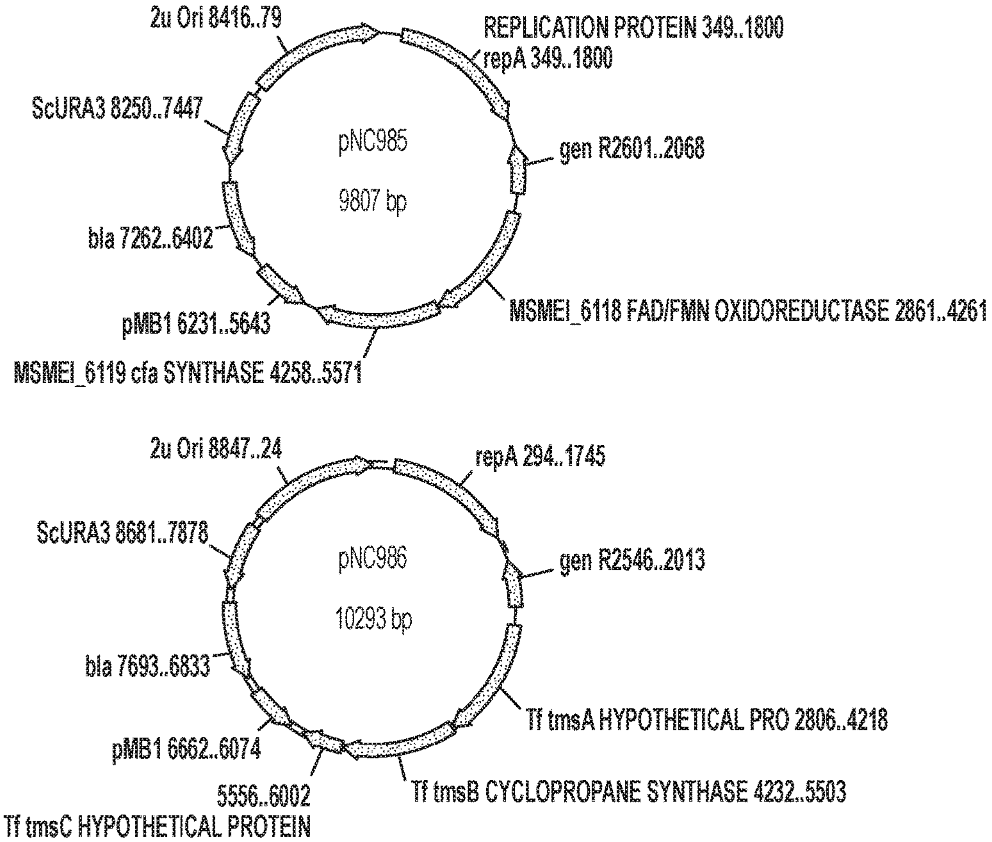

FIG. 10 depicts maps of vectors pNC985 (SEQ ID NO:93), which can be used to express the *M. smegmatis* tmsAB genes in *Rhodococcus* bacteria, and pNC986 (SEQ ID NO:94), which can be used to express the *T. fusca* tmsAB genes in *Rhodococcus* bacteria.

Figure 11:
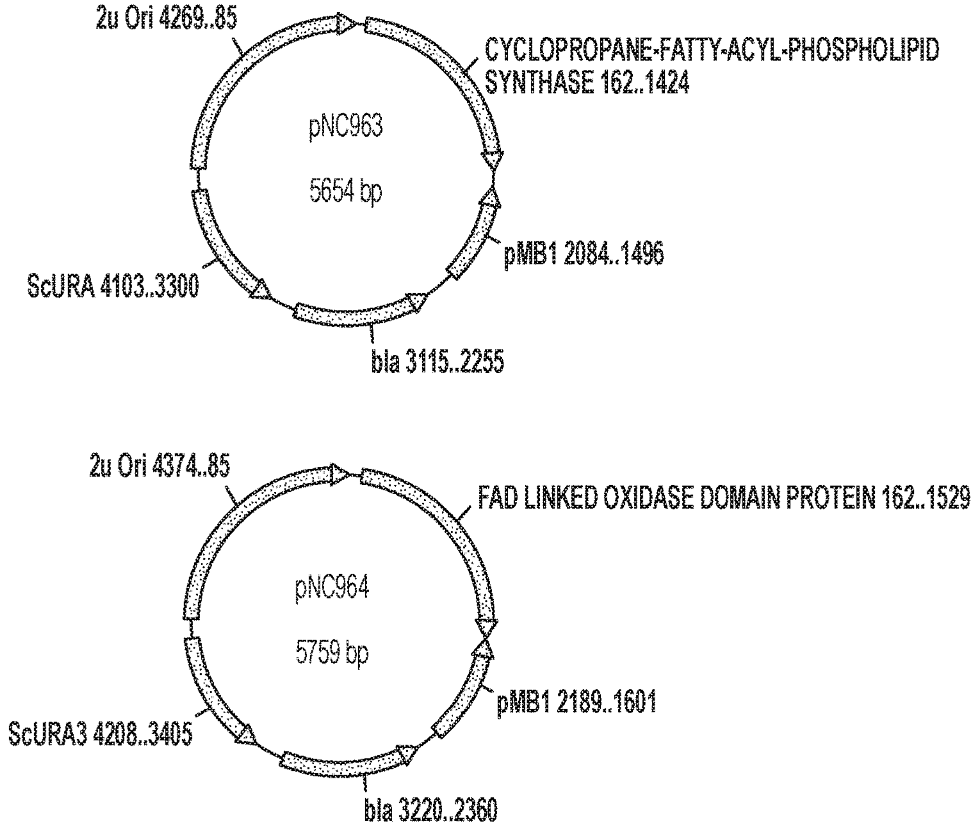

FIG. 11 depicts maps of vectors pNC963 (SEQ ID NO:95), which encodes the *T. curvata* tmsB gene under control of the constitutive tac promoter, and pNC964 (SEQ ID NO:96), which encodes the T *curvata* tmsA gene under control of the constitutive tac promoter.

Figure 12:
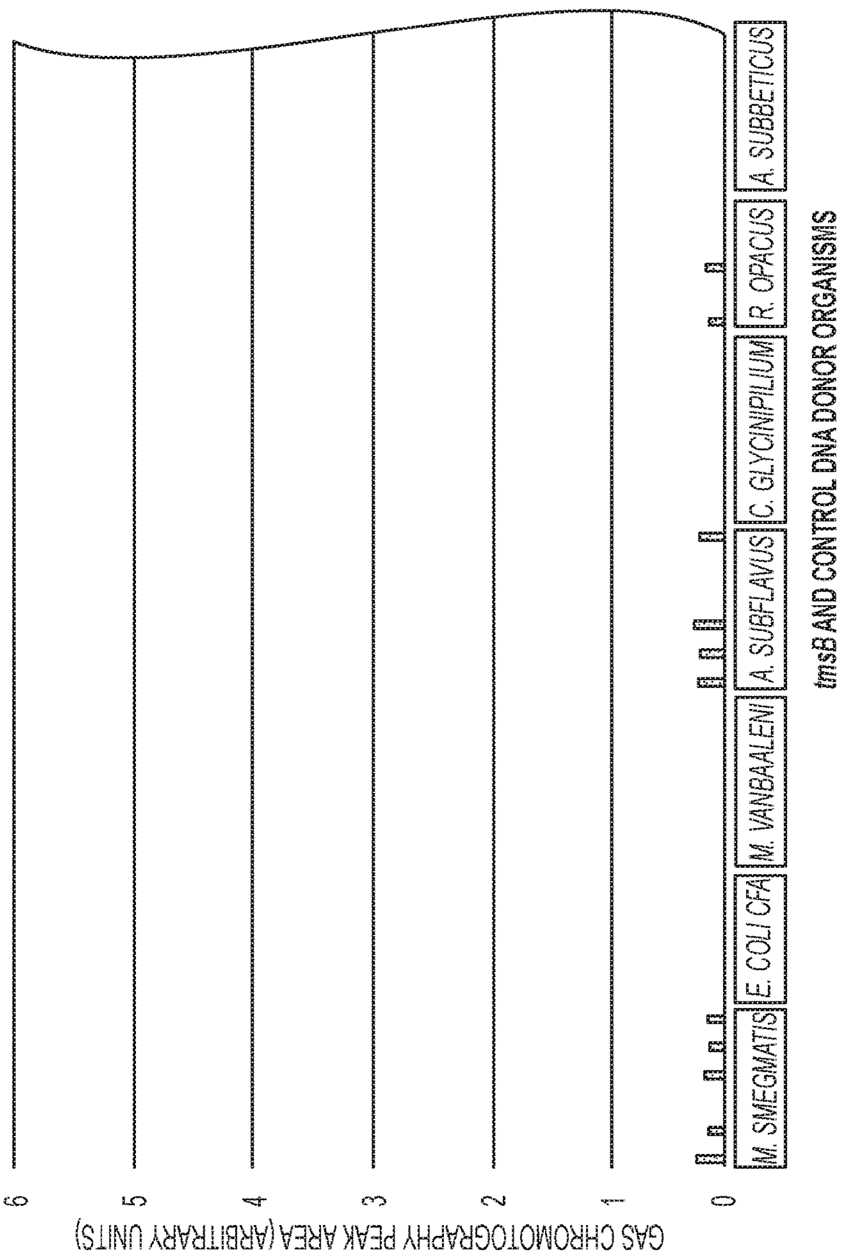
Figure 12:
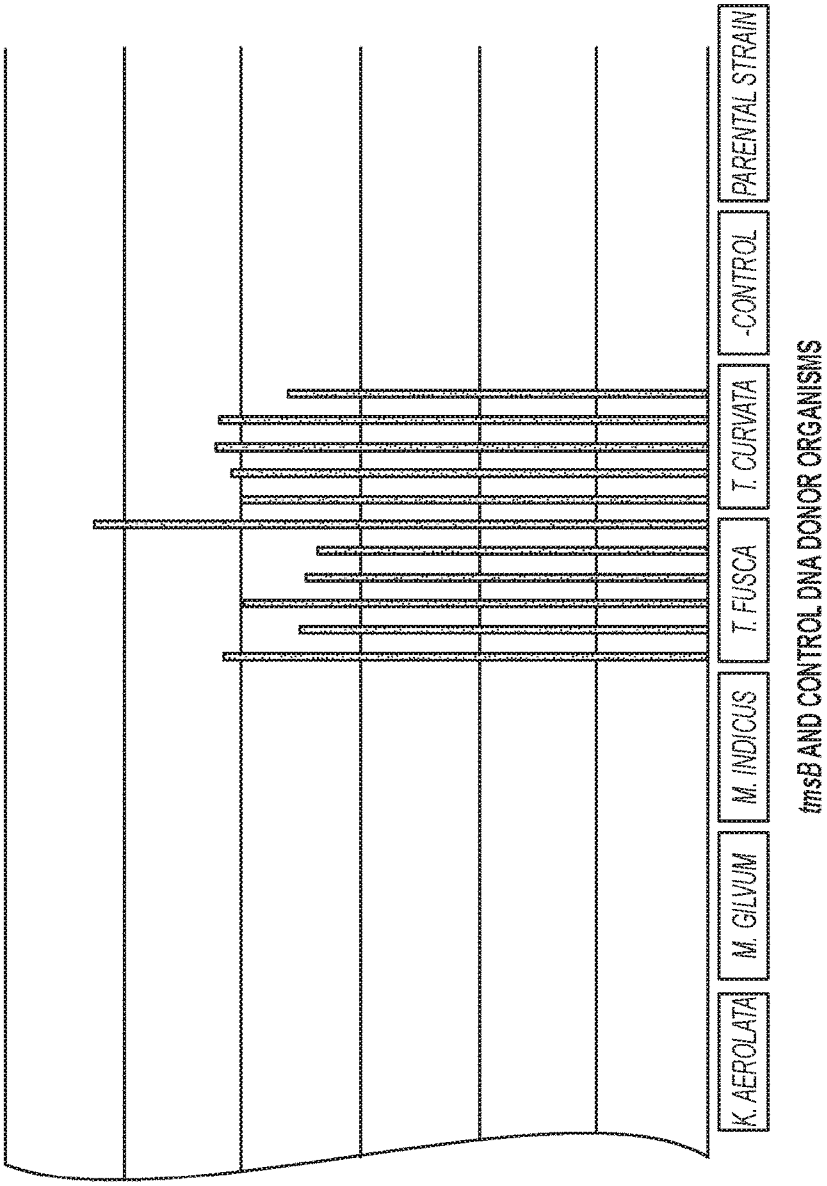

FIG. 12 is a graph showing gas chromatographic detection of 10-methylene stearic acid in *Y. lipolytica* expressing tmsB genes from various organisms.

Figure 13:
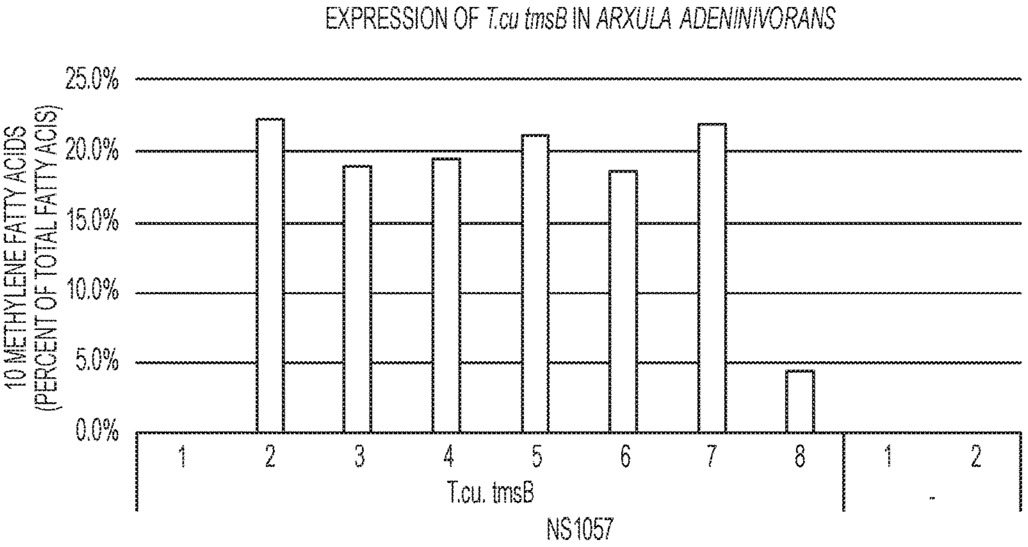

FIG. 13 is a graph showing percentage of 10-methylene fatty acids as compared to total fatty acids in 8 transformants of *Arxula adeninivorans* containing a plasmid encoding *T. curvata* tmsB. The two isolates furthest to the right were transformed with empty vector control.

Figure 14:
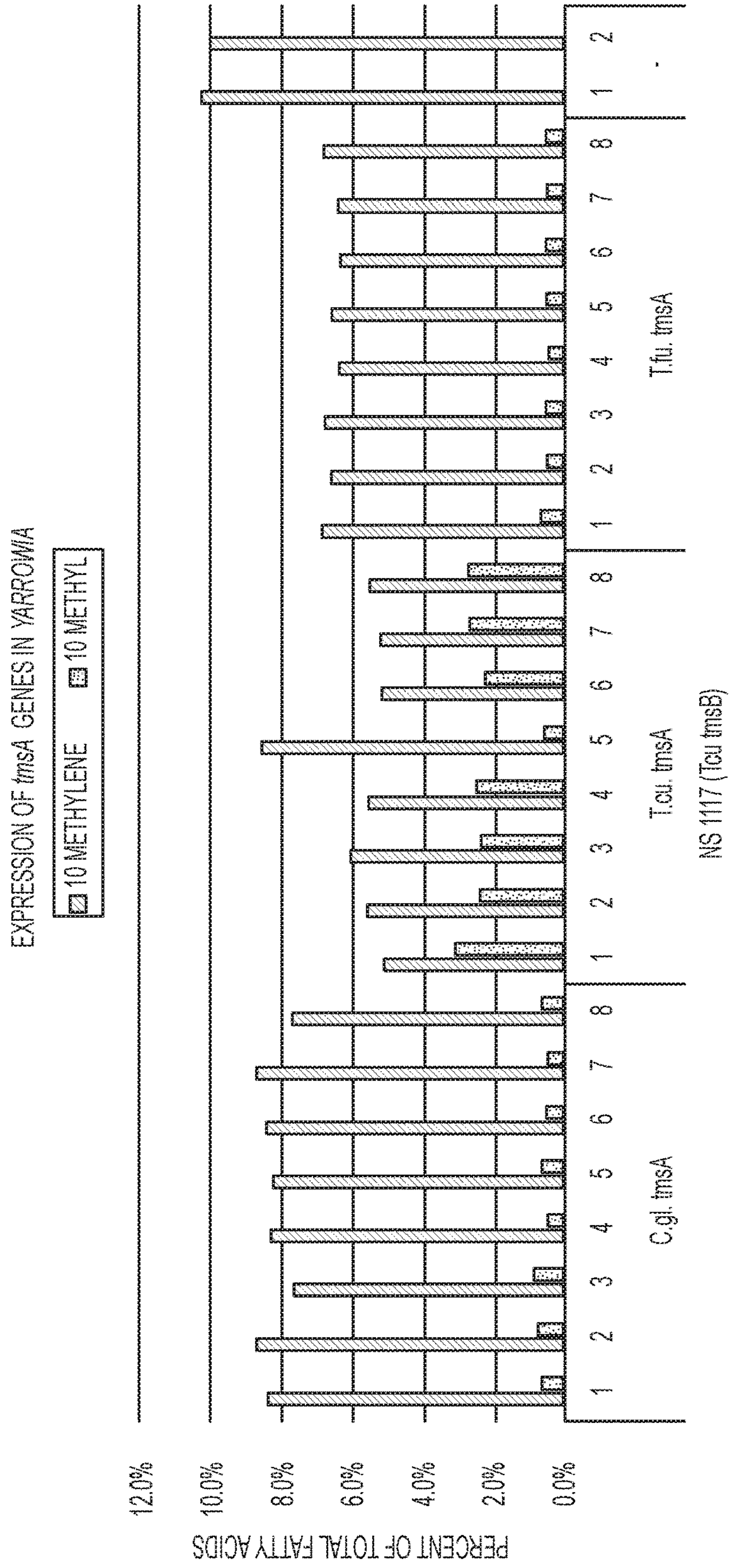

FIG. 14 is a graph showing the percentage by weight of 10-methylene fatty acids and 10-methyl fatty acids in *Yarrowia lipolytica* containing a stably integrated copy of the *T. curvata* tmsB gene and transformed with plasmids expressing tmsA from *C. glutamicum* (C.gl.), *T. curvata* (T.cu.), or *T. fusca* (T.fu.), or an empty vector control (the two transformants furthest to the right).

Figure 15:
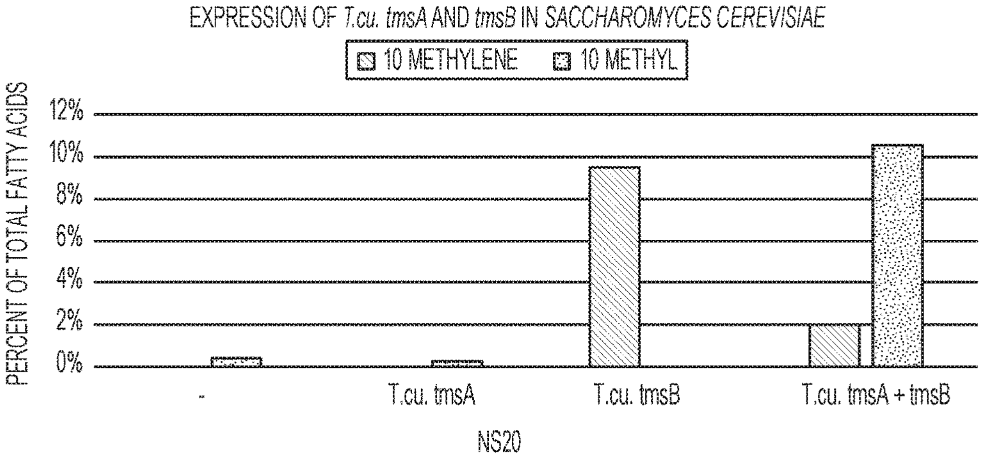

FIG. 15 is a graph showing the percentage by weight of 10-methylene fatty acids and 10-methyl fatty acids as compared to total fatty acids in transformants of *S. cerevisiae* transformed with empty vector (-) or vectors encoding *T. curvata* tmsA (T.cu. tmsA), *T. curvata* tmsB (T.cu. tmsB), or both *T. curvata* tmsA and tmsB (T.cu. tmsA+tmsB).

Figure 16:
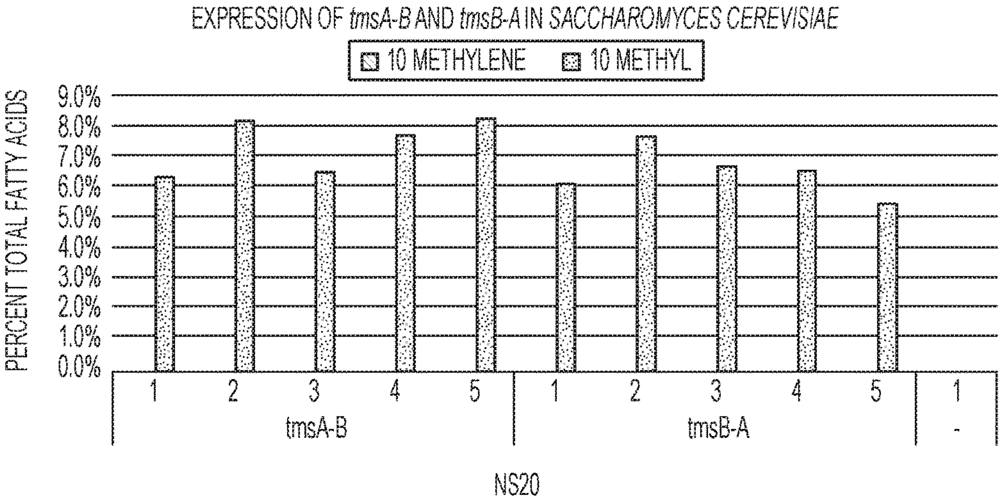

FIG. 16 is a graph showing the percentage by weight of 10-methylene fatty acids and 10-methyl fatty acids as compared to total fatty acids in transformants of *S. cerevisiae* containing the tmsA-B fusion protein, the tmsB-A fusion protein, or empty vector (-).

Figure 17:
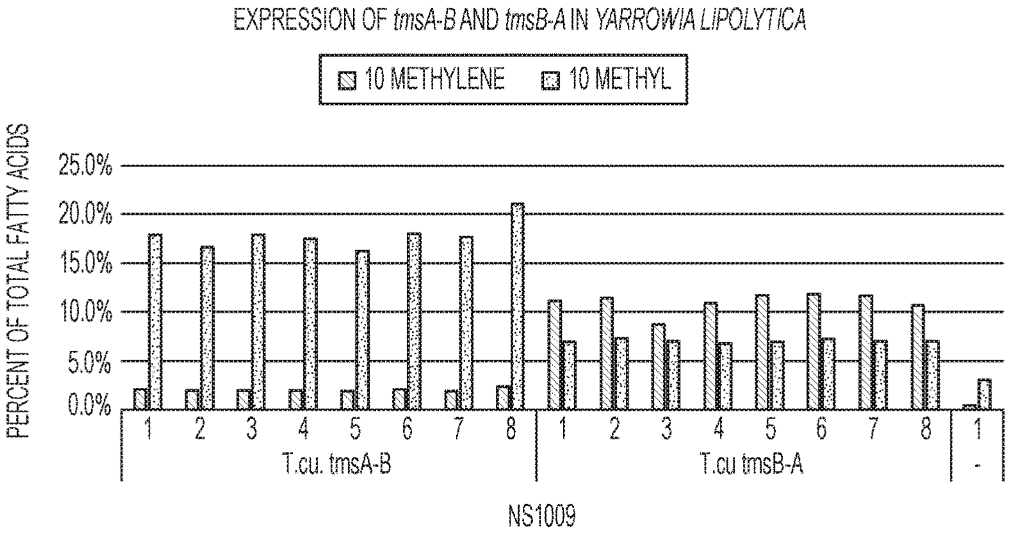

FIG. 17 is a graph showing the percentage by weight of 10-methylene fatty acids and 10-methyl fatty acids as compared to total fatty acids in transformants of *Y. lipolytica* containing the tmsA-B fusion protein, the tmsB-A fusion protein, or empty vector (-).

Figure 18:
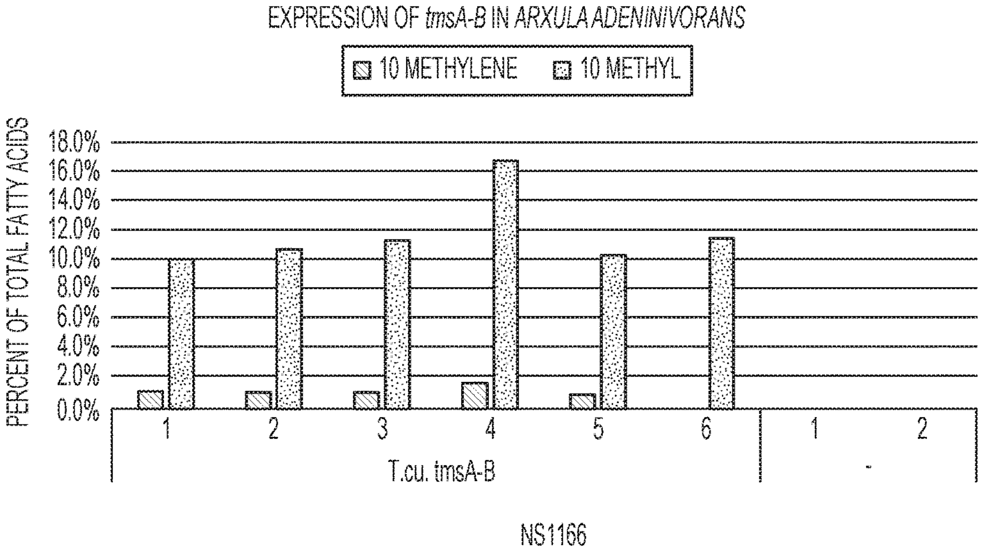

FIG. 18 is a graph showing the percentage by weight of 10-methylene fatty acids and 10-methyl fatty acids as compared to total fatty acids in transformants of *A. adeninivorans* containing the tmsA-B fusion protein or empty vector (-).

FIGS. 19A-19D show a CLUSTAL OMEGA alignment of TmsB protein sequences encoded by the tmsB genes from *Mycobacterium smegmatis* (SEQ ID NO:4), *Mycobacterium vanbaaleni* (SEQ ID NO:54), *Amycolicicoccus subflavus* (SEQ ID NO:12), *Corynebacterium glyciniphilum* (SEQ ID NO:20), *Corynebacterium glutamicum* (SEQ ID NO:16), *Rhodococcus opacus* (SEQ ID NO:60), *Agromyces subbeticus* (SEQ ID NO:8), *Knoellia aerolata* (SEQ ID NO:26), *Mycobacterium gilvum* (SEQ ID NO:36), *Mycobacterium* sp. *Indicus* (SEQ ID NO:42), *Thermobifida fusca* (SEQ ID NO:70), and *Thermomonospora curvata* (SEQ ID NO:76), along with the cyclopropane fatty acid synthase (Cfa) enzyme from *Escherichia coli*.

FIGS. 20A-20E show a CLUSTAL OMEGA alignment of TmsA protein sequences encoded by the tmsA genes from *Mycobacterium smegmatis* (SEQ ID NO:2), *Mycobacterium vanbaaleni* (SEQ ID NO:52), *Amycolicicoccus subflavus* (SEQ ID NO: 10), *Corynebacterium glyciniphilum* (SEQ ID NO: 18), *Corynebacterium glutamicum* (SEQ ID NO:14), *Rhodococcus opacus* (SEQ ID NO:58), *Agromyces subbeticus* (SEQ ID NO:6), *Knoellia aerolata* (SEQ ID NO:24), *Mycobacterium gilvum* (SEQ ID NO:34), *Mycobacterium* sp. *Indicus* (SEQ ID NO:40), *Thermobifida fusca* (SEQ ID NO:68), and *Thermomonospora curvata* (SEQ ID NO:74), along with the Glycolate oxidase subunit GlcD enzyme from *Escherichia coli*.

DETAILED DESCRIPTION

Definitions

The articles "a" and "an" are used herein to refer to one or to more than one (i.e., to at least one) of the grammatical object of the article. By way of example, "an element" means one element or more than one element.

The term "biologically-active portion" refers to an amino acid sequence that is less than a full-length amino acid sequence, but exhibits at least one activity of the full length sequence. For example, a biologically-active portion of a methyltransferase may refer to one or more domains of tmsB having biological activity for converting oleic acid (e.g., a phospholipid comprising an ester of oleate) and methionine (e.g., S-adenosyl methionine) into 10-methylenestearic acid (e.g., a phospholipid comprising an ester of 10-methylenestearate). A biologically-active portion of a reductase may refer to one or more domains of tmsA having biological activity for converting 10-methylenestearic acid (e.g., a phospholipid comprising an ester of 10-methylenestearate) and a reducing agent (e.g., NADH, NADPH, FAD, FADH2, FMNH2) into 10-methylstearic acid (e.g., a phospholipid comprising an ester of 10-methylstearate). Biologically-active portions of a protein include peptides or polypeptides comprising amino acid sequences sufficiently identical to or derived from the amino acid sequence of the protein, e.g., the amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, or 76, which include fewer amino acids than the full length protein, and exhibit at least one activity of the protein, especially methyltransferase or reductase activity. A biologically-active portion of a protein may comprise, comprise at least, or comprise the most, for example, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or more amino acids or any range derivable therein. Typically, biologically-active portions comprise a domain or motif having a catalytic activity, such as catalytic activity for producing 10-methylenestearic acid or 10-methylstearic acid. A biologically-active portion of a protein includes portions of the protein that have the same activity as the full-length peptide and every portion that has more activity than background. For example, a biologically-active portion of an enzyme may have, have at least, or have at most 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, 400% or higher activity relative to the full-length enzyme (or any range derivable therein). A biologically-active portion of a protein may include portions of a protein that lack a domain that targets the protein to a cellular compartment.

The terms "codon optimized" and "codon-optimized for the cell" refer to coding nucleotide sequences (e.g., genes) that have been altered to substitute at least one codon that is relatively rare in a desired host cell with a synonymous codon that is relatively prevalent in the host cell. Codon optimization thereby allows for better utilization of the tRNA of a host cell by matching the codons of a recombinant gene with the tRNA of the host cell. For example, the codon usage of the species of Actinobacteria (prokaryotes) varies from the codon usage of yeast (eukaryotes). The translation efficiency in a yeast host cell of an mRNA encoding a Actinobacteria protein may be increased by substituting the codons of the corresponding Actinobacteria gene with codons that are more prevalent in the particular species of yeast. A codon optimized gene thereby has a nucleotide sequence that varies from a naturally-occurring gene.

The term "constitutive promoter" refers to a promoter that mediates the transcription of an operably linked gene independent of a particular stimulus (e.g., independent of the presence of a reagent such as isopropyl β-D-1-thiogalactopyranoside).

The term "DGAT1" refers to a gene that encodes a type 1 diacylglycerol acyltransferase protein, such as a gene that encodes a yeast DGA2 protein.

The term "DGAT2" refers to a gene that encodes a type 2 diacylglycerol acyltransferase protein, such as a gene that encodes a yeast DGA1 protein.

"Diacylglyceride," "diacylglycerol," and "diglyceride," are esters comprised of glycerol and two fatty acids.

The terms "diacylglycerol acyltransferase" and "DGA" refer to any protein that catalyzes the formation of triacylglycerides from diacylglycerol. Diacylglycerol acyltransferases include type 1 diacylglycerol acyltransferases (DGA2), type 2 diacylglycerol acyltransferases (DGA1), and type 3 diacylglycerol acyltransferases (DGA3) and all homologs that catalyze the above-mentioned reaction.

The terms "diacylglycerol acyltransferase, type 1" and "type 1 diacylglycerol acyltransferases" refer to DGA2 and DGA2 orthologs.

The terms "diacylglycerol acyltransferase, type 2" and "type 2 diacylglycerol acyltransferases" refer to DGA1 and DGA1 orthologs.

The term "domain" refers to a part of the amino acid sequence of a protein that is able to fold into a stable three-dimensional structure independent of the rest of the protein.

The term "drug" refers to any molecule that inhibits cell growth or proliferation, thereby providing a selective advantage to cells that contain a gene that confers resistance to the drug. Drugs include antibiotics, antimicrobials, toxins, and pesticides.

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed. The term "% dry weight," when referring to a specific fatty acid (e.g., oleic acid or 10-methylstearic acid), includes fatty acids that are present as carboxylates, esters, thioesters, and amides. For example, a cell that comprises 10-methylstearic acid as a percentage of total fatty acids by % dry cell weight includes 10-methylstearic acid, 10-methylstearate, the 10-methylstearate portion of a diacylglycerol comprising a 10-methylstearate ester, the 10-methylstearate portion of a triacylglycerol comprising a 10-methylstearate ester, the 10-methylstearate portion of a phospholipid comprising a 10-methylstearate ester, and the 10-methylstearate portion of 10-methylstearate CoA. The term "% dry weight," when referring to a specific type of fatty acid (e.g., C16 fatty acids, C18 fatty acids), includes fatty acids that are present as carboxylates, esters, thioesters, and amides as described above (e.g., for 10 methylstearic acid).

The term "encode" refers to nucleic acids that comprise a coding region, portion of a coding region, or compliments thereof. Both DNA and RNA may encode a gene. Both DNA and RNA may encode a protein.

The term "enzyme" as used herein refers to a protein that can catalyze a chemical reaction.

The term "expression" refers to the amount of a nucleic acid or amino acid sequence (e.g., peptide, polypeptide, or protein) in a cell. The increased expression of a gene refers to the increased transcription of that gene. The increased expression of an amino acid sequence, peptide, polypeptide, or protein refers to the increased translation of a nucleic acid encoding the amino acid sequence, peptide, polypeptide, or protein.

The term "gene," as used herein, may encompass genomic sequences that contain exons, particularly polynucleotide sequences encoding polypeptide sequences involved in a specific activity. The term further encompasses synthetic nucleic acids that did not derive from genomic sequence. In certain embodiments, the genes lack introns, as they are synthesized based on the known DNA sequence of cDNA and protein sequence. In other embodiments, the genes are synthesized, non-native cDNA wherein the codons have been optimized for expression in *Y. lipolytica* or *A. adeninivorans* based on codon usage. The term can further include nucleic acid molecules comprising upstream, downstream, and/or intron nucleotide sequences.

The term "inducible promoter" refers to a promoter that mediates the transcription of an operably linked gene in response to a particular stimulus.

The term "integrated" refers to a nucleic acid that is maintained in a cell as an insertion into the cell's genome, such as insertion into a chromosome, including insertions into a plastid genome.

"In operable linkage" refers to a functional linkage between two nucleic acid sequences, such a control sequence (typically a promoter) and the linked sequence (typically a sequence that encodes a protein, also called a coding sequence). A promoter is in operable linkage with a gene if it can mediate transcription of the gene.

The term "knockout mutation" or "knockout" refers to a genetic modification that prevents a native gene from being transcribed and translated into a functional protein.

The term "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "phospholipid" refers to esters comprising glycerol, two fatty acids, and a phosphate. The phosphate may be covalently linked to carbon-3 of the glycerol and comprise no further substitution, i.e., the phospholipid may be a phosphatidic acid. The phosphate may be substituted with ethanolamine (e.g., phosphatidylethanolamine), choline (e.g., phosphatidylcholine), serine (e.g., phosphatidylserine), inositol (e.g., phosphatidylinositol), inositol phosphate (e.g., phosphatidylinositol-3-phosphate, phosphatidylinositol-4-phosphate, phosphatidylinositol-5-phosphate), inositol bisphosphate (e.g., phosphatidylinositol-4,5-bisphosphate), or inositol triphosphate (e.g., phosphatidylinositol-3,4,5-bisphosphate).

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be self-replicating, but may integrate into and be replicated with the genomic DNA of an organism.

A "promoter" is a nucleic acid control sequence that directs the transcription of a nucleic acid. As used herein, a promoter includes the necessary nucleic acid sequences near the start site of transcription.

The term "protein" refers to molecules that comprise an amino acid sequence, wherein the amino acids are linked by peptide bonds.

"Transformation" refers to the transfer of a nucleic acid into a host organism or into the genome of a host organism, resulting in genetically stable inheritance. Host organisms containing the transformed nucleic acid are referred to as "recombinant," "transgenic," or "transformed" organisms. Thus, nucleic acids of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

The term "transformed cell" refers to a cell that has undergone a transformation. Thus, a transformed cell comprises the parent's genome and an inheritable genetic modification.

The terms "triacylglyceride," "triacylglycerol," "triglyceride," and "TAG" are esters comprised of glycerol and three fatty acids.

Microbe Engineering

A. Overview

Genes and gene products may be introduced into microbial host cells. Suitable host cells for expression of the genes and nucleic acid molecules are microbial hosts that can be found broadly within the fungal or bacterial families. Examples of suitable host strains include but are not limited to fungal or yeast species, such as *Arxula, Aspegillus, Aurantiochytrium, Candida, Claviceps, Cryptococcus, Cunninghamella, Hansenula, Kluyveromyces, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Yarrowia*, or bacterial species, such as members of proteobacteria and actinomycetes, as well as the genera *Acinetobacter, Arthrobacter, Brevibacterium, Acidovorax, Bacillus, Clostridia, Streptomyces, Escherichia, Salmonella, Pseudomonas*, and *Cornyebacterium. Yarrowia lipolytica* and *Arxula adeninivorans* are suited for use as a host microorganism because they can accumulate a large percentage of their weight as triacylglycerols.

Microbial expression systems and expression vectors containing regulatory sequences that direct high level expression of foreign proteins are known to those skilled in the art. Any of these could be used to construct chimeric genes to produce any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and an aforementioned starting parent strain as a host can be transformed with the resulting plasmid. This approach can increase the copy number of each of the genes encoding the enzymes and, as a result, the activities of the enzymes can be increased. The plasmid is not particularly limited so long as it renders a desired genetic modification inheritable to the microorganism's progeny.

Vectors or cassettes useful for the transformation of suitable host cells are well known. Typically the vector or cassette contains sequences that direct the transcription and translation of the relevant gene, a selectable marker, and sequences that allow autonomous replication or chromosomal integration. Suitable vectors comprise a region 5' of the gene harboring transcriptional initiation controls and a region 3' of the DNA fragment which controls transcriptional termination. In certain embodiments both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (see, e.g., Green & Sambrook, *Molecular Cloning: A Laboratory Manual*, (4th ed., 2012); U.S. Pat. No. 4,683,202 (incorporated by reference)). Alternatively, elements can be generated synthetically using known methods (see, e.g., Gene 164:49-53 (1995)).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding homologous genomic sequences.

The ability to carry out homologous recombination in a host organism has many practical implications for what can be carried out at the molecular genetic level and is useful in the generation of a microbe that can produce a desired product. By its nature homologous recombination is a precise gene targeting event and, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from exogenous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements, such as promoters/UTRs, to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, thereby affecting a desired change in the metabolism of the host cell. Homologous recombination provides a powerful means to manipulate the host genome resulting in gene targeting, gene conversion, gene deletion, gene duplication, gene inversion, and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) by cutting the transgenic DNA with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transforming microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location inside or outside the cell.

Thus, an exemplary vector design for expression of a gene in a microbe contains a coding sequence for a desired gene product (for example, a selectable marker, or an enzyme) in operable linkage with a promoter active in yeast. Alternatively, if the vector does not contain a promoter in operable linkage with the coding sequence of interest, the coding sequence can be transformed into the cells such that it becomes operably linked to an endogenous promoter at the point of vector integration.

The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, e.g., substantially, transcription of an operably linked gene that is transcribed at a low level.

Inclusion of termination region control sequence is optional, and if employed, then the choice is primarily one of convenience, as the termination region is relatively interchangeable. The termination region may be native to the transcriptional initiation region (the promoter), may be native to the DNA sequence of interest, or may be obtainable from another source (See, e.g., Chen & Orozco, Nucleic Acids Research 16:8411 (1988)).

2. Genes and Codon Optimization

Typically, a gene includes a promoter, a coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the transgenic mRNA resulting in ribosomal stalling and termination and possible instability of the transgenic mRNA. Resources for codon-optimization of gene sequences are described in Puigbo et al. (Nucleic Acids Research 35:W126-31 (2007)), and principles underlying codon optimization strategies are described in Angov (Biotechnology Journal 6:650-69 (2011)). Public databases providing statistics for codon usage by different organisms are available, including at www.kazusa.or.jp/codon/and other publicly available databases and resources.

D. Transformation

Cells can be transformed by any suitable technique including, e.g., biolistics, electroporation, glass bead transformation, and silicon carbide whisker transformation. Any convenient technique for introducing a transgene into a microorganism can be employed in the present invention. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like.

Examples of expression of transgenes in oleaginous yeast (e.g., *Yarrowia lipolytica*) can be found in the literature (Bordes et al., J. Microbiological Methods, 70:493 (2007); Chen et al., Applied Microbiology & Biotechnology 48:232 (1997)). Examples of expression of exogenous genes in bacteria such as *E. coli* are well known (Green & Sambrook, *Molecular Cloning: A Laboratory Manual*, (4th ed., 2012)).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to a native promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (Protist 155:381-93 (2004)). The transformed cells can be optionally selected based upon the ability to grow in the presence of the antibiotic or other selectable marker under conditions in which cells lacking the resistance cassette would not grow.

Exemplary Cells, Nucleic Acids, Compositions, and Methods

A. Transformed Cell

In some embodiments, the transformed cell is a prokaryotic cell, such as a bacterial cell. In some embodiments, the cell is a eukaryotic cell, such as a mammalian cell, a yeast cell, a filamentous fungi cell, a protist cell, an algae cell, an avian cell, a plant cell, or an insect cell. In some embodiments, the cell is a yeast. Those with skill in the art will recognize that many forms of filamentous fungi produce yeast-like growth, and the definition of yeast herein encompasses such cells. The cell may cell may be selected from the group consisting of algae, bacteria, molds, fungi, plants, and yeasts. The cell may be a yeast, fungus, or yeast-like algae. The cell may be selected from thraustochytrids (*Aurantiochytrium*) and achlorophylic unicellular algae (*Prototheca*).

The cell may be selected from the group consisting of *Arxula, Aspegillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, and *Yarrowia*. It is specifically contemplated that one or more of these cell types may be excluded from embodiments of this invention.

The cell may be selected from the group of consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii*, and *Yarrowia lipolytica*. It is specifically contemplated that one or more of these cell types may be excluded from embodiments of this invention.

The cell may be *Saccharomyces cerevisiae, Yarrowia lipolytica*, or *Arxula adeninivorans.*

In certain embodiments, the transformed cell comprises at least 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more lipid as measured by % dry cell weight, or any range derivable therein. In some embodiments, the transformed cell comprises C18 fatty acids at a concentration of at least 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or higher as a percentage of total C16 and C18 fatty acids in the cell, or any range derivable therein.

In some embodiments, the transformed cell comprises oleic acid at a concentration of at least 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, or higher as a percentage of total C16 and C18 fatty acids in the cell, or any range derivable therein. In some embodiments, the transformed cell comprises a linear fatty acid with a chain length of 14-20 carbons with a methyl branch at the Δ9, Δ10, or Δ11 position (e.g., 10-methylstearic acid) at a concentration of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight or higher as a percentage of total fatty acids in the cell, or any range derivable therein. In some embodiments, the fatty acid has a chain length of 14, 15, 16, 17, 18, 19, or 20 carbons, or any range derivable therein.

A cell may be modified to increase its oleate content, which serves as a substrate for 10-methylstearate synthesis. Genetic modifications that increase oleate content are known (see, e.g., PCT Patent Application Publication No. WO16/094520, published Jun. 16, 2016, hereby incorporated by reference in its entirety). For example, a cell may comprise a Δ12 desaturase knockdown or knockout, which favors the accumulation of oleate and disfavors the production of linoleate. A cell may comprise a recombinant Δ9 desaturase gene, which favors the production of oleate and disfavors the accumulation of stearate. The recombinant Δ9 desaturase gene may be, for example, the Δ9 desaturase gene from *Y. lipolytica, Arxula adeninivorans*, or *Puccinia graminis*. A cell may comprise a recombinant elongase 1 gene, which favors the production of oleate and disfavors the accumulation of palmitate and palmitoleate. The recombinant elongase 1 gene may be the elongase 1 gene from *Y. lipolytica*. A cell may comprise a recombinant elongase 2 gene, which favors the production of oleate and disfavors the accumulation of palmitate and palmitoleate. The recombinant elongase 2 gene may be the elongase 2 gene from *R. norvegicus*.

A cell may be modified to increase its triacylglycerol content, thereby increasing its 10-methylstearate content. Genetic modifications that increase triacylglycerol content are known (see, e.g., PCT Patent Application Publication No. WO16/094520, published Jun. 16, 2016, hereby incorporated by reference in its entirety). A cell may comprise a recombinant diacylglycerol acyltransferase gene (e.g., DGAT1, DGAT2, or DGAT3), which favors the production of triacylglycerols and disfavors the accumulation of diacylglycerols. The recombinant diacylglycerol acyltransferase gene may be, for example, DGAT2 (encoding protein DGA1) from *Y. lipolytica*, DGAT1 (encoding protein DGA2) from *C. purpurea*, or DGAT2 (encoding protein DGA1) from *R. toruloides*. The cell may comprise a glycerol-3-phosphate acyltransferase gene (Sct1) knockdown or knockout, which may favor the accumulation of triacylglycerols, depending on the cell type. The cell may comprise a recombinant glycerol-3-phosphate acyltransferase gene (Sct1) such as the Sct1 gene from *A. adeninivorans*, which may favor the accumulation of triacylglycerols. The cell may comprise a triacylglycerol lipase gene (TGL) knockdown or knockout, which may favor the accumulation of triacylglycerols in the cell.

Various aspects of the invention relate to a transformed cell. The transformed cell may comprise a recombinant methyltransferase gene (e.g., a tmsB gene), a recombinant reductase gene (e.g., a tmsA gene), an exomethylene-substituted lipid, and/or a branched (methyl)lipid. A transformed cell may comprise a tmsC gene. A branched (methyl) lipid may be a carboxylic acid (e.g., 10-methylstearic acid, 10-methylpalmitic acid, 12-methyloleic acid, 13-methyloleic acid, 10-methyl-octadec-12-enoic acid), carboxylate (e.g., 10-methylstearate, 10-methylpalmitate, 12-methyloleate, 13-methyloleate, 10-methyl-octadec-12-enoate), ester (e.g., diacylglycerol, triacylglycerol, phospholipid), thioester (e.g., 10-methylstearyl CoA, 10-methylpalmityl CoA, 12-methyloleoyl CoA, 13-methyloleoyl CoA, 10-methyl-octadec-12-enoyl CoA), or amide. An exomethylene-substituted lipid may be a carboxylic acid (e.g., 10-methylenestearic acid, 10-methylenepalmitic acid, 12-methyleneoleic acid, 13-methyleneoleic acid, 10-methylene-octadec-12-enoic acid), carboxylate (e.g., 10-methylenestearate, 10-methylenepalmitate, 12-methyleneoleate, 13-methyleneoleate, 10-methylene-octadec-12-enoate), ester (e.g., diacylglycerol, triacylglycerol, phospholipid), thioester (e.g., 10-methylenestearyl CoA, 10-methylenepalmityl CoA, 12-methyleneoleoyl CoA, 13-methyleneoleoyl CoA, 10-methylene-octadec-12-enoyl CoA), or amide. It is specifically contemplated that one or more of the above lipids may be excluded from embodiments of this invention.

"Fatty acids" generally exist in a cell as a phospholipid or triacylglycerol, although they may also exist as a monoacylglycerol or diacylglycerol, for example, as a metabolic intermediate. Free fatty acids also exist in the cell in equilibrium between a relatively abundant carboxylate anion and a relatively scarce, neutrally-charged acid. A fatty acid may exist in a cell as a thioester, especially as a thioester with coenzyme A (CoA), during biosynthesis or oxidation. A fatty acid may exist in a cell as an amide, for example, when covalently bound to a protein to anchor the protein to a membrane.

A cell may comprise any one of the nucleic acids described herein, infra (see, e.g., Section B, below).

A branched (methyl)lipid may comprise a saturated branched aliphatic chain (e.g., 10-methylstearic acid, 10-methylpalmitic acid) or an unsaturated branched aliphatic chain (e.g., 12-methyloleic acid, 13-methyloleic acid, 10-methyl-octadec-12-enoic acid). The branched (methyl) lipid may comprise a saturated or unsaturated branched aliphatic chain comprising a branching methyl group.

An exomethylene-substituted lipid may comprise a branched aliphatic chain (e.g., 10-methylenestearic acid, 10-methylenepalmitic acid, 12-methyleneoleic acid, 13-methyleneoleic acid, 10-methylene-octadec-12-enoic acid). The aliphatic chain may be branched because the aliphatic chain is substituted with an exomethylene group.

A branched (methyl)lipid may be 10-methylstearate, or an acid (10-methylstearic acid), ester (e.g., diacylglycerol, triacylglycerol, phospholipid), thioester (e.g., 10-methylstearyl CoA), or amide (e.g., 10-methylstearyl amide) thereof. For example, the branched (methyl)lipid may be a diacylglycerol, triacylglycerol, or phospholipid, and the diacylglycerol, triacylglycerol, or phospholipid may comprise an ester of 10-methylstearate.

An exomethylene-substituted lipid may be 10-methylenestearate, or an acid (10-methylenestearic acid), ester (e.g., diacylglycerol, triacylglycerol, phospholipid), thioester (e.g., 10-methylenestearyl CoA), or amide (e.g., 10-methylenestearyl amide) thereof. For example, the exomethylene-substituted lipid may be a diacylglycerol, triacylglycerol, or phospholipid, and the diacylglycerol, triacylglycerol, or phospholipid may comprise an ester of 10-methylenestearate.

In some embodiments, about, at most about, or at least about 1% of the fatty acids of the cell may be 10-methylstearic acid as measured by % dry cell weight. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the fatty acids of the cell may be 10-methylstearic acid as measured by % dry cell weight, or any range derivable therein.

In some embodiments, about, at least about, or at most about 1% of the fatty acids of the cell may be 10-methylenestearic acid as measured by % dry cell weight. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the fatty acids of the cell may be 10-methylenestearic acid as measured by % dry cell weight, or any range derivable therein.

In some embodiments, about, at least about, or at most about 1% by weight of the fatty acids of the cell may be one or more of the branched (methyl)lipids described herein. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids of the cell may be one or more of the branched (methyl)lipids described herein, or any range derivable therein.

In some embodiments, about, at least about, or at most about 1% by weight of the fatty acids of the cell may one or more of the branched (methyl)lipids described herein (e.g., a linear fatty acid with a chain length of 14-20 carbons with a methyl branch at the Δ9, Δ10, or Δ11 position). About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the fatty acids of the cell may one or more of the branched (methyl)lipids described herein (e.g., a linear fatty acid with a chain length of 14-20 carbons with a methyl branch at the Δ9, Δ10, or Δ11 position), or any range derivable therein.

In some embodiments, the cell may comprise about, at least about, or at most about 1% 10-methylstearic acid as measured by % dry cell weight. The cell may comprise about, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% 10-methylstearic acid as measured by % dry cell weight, or any range derivable therein.

In some embodiments, the cell may comprise about, at least about, or at most about 1% 10-methylenestearic acid as measured by % dry cell weight. The cell may comprise about, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% 10-methylenestearic acid as measured by % dry cell weight, or any range derivable therein.

An unmodified cell of the same type (e.g., species) as a cell of the invention may not comprise 10-methylstearate, or an acid (10-methylstearic acid), ester (e.g., diacylglycerol, triacylglycerol, phospholipid), thioester (e.g., 10-methylstearyl CoA), or amide (e.g., 10-methylstearyl amide) thereof (e.g., wherein the unmodified cell does not comprise a recombinant methyltransferase gene or a recombinant reductase gene). An unmodified cell of the same type (e.g., species) as a cell of the invention may not comprise 10-methylenestearate, or an acid (10-methylenestearic acid), ester (e.g., diacylglycerol, triacylglycerol, phospholipid), thioester (e.g., 10-methylenestearyl CoA), or amide (e.g., 10-methylenestearyl amide) thereof (e.g., wherein the unmodified cell does not comprise a recombinant methyltransferase gene or a recombinant reductase gene). In some embodiments, an unmodified cell of the same species as the cell does not comprise a branched (methyl)lipid and/or an exomethylene-substituted lipid. In some embodiments, an unmodified cell of the same species as the cell does not comprise one or more of the branched (methyl)lipids or exomethylene-substituted lipids described herein.

A cell may constitutively express the protein encoded by a recombinant methyltransferase gene. A cell may constitutively express the protein encoded by a recombinant reductase gene. A cell may constitutively express the protein encoded by a recombinant tmsC gene. A cell may constitutively express a methyltransferase protein. A cell may constitutively express a reductase protein. A cell may constitutively express a tmsC protein.

B. Nucleic Acids

Various aspects of the invention relate to a nucleic acid comprising a recombinant methyltransferase gene, a recombinant reductase gene, or both. The nucleic acid may be, for example, a plasmid. In some embodiments, a recombinant methyltransferase gene and/or a recombinant reductase gene is integrated into the genome of a cell, and thus, the nucleic acid may be a chromosome. In some embodiments, the invention relates to a cell comprising a recombinant methyltransferase gene, e.g., wherein the recombinant methyltransferase gene is present in a plasmid or chromosome. In some embodiments, the invention relates to a cell comprising a recombinant reductase gene, e.g., wherein the recombinant reductase gene is present in a plasmid or chromosome. A recombinant methyltransferase gene and a recombinant reductase gene may be present in a cell in the same nucleic acid (e.g., same plasmid or chromosome) or in different nucleic acids (e.g., different plasmids or chromosomes).

A nucleic acid may be inheritable to the progeny of a transformed cell. A gene such as a recombinant methyltransferase gene or recombinant reductase gene may be inheritable because it resides on a plasmid or chromosome. In certain embodiments, a gene may be inheritable because it is integrated into the genome of the transformed cell.

A gene may comprise conservative substitutions, deletions, and/or insertions while still encoding a protein that has activity. For example, codons may be optimized for a particular host cell, different codons may be substituted for convenience, such as to introduce a restriction site or to create optimal PCR primers, or codons may be substituted for another purpose. Similarly, the nucleotide sequence may be altered to create conservative amino acid substitutions, deletions, and/or insertions.

Proteins may comprise conservative substitutions, deletions, and/or insertions while still maintaining activity. Conservative substitution tables are well known in the art (Creighton, *Proteins* (2d. ed., 1992)).

Amino acid substitutions, deletions and/or insertions may readily be made using recombinant DNA manipulation techniques. Methods for the manipulation of DNA sequences to produce substitution, insertion or deletion variants of a protein are well known in the art. These methods include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis, and other site-directed mutagenesis protocols.

To determine the percent identity of two amino acid sequences or two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. Unless otherwise specified, when percent identity between two amino acid sequences is referred to herein, it refers to the percent identity as determined using the Needleman and Wunsch (J. Molecular Biology 48:444-453 (1970)) algorithm which has been incorporated into the GAP program in the GCG software package (available at www.gcg.com), using a Blosum 62 matrix, a gap weight of 10, and a length weight of 4. In some embodiments, the percent identity between two amino acid sequences is determined the Needleman and Wunsch algorithm using a Blosum 62 matrix or a PAM250 matrix, and a gap weight of 16, 14, 12, 10, 8, 6, or 4 and a length weight of 1, 2, 3, 4, 5, or 6. Unless otherwise specified, when percent identity between two nucleotide sequences is referred to herein, it refers to percent identity as determined using the GAP program in the GCG software package (available at www.gcg.com), using a NWSgapdna.CMP matrix and a gap weight of 60 and a length weight of 4. In yet another embodiment, the percent identity between two nucleotide sequences can be determined using a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0 U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, MEGABLAST, BLASTX, TBLASTN, TBLASTX, and BLASTP, and Clustal programs, e.g., ClustalW, ClustalX, and Clustal Omega.

Sequence searches are typically carried out using the BLASTN program, when evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

Any nucleic acid that is referred to herein as having a certain percent sequence identity to a sequence set forth in a SEQ ID NO, includes nucleic acids that have the certain percent sequence identity to the complement of the sequence set forth in the SEQ ID NO.

i. Nucleic Acids Comprising a Recombinant Methyltransferase Gene

A methyltransferase gene (e.g., a recombinant methyltransferase gene) encodes a methyltransferase protein, which is an enzyme capable of transferring a carbon atom and one or more protons bound thereto from a substrate such as S-adenosyl methionine to a fatty acid such as oleic acid (e.g., wherein the fatty acid is present as a free fatty acid, carboxylate, phospholipid, diacylglycerol, or triacylglycerol). A methyltransferase gene (e.g., a recombinant methyltransferase gene) may comprise any one of the nucleotide sequences set forth in SEQ ID NO:3, SEQ ID NO:7, SEQ ID NO: 11, SEQ ID NO: 15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, and SEQ ID NO:81. A methyltransferase gene (e.g., a recombinant methyltransferase gene) may be a 10-methylstearic B gene (tmsB) as described herein, or a biologically-active portion thereof (i.e., wherein the biologically-active portion thereof comprises methyltransferase activity).

A methyltransferase gene (e.g., a recombinant methyltransferase gene) may be derived from a gram-positive species of Actinobacteria, such as *Mycobacteria, Corynebacteria, Nocardia, Streptomyces,* or *Rhodococcus*. A methyltransferase gene (e.g., a recombinant methyltransferase gene) may be selected from the group consisting of *Mycobacterium smegmatis* gene tmsB, *Agromyces subbeticus* gene tmsB, *Amycolicicoccus subflavus* gene tmsB, *Corynebacterium glutamicum* gene tmsB, *Corynebacterium glyciniphilium* gene tmsB, *Knoella aerolata* gene tmsB, *Mycobacterium austroafricanum* gene tmsB, *Mycobacterium gilvum* gene tmsB, *Mycobacterium indicus pranii* gene tmsB, *Mycobacterium phlei* gene tmsB, *Mycobacterium tuberculosis* gene tmsB, *Mycobacterium vanbaalenii* gene tmsB, *Rhodococcus opacus* gene tmsB, *Streptomyces regnsis* gene tmsB, *Thermobifida fusca* gene tmsB, and *Thermomonospora curvata* gene tmsB. It is specifically contemplated that one or more of the above methyltransferase genes may be excluded from embodiments of this invention.

A recombinant methyltransferase gene may be recombinant because it is operably-linked to a promoter other than the naturally-occurring promoter of the methyltransferase gene. Such genes may be useful to drive transcription in a particular species of cell. A recombinant methyltransferase gene may be recombinant because it contains one or more nucleotide substitutions relative to a naturally-occurring methyltransferase gene. Such genes may be useful to increase the translation efficiency of the methyltransferase gene's mRNA transcript in a particular species of cell.

A nucleic acid may comprise a recombinant methyltransferase gene and a promoter, wherein the recombinant methyltransferase gene and promoter are operably-linked. The recombinant methyltransferase gene and promoter may be derived from different species. For example, the recombinant methyltransferase gene may encode the methyltransferase protein of a gram-positive species of Actinobacteria, and the recombinant methyltransferase gene may be operably-linked to a promoter that can drive transcription in another phylum of bacteria (e.g., a Proteobacterium, such as *E. coli*) or a eukaryote (e.g., an algae cell, yeast cell, or plant cell). The promoter may be a eukaryotic promoter. A cell may comprise the nucleic acid, and the promoter may be capable of driving transcription in the cell. A cell may comprise a recombinant methyltransferase gene, and the recombinant methyltransferase gene may be operably-linked to a promoter capable of driving transcription of the recombinant methyltransferase gene in the cell. The cell may be a species of yeast, and the promoter may be a yeast promoter. The cell may be a species of bacteria, and the promoter may be a bacterial promoter (e.g., wherein the bacterial promoter is not a promoter from Actinobacteria). The cell may be a species of algae, and the promoter may be an algae promoter. The cell may be a species of plant, and the promoter may be a plant promoter.

A recombinant methyltransferase gene may be operably-linked to a promoter that cannot drive transcription in the cell from which the recombinant methyltransferase gene originated. For example, the promoter may not be capable of binding an RNA polymerase of the cell from which a recombinant methyltransferase gene originated. In some embodiments, the promoter cannot bind a prokaryotic RNA polymerase and/or initiate transcription mediated by a prokaryotic RNA polymerase. In some embodiments, a recombinant methyltransferase gene is operably-linked to a promoter that cannot drive transcription in the cell from which the protein encoded by the gene originated. For example, the promoter may not be capable of binding an RNA polymerase of a cell that naturally expresses the methyltransferase enzyme encoded by a recombinant methyltransferase gene.

A promoter may be an inducible promoter or a constitutive promoter. A promoter may be any one of the promoters described in PCT Patent Application Publication No. WO 2016/014900, published Jan. 28, 2016 (hereby incorporated by reference in its entirety). WO 2016/014900 describes various promoters derived from yeast species *Yarrowia lipolytica* and *Arxula adeninivorans*, which may be particularly useful as promoters for driving the transcription of a recombinant gene in a yeast cell. A promoter may be a promoter from a gene encoding a Translation Elongation factor EF-1α; Glycerol-3-phosphate dehydrogenase; Triose-phosphate isomerase 1; Fructose-1,6-bisphosphate aldolase; Phosphoglycerate mutase; Pyruvate kinase; Export protein EXP1; Ribosomal protein S7; Alcohol dehydrogenase; Phosphoglycerate kinase; Hexose Transporter; General amino acid permease; Serine protease; Isocitrate lyase; Acyl-CoA oxidase; ATP-sulfurylase; Hexokinase; 3-phosphoglycerate dehydrogenase; Pyruvate Dehydrogenase Alpha subunit; Pyruvate Dehydrogenase Beta subunit; Aconitase; Enolase; Actin; Multidrug resistance protein (ABC-transporter); Ubiquitin; GTPase; Plasma membrane Na+/$P_i$ cotransporter; Pyruvate decarboxylase; Phytase; or Alpha-amylase, e.g., wherein the gene is a yeast gene, such as a gene from *Yarrowia lipolytica* or *Arxula adeninivorans*.

A recombinant methyltransferase gene may comprise a nucleotide sequence with at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:3, SEQ ID NO:7, SEQ ID NO: 1, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81. A recombinant methyltransferase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity (or any range derivable therein) with 150, 200, 250, 300, 350, 400, 450, 500, 550, 600, 650, 700, 750, 800, 850, 900, 950, 1000, 1050, 1100, 1150, 1200, 1250, or 1300 contiguous base pairs (or any range derivable therein) starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, or 1200 of the nucleotide sequence set forth in SEQ ID NO:3, SEQ ID NO:7, SEQ ID NO: 11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81. A recombinant methyltransferase may or may not have 100% sequence identity with any one of the nucleotide sequences set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81. A recombinant methyltransferase gene may or may not have 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs of the nucleotide sequence set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81. A recombinant methyltransferase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, SEQ ID NO:75, or SEQ ID NO:81, and the recombinant methyltransferase gene may encode a methyltransferase protein with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the amino acid sequence set forth in SEQ ID NO:4, SEQ ID NO:8, SEQ ID NO:12, SEQ ID NO: 16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. For example, SEQ ID NO:81 is a gene that is codon-optimized for expression in yeast. SEQ ID NO:81 has about 70% sequence identity (69.86% sequence identity) with SEQ ID NO:3, and the protein encoded by SEQ ID NO:81 has 100% sequence identity with the amino acid sequence set forth in by SEQ ID NO:4. Thus, even though SEQ ID NO:81 and SEQ ID NO:3 have 69.86% sequence identity, the two nucleotide sequences encode the same amino acid sequence.

A recombinant methyltransferase gene may vary from a naturally-occurring methyltransferase gene because the recombinant methyltransferase gene may be codon-optimized for expression in a eukaryotic cell, such as a plant cell, algae cell, or yeast cell.

A cell may comprise a recombinant methyltransferase gene, wherein the recombinant methyltransferase gene is codon-optimized for the cell.

Exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 codons of a recombinant methyltransferase gene may vary from a naturally-occurring methyltransferase gene or may be unchanged from a naturally-occurring methyltransferase gene. For example, a recombinant methyltransferase gene may comprise a nucleotide sequence with at least about 65% sequence identity with the naturally-occurring nucleotide sequence set forth in SEQ ID NO:3, SEQ ID NO:7, SEQ ID NO:11, SEQ ID NO:15, SEQ ID NO:19, SEQ ID NO:25, SEQ ID NO:29, SEQ ID NO:35, SEQ ID NO:41, SEQ ID NO:45, SEQ ID NO:49, SEQ ID NO:53, SEQ ID NO:59, SEQ ID NO:63, SEQ ID NO:69, or SEQ ID NO:75 (e.g., at least 70%, 75%, 80%, 85%, 90%, 95%, 96%, 97%, 98%, or 99% sequence identity), and at least 5 codons of the nucleotide sequence of the recombinant methyltransferase gene may vary from the naturally-occurring nucleotide sequence (e.g., at least 10, 15, 20, 25, 30, 35, 40, 45, 50, 60, 70, 80, 90, or 100 codons (or any range derivable therein)).

A methyltransferase gene encodes a methyltransferase protein. A methyltransferase protein may be a protein expressed by a gram-positive species of Actinobacteria, such as *Mycobacteria, Corynebacteria, Nocardia, Streptomyces*, or *Rhodococcus*. A recombinant methyltransferase gene may encode a naturally-occurring methyltransferase protein even if the recombinant methyltransferase gene is not a naturally-occurring methyltransferase gene. For example, a recombinant methyltransferase gene may vary from a naturally-occurring methyltransferase gene because the recombinant methyltransferase gene is codon-optimized for expression in a specific cell. The codon-optimized, recombinant methyltransferase gene and the naturally-occurring methyltransferase gene may nevertheless encode the same naturally-occurring methyltransferase protein.

A recombinant methyltransferase gene may encode a methyltransferase protein selected from *Mycobacterium smegmatis* enzyme tmsB, *Agromyces subbeticus* enzyme tmsB, *Amycolicicoccus subflavus* enzyme tmsB, *Corynebacterium glutamicum* enzyme tmsB, *Corynebacterium glyciniphilium* enzyme tmsB, *Knoella aerolata* enzyme tmsB, *Mycobacterium austroafricanum* enzyme tmsB, *Mycobacterium gilvum* enzyme tmsB, *Mycobacterium indicus pranii* enzyme tmsB, *Mycobacterium phlei* enzyme tmsB, *Mycobacterium tuberculosis* enzyme tmsB, *Mycobacterium vanbaalenii* enzyme tmsB, *Rhodococcus opacus* enzyme tmsB, *Streptomyces regnsis* enzyme tmsB, *Thermobifida fusca* enzyme tmsB, and *Thermomonospora curvata* enzyme tmsB. It is specifically contemplated that one or more of the above methyltransferase proteins may be excluded from embodiments of this invention. A recombinant methyltransferase gene may encode a methyltransferase protein, and the methyltransferase protein may be substantially identical to any one of the foregoing enzymes, but the recombinant methyltransferase gene may vary from the naturally-occurring gene that encodes the enzyme. The recombinant methyltransferase gene may vary from the naturally-occurring gene because the recombinant methyltransferase gene may be codon-optimized for expression in a specific phylum, class, order, family, genus, species, or strain of cell.

The sequences of naturally-occurring methyltransferase proteins are set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. A recombinant methyltransferase gene may or may not encode a protein comprising 100% sequence identity with the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. For example, a recombinant methyltransferase gene may encode a protein having 100% sequence identity with a biologically-active portion of an amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76.

A recombinant methyltransferase gene may encode a methyltransferase protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity (or any range derivable therein) with the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76, or a biologically-active portion thereof. A recombinant methyltransferase gene may encode a methyltransferase protein having at least about 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, or 400% methyltransferase activity (or any range derivable therein) relative to a protein comprising the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. A recombinant methyltransferase gene may encode a protein having at least 70%, 75%, 80%, 85%, 90%, 91%, 92%, 93%, 94%, 95%, 96%, 97%, 98%, 99%, 99.9%, or 100% sequence identity with 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous amino acids starting at amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 of SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76.

Substrates for the methyltransferase protein may include any fatty acid from 14 to 20 carbons long with an unsaturated double bond in the Δ9, Δ10, or Δ11 position. The methyltransferase protein may be capable of catalyzing the formation of a methylene substitution at the Δ9, Δ10, or Δ11 position of such a substrate.

In some embodiments, the recombinant methyltransferase gene encodes a methyltransferase protein that includes an S-adenosylmethionine-dependent methyltransferase domain. In some embodiments the S-adenosylmethionine-dependent methyltransferase domain has, has at least, or has at most 70%, 75%, 80%, 85%, 90%, 91%, 92%, 93%, 94%, 95%, 96%, 97%, 98%, 99%, 99.9%, or 100% sequence identity to amino acids 192-291 of *T. curvata* TmsB (SEQ ID NO:76) or to a corresponding portion of TmsB from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus*, or *Thermobifida fusca*, according to the alignment set forth in FIGS. 19A-D.

In some embodiments, the recombinant methyltransferase gene encodes a methyltransferase protein that has specific amino acids unchanged from the amino acid sequence set forth in SEQ ID NO:4, SEQ ID NO:8, SEQ ID NO:12, SEQ ID NO:16, SEQ ID NO:20, SEQ ID NO:26, SEQ ID NO:30, SEQ ID NO:36, SEQ ID NO:42, SEQ ID NO:46, SEQ ID NO:50, SEQ ID NO:54, SEQ ID NO:60, SEQ ID NO:64, SEQ ID NO:70, or SEQ ID NO:76. The unchanged amino acids can include 1, 2, 3, 4, 5, 6, 7, 8, 9, 10, 11, 12, 13, 14, 15, 16, 17, 18, 19, 20, 21, 22, 23, 24, 25, 26, 27, 28, or 29 amino acids selected from D23, G24, A59, H128, F147, Y148, L180, L193, M203, G236, A241, R313, R318, E320, L359, L400, V196, G197, C198, G199, W200, G201, G202, T219, L220, Q246, D247, Y248, and D262 of *T. curvata* TmsB (SEQ ID NO:76) or corresponding amino acids in TmsB from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus*, or *Thermobifida fusca*, according to the alignment set forth in FIGS. 19A-D.

ii. Nucleic Acids Comprising a Recombinant Reductase Gene

A reductase gene (e.g., a recombinant reductase gene) encodes a reductase protein, which is an enzyme capable of reducing, often in an NADPH-dependent manner, a double bond of a fatty acid (e.g., wherein the fatty acid is present as a free fatty acid, carboxylate, phospholipid, diacylglycerol, or triacylglycerol). A reductase gene (e.g., a recombinant reductase gene) may comprise any one of the nucleotide sequences set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, and SEQ ID NO:80. A reductase gene (e.g., a recombinant reductase gene) may be a 10-methylstearic A gene (tmsA) as described herein, or a biologically-active portion thereof (i.e., wherein the biologically-active portion thereof comprises reductase activity).

A reductase gene (e.g., a recombinant reductase gene) may be derived from a gram-positive species of Actinobacteria, such as *Mycobacteria, Corynebacteria, Nocardia, Streptomyces*, or *Rhodococcus*. A reductase gene (e.g., a recombinant reductase gene) may be selected from the group consisting of *Mycobacterium smegmatis* gene tmsA, *Agromyces subbeticus* gene tmsA, *Amycolicicoccus subflavus* gene tmsA, *Corynebacterium glutamicum* gene tmsA, *Corynebacterium glyciniphilium* gene tmsA, *Knoella aerolata* gene tmsA, *Mycobacterium austroafricanum* gene tmsA, *Mycobacterium gilvum* gene tmsA, *Mycobacterium indicus pranii* gene tmsA, *Mycobacterium phlei* gene tmsA, *Mycobacterium tuberculosis* gene tmsA, *Mycobacterium vanbaalenii* gene tmsA, *Rhodococcus opacus* gene tmsA, *Streptomyces regnsis* gene tmsA, *Thermobifida fusca* gene tmsA, and *Thermomonospora curvata* gene tmsA. It is specifically contemplated that one or more of the above reductase genes may be excluded from embodiments of this invention.

A recombinant reductase gene may be recombinant because it is operably-linked to a promoter other than the naturally-occurring promoter of the reductase gene. Such genes may be useful to drive transcription in a particular species of cell. A recombinant reductase gene may be recombinant because it contains one or more nucleotide substitutions relative to a naturally-occurring reductase gene. Such genes may be useful to increase the translation efficiency of the reductase gene's mRNA transcript in a particular species of cell.

A nucleic acid may comprise a recombinant reductase gene and a promoter, wherein the recombinant reductase gene and promoter are operably-linked. The recombinant reductase gene and promoter may be derived from different species. For example, the recombinant reductase gene may encode the reductase protein of a gram-positive species of Actinobacteria, and the recombinant reductase gene may be operably-linked to a promoter that can drive transcription in another phylum of bacteria (e.g., a Proteobacterium, such as *E. coli*) or a eukaryote (e.g., an algae cell, yeast cell, or plant cell). The promoter may be a eukaryotic promoter. A cell may comprise the nucleic acid, and the promoter may be capable of driving transcription in the cell. A cell may comprise a recombinant reductase gene, and the recombinant reductase gene may be operably-linked to a promoter capable of driving transcription of the recombinant reductase gene in the cell. The cell may be a species of yeast, and the promoter may be a yeast promoter. The cell may be a species of bacteria, and the promoter may be a bacterial promoter (e.g., wherein the bacterial promoter is not a promoter from Actinobacteria). The cell may be a species of algae, and the promoter may be an algae promoter. The cell may be a species of plant, and the promoter may be a plant promoter.

A recombinant reductase gene may be operably-linked to a promoter that cannot drive transcription in the cell from which the recombinant reductase gene originated. For example, the promoter may not be capable of binding an RNA polymerase of the cell from which a recombinant reductase gene originated. In some embodiments, the promoter cannot bind a prokaryotic RNA polymerase and/or initiate transcription mediated by a prokaryotic RNA polymerase. In some embodiments, a recombinant reductase gene is operably-linked to a promoter that cannot drive transcription in the cell from which the protein encoded by the gene originated. For example, the promoter may not be capable of binding an RNA polymerase of a cell that naturally expresses the reductase enzyme encoded by a recombinant reductase gene.

A promoter may be an inducible promoter or a constitutive promoter. A promoter may be any one of the promoters described in PCT Patent Application Publication No. WO 2016/014900, published Jan. 28, 2016 (hereby incorporated by reference in its entirety). WO 2016/014900 describes various promoters derived from yeast species *Yarrowia lipolytica* and *Arxula adeninivorans*, which may be particularly useful as promoters for driving the transcription of a recombinant gene in a yeast cell. A promoter may be a promoter from a gene encoding a Translation Elongation factor EF-1α; Glycerol-3-phosphate dehydrogenase; Triosephosphate isomerase 1; Fructose-1,6-bisphosphate aldolase; Phosphoglycerate mutase; Pyruvate kinase; Export protein EXP1; Ribosomal protein S7; Alcohol dehydrogenase; Phosphoglycerate kinase; Hexose Transporter; General amino acid permease; Serine protease; Isocitrate lyase; Acyl-CoA oxidase; ATP-sulfurylase; Hexokinase; 3-phosphoglycerate dehydrogenase; Pyruvate Dehydrogenase Alpha subunit; Pyruvate Dehydrogenase Beta subunit; Aconitase; Enolase; Actin; Multidrug resistance protein (ABC-transporter); Ubiquitin; GTPase; Plasma membrane Na+/$P_i$ cotransporter; Pyruvate decarboxylase; Phytase; or Alpha-amylase, e.g., wherein the gene is a yeast gene, such as a gene from *Yarrowia lipolytica* or *Arxula adeninivorans*.

A recombinant reductase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80. A recombinant reductase gene may comprise a nucleotide sequence with, with at least, with at most 65%, 70%, 75%, 80%, 85%, 90%, 95%, 96%, 97%, 98%, or 99% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, or 1200 of the nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80. A recombinant reductase may or may not have 100% sequence identity with any one of the nucleotide sequences set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80. A recombinant reductase gene may or may not have 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs of the nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80. A recombinant reductase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, SEQ ID NO:73, or SEQ ID NO:80, and the recombinant reductase gene may encode a reductase protein with at least about 95%, 96%, 97%, 98%, 99%, or 100% sequence identity with the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. For example, SEQ ID NO:80 is a gene that is codon-optimized for expression in yeast. SEQ ID NO:80 has about 70% sequence identity (70.09% sequence identity) with SEQ ID NO: 1, and the protein encoded by SEQ ID NO:80 has at least about 99% sequence identity with the amino acid sequence set forth in SEQ ID NO:2. The protein encoded by SEQ ID NO:1 has 100% sequence identity with the amino acid sequence set forth in SEQ ID NO:2.

A recombinant reductase gene may vary from a naturally-occurring reductase gene because the recombinant reductase gene may be codon-optimized for expression in a eukaryotic cell, such as a plant cell, algae cell, or yeast cell. A cell may comprise a recombinant reductase gene, wherein the recombinant reductase gene is codon-optimized for the cell.

Exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 codons of a recombinant reductase gene may vary from a naturally-occurring reductase gene or may be unchanged from a naturally-occurring reductase gene. For example, a recombinant reductase gene may comprise a nucleotide sequence with at least 65% sequence identity with the naturally-occurring nucleotide sequence set forth in SEQ ID NO:1, SEQ ID NO:5, SEQ ID NO:9, SEQ ID NO:13, SEQ ID NO:17, SEQ ID NO:23, SEQ ID NO:27, SEQ ID NO:33, SEQ ID NO:39, SEQ ID NO:43, SEQ ID NO:47, SEQ ID NO:51, SEQ ID NO:57, SEQ ID NO:61, SEQ ID NO:67, or SEQ ID NO:73 (e.g., at least 70%, 75%, 80%, 85%, 90%, 95%, 96%, 97%, 98%, or 99% sequence identity), and at least 5 codons of the nucleotide sequence of the recombinant reductase gene may vary from the naturally-occurring nucleotide sequence (e.g., at least 10, 15, 20, 25, 30, 35, 40, 45, 50, 60, 70, 80, 90, or 100 codons).

A reductase gene encodes a reductase protein. A reductase protein may be a protein expressed by a gram-positive species of Actinobacteria, such as *Mycobacteria, Corynebacteria, Nocardia, Streptomyces*, or *Rhodococcus*. A recombinant reductase gene may encode a naturally-occurring reductase protein even if the recombinant reductase gene is not a naturally-occurring reductase gene. For example, a recombinant reductase gene may vary from a naturally-occurring reductase gene because the recombinant reductase gene is codon-optimized for expression in a specific cell. The codon-optimized, recombinant reductase gene and the naturally-occurring reductase gene may nevertheless encode the same naturally-occurring reductase protein.

A recombinant reductase gene may encode a reductase protein selected from *Mycobacterium smegmatis* enzyme tmsA, *Agromyces subbeticus* enzyme tmsA, *Amycolicicoccus subflavus* enzyme tmsA, *Corynebacterium glutamicum* enzyme tmsA, *Corynebacterium glyciniphilium* enzyme tmsA, *Knoella aerolata* enzyme tmsA, *Mycobacterium austroafricanum* enzyme tmsA, *Mycobacterium gilvum* enzyme tmsA, *Mycobacterium indicus pranii* enzyme tmsA, *Mycobacterium phlei* enzyme tmsA, *Mycobacterium tuberculosis* enzyme tmsA, *Mycobacterium vanbaalenii* enzyme tmsA, *Rhodococcus opacus* enzyme tmsA, *Streptomyces regnsis* enzyme tmsA, *Thermobifida fusca* enzyme tmsA, and *Thermomonospora curvata* enzyme tmsA. It is specifically contemplated that one or more of the above reductase proteins may be excluded from embodiments of this invention. A recombinant reductase gene may encode a reductase protein, and the reductase protein may be substantially identical to any one of the foregoing enzymes, but the recombinant reductase gene may vary from the naturally-occurring gene that encodes the enzyme. The recombinant reductase gene may vary from the naturally-occurring gene because the recombinant reductase gene may be codon-optimized for expression in a specific phylum, class, order, family, genus, species, or strain of cell.

The sequences of naturally-occurring reductase proteins are set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. A recombinant reductase gene may or may not encode a protein comprising 100% sequence identity with the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. For example, a recombinant reductase gene may encode a protein having 100% sequence identity with a biologically-active portion of an amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74.

A recombinant reductase gene may encode a reductase protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74, or a biologically-active portion thereof. A recombinant reductase gene may encode a reductase protein having about, at least about, or at most about 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, or 400% reductase activity relative to a protein comprising the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. A recombinant reductase gene may encode a protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous amino acids starting at amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 of the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74.

Substrates for the reductase protein may include any fatty acid from 14 to 20 carbons long with a methylene substitution in the Δ9, Δ10, or Δ11 position. The fatty acid substrate may be 14, 15, 16, 17, 18, 19, or 20 carbons long, or any range derivable therein. The reductase protein may be capable of catalyzing the reduction of a methylene-substituted fatty acid substrate to a (methyl)lipid. The reductase protein, together with a methyltransferase protein, may be capable of catalyzing the production of a methylated branch from any fatty acid from 14 to 20 carbons long with an unsaturated double bond in the Δ9, Δ10, or Δ11 position.

In some embodiments, the recombinant reductase gene encodes a reductase protein that includes a Flavin adenine dinucleotide (FAD) binding domain. In some embodiments, the FAD binding domain has at least 80%, 85%, 90%, 91%, 92%, 93%, 94%, 95%, 96%, 97%, 98%, 99%, 99.9%, or 100% sequence identity to amino acids 9-141 of *T. curvata* TmsA (SEQ ID NO:74) or to a corresponding portion of TmsA from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus*, or *Thermobifida fusca*, according to the alignment set forth in FIGS. 20A-E.

In some embodiments, the recombinant reductase gene encodes a reductase protein that includes a FAD/FMN-containing dehydrogenase domain. In some embodiments, the FAD/FMN-containing dehydrogenase domain has, has at least, or has at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to amino acids 22-444 of *T. curvata* TmsA (SEQ ID NO:74) or to a corresponding portion of TmsA from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus*, or *Thermobifida fusca*, according to the alignment set forth in FIGS. 20A-E.

In some embodiments, the recombinant reductase gene encodes a reductase protein that has specific amino acids unchanged from the amino acid sequence set forth in SEQ ID NO:2, SEQ ID NO:6, SEQ ID NO:10, SEQ ID NO:14, SEQ ID NO:18, SEQ ID NO:24, SEQ ID NO:28, SEQ ID NO:34, SEQ ID NO:40, SEQ ID NO:44, SEQ ID NO:48, SEQ ID NO:52, SEQ ID NO:58, SEQ ID NO:62, SEQ ID NO:68, or SEQ ID NO:74. The unchanged amino acids can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, or amino acids selected from R31, A33, S37, N38, L39, F40, R43, D52, V59, D63, G73, M74, T76, Y77, D79, L80, V81, L85, P91, V93, V94, Q96, L97, T99, 1100, T101, A105, G108, G110, E112, S113, S115, F116, R117, N118, P121, H122, E123, V125, E127, G133, P154, N155, Y157, Y162, L166, E171, V173, V177, H181, V208, G213, F216, Y222, L223, S236, D237, Y238, T239, Y245, S247, D254, T257, Y261, W263, R264, W265, D266, D268, W269, C272, A275, G277, Q279, R284, W287, R293, S294, G318, E232, V325, P328, E330, F339, F343, W353, C355, P356, W363, L365, Y366, P367, N376, F379, W380, V383, P384, N395, E399, G407, H408, K409, S410, L411, Y412, S413, Y417, F422, Y426, G428, R443, L447, and V452 of *T. curvata* TmsA (SEQ ID NO:74) or corresponding amino acids in TmsA from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus*, or *Thermobifida fusca*, according to the alignment set forth in FIGS. 20A-E.

iii. Nucleic Acids Comprising a Recombinant tmsC Gene.

A nucleic acid may comprise a 10-methylstearic C gene (tmsC), as described herein. A tmsC gene (e.g., a recombinant tmsC gene) may comprise any one of the nucleotide sequences set forth in SEQ ID NO:21, SEQ ID NO:31, SEQ ID NO:37, SEQ ID NO:55, SEQ ID NO:65, and SEQ ID NO:71. A tmsC gene (e.g., a recombinant tmsC gene) may be derived from a gram-positive species of Actinobacteria, such as *Mycobacteria, Corynebacteria, Nocardia, Streptomyces*, or *Rhodococcus*. A tmsC gene (e.g., a recombinant tmsC gene) may be selected from the group consisting of *Corynebacterium glyciniphilium* gene tmsC, *Mycobacterium austroafricanum* gene tmsC, *Mycobacterium gilvum* gene tmsC, *Mycobacterium vanbaalenii* gene tmsC, *Streptomyces regnsis* gene tmsC, and *Thermobifida fusca* gene tmsC.

A recombinant tmsC gene may be recombinant because it is operably-linked to a promoter other than the naturally-occurring promoter of the tmsC gene. Such genes may be useful to drive transcription in a particular species of cell. A recombinant tmsC gene may be recombinant because it contains one or more nucleotide substitutions relative to a naturally-occurring tmsC gene. Such genes may be useful to increase the translation efficiency of the tmsC gene's mRNA transcript in a particular species of cell.

A nucleic acid may comprise a recombinant tmsC gene and a promoter, wherein the recombinant tmsC gene and promoter are operably-linked. The recombinant tmsC gene and promoter may be derived from different species. For example, the recombinant tmsC gene may encode the tmsC protein of a gram-positive species of Actinobacteria, and the recombinant tmsC gene may be operably-linked to a promoter that can drive transcription in another phylum of bacteria (e.g., a Proteobacterium, such as *E. coli*) or a eukaryote (e.g., an algae cell, yeast cell, or plant cell). The promoter may be a eukaryotic promoter. A cell may comprise the nucleic acid, and the promoter may be capable of driving transcription in the cell. A cell may comprise a recombinant tmsC gene, and the recombinant tmsC gene may be operably-linked to a promoter capable of driving transcription of the recombinant tmsC gene in the cell. The cell may be a species of yeast, and the promoter may be a yeast promoter. The cell may be a species of bacteria, and the promoter may be a bacterial promoter (e.g., wherein the bacterial promoter is not a promoter from Actinobacteria). The cell may be a species of algae, and the promoter may be an algae promoter. The cell may be a species of plant, and the promoter may be a plant promoter.

A recombinant tmsC gene may be operably-linked to a promoter that cannot drive transcription in the cell from which the recombinant tmsC gene originated. For example, the promoter may not be capable of binding an RNA polymerase of the cell from which a recombinant tmsC gene originated. In some embodiments, the promoter cannot bind a prokaryotic RNA polymerase and/or initiate transcription mediated by a prokaryotic RNA polymerase. In some embodiments, a recombinant tmsC gene is operably-linked to a promoter that cannot drive transcription in the cell from which the protein encoded by the gene originated. For example, the promoter may not be capable of binding an RNA polymerase of a cell that naturally expresses the tmsC enzyme encoded by a recombinant tmsC gene.

A promoter may be an inducible promoter or a constitutive promoter. A promoter may be any one of the promoters described in PCT Patent Application Publication No. WO 2016/014900, published Jan. 28, 2016 (hereby incorporated by reference in its entirety). WO 2016/014900 describes various promoters derived from yeast species *Yarrowia lipolytica* and *Arxula adeninivorans*, which may be particularly useful as promoters for driving the transcription of a recombinant gene in a yeast cell. A promoter may be a promoter from a gene encoding a Translation Elongation factor EF-1$\alpha$; Glycerol-3-phosphate dehydrogenase; Triosephosphate isomerase 1; Fructose-1,6-bisphosphate aldolase; Phosphoglycerate mutase; Pyruvate kinase; Export protein EXP1; Ribosomal protein S7; Alcohol dehydrogenase; Phosphoglycerate kinase; Hexose Transporter; General amino acid permease; Serine protease; Isocitrate lyase; Acyl-CoA oxidase; ATP-sulfurylase; Hexokinase; 3-phosphoglycerate dehydrogenase; Pyruvate Dehydrogenase Alpha subunit; Pyruvate Dehydrogenase Beta subunit; Aconitase; Enolase; Actin; Multidrug resistance protein (ABC-transporter); Ubiquitin; GTPase; Plasma membrane Na+/$P_i$ cotransporter; Pyruvate decarboxylase; Phytase; or Alpha-amylase, e.g., wherein the gene is a yeast gene, such as a gene from *Yarrowia lipolytica* or *Arxula adeninivorans.*

A recombinant tmsC gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:21, SEQ ID NO:31, SEQ ID NO:37, SEQ ID NO:55, SEQ ID NO:65, or SEQ ID NO:71. A recombinant tmsC may or may not have 100% sequence identity with any one of the nucleotide sequences set forth in SEQ ID NO:21, SEQ ID NO:31, SEQ ID NO:37, SEQ ID NO:55, SEQ ID NO:65, and SEQ ID NO:71. A recombinant tmsC gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:21, SEQ ID NO:31, SEQ ID NO:37, SEQ ID NO:55, SEQ ID NO:65, and SEQ ID NO:71, and the recombinant tmsC gene may encode a tmsC protein with at least about 95%, 96%, 97%, 98%, 99%, or 100% sequence identity with the amino acid sequence set forth in SEQ ID NO:22, SEQ ID NO:32, SEQ ID NO:38, SEQ ID NO:56, SEQ ID NO:66, and SEQ ID NO:72.

A recombinant tmsC gene may vary from a naturally-occurring tmsC gene because the recombinant tmsC gene may be codon-optimized for expression in a eukaryotic cell, such as a plant cell, algae cell, or yeast cell. A cell may comprise a recombinant tmsC gene, wherein the recombinant tmsC gene is codon-optimized for the cell.

Exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 codons of a recombinant tmsC gene may vary from a naturally-occurring tmsC gene or may remain unchanged from a naturally-occurring tmsC gene. For example, a recombinant tmsC gene may comprise a nucleotide sequence with at least about 65% sequence identity with the naturally-occurring nucleotide sequence set forth in SEQ ID NO:21, SEQ ID NO:31, SEQ ID NO:37, SEQ ID NO:55, SEQ ID NO:65, or SEQ ID NO:71 (e.g., at least about 70%, 75%, 80%, 85%, 90%, 95%, 96%, 97%, 98%, or 99% sequence identity), and at least 5 codons of the nucleotide sequence of the recombinant tmsC gene may vary from the naturally-occurring nucleotide sequence (e.g., at least about 10, 15, 20, 25, 30, 35, 40, 45, 50, 60, 70, 80, 90, or 100 codons).

A tmsC gene encodes a tmsC protein. A tmsC protein may be a protein expressed by a gram-positive species of Actinobacteria, such as *Mycobacteria, Corynebacteria, Nocardia, Streptomyces*, or *Rhodococcus*. A recombinant tmsC gene may encode a naturally-occurring tmsC protein even if the recombinant tmsC gene is not a naturally-occurring tmsC gene. For example, a recombinant tmsC gene may vary from a naturally-occurring tmsC gene because the recombinant tmsC gene is codon-optimized for expression in a specific cell. The codon-optimized, recombinant tmsC gene and the naturally-occurring tmsC gene may nevertheless encode the same naturally-occurring tmsC protein.

A recombinant tmsC gene may encode a tmsC protein selected from *Corynebacterium glyciniphilium* enzyme tmsC, *Mycobacterium austroafricanum* enzyme tmsC, *Mycobacterium gilvum* enzyme tmsC, *Mycobacterium vanbaalenii* enzyme tmsC, *Streptomyces regnsis* enzyme tmsC, and *Thermobifida fusca* enzyme tmsC. A recombinant tmsC gene may encode a tmsC protein, and the tmsC protein may be substantially identical to any one of the foregoing enzymes, but the recombinant tmsC gene may vary from the naturally-occurring gene that encodes the enzyme. The recombinant tmsC gene may vary from the naturally-occurring gene because the recombinant tmsC gene may be codon-optimized for expression in a specific phylum, class, order, family, genus, species, or strain of cell.

The sequences of naturally-occurring tmsC proteins are set forth in SEQ ID NO:22, SEQ ID NO:32, SEQ ID NO:38, SEQ ID NO:56, SEQ ID NO:66, and SEQ ID NO:72. A recombinant tmsC gene may or may not encode a protein comprising 100% sequence identity with the amino acid sequence set forth in SEQ ID NO:22, SEQ ID NO:32, SEQ ID NO:38, SEQ ID NO:56, SEQ ID NO:66, and SEQ ID NO:72. For example, a recombinant tmsC gene may encode a protein having 100% sequence identity with a biologically-active portion of an amino acid sequence set forth in SEQ ID NO:22, SEQ ID NO:32, SEQ ID NO:38, SEQ ID NO:38, SEQ ID NO:56, SEQ ID NO:66, and SEQ ID NO:72. A recombinant tmsC gene may encode a tmsC protein having at least about 95%, 96%, 97%, 98%, or 99% sequence identity with the amino acid sequence set forth in SEQ ID NO:22, SEQ ID NO:32, SEQ ID NO:38, SEQ ID NO:56, SEQ ID NO:66, or SEQ ID NO:72, or a biologically-active portion thereof.

iv. Nucleic Acids Comprising a Recombinant Methyltransferase Gene and a Recombinant Reductase Gene A nucleic acid may comprise both a recombinant methyltransferase gene and a recombinant reductase gene. The recombinant methyltransferase gene and the recombinant reductase gene may encode proteins from the same species or from different species. A nucleic acid may comprise a recombinant methyltransferase gene, a recombinant reductase gene, and/or a tmsC gene. A recombinant methyltransferase gene, recombinant reductase gene, and a tmsC gene may encode proteins from 1, 2, or 3 different species (i.e., the genes may each be from the same species, two genes may be from the same species, or all three genes may be from different species).

A nucleic acid may comprise the nucleotide sequence set forth in SEQ ID NO:77, SEQ ID NO:78, or SEQ ID NO:79. A nucleic acid may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:77, SEQ ID NO:78, SEQ ID NO:79, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, or SEQ ID NO:92.

In some embodiments, the nucleic acid encodes a fusion protein that includes both a methyltransferase and a reductase or fragments thereof. In the context of the present invention, "fusion protein" means a single protein molecule containing two or more distinct proteins or fragments thereof, covalently linked via peptide bond in a single peptide chain. In some embodiments, the fusion protein comprises enzymatically active domains from both a methyltransferase protein and a reductase protein. The nucleic acid may further encode a linker peptide between the methyltransferase and the reductase. In some embodiments, the linker peptide comprises the amino acid sequence AGGAEGGNGGGA. The linker may comprise about or at least about 2, 3, 4, 5, 6, 7, 8, 9, 10, 15, 20, 25, or 30 amino acids, or any range derivable therein. The nucleic acid may comprise any of the methyltransferase and reductase genes described herein, and the fusion protein encoded by the nucleic acid can comprise any of the methyltransferase and reductase proteins described herein, including biologically active fragments thereof. In some embodiments, the fusion protein is a tmsA-B protein, in which the TmsA protein is closer to the N-terminus than the TmsB protein. An example of such a tmsA-B protein is encoded by the nucleic acid sequence of SEQ ID NO:97. In some embodiments, the fusion protein is a tmsB-A protein, in which the tmsB protein is closer to the N-terminus than the tmsA protein. An example of such a tmsB-A protein is encoded by the nucleic acid sequence of SEQ ID NO:98. In some embodiments, the fusion protein has at least about 80%, 85%, 90%, 91%, 92%, 93%, 94%, 95%, 96%, 97%, 98%, 99%, or 99.9% identity to the amino acid sequence of a fusion protein encoded by SEQ ID NO:97 or SEQ ID NO:98.

C. Compositions

Various aspects of the invention relate to compositions produced by the cells described herein. The composition may be an oil composition comprised of about or at least about 75%, 80%, 85%, 90%, 95%, or 99% lipids. The composition may comprise branched (methyl)lipids and/or exomethylene-substituted lipids. The branched (methyl) lipid may be a carboxylic acid (e.g., 10-methylstearic acid, 10-methylpalmitic acid, 12-methyloleic acid, 13-methyloleic acid, 10-methyl-octadec-12-enoic acid), carboxylate (e.g., 10-methylstearate, 10-methylpalmitate, 12-methyloleate, 13-methyloleate, 10-methyl-octadec-12-enoate), ester (e.g., diacylglycerol, triacylglycerol, phospholipid), thioester (e.g., 10-methylstearyl CoA, 10-methylpalmityl CoA, 12-methyloleoyl CoA, 13-methyloleoyl CoA, 10-methyl-octadec-12-enoyl CoA), or amide. The exomethylene-substituted lipid may be a carboxylic acid (e.g., 10-methylenestearic acid, 10-methylenepalmitic acid, 12-methyleneoleic acid, 13-methyleneoleic acid, 10-methylene-octadec-12-enoic acid), carboxylate (e.g., 10-methylenestearate, 10-methylenepalmitate, 12-methyleneoleate, 13-methyleneoleate, 10-methylene-octadec-12-enoate), ester (e.g., diacylglycerol, triacylglycerol, phospholipid), thioester (e.g., 10-methylenestearyl CoA, 10-methylenepalmityl CoA, 12-methyleneoleoyl CoA, 13-methyleneoleoyl CoA, 10-methylene-octadec-12-enoyl CoA), or amide.

10-methyl lipids, 10-methylene lipids, or both. It is specifically contemplated that one or more of the above lipids may be excluded from certain embodiments.

In some aspects, the composition is produced by cultivating a culture comprising any of the cells described herein and recovering the oil composition from the cell culture. The cells in the culture may contain any of the recombinant methyltransferase genes described herein and/or any of the recombinant reductase genes described herein. The culture medium and conditions can be chosen based on the species of the cell to be cultured and can be optimized to provide for maximal production of the desired lipid profile.

Various methods are known for recovering an oil composition from a culture of cells. For example, lipids, lipid derivatives, and hydrocarbons can be extracted with a hydrophobic solvent such as hexane. Lipids and lipid derivatives can also be extracted using liquefaction, oil liquefaction, and supercritical $CO_2$ extraction. The recovery process may include harvesting cultured cells, such as by filtration or centrifugation, lysing cells to create a lysate, and extracting the lipid/hydrocarbon components using a hydrophobic solvent.

In addition to accumulating within cells, the lipids described herein may be secreted by the cells. In that case, a process for recovering the lipid may not require creating a lysate from the cells, but collecting the secreted lipid from the culture medium. Thus, the compositions described herein may be made by culturing a cell that secretes one of the lipids described herein, such as a linear fatty acid with a chain length of 14-20 carbons with a methyl branch at the Δ9, Δ10, or Δ11 position.

In some embodiments, the oil composition comprises about, at least about, or at most about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of a branched (methyl)lipid, such as a 10-methyl fatty acid, or any range derivable therein. In some embodiments, 10-methyl fatty acids comprise about, at least about, or at most about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids in the composition, or any range derivable therein.

D. Methods of Producing a Branched (Methyl)Lipid

Various aspects of the invention relate to a method of producing a branched (methyl)lipid. The method may comprise incubating a cell or plurality of cells as described herein, supra, with media. The media may optionally be supplemented with an unbranched, unsaturated fatty acid, such as oleic acid, that serves as a substrate for methylation. The media may optionally be supplemented with methionine or s-adenosyl methionine, which may similarly serve as a substrate. Thus, the method may comprise contacting a cell or plurality of cells with oleic acid, methionine, or both. The method may comprise incubating a cell or plurality of cells as described herein, supra, in a bioreactor. The method may comprise recovering lipids from the cells and/or from the culture medium, such as by extraction with an organic solvent.

The method may comprise degumming the cell or plurality of cells, e.g., to remove proteins. The method may comprise transesterification or esterification of the lipids of the cells. An alcohol such as methanol or ethanol may be used for transesterification or esterification, e.g., thereby producing a fatty acid methyl ester or fatty acid ethyl ester.

EXEMPLIFICATION

The present description is further illustrated by the following examples, which should not be construed as limiting in any way.

Example 1: Identification of 10-Methylstearic Genes tmsA, tmsB, and tmsC

Two different genes have been identified as responsible for 10-methylstearate production in *M. tuberculosis* (see Meena, L. S., and P. E. Kolattukudy, Biotechnology & Applied Biochemistry 60(4):412 (2013) and Meena, L. S., et al. Biological Chemistry 394(7):871 (2013)). Curiously, neither gene is conserved throughout each Actinobacteria species that produces 10-methylstearate. While it is possible that different species of Actinobacteria each independently evolved genes that synthesize 10-methylstearate, such convergent evolution is rare. A simpler explanation is that a single common gene or set of genes is responsible for 10-methylstearate production in Actinobacteria.

To identify genes that may be responsible for 10-methylstearate production in Actinobacteria, genes with sequence homology to those that encode enzymes that catalyze lipid synthesis reactions were aligned from various species of 10-methylstearate-producing Actinobacteria. Two unique genes were identified and named 10-methystearic A (tmsA) and 10-methylstearic B (tmsB), which each occur in the same operon within each 10-methystearate producing species of Actinobacteria (FIG. 3). A third gene named 10-methylstearic C (tmsC) was identified as occurring in the same operon as tmsA and tmsB for some of the 10-methylstearate-producing species.

The 10-methylstearate B gene has sequence homology with cyclopropane synthases, which suggests that the 10-methylstearate B gene may be capable of transferring a methyl group to a fatty acid. The 10-methylstearic A gene has sequence homology with oxidoreductases, which suggests that it may be capable of reducing the exomethylene group of a branched fatty acid.

Figure 1:
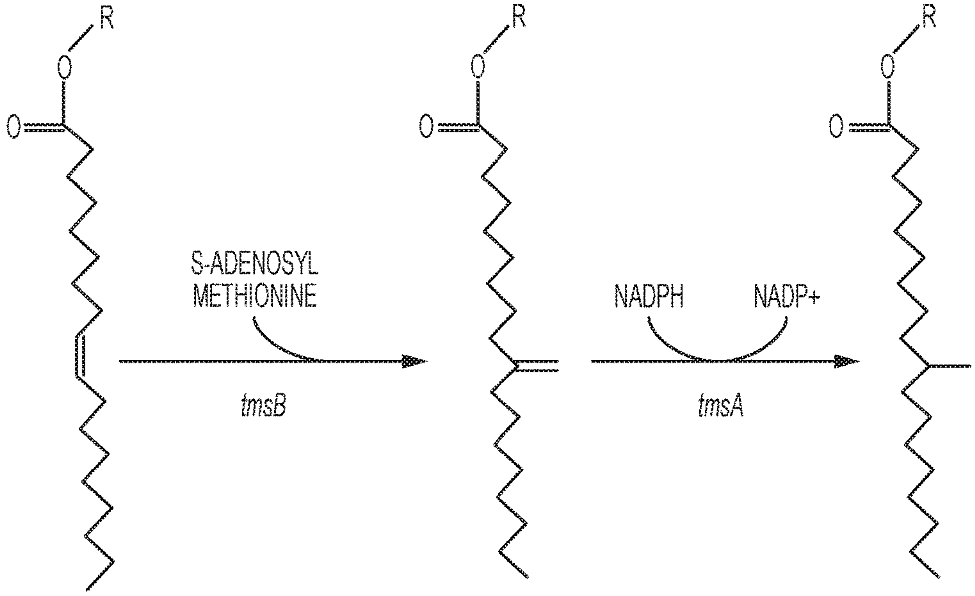
FIG. 1 depicts one possible mechanism for the conversion of oleic acid to 10-methylstearic acid. An oleic acid substrate may be present as an acyl chain of a glycerolipid or phospholipid. A methionine substrate, which donates the methyl group, may be present as S-adenosyl methionine. The oleic acid and methionine substrates may be converted to 10-methylenestearic acid (e.g., present as an acyl chain of a glycerolipid or phospholipid) and homocysteine (e.g., present as S-adenosyl homocysteine). This reaction may be catalyzed by a tmsB protein as described herein, infra. 10-methylenestearic acid (e.g., present as an acyl chain of a glycerolipid or phospholipid) may be reduced to 10-methylstearic acid. The reduction may be catalyzed by a tmsA protein as describe herein, infra, for example, using NADPH as a reducing agent. The language of the specification and claims, however, is not limited to any particular reaction mechanism.
Figure 2:
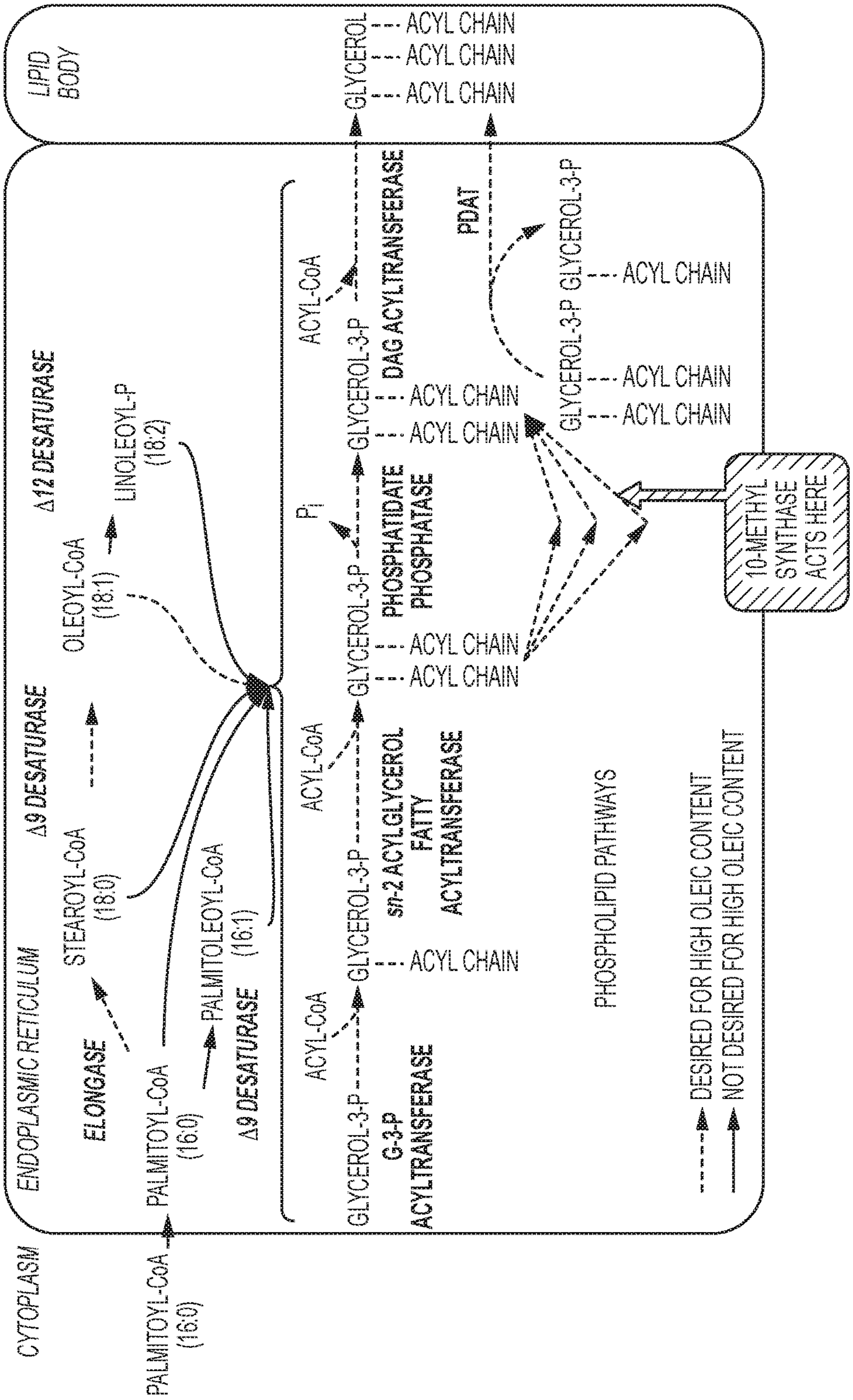
FIG. 2 depicts one possible mechanism for the conversion of oleic acid to 10-methylstearic acid. Oleic acid, present as a carboxylic acid in the cytosol, may be added to monoacylglycerol-3-phosphate to form a diacylglycerol-3-phosphate comprising an oleate acyl group. "10-methyl synthase" may convert diacylglycerol-3-phosphate comprising an oleate acyl group to diacylglycerol-3-phosphate comprising a 10-methylsterate acyl group. The diacyl-3-phosphate may subsequently be converted to a triacylglycerol, converted into another phospholipid, such as phosphatidylcholine, or converted back into a monoacylglycerol-3-phosphate (e.g., thereby releasing free 10-methylstearate into the cytosol). The language of the specification and claims, however, is not limited to any particular reaction mechanism.
Figure 4:
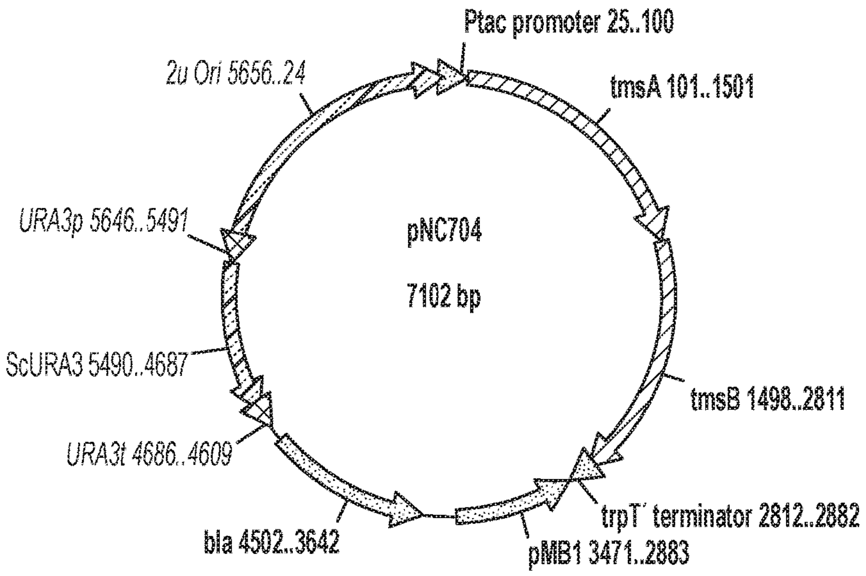
FIG. 4 is a map of plasmid pNC704, which may be used to express *Mycobacterium smegmatis* genes tmsA (SEQ ID NO:1) and tmsB (SEQ ID NO:3) in *E. coli*. The nucleotide sequence of plasmid pNC738 is set forth in SEQ ID NO:77.
Figure 5:
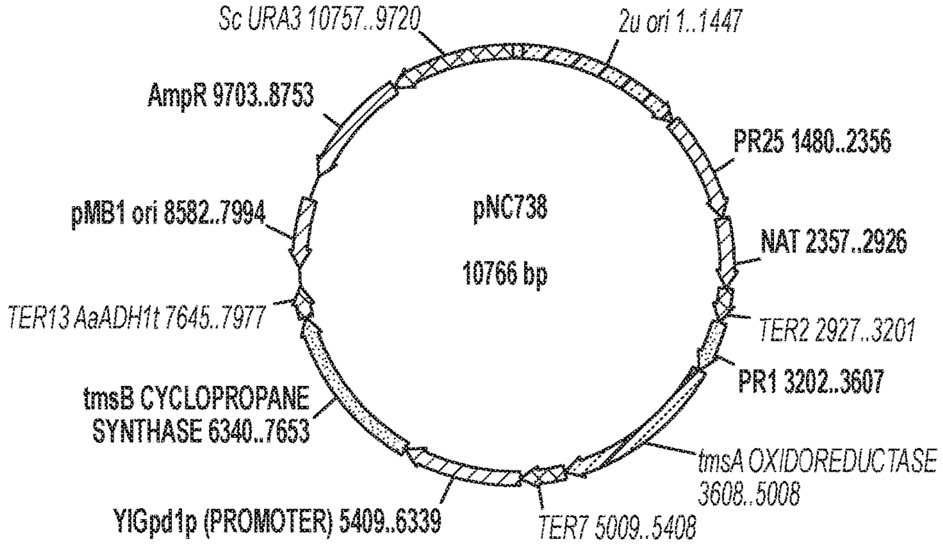
FIG. 5 is a map of plasmid pNC738, which may be used to express codon-optimized versions of *Mycobacterium smegmatis* genes tmsA (SEQ ID NO:80) and tmsB (SEQ ID NO:81) in yeast, such as *Arxula adeninivorans, Saccharomyces cerevisiae*, and *Yarrowia lipolytica*. The nucleotide sequence of plasmid pNC738 is set forth in SEQ ID NO:78.
Figure 6:
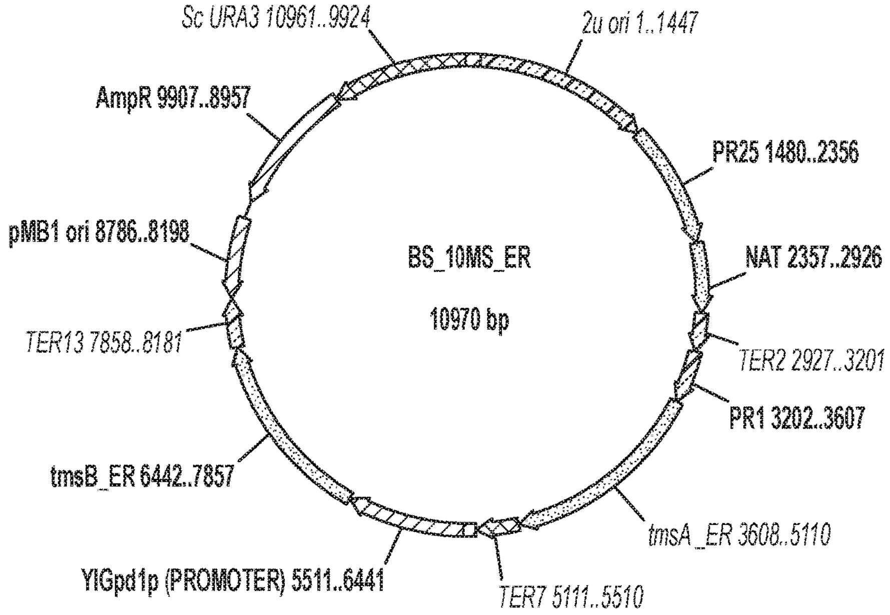
FIG. 6 is a map of plasmid BS-10MS_ER, which may be used to express codon-optimized versions of *Mycobacterium smegmatis* genes tmsA (SEQ ID NO:80) and tmsB (SEQ ID NO:81) in yeast, such as *Arxula adeninivorans,*

The 10-methylstearate A and 10-methylstearate B genes from *M. smegmatis* were cloned into a plasmid (named pNC704) for expression in *E. coli* (FIG. 4). The pNC704 plasmid harboring *M. smegmatis* tmsA and tmsB was used to transform *E. coli*. The transformed cells were grown for 20 hours at 37° C. in LB media supplemented with 100 lag/mL oleic acid. *E. coli* was transformed with an empty vector pNC53 (SEQ ID NO:81) and grown in parallel as a control. Each of two *E. coli* colonies transformed with pNC704 produced 10-methylstearate at a concentration of 2.0% and 2.1% of the total fatty acids in the cell (Table 1). The control did not produce 10-methylstearate

TABLE 1

Fatty acid concentration as a percentage of total cellular fatty acids. "10-MS" corresponds to 10-methylstearate

| | Fatty acid composition | | | | |
|---|---|---|---|---|---|
| | % 10-MS | % 16:1 | % 16:0 | % 18:0 | % 18:1 |
| *E. coli* TOP10 + pNC53 | 0.0 | 4.0 | 56.8 | 1.4 | 30.6 |
| *E. coli* TOP10 + pNC704 isolate 1 | 2.1 | 4.2 | 55.0 | 0.8 | 30.9 |
| *E. coli* TOP10 + pNC704 isolate 2 | 2.0 | 3.9 | 55.5 | 0.8 | 30.8 |

Cellular lipids were transesterified to produce fatty acid methyl esters (FAMEs) in a solution of HCl in methanol. Stearic acid, 10-methylstearic acid, and oleic acid were transesterified into FAMEs as standards. Each sample/standard was extracted into isooctane and analyzed by various gas chromatography methods (FIGS. 7 and 8). FAMEs were first analyzed by capillary gas chromatography using a flame-ionization detector (GC-FID). The FAMEs produced from *E. coli* displayed a GC peak corresponding to the 10-methylstearic acid FAME standard, which suggests that the *M. smegmatis* tmsA and tmsB genes express proteins that are capable of synthesizing 10-methylstearic acid (FIG. 7A).

FAMEs were also produced from *E. coli* that was transformed with the empty vector pNC53 and analyzed by GC-FID as above. This sample did not display a GC peak corresponding to the 10-methylstearic acid FAME, further suggesting that the *M. smegmatis* tmsA and tmsB genes express proteins that are capable of synthesizing 10-methylstearic acid (FIG. 7B).

The FAMEs produced from the tmsA/tmsB sample were analyzed using a GC-MS configured in single-ion monitoring mode (SIM), which monitored m/z at 312.3 and 313.3 amu. The mass spectrum displayed a peak at 312.3 amu, corresponding to the molecular weight of a 10-methylstearate methyl ester (FIG. 8B). Additionally, the ratio of the peak at 312.3 amu to 313.3 amu suggests that the ion observed at 312.3 amu contains 20.6 carbons, which corresponds to the actual number of carbons (20) in the 10-methylstearate methyl ester.

Example 2: Production of 10-Methyl Fatty Acid in *E. coli* Using tmsB and tmsA Genes from Different Donor Organisms Methods:

Donor bacteria genomic DNA was obtained from Deutsche Sammlung von Mikroorganismen und Zellkulturen (DSMZ), Germany. Plasmids were constructed with standard molecular biology techniques using the "yeast gap repair" method (Shanks, et al., Appl. Microbiol. Biotechnol., 48:232 (1997)). The empty *E. coli* expression vector pNC53 (SEQ ID NO:82) was restriction digested with enzyme PmeI (New England Biolabs, MA), creating a double strand break between the tac promoter and trpT' terminator sequences on this vector. tmsAB gene operons were PCR amplified from genomic DNA with primer flanking sequence such that the tmsB ATG start site integrated into the end of the tac promoter via homologous recombination. *E. coli* transcription and translation was driven by the tac promoter. The stop codon of the tmsA gene similarly integrated into the beginning of the trpT' terminator region. *E. coli* translation of the operon-embedded tmsA gene relied on native translation signals from the donor organism DNA. Where necessary, the first codon of tmsB was altered from GTG or TTG to ATG; otherwise the native codon sequence was kept in the *E. coli* expression vectors.

Vectors were checked by DNA sequencing and restriction digest for correct construction. The vectors created for this example are illustrated in FIG. 9. Vectors transformed into *E. coli* Top 10 (Invitrogen) were then used for fermentation studies. Cells were inoculated in 50 mL LB medium supplemented with 100 mg/L ampicillin and 100 mg/L oleic acid from a stock solution of 100 mg/mL oleic acid in ethanol. Cultures were incubated at 37° C. and 200 rpm in baffled shake flasks for 41 hours. At the end of cultivation, cells were harvested by centrifugation at 4000 rpm for 15 minutes in an Eppendorf 5810 R clinical centrifuge, washed once with and equal volume of deionized water, resuspended in 0.1 mL deionized water, and frozen at −80° C. Cells were then lyophilized to dryness and used to perform an acid-catalyzed transesterification with a solution of 0.5 N HCl in methanol (20×1 mL ampule, Sigma) at 85° C. for 90 minutes. After the transesterification was completed, the lipid-soluble components of the reaction mixture were separated from the water-soluble components using a two-phase liquid extraction by adding water and isooctane and subsequently analyzed with a capillary gas chromatograph (GC) equipped with a robotic injector, flame ionization detector (Agilent Technologies 7890B GC system and 7396 Autosampler) and HP-INNOWAX capillary column (30 m×0.25 mm×0.15 micrometers, Agilent). A 10-methylstearic acid reference standard was obtained from Larodan AB, Sweden.

Results:

Conversion of oleic acid to 10-methylstearic acid was observed for 4 of the 11 vectors tested. Highest percent conversion occurred with tmsAB genes from *Thermobifida fusca* (22%) and *Thermomonospora curvata* (38%), as indicated in Table 2 below.

TABLE 2

| *E. coli* vector | Sequence | Donor organism | % oleic acid conversion to 10-methylstearic acid |
|---|---|---|---|
| pNC704 | SEQ ID NO: 77 | *Mycobacterium smegmatis* | 4.9% ± 0.6% |
| pNC721 | SEQ ID NO: 83 | *Mycobacterium vanbaaleni* | 0 |
| pNC755 | SEQ ID NO: 84 | *Amycolicicoccus subflavus* | 0 |
| pNC757 | SEQ ID NO: 85 | *Corynebacterium glyciniphilum* | |
| pNC904 | SEQ ID NO: 86 | *Rhodococcus opacus* | 1.2% ± 0.2% |
| pNC905 | SEQ ID NO: 87 | *Thermobifida fusca* | 22.0% ± 0.3% |
| pNC906 | SEQ ID NO: 88 | *Thermomonospora curvata* | 38.3% ± 0.5% |
| pNC907 | SEQ ID NO: 89 | *Corynebacterium glutamicum* | 0 |
| pNC908 | SEQ ID NO: 90 | *Agromyces subbeticus* | 0 |
| pNC910 | SEQ ID NO: 91 | *Mycobacterium gilvum* | 0 |
| pNC911 | SEQ ID NO: 92 | *Mycobacterium* sp. *indicus* | 0 |

Example 3: tmsB and tmsA expression in *Rhocococcus opacus* PD630

The oleaginous bacteria *Rhocococcus opacus* can produce 10-methyl fatty acids natively at low levels (0.2% of total fatty acids (Wiltermann et al., Microbiology, 72:5027 (2006)), and additionally possesses native homologs of the tmsB and tmsA gens, although they have not been identified as such in the literature. In this Example, the inventors tested whether overexpression of the tmsB and tmsA genes in *R. opacus* can increase 10-methyl branched fatty acid content.

Methods:

*Rhodococcus opacus* PD630 was obtained from the German Collection of Microorganisms and Cell Cultures (DSMZ) from stock DSM 44193. The culture was revived by dilution with 4 mL LB media and incubated at 30° C. for 3 days in a drum roller. Once visible growth occurred, 10 μL broth was struck to single colonies on an LB plate and incubated an additional 3 days at 30° C. One colony was isolated and designated strain NS1104.

All *R. opacus* growth was performed at 30° C. Routine culturing was performed in LB medium supplemented with appropriate antibiotics. Genetic transformation was performed in Nutrient Broth medium as modified by Kalscheuer et al. (Appl. Microbiol. and Biotechnol., 52:508 (1999)), which contained 5 g/L peptone, 2 g/L yeast extract, 1 g/L beef extract, 5 g/L NaCl, 8.5 g/L glycine, and 10 g/L sucrose. Lipid production was performed in defined medium containing the following components and adjusted to pH 7.6 with NaOH and filter sterilized before use.

*R. opacus* fermentation medium

| Component | g/L |
|---|---|
| Glucose | 40 |
| $(NH_4)_2SO_4$ | 1.4 |
| $MgSO_4$•$7H_2O$ | 1 |
| $CaCl_2$•$6H_2O$ | 0.02 |
| $KH_2PO_4$ | 0.4 |
| MOPS acid | 5 |
| Trace element solution | 1 mL |
| **Trace element solution** | **g/L stock solution** |
| $FeSO_4$•$7H_2O$ | 0.5 |
| $CuSO_4$•$5H_2O$ | 0.005 |
| $ZnSO_4$•$7H_2O$ | 0.4 |
| $MnCl_2$•$2H_2O$ | 0.02 |
| $Na_2MoO_4$•$2H_2O$ | 0.02 |
| $CoCl_2$•$6H_2O$ | 0.05 |
| EDTA | 0.25 |
| $H_3BO_3$ | 0.015 |
| $NiCl_2$•$6H_2O$ | 0.01 |

Plasmids were constructed with standard molecular biology techniques using the "yeast gap repair" method (Shanks et al., Applied and Environmental Biology 72:5207-36 (2006)). A synthetic DNA sequence containing the *Rhodococcus* repA origin of replication and gentamicin resistance marker (Lessard, BMC Microbiol., 4:15 (2004)) was used to create a *R. opacus*-*E. coli*-*S. cerevisiae* shuttle vector from two plasmids containing the tmsAB genes from *Mycobacterium smegmatis* and *Thermobifida fusca* under control of the tac promoter. Briefly, the repA and $gen^R$ synthetic DNA was constructed with approximately 50 bp flanking homology regions to the tmsAB destination plasmids. Destination plasmids were restriction digested with PacI, and the flanking homology regions repaired the gap, enabling genetic selection via the ura3 gene in *S. cerevisiae*. DNA was isolated from *S. cerevisiae* by phenol/chloroform extraction and ethanol precipitation and used to transform *E. coli*. Correct plasmid constructions were isolated by mini-prep (Qiagen, USA) and screened by restriction digest. Plasmids pNC985 (SEQ ID NO:93), containing *M. smegmatis* tmsAB, and pNC986 (SEQ ID NO:94) (FIG. 10), containing *T. fusca* tmsAB were isolated and used to transform *R. opacus*.

*R. opacus* was transformed following the protocol described by Kalscheuer et al. (Kalscheuer 1999). Cells were grown overnight in modified nutrient broth, then transferred to 50 mL modified nutrient broth medium at a starting optical density of 0.13. Cells were harvested at OD 0.36, washed twice in 50 mL ice cold water, and resuspended in 1.7 mL ice cold water. Cells were then subdivided to 350 μL volumes and 2 μL plasmid DNA at 400-600 ng/μL concentration. Cells plus DNA were incubated at 39° C. for 5 minutes immediately prior to cooling on ice and electrotransformation. Electric pulses were delivered using 2 mm gap cuvettes with a 2 kV pulse (600Ω, 25 μF, 12 ms time constant). Cells were then diluted with 600 μL SOC medium and incubated overnight at 30° C. 200 μL overnight cell broth was then plated on LB agar containing 10 μg/mL gentamicin and incubated an additional 4 days at 30° C. for colony formation. Gentamicin resistant colonies were picked for further analysis, no resistant colonies were seen on control plates without added plasmid DNA.

Fermentation was performed at 30° C. for 4 days in 250 mL shake flasks (25 mL working volume with defined medium, 10 μg/mL gentamicin added as appropriate) at 200 rpm. Inoculum was prepared from 48 hour grown cultures in LB+10 μg/mL gentamicin. Inoculation amount was 1:25 v/v of the final volume. At the end of fermentation cells were harvested and resuspended in 1 mL distilled water and frozen at −80° C. After freezing, cells were lyophilized to dryness and then whole cells were transesterified in situ with methanolic HCl at 80° C. before extraction into isooctane and quantification by gas chromatography with flame ionization detection.

Results:

*R. opacus* was transformed with two vectors, pNC985 expressing the *M. smegmatis* tmsAB genes, and pNC986 expressing the *T. fusca* tmsAB genes. As shown in Table 3 below, one isolate of the pNC986 transformation, strain NS1155, produced 10-methylstearic acid at 7.2% by weight of total fatty acids, as compared to the control strain NS1104 at 3.6% by weight of total fatty acids.

TABLE 3

Weight percent 10-methylstearic acid measured in *R. opacus* strains transformed with tmsAB expression vectors.

| Description | 10-methylstearic acid (% of total FA) |
|---|---|
| *R. opacus* PD630 (NS1104) | 3.6 |
| *R. opacus* + pNC985 #1 (Msm tmsAB) | 3.9 |
| *R. opacus* + pNC985 #2 | 3.3 |
| *R. opacus* + pNC985 #3 | 3.3 |
| *R. opacus* + pNC986 #1 (Tfu tmsAB) | 7.2 |
| *R. opacus* + pNC986 #2 | 3.0 |
| *R. opacus* + pNC986 #3 | 3.1 |

Example 4: Acyl Chain Substrate Range for tmsB and tmsA

The inventors performed the following experiments to determine the acyl-chain substrate range of the tmsB and tmsA enzymes from *Thermomonospora curvata*, particularly the fatty acid chain length and double bond position.

Methods:

Unsaturated fatty acids were purchased from Nu-Check Prep, Inc., Elysian Minn. Fatty acids were dissolved in DMSO at a concentration of 100 mg/mL, with the exceptions of palmitoleic acid, oleic acid, and vaccenic acid, which were dissolved in ethanol at a concentration of 100 mg/mL. A 10-methyl stearic acid reference standard was obtained from Larodan AB, Sweden.

*E. coli* strains NS1161 and NS1162 were used in this experiment; strain NS1161 was constructed by transforming the control (empty) vector plasmid into *E. coli* CGSC 9407 (aka JW1653-1 Keio collection) which holds a kan$^R$ disruption of the native *E. coli* cyclopropane fatty acid synthase (cfa) gene. Strain NS1162 was constructed by transforming plasmid pNC906 (SEQ ID NO:88) (FIG. 9B), containing the *T. curvata* tmsB and tmsA genes under control of the constitutive tac promoter, into *E. coli* CGSC 9407.

*E. coli* strains were grown in LB media supplemented with 100 mg/L ampicillin and 100 mg/L of fatty acid. Cultures were inoculated with a 1:1000 dilution of overnight pre-culture and grown in 14 mL plastic culture tubes with a 5 mL working volume at 37° C. in a rotary drum roller for 24 hours. At the end of cultivation cells were harvested by centrifugation at 4000 rpm for 15 minutes in an Eppendorf 5810 R clinical centrifuge, washed once with and equal volume of deionized water, resuspended in 0.1 mL deionized water, and frozen at −80° C. Cells were then lyophilized to dryness and used to perform a HCl-methanol catalyzed transesterification reaction to produce fatty acid methyl esters (FAME). These samples were dissolved in isooctane and injected into a gas chromatography system (Agilent Technologies) equipped with a flame ionization detector.

Results:

When fed exogenous free fatty acids, *E. coli* can incorporate them into its phospholipids and other lipid structures. Strains NS1161 and NS1162 were cultured with 18 different unsaturated fatty acids and in a control medium with no fatty acid supplementation, and FAME profiles for the two strains were compared. To identify new unsaturated fatty acids, a GC peak corresponding to the supplemented fatty acid was identified via the strain NS1161 FAME profile as compared to the un-supplemented reference culture. and then the strain NS1162 FAME profile was checked for the same GC peak, and a new peak at a characteristic retention time shift (0.24 to 0.08 minutes forward, with the relative shift decreasing as overall retention time increases) corresponding to a methylated fatty acid. A 10-methyl stearic acid reference standard (Larodan AB, Sweden) was used as a control to assign retention time to 10-methylstearic acid.

As observed in Table 4 below, methylation occurred on fatty acids with 14, 15, 16, 17, 18, 19 and 20 carbons, and on Δ9, Δ10, and Δ11 double bond positions. The highest percent conversion to methylated fatty acids occurred at 16 and 18 carbon fatty acids at the Δ9 and Δ11 positions.

TABLE 4

| Fatty acid | Name | Unsaturated FA Retention time (min) | Methyl-branched FA retention time (min) | % conversion to methyl branched FA |
|---|---|---|---|---|
| 12:1Δ11 | 11-Dodecenoic acid | 4.627 | — | 0.0% |
| 13:1Δ12 | 12-Tridecenoic acid | 5.765 | — | 0.0% |
| 14:1Δ9 | Myristoleic acid | 6.785 | 6.546 | 3.4% |
| 15:1Δ10 | 10-Pentadecenoic acid | 7.926 | 7.715 | 1.7% |
| 16:1Δ9 | Palmitoleic acid | 8.907 | 8.772 | 30.4% |
| 17:1Δ110 | 10-Heptadecenoic acid | 9.999 | 9.859 | 11.1% |
| 18:1Δ6 | Petroselinic acid | 10.943 | — | 0.0% |

TABLE 4-continued

| Fatty acid | Name | Unsaturated FA Retention time (min) | Methyl-branched FA retention time (min) | % conversion to methyl branched FA |
|---|---|---|---|---|
| 18:1Δ9 | Oleic acid | 10.978 | 10.862 | 33.7% |
| 18:1Δ11 | Vaccenic acid | 11.065 | 10.917 | 21.8% |
| 18:1Δ9, 12-OH | Ricinoleic acid | 12.737 | — | 0.0% |
| 18:1Δ9, 12 | Linoleic acid | 11.656 | — | 0.0% |
| 19:1Δ7 | 7-Nondecenoic acid | 11.941 | — | 0.0% |
| 19:1Δ10 | 10-Nondecenoic acid | 12.01 | 11.888 | 6.1% |
| 20:1Δ5 | 5-Eicosenoic acid | 12.652 | — | 0.0% |
| 20:1Δ8 | 8-Eicosenoic acid | 12.713 | — | 0.0% |
| 20:1Δ11 | 11-Eicosenoic acid | 12.743 | 12.666 | 2.2% |
| 22:1Δ13 | Erucic acid | 13.406 | — | 0.0% |
| 24:1Δ15 | Nervonic acid | 13.86 | — | 0.0% |

Example 5: tmsA Co-Factor Usage

The inventors performed the following experiments to determine which redox co-factor the tmsA enzyme (10-methylene reductase) uses to produce fully saturated 10-methyl fatty acids from the intermediate 10-methylene fatty acids.

Methods:

*E. coli* strains NS1161, NS1163, and NS1164 were used in this experiment; strain NS1161 was constructed by transforming the control (empty) vector plasmid pNC53 into *E. coli* CGSC 9407 (aka JW1653-1 Keio collection) which holds a kan$^R$ disruption of the native *E. coli* cyclopropane fatty acid synthase (cfa) gene. Strain NS1163 was constructed by transforming plasmid pNC963 (SEQ ID NO:95) (FIG. 11), containing the *T. curvata* tmsB gene under control of the constitutive tac promoter, into *E. coli* CGSC 9407. Strain NS1164 was constructed by transforming plasmid pNC964 (SEQ ID NO:96) (FIG. 11), containing the *T. curvata* tmsA gene under control of the constitutive tac promoter, into *E. coli* CGSC 9407.

Strain NS1163 was grown in 1 L LB media supplemented with 100 mg/L ampicillin for 24 hours at 37° C. (2×500 mL in 2 L baffled flasks). After cultivation, cells were harvested by centrifugation at 4000 rpm for 15 minutes in an Eppendorf 5810 R clinical centrifuge and washed twice in 100 mL PBS buffer. After concentration to 40 mL PBS buffer, cells were heat inactivated at 85° C. for 30 min. Inactivated cells were then dispensed into 1 mL aliquots and disrupted with 0.3 grams of 0.1 mm glass beads using a MP fastprep-24 on "*E. coli*" setting (MP biomedicals, LLC). Whole cell lysed suspension was collected by micro-centrifugation at 2000×g for 30 seconds to remove beads and then 0.7 mL of suspension per tube was transferred to new tubes and frozen at −80° C. until further use.

On the day of assay, strains NS1161 and NS1164 were grown via inoculation from overnight cultures (1:1000 dilution) in 50 mL LB medium supplemented with 100 mg/L ampicillin in 37° C. and 200 rpm in baffled shake flasks. After 4 hours of cultivation, cells were harvested at 5° C., washed 1× in ice cold PBS and then resuspended in 750 μL PBS in 1 mL plastic screw tubes. 0.3 grams of 0.1 mm glass beads were added and cells were lysed with a MP fastprep-24 on the "*E. coli*" setting. The cell suspension was then micro-centrifuged for 5 min at 12,000×g, and the supernatant transferred to a fresh tube and held on ice until assay.

Assay reaction: 700 μL of NS1163 whole lysate, 200 μL of 37.2 mg/mL NADPH solution (assay concentration 10 mM), 33.2 mg/mL NADH solution (assay concentration 10 mM), or PBS buffer, and 100 μL of cell free extract or PBS buffer. Assay tubes were sealed and rotated on a drum roller at 37° C. for 16 hours. To end the assay, tubes were frozen at −80° C., then lyophilized to dryness followed by in situ extraction and transesterification with methanolic HCL. Fatty acid profiles were determined by GC with flame ionization detection, and the 10-methyl fatty acid peak area was compared to the total fatty acid peak area to determine assay activity.

Results:

Strain NS1163, which accumulates 10-methylene intermediate fatty acids via expression of the *Thermomonospora curvata* tmsB gene, was grown, harvested, inactivated, and lysed for use as a substrate for the tmsA (10-methylene reductase) assay. To this substrate cell-free extract *E. coli* strain NS1164 expressing the *T. curvata* tmsA gene or *E. coli* strain NS1161 containing an empty expression vector were added, along with NADPH or NADH. As observed Table 5 below, only the presence of *T. curvata* tmsA and NADPH resulted in synthesis of 10-methyl fatty acids in this assay.

TABLE 5

| E. coli (Δcfa background) cell free extract | co-factor | relative 10Me16 + 10Me18 peak area | SD |
|---|---|---|---|
| Tcu tmsA | NADPH | 0.059 | 0.003 |
| Tcu tmsA | NADH | ND | |
| Tcu tmsA | none | ND | |
| empty vector | NADPH | ND | |
| empty vector | NADH | ND | |
| empty vector | none | ND | |
| none | NADPH | ND | |
| none | NADH | ND | |
| none | none | ND | |

ND = Not detected by this assay

Example 6: Expression of tmsB Genes in Yeast *Yarrowia lipolytica* and *Arxula adeninivorans*

Sequences encoding the native bacterial codon tmsB sequences from *Mycobacterium smegmatis, Mycobacterium vanbaaleni, Amycolicicoccus subflavus, Corynebacterium glyciniphilum, Rhodococcus opacus, Agromyces subbeticus, Knoellia aerolata, Mycobacterium gilvum, Mycobacterium* sp. *Indicus, Thermobifida fusca*, and *Thermomonospora curvata* were cloned into a standard *Yarrowia* expression vector driven by the *Y. lipolytica* TEF1 promoter and containing an ARS68 *Y. lipolytica* replication origin, a nourseothricin antibiotic resistance gene for selection, and the 2 origin and URA3 gene for high copy maintenance in *Saccharomyces cerevisiae*. Cloning was performed using the yeast-gap repair method (Shanks 2006) with selection on uracil dropout media. *Y. lipolytica* was transformed following a standard lithium acetate heat-shock protocol with selection on YPD medium supplemented with 500 μg/mL nourseothricin. Colonies were selected and transferred to a 96 well plate containing 300 μL nitrogen-limited lipid production media per well and incubated at 30° C. with shaking at 900 rpm for 96 hours. The medium contained 100 g/L glucose, 0.5 g/L urea, 1.5 g/L yeast extract, 0.85 g/L casamino acids, 1.7 g/L YNB base without amino acids, and 5.1 g/L potassium hydrogen phthalate at pH 5.5. After fermentation, cells were centrifuged, washed with distilled water, and frozen at −80° C. prior to lyophilization to dryness. Dried cells were transesterified in situ with 0.5 N HCl in methanol at 85° C. for 90 minutes to produce fatty acid methyl esters (FAME) suitable for gas chromatography analysis. These samples were dissolved in isooctane and injected into a gas chromatography system (Agilent Technologies) equipped with a flame ionization detector. Total C16 and C18 branched fatty acids were identified and quantified based on known standards and the 10 methylene and 10 methyl fatty acids identified in *E. coli* tms expression experiments. 10-methyl and 10-methylene fatty acid identities were verified by mass spec in an independent experiment. FIG. 12 shows that *Y. lipolytica* transformed with tmsB from *T. fusca* and *T. curvata* produced the highest amounts of 10-methylene stearic acid.

To test tmsB activity in *Arxula adeninivorans*, the top performing tmsB gene from *Yarrowia, T. curvata* tmsB (SEQ ID NO:75) was cloned into a constitutive expression vector under the *Arxula* ADH1 promoter, resulting in plasmid pNC1065. Individual transformant colonies were isolated and grown in a standard industrial media (with a high C:N ratio to promote lipid accumulation) for 4 days at 40° C. Cell pellets were isolated, washed once with water, and lyophilized. Total C16 and C18 fatty acids were transesterified as for *Yarrowia* strains and were analyzed by GC. FIG. 13 shows that *A. adeninivorans* transformed with tmsB from *T. curvata* produce 10-methylene fatty acids.

Example 7: tmsA and tmsB Coexpression in *Yarrowia lipolytica* and *Saccharomyces cerevisiae*

The inventors discovered that simultaneous expression of tmsA and tmsB genes can produce branched 10-methyl and 10-methylene fatty acids, respectively, in *Saccharomyces* and *Yarrowia* yeast strains. For expression in *Yarrowia*, plasmids constitutively expressing the native bacterial sequences for tmsA from *T. curvata* (pNC984), *T. fusca* (pNC983) and *C. glutamicum* (pNC991) were each transformed into strain NS1117 containing a stably integrated copy of the *T. curvata* tmsB gene (isolated from Example 6 above). Individual transformants were isolated and grown for 4 days at 30° C. in shake flask medium. Fatty acids were isolated and analyzed by GC as in Example 6. As shown in FIG. 14, all tmsA genes analyzed produce at detectable levels of 10 methyl fatty acids in *Yarrowia*, compared to the parental strain. The *T. curvata* tmsA gene produced more 10-methyl fatty acids than the other tmsA genes analyzed.

For expression in *Saccharomyces*, plasmids with demonstrated gene activity in *Yarrowia*, pNC984 (*T. curvata* tmsA with a NAT marker) and pNC1025 (*T. curvata* tmsB with a HYG marker) were transformed individually and together into *S. cerevisiae* strain NS20, and transformants were selected on media containing the appropriate antibiotic(s). Individual transformation isolates were grown for 2 days in YPD medium at 30° C. Cell pellets were processed, and total fatty acids were analyzed as for *Yarrowia*. As shown in FIG. 15, the strain transformed with only tmsB produced only 10-methylene fatty acids, and the strain transformed with both tmsA and tmsB produced a relatively high percentage of 10-methyl fatty acids.

Example 8: Expression of a tmsA-B Fusion Protein in *E. coli, Saccharomyces ceverisiae, Yarrowia lipolytica* and *Arxula adeninivorans*

The inventors discovered that expressing the tmsA and tmsB enzymes in a single polypeptide improves conversion of 10-methylene fatty acids to 10-methyl fatty acids. Single proteins containing both tmsA and tmsB activity were created by fusing the genes for *Thermomonospora curvata* tmsA and tmsB in frame, separated by a flexible linker domain. The *Thermomonospora curvata* tmsA and tmsB enzymes were chosen because they produced the most 10-methyl branched fatty acids in yeast. A short 12 amino acid linker with the sequence AGGAEGGNGGGA which occurs naturally in the *Yarrowia* FAS2 gene was chosen to connect the two enzymes. Two fusion enzymes were tested for activity in bacteria and yeast, tmsA-B (NG540; encoded by SEQ ID NO:97) and tmsB-A (NG541; encoded by SEQ ID NO:98).

For *E. coli* expression, plasmids pNC1069 and pNC1070 containing the *T. curvata* tmsA-B and tmsB-A genes with the tac promoter and trpT' terminator were each transformed into *E. coli* CGSC 9407. Individual transformed strains were grown and total fatty acids were assayed as in Example 2 above. As shown in Table 6 below, both the tmsA-B and tmsB-A genes resulted in production of methylated stearic acid in *E. coli*.

TABLE 6

Methylation of oleic and vaccenic acid was calculated as the percent of C18:1 fatty acids converted into 10- and 12-methyl fatty acids.

| Vector | % C18:1 methylated |
|---|---|
| None | 0 |
| *T.curvata* tmsA-B | 19.4 |
| *T.curvata* tmsB-A | 26.25 |

For *Saccharomyces cerevisiae* and *Yarrowia lipolytica* expression, NG540 (SEQ ID NO:97) and NG541 (SEQ ID NO:98) were individually cloned into standard *Yarrowia* expression vectors containing a yeast 2u origin of replication for high copy retention in *Saccharomyces*, resulting in the respective vectors pNC1067 and pNC1068.

Plasmids pNC1067 and pNC1068 were transformed into *Saccharomyces* strain NS20 by a standard protocol and individual transformed strains were selected for assay of branched fatty acid production. Strains were grown for 2 days at 30° C. in 25 ml YPD medium. Cell pellets were lyophilized and total fatty acids were analyzed by basic transesterification and GC analysis as in Example 2. FIG. 16 shows that expression of both tmsA-B and tmsB-A in *S. cerevisiae* led to production of 10 methyl fatty acids.

Plasmids pNC1067 and pNC1068 were transformed into *Yarrowia lipolytica* by a standard heat shock protocol. Individual resulting transformant strains were chosen for analysis of 10-methylene and 10-methyl fatty acid production. Strains were grown and analyzed by GC as in Example 7. FIG. 17 shows that expression of both tmsA-B and tmsB-A in *Y. lipolytica* led to production of 10 methyl fatty acids, although tmsA-B was more efficient at converting 10-methylene fatty acids to 10-methyl fatty acids.

For expression in *Arxula adeninivorans*, NG540 was cloned into a standard expression vector containing the constitutive *Arxula* ADH1 promoter resulting in pNC1151. pNC1151 was transformed into *Arxula* strain NS1166 and individual transformants were selected to assay of 10-methyl fatty acid production. *Arxula* strains were grown and analyzed by GC as in Example 7.

These experiments showed that 10-methyl C16 and C18 fatty acids were detected in *E. coli*. (Table 6), *Saccharomyces cerevisiae* (FIG. 16), *Yarrowia lipolytica* (FIG. 17), and *Arxula adeninivorans* (FIG. 18), indicating that the fusion enzymes contain both tmsA and tmsB activities. The low production of 10-methylene intermediates (undetectable in *E. coli* and *Saccharomyces*, at low levels in *Yarrowia* and *Arxula*) indicate that the fusion protein efficiently converts unsaturated fatty acids into 10 methyl fatty acids.

Example 9: tmsB Sequence Analysis

TmsB protein sequences coded by the tmsB genes from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus, Thermobifida fusca*, and *Thermomonospora curvata* were aligned with the cyclopropane fatty acid synthase (Cfa) enzyme from *Escherichia coli* with the CLUSTAL OMEGA software program (European Molecular Biology Laboratory, EMBL). FIGS. 19A-D show the alignment of these protein sequences. *E. coli* Cfa shares homology to the TmsB enzyme and carries out a similar reaction to TmsB, with methylation of a fatty acid phospholipid double bond, but produces a cyclopropane moiety rather than a methylene moiety.

Certain amino acids of the *E. coli* Cfa enzyme are thought to bind the active site bicarbonate ion. Iwig et al., J. Am. Chem. Soc. 127:11612-13(2005). These amino acids are C139, E239, H266, 1268, and Y317 of the *E. coli* enzyme, which are conserved in the consensus tmsB protein sequence (C160, E266, H293, 1295, and Y348 on the *T. curvata* TmsB sequence SEQ ID NO:76).

Additionally, there are sixteen amino acid residues that are conserved for all twelve TmsB protein sequences, but not in the *E. coli* Cfa sequence. These amino acids may be specific for 10-methylene addition to fatty acid phospholipids rather than the cyclopropane addition performed by the *E. coli* Cfa protein. These conserved amino acids, numbered with the *T. curvata* TmsB sequence, are D23, G24, Δ59, H128, F147, Y148, L180, L193, M203, G236, Δ241, R313, R318, E320, L359, L400 of SEQ ID NO:76.

A BLASTp conserved domains analysis (National Center for Biotechnology Information, NCBI) identifies a S-adenosylmethionine-dependent methyltransferase domain from amino acids 192-291 of *T. curvata* TmsB. S-adenosylmethionine binding site amino acid residues are identified as V196, G197, C198, G199, W200, G201, G202, T219, L220, Q246, D247, Y248, and D262.

Table 7 shows the percent sequence identity of the indicated protein relative to *T. curvata* tmsB:

TABLE 7

| Species | % Identity |
|---|---|
| *Thermomonospora curvata* tmsB | 100 |
| *Mycobacterium smegmatis* tmsB | 60 |
| *Mycobacterium vanbaaleni* tmsB | 59 |
| *Amycolicicoccus subflavus* tmsB | 55 |
| *Corynebacterium glyciniphilum* tmsB | 47 |
| *Corynebacterium glutamicum* tmsB | 50 |
| *Rhodococcus opacus* tmsB | 59 |
| *Agromyces subbeticus* tmsB | 57 |
| *Knoellia aerolata* tmsB | 47 |
| *Mycobacterium gilvum* tmsB | 58 |
| *Mycobacterium* sp. *Indicus* tmsB | 58 |
| *Thermobifida fusca* tmsB | 67 |
| *Escherichia coli* Cfa | 34 |

As shown in Table 7, there is a great deal of variation among the tmsB protein sequences from the different species. Nevertheless, despite the sequence variation, several of the proteins are shown herein to have the same ability to catalyze the production of a methylene-substituted lipid.

Example 10: tmsA Sequence Analysis

TmsA protein sequences coded by the tmsA genes from *Mycobacterium smegmatis, Mycobacterium vanbaaleni, Amycolicicoccus subflavus, Corynebacterium glyciniphilum, Corynebacterium glutamicum, Rhodococcus opacus, Agromyces subbeticus, Knoellia aerolata, Mycobacterium gilvum, Mycobacterium* sp. *Indicus, Thermobifida fusca*, and *Thermomonospora curvata* were aligned with the Glycolate oxidase subunit GlcD enzyme from *Escherichia coli* with the CLUSTAL OMEGA software program (European Molecular Biology Laboratory, EMBL). The *E. coli* GlcD enzyme does not appear to perform a similar enzymatic reaction as TmsA, but it is the most closely homologous protein to TmsA in the *E. coli* genome.

FIGS. 20A-E show the alignment of the TmsA proteins. There are 114 amino acid residues that are conserved for all twelve TmsA protein sequences, but not in the *E. coli* GlcD sequence. These amino acids are (numbered according to the *T. curvata* sequence (SEQ ID NO:74)): R31, A33, S37, N38, L39, F40, R43, D52, V59, D63, G73, M74, T76, Y77, D79, L80, V81, L85, P91, V93, V94, Q96, L97, T99, 1100, T101, A105, G108, G110, E112, S113, S115, F116, R117, N118, P121, H122, E123, V125, E127, G133, P154, N155, Y157, Y162, L166, E171, V173, V177, H181, V208, G213, F216, Y222, L223, S236, D237, Y238, T239, Y245, S247, D254, T257, Y261, W263, R264, W265, D266, D268, W269, C272, Δ275, G277, Q279, R284, W287, R293, S294, G318, E232, V325, P328, E330, F339, F343, W353, C355, P356, W363, L365, Y366, P367, N376, F379, W380, V383, P384, N395, E399, G407, H408, K409, S410, L411, Y412, S413, Y417, F422, Y426, G428, R443, L447, and V452.

A BLASTp conserved domains analysis (National Center for Biotechnology Information, NCBI) identifies a Flavin adenine dinucleotide (FAD) binding domain from amino acids 9-141 of *T. curvata* TmsA (SEQ ID NO:74), as well as a FAD/FMN-containing dehydrogenase domain from amino acids 22-444. Table 8 shows the percent sequence identity of the indicated protein relative to *T. curvata* tmsA:

TABLE 8

| Species | % Identity |
|---|---|
| *Thermomonospora curvata* tmsA | 100 |
| *Mycobacterium smegmatis* tmsA | 61 |
| *Mycobacterium vanbaaleni* tmsA | 61 |
| *Amycolicicoccus subflavus* tmsA | 60 |
| *Corynebacterium glyciniphilum* tmsA | 55 |
| *Corynebacterium glutamicum* tmsA | 53 |
| *Rhodococcus opacus* tmsA | 61 |
| *Agromyces subbeticus* tmsA | 59 |
| *Knoellia aerolata* tmsA | 60 |
| *Mycobacterium gilvum* tmsA | 59 |
| *Mycobacterium* sp. *Indicus* tmsA | 58 |
| *Thermobifida fusca* tmsA | 64 |
| *Escherichia coli* GlcD | 28 |

As shown in Table 8, there is a great deal of variation among the tmsA protein sequences from the different species. Nevertheless, despite the sequence variation, several of the proteins are shown herein to have the same ability to catalyze the production of a methyl-substituted lipid.

INCORPORATION BY REFERENCE

Each of the patents, published patent applications, and non-patent references cited herein is hereby incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A yeast cell comprising a methyltransferase gene encoding a *Thermomonospora curvata* enzyme tmsB and either a branched (methyl)lipid or an exomethylene-substituted lipid, wherein:
   the branched (methyl)lipid or exomethylene-substituted lipid is a carboxylic acid, carboxylate, ester, thioester, or amide, and
   the branched (methyl)lipid comprises a saturated or unsaturated branched aliphatic chain comprising a branching methyl group or the exomethylene-substituted lipid comprises a branched aliphatic chain that is branched because the aliphatic chain is substituted with an exomethylene group.

2. The cell of claim 1, wherein the branched (methyl)lipid or the exomethylene-substituted lipid comprises a linear lipid with a chain length of 14-20 carbons and a methyl branch at the Δ9, Δ10, or Δ11 position.

3. The cell of claim 2, wherein the branched (methyl)lipid or the exomethylene-substituted lipid is a diacylglycerol, triacylglycerol, or phospholipid, and the diacylglycerol, triacylglycerol, or phospholipid comprises an ester of 10-methylstearate or an ester of 10-methylenestearate.

4. The cell of claim 1, wherein at least 1% by weight of the fatty acids of the cell are one or more linear fatty acids with a chain length of 14-20 carbons and a methyl branch at the Δ9, Δ10, or Δ11 position.

5. The cell of claim 1, wherein the cell comprises at least 1% lipid as measured by % dry cell weight.

6. The cell of claim 1, further comprising a recombinant reductase gene.

7. The cell of claim 6, wherein the reductase gene encodes tmsA from *Thermomonospora curvata*.

8. The cell of claim 1, wherein:
   the methyltransferase gene is codon-optimized for the cell; or
   the cell further comprises a reductase gene and the reductase gene is codon-optimized for the cell.

9. The cell of claim 1, wherein the cell is selected from the group consisting of *Arxula*, *Saccharomyces*, and *Yarrowia*.

10. The cell of claim 9, wherein the cell is selected from the group consisting of *Arxula adeninivorans*, *Saccharomyces cerevisiae*, and *Yarrowia lipolytica*.

11. The cell of claim 1, wherein the cell comprises a methyltransferase protein encoded by the methyltransferase gene, and the methyltransferase protein comprises either: an amino acid sequence with at least 95% sequence identity with the amino acid sequence of SEQ ID NO:76; or the amino acid sequence of SEQ ID NO:76.

12. The cell of claim 1, wherein the methyltransferase gene comprises either: a nucleotide sequence with at least 95% sequence identity with the nucleotide sequence of SEQ ID NO:75; or the nucleotide sequence of SEQ ID NO:75.

13. A method of producing a branched (methyl)lipid or exomethylene-substituted lipid, comprising contacting the cell of claim 1 with oleic acid, methionine, or both oleic acid and methionine.

14. The cell of claim 6, wherein the reductase protein is in a fusion protein with the tmsB enzyme.

* * * * *